(12) United States Patent
Dininno et al.

(10) Patent No.: US 8,440,643 B2
(45) Date of Patent: May 14, 2013

(54) INHIBITORS OF BETA-LACTAMASE

(75) Inventors: Frank Dininno, Barnegat, NJ (US); Milton L. Hammond, Somerville, NJ (US); Kevin Dykstra, West Milford, NJ (US); Seongkon Kim, Holmdel, NJ (US); Qiang Tan, Westfield, NJ (US); Katherine Young, Metuchen, NJ (US); Jeffrey Donald Hermes, Warren, NJ (US); Helen Chen, Marlboro, NJ (US); Stephane Raeppel, St. Lazare (CA); Michael Mannion, Montreal (CA); Frederic Gaudette, Laval (CA); Arkadii Vaisburg, Kirkland (CA); Jubrail Rahil, Dollard des Ormeaux (CA); Nafsika Georgopapadakou, Vaudreuil (CA); Nancy Z. Zhou, Kirkland (CA)

(73) Assignee: MethylGene Inc., Montreal (CA)

( * ) Notice: Subject to any disclaimer, the term of this patent is extended or adjusted under 35 U.S.C. 154(b) by 614 days.

(21) Appl. No.: 12/301,797

(22) PCT Filed: May 21, 2007

(86) PCT No.: PCT/US2007/011979
§ 371 (c)(1), (2), (4) Date: Jun. 29, 2010

(87) PCT Pub. No.: WO2008/073142
PCT Pub. Date: Jun. 19, 2008

(65) Prior Publication Data
US 2010/0279983 A1   Nov. 4, 2010

Related U.S. Application Data

(60) Provisional application No. 60/802,141, filed on May 22, 2006, provisional application No. 60/840,001, filed on Aug. 25, 2006.

(51) Int. Cl.
*A61K 31/675* (2006.01)
*A61K 31/67* (2006.01)
*A61K 31/665* (2006.01)

(52) U.S. Cl.
USPC .................. 514/80; 514/89; 514/92; 514/96; 514/100

(58) Field of Classification Search .................... 514/80, 514/89, 92, 96, 100
See application file for complete search history.

(56) References Cited

U.S. PATENT DOCUMENTS

| 2004/0029836 A1 | 2/2004 | Besterman et al. |
| 2004/0059115 A1* | 3/2004 | Besterman et al. ............. 546/22 |

FOREIGN PATENT DOCUMENTS

| WO | WO 01/02411 A1 | 1/2001 |
| WO | WO 2004/048393 A2 | 6/2004 |
| WO | WO 2007/139729 A1 | 12/2007 |

OTHER PUBLICATIONS

Wolff, Burger's medicinal Chemistry and Drug Discovery, vol. 1, Principles and Practice, John Wiley & sons, New York, 1997.*
Li et al. Bioorganic & Medicinal Chemistry, 1997, 5(9), 1783-1788.*

* cited by examiner

*Primary Examiner* — Nizal Chandrakumar
(74) *Attorney, Agent, or Firm* — McDonnell Boehnen Hulbert & Berghoff LLP

(57) ABSTRACT

This invention provides novel β-lactamase inhibitors of the aryl- and heteroaryl-sulfonamidomethylphosphonate monoester class having nitrogen-based cations or quarternary ammomium groups. The compounds inhibit three classes of β-lactamases and synergize the antibacterial effects of β-lactam antibiotics (e.g., imipenem and ceftazimdime) against those micro-organisms normally resistant to the β-lactam antibiotics as a result of the presence of the β-lactamases.

21 Claims, No Drawings

INHIBITORS OF BETA-LACTAMASE

RELATED APPLICATIONS

This application is the U.S. National Phase under 35 U.S.C. §371 of International Application No. PCT/US2007/011979, filed on May 21, 2007, which in turn claims the benefit of U.S. Provisional Application Nos. 60/802,141, filed on May 22, 2006 and 60/840,001, filed on Aug. 25, 2006, the disclosures of which Applications are incorporated by reference herein.

BACKGROUND OF THE INVENTION

Bacterial antibiotic resistance has become one of the most important threats to modern health care. Cohen, Science 257: 1051-1055 (1992) discloses that infections caused by resistant bacteria frequently result in longer hospital stays, higher mortality and increased cost of treatment. Neu, Science 257: 10641073 (1992) discloses that the need for new antibiotics will continue to escalate because bacteria have a remarkable ability to develop resistance to new agents rendering them quickly ineffective.

The present crisis has prompted various efforts to elucidate the mechanisms responsible for bacterial resistance, Coulton et al., Progress in Medicinal Chemistry 31:297-349 (1994) teaches that the widespread use of penicillins and cephalosporins has resulted in the emergence of β lactamases, a family of bacterial enzymes that catalyze the hydrolysis of the β-lactam ring common to numerous presently used antibiotics. More recently, Dudley, Pharmacotherapy 15: 9S-14S (1995) has disclosed that resistance mediated by β-lactamases is a critical aspect at the core of the development of bacterial antibiotic resistance. Clavulanic acid, which is a metabolite of *Streptomyces clavuligerus*, and two semi-synthetic inhibitors, sulbactam and tazobactam are presently available semi-synthetic or natural product β-lactamase inhibitors. U.S. Pat. No. 6,472,406, incorporated herein in its entirety, discloses certain synthetic β-lactamase inhibitors.

The availability of only a few β-lactamase inhibitors, however, is insufficient to counter the constantly increasing diversity of β-lactamases, for which a variety of novel and distinct inhibitors has become a necessity. There is, therefore, a need for the ability to identify new β-lactamase inhibitors.

This invention relates to novel beta-lactamase inhibitors and their use against bacterial antibiotic resistance. More particularly, the invention relates to compositions and methods for overcoming bacterial antibiotic resistance.

SUMMARY OF THE INVENTION

This invention provides novel β-lactamase inhibitors of the aryl- and heteroaryl-sulfonamidomethylphosphonate monoester class having nitrogen-based cations or quarternary ammonium groups. The compounds inhibit three classes of β-lactamases and synergize the antibacterial effects of β-lactam antibiotics (e.g., imipenem and ceftazidime) against those micro-organisms normally resistant to the β-lactam antibiotics as a result of the presence of the β-lactamases. In addition, the exhibited in vitro synergy effect is not significantly altered by the presence of either mouse or human serum; an effect which plagues the prior-art compounds of the class rendering them potentially less effectual. This invention also relates to the combination of the claimed compounds with all relevant β-lactam antibiotics to extend the spectrum of antimicrobial activity of the antibiotic against β-lactamase producing bacteria such as *Pseudomonas* spp. The invention further relates to compositions containing compounds of this invention and a pharmaceutically acceptable carrier or carriers. It also relates to methods for treating bacterial infections and inhibiting bacterial growth using the compounds or compositions of this invention. This and other aspects of the invention are realized upon consideration of the specification in its entirety.

DETAILED DESCRIPTION OF THE INVENTION

The present invention is directed to novel compounds of Formula I:

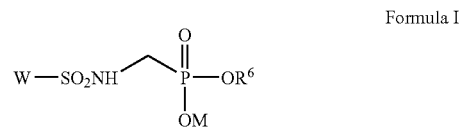

Formula I or a pro-drug or pharmaceutically acceptable salt thereof, wherein:
W represents:

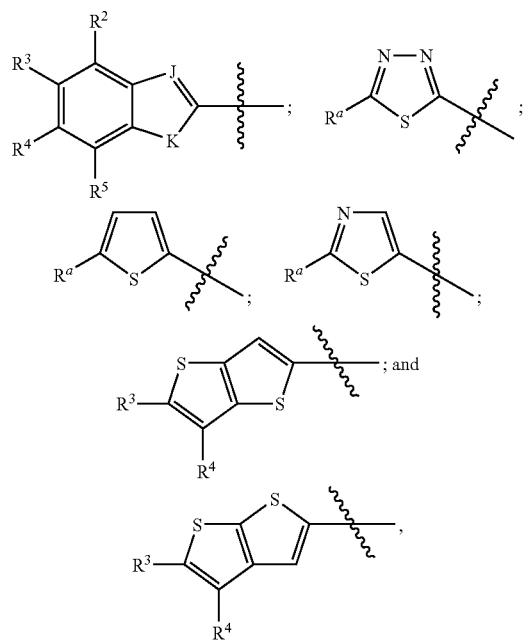

$R^a$ represents: $(CH_2)_n R^{aa}$, or $R^{aa}$;
$R^{aa}$ represents:

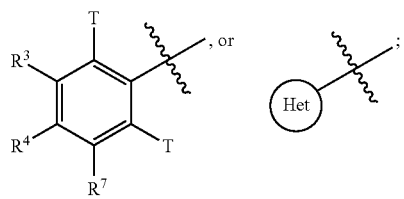

J represents N or $CR^1$;
K represents O, S, or $NR^1$;
Het represents a 5-6 membered nitrogen containing heterocycle substituted with 0 to 4 groups of $R^2$;
T represents hydrogen, halogen, $OR^1$, or $C_{1-6}$ alkyl;

$R^1$ independently represents hydrogen, or $C_{1-6}$ alkyl;

M is a negative charge, H, or a pharmaceutically acceptable metal or ammonium salt, and provided that when W contains a moiety with multiple positive charges, there is an appropriate number of $L^\ominus$ present to provide overall neutrality;

$R^2$ and $R^5$ independently represent hydrogen, halogen, cyano, —$OR^1$, or $C_{1-6}$ alkyl;

$R^3$, $R^4$, and $R^7$ independently represent hydrogen, halogen, cyano, —$OR^1$, $C_{1-6}$ alkyl, —$X_m$—$Y_m$—$Z^*_m$—$R^8$, or —$X_m$—$Y_m$—$Z^*_m$-$Q^+$;

X and Y independently are O, $NR^x$, (C=O), $SO_2$, $(CH_2)_n$, —$(CH_2)_nNR^1C(O)$—, —$(CH_2)_nS$—, or —$(CH_2)_nN(R^x)_2$—;

$Z^*$ is $(CH_2)$, which may be substituted with one to four $R^b$, $R^6$ represents $C_{6-10}$ aryl, or $C_{5-10}$ heteroaryl, said aryl and heteroaryl optionally substituted;

$R^8$ represents hydrogen, halo, $N(R^c)_2$, —$C(O)R^5$, $NR^cC(NH)NH_2$, $NR^cC(NH)H$, $(CH_2)_nC_{5-10}$ heterocyclyl, or $(CH_2)_nC_{5-10}$ aryl, said heterocyclyl and aryl optionally substituted;

Q is selected from the group consisting of:

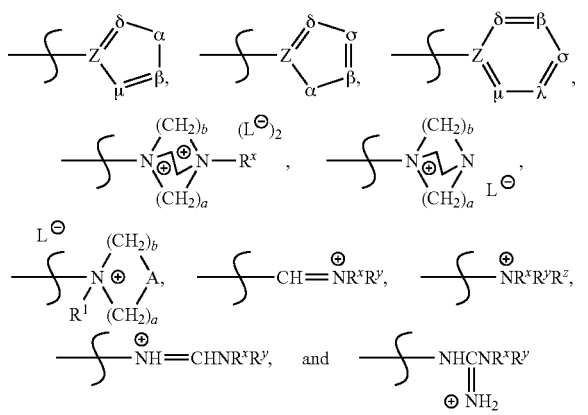

wherein Z represents $N^+$ or carbon; and A is O, $CH_2$, $S(O)_{0-2}$, $NR^x$, or $N^+(R^x)_2$;

$^+$ represents a positive charged ion;

$L^\ominus$ represents a pharmaceutically acceptable counterion that is present as needed to provide charge balance on the molecule;

a and b are 1, 2 or 3;

α represents O, S or $NR^s$;

β, δ, λ, μ and a represent $CR^t$, N or $N^\oplus R^s$, provided that no more than one of β, ε, λ, μ and σ is $N^\oplus R^s$;

each $R^b$ independently represents halo; —CN; —$NO_2$; phenyl; —$NHSO_2R^c$; —$OR^c$; —$SR^c$; —$N(R^c)_2$; —$N^+(R^c)_3$; —$C(O)N(R^c)_2$; —$SO_2N(R^c)_2$; heteroaryl; heteroarylium; formamidinyl, —$CO_2R^c$; —$C(O)R^c$; —OC(O)$R^c$; —NHC(O)$R^c$; —NHC(O)$_2R^c$; guanidinyl; carbamimidoyl or ureido, said phenyl and heteroaryl optionally substituted;

each $R^c$ independently represents hydrogen, a —$C_{1-6}$ straight or branched-chain alkyl group, a —$C_3$-$C_6$ cycloalkyl group or $C_{6-10}$ aryl, said aryl optionally substituted with one to four groups of halogen; —CN; —$NO_2$; phenyl; —$NHSO_2R^j$; —$OR^1$, —SW; —$N(R^j)_2$; —$N^+(R^j)_3$; —$C(O)N(R^j)_2$; —$SO_2N(R^j)_2$; heteroaryl; heteroarylium; formamidinyl, —$CO_2R^j$; —$C(O)R^j$; —OC(O)$R^j$; —NHC(O)$R^j$; —NHC(O)$_2R^j$; guanidinyl; carbamimidoyl or ureido, said phenyl and heteroaryl optionally substituted, wherein Rj is selected from the group consisting of hydrogen, a —$C_{1-6}$ straight or branched-chain alkyl group, a —$C_3$-$C_6$ cycloalkyl group or $C_{6-10}$ aryl.

each $R^s$ independently represents hydrogen; phenyl or —$C_{1-6}$ straight- or branched-chain alkyl, unsubstituted or substituted with one to four $R^b$ groups;

each $R^t$ independently represents hydrogen; halo; phenyl; —CN; —$NO_2$; —$NR^uR^v$; —$OR^u$; —$SR^u$; —C(O)$NR^uR^v$; —$COOR^c$; —$SOR^u$; —$SO_2R^u$; —$SO_2NR^uR^v$; —$NR^uSO_2R^v$; —C(O)$R^u$; —$NR^uC(O)R^v$; —OC(O)$R^u$; —OC(O)$NR^uR^v$; —$NR^uCO_2R^v$; —$NR^uC(O)NR^vR^w$; —$OCO_2R^v$; —$C_{1-6}$ straight- or branched-chain alkyl, unsubstituted or substituted with one to four $R^b$ groups;

$R^u$ and $R^v$ represent hydrogen or —$C_{1-6}$ straight- or branched-chain alkyl, unsubstituted or substituted with one to four $R^b$ groups;

each $R^w$ independently represents hydrogen; —$C_{1-6}$ straight- or branched-chain alkyl, unsubstituted or substituted with one to four $R^b$ groups; $C_{3-6}$ cycloalkyl optionally substituted with one to four $R^b$ groups; phenyl optionally substituted with one to four $R^b$ groups, or heteroaryl optionally substituted with one to four $R^b$ groups;

$R^x$ represents hydrogen or a $C_{1-8}$ straight- or branched-alkyl chain, optionally interrupted by one or two of O, S, SO, $SO_2$, $NR^w$, $N^+R^cR^w$, or —C(O)—, said alkyl chain being unsubstituted or substituted with one to four of halo, CN, $NO_2$, —$N_3$, $OR^w$, $SR^w$, $SOR^w$, $SO_2R^w$, $NR^cR^w$, $N^+(R^c)_2R^w$, Q, —C(O)—$R^w$, C(O)$NR^cR^w$, $SO_2NR^cR^w$, $CO_2R^w$, OC(O)$R^w$, OC(O)$NR^cR^w$, $NR^cC(O)R^w$, $NR^cC(NH)NH_2$, $NR^cC(NH)H$, $NR^cC(O)NR^cR^w$, phenyl, napthyl, heteroaryl, or heterocyclic group said phenyl, heteroaryl, and heterocyclic group optionally substituted with from one to four $R^b$ groups or with one to two $C_{1-3}$ straight- or branched-chain alkyl groups, said alkyl groups being unsubstituted or substituted with one to four $R^b$ groups;

$R^y$ and $R^z$ represent hydrogen; phenyl; —$C_{1-6}$ straight or branched chain alkyl, unsubstituted or substituted with one to four $R^b$ groups, and optionally interrupted by O, S, $NR^w$, $N^+R^cR^w$ or —C(O)—; and m represents 0 to 1; n represents 0 to 6; wherein it is understood that when a value is zero, a bond exists.

The invention further relates to bacterial antibiotic resistance. More particularly, the invention relates to compositions and methods for overcoming bacterial antibiotic resistance. The patents and publications identified in this specification indicate the knowledge in this field and are hereby incorporated by reference in their entirety. In the case of inconsistencies, the present disclosure will prevail.

The invention provides novel β-lactamase inhibitors, which are structurally unrelated to the natural product and semi-synthetic β-lactamase inhibitors presently available, and which do not require a β-lactam pharmacophore. Certain embodiments of these new inhibitors may also bind bacterial DD-peptidases, and thus may potentially act both as β-lactamase inhibitors and as antibiotic agents.

For purposes of the present invention, the following definitions will be used:

As used herein, the term "β-lactamase inhibitor" is used to identify a compound having a structure as defined herein, which is capable of inhibiting β-lactamase activity. Inhibiting β-lactamase activity means inhibiting the activity of a class A, C, or D β-lactamase. Preferably, for antimicrobial applications such inhibition should be at a 50% inhibitory concentration below 100 micrograms/mL, more preferably below 30 micrograms/mL and most preferably below 10 micrograms/ mL. The terms "class A", "class C", and "class D" β-lactamases are understood by those skilled in the art and can be found described in Waley, *The Chemistry of β-lactamase*, Page Ed., Chapman & Hall, London, (1992) 198-228.

In some embodiments of the invention, the β-lactamase inhibitor may also be capable-of acting as an antibiotic agent by inhibiting bacterial cell-wall cross-linking enzymes. Thus, the term β-lactamase inhibitor is intended to encompass such dual-acting inhibitors. In certain preferred embodiments, the β-lactamase inhibitor may be capable of inhibiting D-alanyl-D-alaninecarboxypeptidases/transpeptidases (hereinafter DD-peptidases). The term "DD-peptidase" is used in its usual sense to denote penicillin-binding proteins involved in bacterial cell wall biosynthesis (see, e.g., Ghysen, Prospect. Biotechnol. 128:67-9a (1987)). In certain particularly preferred embodiments, the D-alanyl-D-alanine-carboxypeptidase/transpeptidase, which may be inhibited is the *Streptomyces* R61DD-peptidase. This enzyme has conservation of active site mechanism with bacterial signal peptidases (see, e.g., Black et al., Current Pharmaceutical Design 4:133-1.54 (1998); Dalbey et al., Protein Science 6:1129-1138 (1997)). It is, therefore, possible that the β-lactamase inhibitors of the invention may also be capable of inhibition of bacterial signal peptidases.

As used herein, the term "β-lactamase" denotes a protein capable of inactivating a β-lactam antibiotic. In one preferred embodiment, the β-lactamase is an enzyme which catalyzes the hydrolysis of the β-lactam ring of a β-lactam antibiotic. In certain preferred embodiments, the β-lactamase is microbial. In certain other preferred embodiments, the β-lactamase is a serine β-lactamase. Examples of such preferred β-lactamases are well known and are disclosed in, e.g., Waley, *The Chemistry of β-Lactamase*, Page Ed., Chapman & Hall, London, (1992) 198-228. In particularly preferred embodiments, the β-lactamase is a class C β-lactamase of *Enterobacter cloacae* P99 (hereinafter P99 β-lactamase), or a class A β-lactamase of the TEM-1 plasmid (hereinafter TEM β-lactamase).

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

As used herein, the term "organism" refers to any multicellular organism. Preferably, the organism is an animal, more preferably a mammal, and most preferably a human For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—. Also, a number of moieties disclosed herein exist in multiple tautomeric forms, all of which are intended to be encompassed by any given tautomeric structure.

The term "alkyl" as employed herein refers to straight and branched chain aliphatic groups having from 1 to 12 carbon atoms, preferably 1-8 carbon atoms, more preferably 1-6 carbon atoms, which is optionally substituted with one, two or three substituents. Unless otherwise specified, the alkyl group may be saturated, unsaturated, or partially unsaturated. As used herein, therefore, the term "alkyl" is specifically intended to include alkenyl and alkynyl groups, as well as saturated alkyl groups. Preferred alkyl groups include, without limitation, methyl, ethyl, propyl, isopropyl, butyl, tert-butyl, isobutyl, pentyl, hexyl, vinyl, alkyl, isobutenyl, ethynyl, and propynyl.

The term "cycloalkyl" as employed herein includes saturated and partially unsaturated cyclic hydrocarbon groups having 3 to 12, preferably 3 to 8 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $C_{1-6}$alkyl(C6-10)aryl including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain preferred embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, 0, and S. Preferred heteroaryl groups include, without limitation, thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other preferred embodiments, the heterocyclic group is fused to an aryl or heteroaryl group. Examples of such fused heterocycles include, without limitation, tetrahydroquinolinyl and dihydrobenzofuranyl.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4fluor-3-propylphenyl. As another non-limiting example, substituted n-octyls include 2,4 dimethyl-5-ethyl-octyl and 3-cyclopentyloctyl. Included within this definition are methylenes (—CH$_2$—) substituted with oxygen to form carbonyl (—CO—).

$\oplus$ represents a positive charged ion(s), said positively charged ion(s) electronically balanced by an appropriate number of negative charged ions $\ominus$ including the phosphonate part of the structure alone or in combination with the appropriate number of negatively charged ions $\ominus$, such as L$^\ominus$. Thus, if the compound contains more than one positive charge, a negatively charged counterion, such as L$^\ominus$, may be present which in combination with the carboxylate anion, provides overall charge neutrality.

L$^\ominus$ is present or absent as necessary to maintain the appropriate charge balance. When present, L$^\ominus$ represents a pharmaceutically acceptable counterion. Most anions derived from inorganic or organic acids are suitable. Representative examples of such counterions are the following: acetate, adipate, aminosalicylate, anhydromethylenecitrate, ascorbate, aspartate, benzoate, benzenesulfonate, bromide, citrate, camphorate, camphorsulfonate, chloride, trifluoroacetate, estolate, ethanesulfonate, fumarate, glucoheptanoate, gluconate, glutamate, lactobionate, malate, maleate, mandelate, methanesulfonate, pantothenate, pectinate, phosphate/diphosphate, polygalacturonate, propionate, salicylate, stearate, succinate, sulfate, tartrate and tosylate. Other suitable anionic species will be apparent to the ordinarily skilled chemist.

Likewise, when L$^\ominus$ represents a species with more than one negative charge, such as malonate, tartrate or ethylenediamine-tetraacetate (EDTA), an appropriate number of compound molecules can be found in association therewith to maintain the overall charge balance and neutrality.

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, aralkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

The term "halogen" or "halo" as employed herein refers to chlorine, bromine, fluorine, or iodine. Preferred halogens are chlorine and fluorine.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

The term "ureido" as employed herein refers to a substituted or unsubstituted urea moiety.

The term heteroarylium refers to heteroaryl groups bearing a quaternary nitrogen atom and thus a positive charge. Examples include the following:

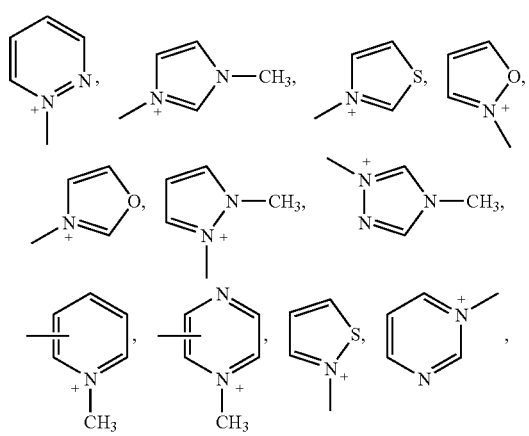

-continued

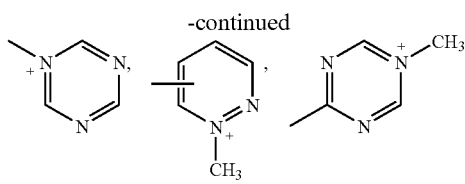

When a charge is shown on a particular nitrogen atom in a ring which contains one or more additional nitrogen atoms, it is understood that the charge may reside on a different nitrogen atom in the ring by virtue of charge resonance that occurs.

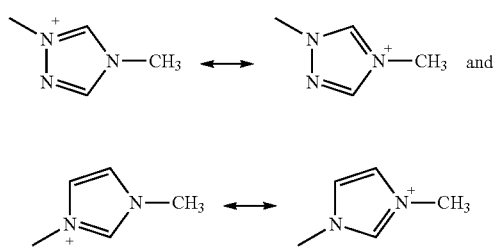

The term "heterocycloalkyl" refers to a cycloalkyl group (nonaromatic) in which one of the carbon atoms in the ring is replaced by a heteroatom selected from O, S or N, and in which up to three additional carbon atoms may be replaced by hetero atoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" means O, S or N, selected on an independent basis.

Alkoxy refers to $C_1$-$C_4$ alkyl-O—, with the alkyl group optionally substituted as described herein.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are contained throughout the specification.

For use in medicine, the salts of the compounds of formula A will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,$N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, iodic, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are acetic, citric, hydrobromic, hydrochloric, maleic, phosphoric, sulfuric and tartaric acids. Examples of particular salts are trifluoroacetate, chloride, methanesulfonate, and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

An embodiment of this invention is realized when T is alkyl and all other variables are as originally described. Another embodiment is realized when T is hydrogen and all other variables are as originally described. Another embodiment of this invention is realized when W contains one or more positively charged moieties and all other variables are as originally described.

Another embodiment of this invention is realized when W contains no positive charge moieties, M is an alkali metal or ammonium salt and all other variables are as originally described.

Another embodiment of this invention is realized when W is

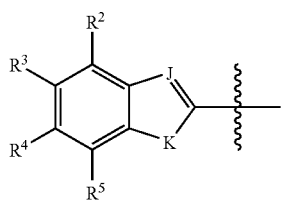

and all other variables are as originally described. A subembodiment of this invention is realized when J is $CR^1$ and K is S. Still another sub-embodiment is realized when J is N and K is S.

Still another embodiment of this invention is realized when W is selected from the group consisting of:

1)

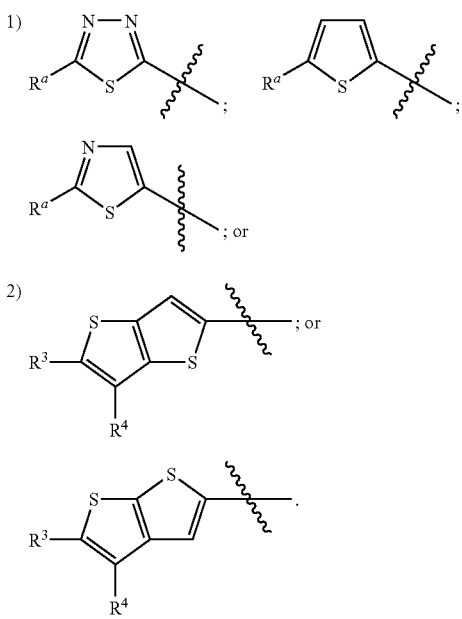

2)

Another embodiment of this invention is realized when at least one of $R^3$, $R^4$, and $R^7$ is $—X_m—Y_m—Z^*_m-Q^+$ and all other variables are as originally described.

Another embodiment of this invention is realized when $R^3$ and $R^4$, are $—X_m—Y_m—Z^*_m-Q^+$ and all other variables are as originally described.

Still another embodiment of this invention is realized when one of $R^3$ and $R^4$ is $—X_m—Y_m—Z^*_m-Q^+$ and the other is $—X_m—Y_m—Z^*_m-R^8$ and all other variables are as originally described.

Another embodiment of this invention is realized when X is O and all other variables are as originally described.

Another embodiment of this invention is realized when Y is $(CH_2)_nNR^1CO—$, $—(CH_2)_nS—$, or $(CH_2)_nN(R^x)_2$ and all other variables are as originally described.

Another embodiment of this invention is realized when X is O, Y is a bond, $Z^*$ is $(CH_2)_n$, and all other variables are as originally described.

Still another embodiment of this invention is realized when X is $(CH_2)_n$, Y is S, and all other variables are as originally described. A sub-embodiment of this invention is realized when Y is $SO_2$.

Another embodiment of this invention is realized when X is $(CH_2)_n$, Y is $NR^x$ and all other variables are as originally described.

Another embodiment of this invention is realized when X is $(CH_2)_n$, Y is $N(R^x)_2$ and all other variables are as originally described.

Another embodiment of this invention is realized when X is CO, Y is $NR^x$ and all other variables are as originally described.

Another embodiment of this invention is realized when X is $NR^x$, Y is CO and all other variables are as originally described.

A sub-embodiment of this invention is realized when $R^3$ and/or $R^4$ is $—(CH_2)_nSCH_2Q^+—$, and all other variables are as originally described. Another sub-embodiment is realized when $R^3$ and/or $R^4$ is $—(CH_2)_nN(R^x)_2$ and all other variables are as originally described. Another embodiment is realized when one of $R^3$ and $R^4$ is $—(CH_2)_nSCH_2Q^+-$ and the other is $—(CH_2)_nN(R^x)_2$.

Another embodiment of this invention is realized when R6 is $C_{6-10}$ aryl, $C_{5-10}$ heteroaryl, said aryl and heteroaryl optionally substituted with 1-4 groups of halogen, cyano, nitro, $C_{1-6}$ alkyl, $OR^1$, $N(R^1)_2$, $COOR^1$, and $CON(R^1)_2$.

Another embodiment of this invention is realized when Q+ is

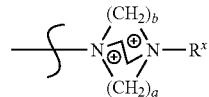

one or more of $L^⊖$ is present if needed and all other variables are as originally described.

Still another embodiment of this invention is realized when Q+ is

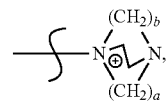

$L^⊖$ is present if needed and all other variables are as originally described.

Still another embodiment of this invention is realized when Q+ is

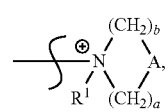

$L^⊖$ is present if needed and all other variables are as originally described.

Yet another embodiment of this invention is realized when Q+ is

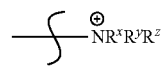

$L^⊖$ is present if needed and all other variables are as originally described.

Yet another embodiment of this invention is realized when Q+ is

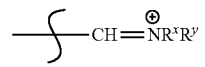

$L^⊖$ is is present if needed and all other variables are as originally described.

Yet another embodiment of this invention is realized when Q+ is

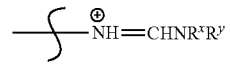

$L^⊖$ is present if needed and all other variables are as originally described.

Yet another embodiment of this invention is realized when Q+ is

$L^{\ominus}$ is present if needed and all other variables are as originally described.

A preferred embodiment of this invention is a compound of formula II:

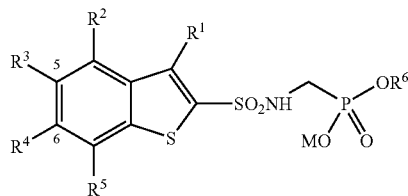

Formula II or a pharmaceutically acceptable salt thereof, wherein: $R^1$, $R^2$, $R^3$. $R^4$, $R^5$, $R^6$ are as previously described. A sub-embodiment of this invention is realized when $R^3$. and $R^4$ both are —$X_m$—$Y_m$—$Z^*$—$R^8$ or —$X_m$—$Y_m$—$Z^*$-Q+.

Another preferred embodiment of this invention is realized when O—$R^6$ is selected from the group consisting of,

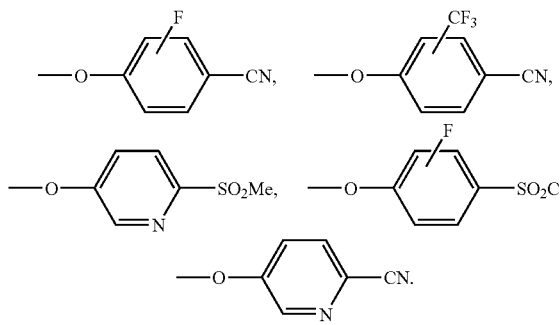

With respect to the positively charged moiety or moieties that are contained in the compounds of formula I or II, it is preferred that from 1-3 positive charges, be present, and most preferably two positive charges be present, balanced by the phosphonate anion and appropriate number of negatively charged counterions, $L^{\ominus}$, to provide overall neutrality. A sub-embodiment of this invention is realized when the positive charges are located at $R^3$, $R^4$, and/or $R^7$.

The compounds of this invention can be combined with beta-lactam antibiotics such as imipenem, Primaxin®, Amoxicillin, Ticarcillin, Ampicillin, Cefoperazone, Piperacillin, and ceftazidime. Thus, another aspect of this invention is realized when the compound of this invention are co-administered with a beta-lactam antibiotic.

Examples of compounds of this invention are:
4-cyano-3-fluorophenyl-[({[5-(2-pyridiniumethoxy)-1-benzothien-2-yl]sulfonyl}amino)methyl]-phosphonate;
4-cyano-3-fluorophenyl-[({[6-(2-pyridiniumethoxy)-4,5,7-trifluoro-1-benzothien-2-yl]-sulfonyl}amino)methyl]phosphonate;
4-cyano-3-fluorophenyl-[({[6-(2-pyridiniumethoxy)-4-fluoro-1-benzothien-2-yl]-sulfonyl}amino)methyl]phosphonate;
4-cyano-3-fluorophenyl-[({[6-(4-pyridiniumbutoxy)-4-fluoro-1-benzothien-2-yl]-sulfonyl}amino)methyl]phosphonate;
4-cyano-3-fluorophenyl[({[5-(2-pyridinium-1-ylethoxy)-1-benzothien-2-yl]-sulfonyl}amino)methyl]phosphonate;
4-cyano-3-fluorophenyl-[({[4-chloro-3-methyl-5-(2-pyridinium-1-ylethoxy)-1-benzothien-2-yl]sulfonyl}amino)methyl]phosphonate;
4-cyano-3-fluorophenyl-[({[7-chloro-3-methyl-5-(2-pyridinium-1-ylethoxy)-1-benzothien-2-yl]-sulfonyl}amino)methyl]phosphonate;
4-cyano-3-fluorophenyl-{[({5-[4-(2-pyridinium-1-ylethoxy)phenyl]-1,3,4-thiadiazol-2-yl}-sulfonyl)amino]methyl}phosphonate;
4-cyano-3-fluorophenyl-{[({5-[4-(3-pyridinium-1-ylpropoxy)phenyl]-1,3,4-thiadiazol-2-yl}sulfonyl)amino]methyl}phosphonate;
4-cyano-3-fluorophenyl-[({[5-(2-pyridinium-1-ylethoxy)-6-(2-chloroethoxy)-1-benzothien-2-yl]-sulfonyl}amino)methyl]phosphonate;
4-cyano-3-fluorophenyl-[({[6-(2-pyridinium-1-ylethoxy)-5-(2-chloroethoxy)-1-benzothien-2-yl]-sulfonyl}amino)methyl]phosphonate;
4-cyano-3-(trifluoromethyl)phenyl[({[5-(2-pyridinium-1-ylethoxy)-1-benzothien-2-yl]sulfonyl}amino)methyl]phosphonate;
4-cyano-3-(trifluoromethyl)phenyl-[({[5-(2-pyridinium-1-ylethoxy)-1-benzothien-2-yl]-sulfonyl}amino)methyl]phosphonate;
4-cyano-3-(trifluoromethyl)phenyl-[({[6-(4-pyridinium-1-ylbutoxy)-1-benzothien-2-yl]-sulfonyl}amino)methyl]phosphonate;
4-cyano-3-(trifluoromethyl)phenyl-[({[6-(5-pyridinium-1-ylpentoxy)-1-benzothien-2-yl]-sulfonyl}amino)methyl]phosphonate;
4-cyano-3-(trifluoromethyl)phenyl-[({[6-(2-pyridinium-1-ylethoxy)-1-benzothien-2-yl]sulfonyl}-amino)methyl]phosphonate;
4-cyano-3-(trifluoromethyl)phenyl-[({[6-(6-pyridinium-1-ylhexoxy)-1-benzothien-2-yl]-sulfonyl}amino)methyl]phosphonate;
4-cyano-3-(trifluoromethyl)phenyl-[({[4-chloro-3-methyl-5-(2-pyridinium-1-ylethoxy)-1-benzothien-2-yl]sulfonyl}amino)methyl]phosphonate;
4-cyano-3-(trifluoromethyl)phenyl-[({[4,5,7-trifluoro-6-(2-pyridinium-1-ylethoxy)-1-benzothien-2-yl]sulfonyl}amino)methyl]phosphonate;
4-cyano-3-(trifluoromethyl)phenyl-[({[7-chloro-3-methyl-5-(2-pyridinium-1-ylethoxy)-1-benzothien-2-yl]sulfonyl}amino)methyl]phosphonate;
4-cyano-3-(trifluoromethyl)phenyl-{[({5-[4-(2-pyridinium-1-ylethoxy)phenyl]-1,3,4-thiadiazol-2-yl}sulfonyl)amino]methyl}phosphonate;
Ammonium 4-cyano-3-fluorophenyl[({[5-(morpholin-4-ylmethyl)-1-benzothien-2-yl]sulfonyl}amino)methyl]phosphonate;
4-Cyano-3-fluorophenyl-({[(4,7-dichloro-5-{[(3-(pyridinium-1-ylpropyl)thio]methyl}-1-benzothien-2-yl)sulfonyl]amino}methyl)phosphonate;
4-cyano-3-(trifluoromethyl)phenyl-({[(4,7-dichloro-5-{[(3-(pyridinium-1-ylpropyl)thio]methyl}-1-benzothien-2-yl)sulfonyl]amino}methyl)phosphonate;
4-cyano-3-fluorophenyl-({[5-(aminomethyl)-thieno[3,2-b]thien-2-yl]sulfonyl}amino)methyl]phosphonate;

4-cyano-3-fluorophenyl-({[(5-{[(3-aminopropyl)thio]methyl}thieno[3,2-b]thien-2-yl)sulfonyl]amino}methyl)phosphonate;

Ammonium-4-cyano-3-fluorophenyl-[({[5-(aminomethyl)thieno[2,3-b]thien-2-yl]sulfonyl}-amino)methyl]phosphonate;

4-cyano-3-fluorophenyl[({[5,6-bis(2-ammonioethoxy)-1-benzothien-2-yl]sulfonyl}amino)methyl]phosphonate trifluoroacetate;

4-cyano-3-(trifluoromethyl)phenyl[({[5,6-bis(2-ammonioethoxy)-1-benzothien-2-yl]-sulfonyl}amino)methyl]phosphonate trifluoroacetate;

3-fluoro-4-[(trifluoromethyl)sulfonyl]phenyl-[({[5,6-bis(2-ammonioethoxy)-1-benzothien-2-yl]-sulfonyl}amino)methyl]phosphonate trifluoroacetate;

6-cyanopyridin-2-yl-[({[5,6-bis(2-ammonioethoxy)-1-benzothien-2-yl]sulfonyl}amino)-methyl]-phosphonate trifluoroacetate;

4-cyano-3-fluorophenyl[({[5,6-bis(3-ammoniopropoxy)-1-benzothien-2-yl]sulfonyl}amino)-methyl]phosphonate trifluoroacetate;

4-cyano-3-fluorophenyl[({[5,6-bis(4-ammoniobutoxy)-1-benzothien-2-yl]sulfonyl}amino)-methyl]phosphonate trifluoroacetate;

4-cyano-3-(trifluoromethyl)phenyl[({[5,6-bis(3-ammoniopropoxy)-1-benzothien-2-yl]sulfonyl}-amino)methyl]phosphonate trifluoroacetate;

4-cyano-3-fluorophenyl[({[5,6-bis(2-ammonioethoxy)-4,7-dichloro-1-benzothien-2-yl]sulfonyl}-amino)methyl]phosphonate trifluoroacetate;

4-cyano-3-(trifluoromethyl)phenyl[({[5,6-bis(2-ammonioethoxy)-4,7-dichloro-1-benzothien-2-yl]sulfonyl}amino)methyl]phosphonate trifluoroacetate;

3-fluoro-4-[(trifluoromethyl)sulfonyl]phenyl-[({[5,6-bis(2-ammonioethoxy)-4,7-dichloro-1-benzothien-2-yl]sulfonyl}amino)methyl]phosphonate trifluoroacetate;

4-cyano-3-fluorophenyl[({[5,6-bis(2-ammonioethoxy)-4,7-difluoro-1-benzothien-2-yl]sulfonyl}-amino)methyl]phosphonate trifluoroacetate;

4-cyano-3-(trifluoromethyl)phenyl[({[5,6-bis(2-ammonioethoxy)-4,7-difluoro-1-benzothien-2-yl]sulfonyl}amino)methyl]phosphonate trifluoroacetate;

4-cyano-3-(trifluoromethyl)phenyl[({[5,6-bis(3-ammoniopropoxy)-4,7-difluoro-1-benzothien-2-yl]sulfonyl}amino)methyl]phosphonate trifluoroacetate;

4-cyano-3-fluorophenyl[({[5,6-bis(3-ammoniopropoxy)-3-methyl-1-benzothien-2-yl]-sulfonyl}amino)methyl]phosphonate trifluoroacetate;

4-cyano-3-fluorophenyl[({[5,6-bis(3-ammoniopropoxy)-4,7-difluoro-3-methyl-1-benzothien-2-yl]sulfonyl}amino)methyl]phosphonate trifluoroacetate;

4-cyano-3-fluorophenyl-[({[5-(2-ammonioethoxy)-1-benzothien-2-yl]sulfonyl}amino)methyl]-phosphonate;

4-cyano-3-(trifluoromethyl)phenyl-[({[5-(2-ammonioethoxy)-1-benzothien-2-yl]sulfonyl}amino) methyl]phosphonate;

6-cyanopyridin-3-yl-[({[5-(2-ammonioethoxy)-1-benzothien-2-yl]sulfonyl}amino)methyl]phosphonate;

6-methylsulfonylpyridin-3-yl-[({[5-(2-ammonioethoxy)-1-benzothien-2-yl]sulfonyl}amino) methyl]phosphonate;

4-cyano-3-fluorophenyl-[({[5-(2-ammonioethoxy)-4-chloro-1-benzothien-2-yl]sulfonyl}amino) methyl]phosphonate;

4-cyano-3-fluorophenyl-[({[5-(2-ammonioethoxy)-7-chloro-1-benzothien-2-yl]sulfonyl}amino) methyl]phosphonate;

4-cyano-3-(trifluoromethyl)phenyl-[({[5-(2-ammonioethoxy)-7-chloro-1-benzothien-2-yl]-sulfonyl}amino)methyl]phosphonate;

3-fluoro-4-[(trifluoromethyl)sulfonyl]phenyl-[({[5-(ammonioethoxy)-7-chloro-1-benzothien-2-yl]sulfonyl}amino)methyl]phosphonate;

4-cyano-3-fluorophenyl-[({[5-(2-ammonioethoxy)-4-chloro-3-methyl-1-benzothien-2-yl]sulfonyl}amino)methyl]phosphonate;

4-cyano-3-(trifluoromethyl)phenyl-[({[5-(2-ammonioethoxy)-4-chloro-3-methyl-1-benzothien-2-yl]sulfonyl}amino)methyl]phosphonate;

4-cyano-3-fluorophenyl-[({[5-(ammonioethoxy)-7-fluoro-3-methyl-1-benzothien-2-yl]sulfonyl}-amino)methyl]phosphonate;

3-fluoro-4-(trifluoromethyl)phenyl-[({[5-(ammonioethoxy)-7-fluoro-3-methyl-1-benzothien-2-yl]sulfonyl}amino)methyl]phosphonate;

3-fluoro-4-[(trifluoromethyl)sulfonyl]phenyl-[({[5-(ammonioethoxy)-7-fluoro-3-methyl-1-benzothien-2-yl]sulfonyl}amino)methyl]phosphonate;

4-cyano-3-[(trifluoromethyl)sulfonyl]-phenyl-[({[5-(2-ammonioethoxy)-4-chloro-3-methyl-1-benzothien-2-yl]sulfonyl}amino)methyl]phosphonate;

4-cyano-3-fluorophenyl-[({[5-(2-ammonioethoxy)-7-chloro-3-methyl-1-benzothien-2-yl]sulfonyl}amino)methyl]phosphonate;

4-cyano-3-(trifluoromethyl)phenyl-[({[5-(2-ammonioethoxy)-7-chloro-3-methyl-1-benzothien-2-yl]sulfonyl}amino)methyl]phosphonate;

4-cyano-3-fluorophenyl-[({[6-(2-ammonioethoxy)-4,5,7-trifluoro-1-benzothien-2-yl]sulfonyl}-amino)methyl]phosphonate;

4-cyano-3-fluorophenyl-{[({5-[4-(2-ammonioethoxy)phenyl]-1,3,4-thiadiazol-2-yl}sulfonyl)-amino]methyl}phosphonate;

4-cyano-3-fluorophenyl-{[({5-[3,4-bis(3-ammoniopropoxy)phenyl]thiophen-2-yl}sulfonyl)-amino]methyl}phosphonate trifluoroacetate;

4-cyano-3-fluorophenyl-{[({5-[3,4-bis(3-ammoniopropoxy)-2-methylphenyl]thiophen-2-yl}sulfonyl)amino]methyl}phosphonate trifluoroacetate;

4-cyano-3-fluorophenyl-{[({5-[4,5-bis(3-ammoniopropoxy)-2-methylphenyl]thiophen-2-yl}-sulfonyl)amino]methyl}phosphonate;

4-cyano-3-fluorophenyl-[({[6-(2-ammonioethoxy)-5-(2-{[2,3-bis(benzyloxy)benzoyl]amino}-ethoxy-1-benzothien-2-yl)-sulfonyl]amino}methyl)phosphonate;

4-cyano-3-fluorophenyl-[({[5-(2-ammonioethoxy)-6-(2-{[2,3-bis(benzyloxy)benzoyl]amino}-ethoxy)-1-benzothien-2-yl)-sulfonyl]amino}methyl)phosphonate;

4-cyano-3-(trifluoromethyl)phenyl-[({[6-(2-ammonioethoxy)-5-(2-{[3,4-bis(benzyloxy)benzoyl]-amino}ethoxy)-1-benzothien-2-yl]sulfonyl}amino)methyl]phosphonate;

4-cyano-3-(trifluoromethyl)phenyl-[({[5-(2-ammonioethoxy)-6-(2-{[3,4-bis(benzyloxy)benzoyl]-amino}ethoxy)-1-benzothien-2-yl]sulfonyl}amino)methyl]phosphonate;

4-cyano-3-fluorophenyl({[(6-(2-ammonioethoxy)-5-{2-[(2,3-dihydroxybenzoyl)amino]ethoxy}-1-benzothien-2-yl)sulfonyl}amino)methyl]phosphonate;

4-cyano-3-fluorophenyl({[(5-(2-ammonioethoxy)-6-{2-[(2,3-dihdroxybenzoyl)amino]ethoxy}-1-benzothien-2-yl)sulfonyl}amino)methyl]phosphonate;

4-cyano-3-(trifluoromethyl)phenyl-({[(6-(2-ammonioethoxy)-5-{2-[(3,4-dihydroxybenzoyl)-amino]ethoxy}-1-benzothien-2-yl)sulfonyl]amino}methyl)phosphonate;
4-cyano-3-(trifluoromethyl)phenyl-({[(5-(2-ammonioethoxy)-6-{2-[(3,4-dihydroxybenzoyl)amino]ethoxy}-1-benzothien-2-yl)sulfonyl]amino}methyl)phosphonate;
4-cyano-3-fluorophenyl {[({5-[2-dimethylammonioethoxy]-1-benzothien-2-yl}sulfonyl)amino]methyl}phosphonate;
4-cyano-3-(trifluoromethyl)phenyl-({[(5-{2-[(iminiomethyl)amino]ethoxy}-1-benzothien-2-yl)sulfonyl]amino}methyl)phosphonate trifluoroacetate;
4-cyano-3-fluorophenyl[({[5-(2-{[(dimethyliminio)-methyl]amino}ethoxy)-1-benzothien-2-yl]sulfonyl}amino)methyl]-phosphonate;
4-cyano-3-fluorophenyl-{[({5-(2-(4-aza-1-azoniabicyclo[2.2.2]oct-1-yl)ethoxy)-1-benzothien-2-yl}sulfonyl)-amino]methyl}phosphonate;
4-cyano-3-fluorophenyl-{[({6-(2-(4-aza-1-azoniabicyclo[2.2.2]oct-1-yl)ethoxy)-4,5,7-trifluoro-1-benzothien-2-yl}sulfonyl)amino]methyl}phosphonate;
4-cyano-3-(trifluoromethyl)phenyl-[({[5-(2-(4-methyl-1,4-diazoniabicyclo[2.2.2]oct-1-yl)ethoxy)-1-benzothien-2-yl]sulfonyl}-amino)methyl}-phosphonate trifluoroacetate;
4-cyano-3-fluorophenyl-({[(5-{2-[4-(3-azidopropyl)-1,4-diazoniabicylco[2.2.2]oct-1-yl]ethoxy}-1-benzothien-2-yl)sulfonyl]-amino}methyl)phosphonate iodide trifluoromethanesulfonate;
4-cyano-3-fluorophenyl-({[(6-{2-[4-(3-azidopropyl)-1,4-diazoniabicylco[2.2.2]oct-1-yl]ethoxy}-4-fluoro-1-benzothien-2-yl)sulfonyl]amino}methyl)phosphonate iodide trifluoromethanesulfonate;
4-cyano-3-fluorophenyl-({[(6-{2-[4-(3-azidopropyl)-1,4-diazoniabicylco[2.2.2]oct-1-yl]ethoxy}-4,5,7-trifluoro-1-benzothien-2-yl)sulfonyl]amino}methyl)phosphonate iodide trifluoromethanesulfonate;
4-cyano-3-fluorophenyl hydrogen[({[5-{2-[bis(2-cyanoethyl)amino]ethoxy}-1-benzothien-2-yl]-sulfonyl}amino)methyl]phosphonate;
4-cyano-3-fluorophenyl[({[5-(2-{4-[3-(1,4-diazoniabicyclo[2.2.2]oct-1-yl)propyl]-1,4-diazoniabicyclo[2.2.2]oct-1-yl}ethoxy)-1-benzothien-2-yl]sulfonyl}amino)methyl]phosphonate bis-trifluoroacetate bis-triflate;
4-cyano-3-fluorophenyl-{[({6-[2-(4-{3-[(2,3-dihydroxybenzoyl)amino]propyl}-1,4-diazoniabicyclo[2.2.2]oct-1-yl)ethoxy]-4,5,7-trifluoro-1-benzothien-2-yl}sulfonyl)-amino]methyl}phosphonate trifluoroacetate;
4-cyano-3-fluorophenyl hydrogen[({[5-{2-[bis(3-ammoniopropoxy)amino]ethoxy}-1-benzothien-2-yl]-sulfonyl}amino)methyl]phoshonate bis-trifluoroacetate;
4-cyano-3-fluorophenyl hydrogen({[(5-{3-[bis(3-aminopropyl)amino]propoxy}-1-benzothien-2-yl)sulfonyl]amino}methyl)phosphonate bis-trifluoroacetate;
4-cyano-3-fluorophenyl hydrogen({[(5-{3-[(4-aminobutyl)-(3-aminopropyl)amino]propoxy}-1-benzothien-2-yl)sulfonyl]amino}methyl)phosphonate bis-trifluoroacetate;
4-cyano-3-fluorophenyl hydrogen({[(5-{3-[bis(3-aminopropyl)amino]propoxy}-3-methyl-1-benzothien-2-yl)sulfonyl]amino}methyl)phosphonate bis-trifluoroacetate;
4-cyano-3-fluorophenyl hydrogen[({[5-(3-{bis[3-({[(4-methoxybenzyl)oxy]carbonyl}amino)propyl]amino}propoxy)-1-benzothien-2-yl]sulfonyl}amino)methyl]phosphonate;
4-cyano-3-fluorophenyl hydrogen[({[5-(3-{[4-({[(4-methoxybenzyl)oxy]carbonyl}amino)butyl][3-({[(4-methoxybenzyl)oxy]carbonyl}amino)propyl]amino}propoxy)-1-benzothien-2-yl]-sulfonyl}amino)-methyl]phosphonate;
4-cyano-3-fluorophenyl hydrogen[({[5-(3-{bis[3-({[(4-methoxybenzyl)oxy]carbonyl}amino)propyl]-amino}propoxy)-3-methyl-1-benzothien-2-yl]sulfonyl}amino)methyl]phosphonate;
4-cyano-3-fluorophenyl hydrogen[({[5-(3-{[4-({[(4-methoxybenzyl)oxy]carbonyl}amino)butyl][3-({[(4-methoxybenzyl)oxy]carbonyl}amino)propyl]amino}propoxy)-3-methyl-1-benzothien-2-yl]sulfonyl}-amino)methyl]phosphonate;
4-cyano-3-fluorophenyl hydrogen({[(5-{3-[4-aminobutyl]-(3-aminopropyl)amino]propoxy}-3-methyl-1-benzothien-2-yl)sulfonyl]amino}methyl)phosphonate bis-trifluoroacetate;
4-cyano-3-fluorophenyl-({[(5-{2-[4-(3-ammoniopropyl)-1,4-diazoniabicylco[2.2.2]oct-1-yl]-ethoxy}-1-benzothien-2-yl)sulfonyl]amino}methyl)phosphonate trifluoroacetate trifluoromethanesulfonate;
4-cyano-3-fluorophenyl-({[(6-{2-[4-(3-ammoniopropyl)-1,4-diazoniabicyclo[2.2.2]oct-1-yl]-ethoxy}-4-fluoro-1-benzothien-2-yl)sulfonyl]amino}methyl)phosphonate bis-trifluoroacetate;
4-cyano-3-fluorophenyl-({[(6-{2-[4-(3-ammoniopropyl)-1,4-diazoniabicyclo[2.2.2]oct-1-yl]-ethoxy}-4,5,7-trifluoro-1-benzothien-2-yl)sulfonyl]amino}methyl)phosphonate bis-trifluoroacetate;
4-{[4-({2-[({[(4-cyano-3-fluorophenoxy)(hydroxyl)-phosphoryl]methyl}amino)sulfonyl]-1-benzothien-6-yl}-oxy)butyl]thio}-1-methylpyridinium;
4-Cyano-3-fluorophenyl-({[(5-{[(3-(pyridinium-1-ylpropyl)thio]methyl}-1-benzothien-2-yl)sulfonyl]amino}methyl)phosphonate;
4-cyano-3-(trifluoromethyl)phenyl-({[(5-{[(3-(pyridinium-1-ylpropyl)thio]methyl}-1-benzothien-2-yl)sulfonyl]amino}methyl)phosphonate;
4-Cyano-3-fluorophenyl-({[(5-{[(3-(pyridinium-1-ylpropyl)sulfonyl]methyl}-1-benzothien-2-yl)sulfonyl]amino}methyl)phosphonate;
4-cyano-3-fluorophenyl[({[5,6-bis(2-ammonioethoxy)-3-methyl-1-benzothien-2-yl]sulfonyl}-amino)methyl]phosphonate trifluoroacetate;
4-cyano-3-fluorophenyl hydrogen[({[5,6-bis(3-ammoniopropoxy)-3-ethyl-1-benzothien-2-yl]-sulfonyl}amino)methyl]phosphonate trifluoroacetate;
4-cyano-3-fluorophenyl hydrogen[({[6-(4-ammoniobutoxy)-5-(3-ammoniopropoxy)-1-benzothien-2-yl]sulfonyl}amino)methyl]phosphonate;
4-cyano-3-fluorophenyl hydrogen[({[5-(4-ammoniobutoxy)-6-(3-ammoniopropoxy)-1-benzothien-2-yl]sulfonyl}amino)methyl]phosphonate;
4-cyano-3-fluorophenyl[({[5,6-bis(2-ammonioethoxy)-3-methyl-4,7-difluoro-1-benzothien-2-yl]sulfonyl}amino)methyl]phosphonate trifluoroacetate;
4-cyano-3-fluorophenyl[({[5,6-bis(2-ammonioethoxy)-3-ethyl-4,7-difluoro-1-benzothien-2-yl]sulfonyl}amino)methyl]phosphonate trifluoroacetate;
4-cyano-3-fluorophenyl[({[5,6-bis(3-ammoniopropoxy)-4,7-difluoro-3-ethyl-1-benzothien-2-yl]-sulfonyl}amino)methyl]phosphonate trifluoroacetate;
N'2',N'2'-bis(2-aminoethyl)-N-{2-[({[(4-cyano-3-fluorophenoxy)(hydroxy)phosphoryl]-methyl}amino)sulfonyl]-1-benzothien-5-yl}glycinamide bis(trifluoroacetate);
2-(2-(N-(((4-cyano-3-fluorophenoxy)(hydroxy)phosphoryl)methyl)sulfamoyl)benzo[b]thiophen-5-ylamino)-N,N,N-trimethyl-2-oxoethanaminium 2,2,2-trifluoroacetate;

4-cyano-3-fluorophenyl hydrogen[({[5,6-bis(3-{[amino(iminio)methyl]amino}propoxy)-4,7-difluoro-1-benzothien-2-yl]sulfonyl}amino)methyl]phosphonate trifluoroacetate;

4-cyano-3-fluorophenyl[({[5,6-bis(3-{[amino(iminio)methyl]amino}propoxy)-3-methyl-1-benzothien-2-yl]sulfonyl}amino)methyl]phosphonate trifluoroacetate;

4-cyano-3-fluorophenyl[({[5,6-bis(3-{[amino(iminio)methyl]amino}propoxy)-4,7-dichloro-1-benzothien-2-yl]sulfonyl}amino)methyl]phosphonate trifluoroacetate;

N'2',N'2'-bis{2-[(tert-butoxycarbonyl)amino]ethyl}-N-{2-[({[(4-cyano-3-fluorophenoxy)-(hydroxy)phosphoryl]methyl}amino)sulfonyl]-1-benzothien-5-yl}glycinamide;

4-cyano-3-fluorophenyl hydrogen[({[5-(2-{bis[3-({[(4-methoxybenzyl)oxy]carbonyl}amino)-propyl]amino}ethoxy)-1-benzothien-2-yl]sulfonyl}amino)methyl]phosphonate;

4-cyano-3-fluorophenyl hydrogen[5-(2-{[(8-hydroxyquinolin-5-yl)methyl](methyl)amino}-acetamido)-benzo[b]thiophene-2-sulfonamido]methyl phosphonate;

4-cyano-3-fluorophenyl[({[5,6-bis(3-{[amino(iminio)methyl]amino}propoxy)-3-ethyl-1-benzothien-2-yl]sulfonyl}amino)methyl]phosphonate trifluoroacetate;

4-cyano-3-fluorophenyl[({[5,6-bis(3-{[amino(iminio)methyl]amino}propoxy)-4,7-fluoro-3-ethyl-1-benzothien-2-yl]sulfonyl}amino)methyl]phosphonate trifluoroacetate;

4-cyano-3-fluorophenyl[({[5,6-bis(2-ammonioethoxy)-3-ethyl-1-benzothien-2-yl]sulfonyl}-amino)methyl]phosphonate trifluoroacetate;

4-cyano-3-fluorophenyl hydrogen[5-((S)-2,6-diaminohexanamido)benzo[b]thiophene-2-sulfonamido]methylphosphonate;

4-cyano-3-fluorophenyl-hydrogen-{5-[(S)-2-amino-3-(1H-imidazol-4-yl)propanamido]-benzo[b]thiophene-2-sulfonamido}methylphosphonate;

4-cyano-3-fluorophenyl hydrogen[({[5-(2-{bis[3-({[(4-methoxybenzyl)oxy]-carbonyl}amino)-propyl]amino}ethoxy)-1-benzothien-2-yl]sulfonyl}amino)methyl]-phosphonate;

4-cyano-3-fluorophenyl(5-(((triethylammonio)methyl)thiophene-2-sulfonamido)methylphosphonate;

4-cyano-3-fluorophenyl(5-((3-(pyridinium-1-yl)propylthio)methyl)benzo[b]thiophene-2-sulfonamido)methylphosphonate;

4-cyano-3-fluorophenyl(5-((3-(pyridinium-1-yl)propylsulfonyl)methyl)benzo[b]thiophene-2-sulfonamido)methylphosphonate;

4-cyano-3-fluorophenyl aminooxy((7-cyano-6-(dimethylamino)benzo[b]thiophene-2-sulfonamido)methyl)phosphinate;

4-cyano-3-fluorophenyl hydrogen(5-(2-(bis(2-(3,4-dimethoxybenzamido)ethyl)-amino)acetamido)-benzo[b]thiophene-2-sulfonamido)methylphosphonate;

4-cyano-3-fluorophenyl hydrogen(5-(2-(bis(2-(3,4-dihydroxybenzamido)ethyl)-amino)acetamido)-benzo[b]thiophene-2-sulfonamido)methylphosphonate;

2,2,2-trifluoroacetic acid compound with 4-cyano-3-fluorophenyl hydrogen(5-(3,4-bis(3-aminopropoxy)benzamido)benzo[b]thiophene-2-sulfonamido)methylphosphonate;

2,2,2-trifluoroacetic acid compound with 4-cyano-3-fluorophenyl hydrogen(5-(3,4,5-tris(3-aminopropoxy)benzamido)-benzo[b]thiophene-2-sulfonamido)methylphosphonate;

2,2,2-trifluoroacetic acid compound with 4-cyano-3-fluorophenyl hydrogen(5-(3,5-bis(3-aminopropoxy)benzamido)benzo[b]thiophene-2-sulfonamido)methylphosphonate;

4-cyano-3-fluorophenyl hydrogen[({[5,6-bis(3-aminopropoxy)-3-methyl-1-benzothien-2-yl]sulfonyl}amino)methyl]phosphonate;

4-cyano-3-fluorophenyl hydrogen({[(5,6-bis{3-[(iminomethyl)amino]propoxy}-3-methyl-1-benzothien-2-yl)sulfonyl]amino}methyl)phosphonate;

4-cyano-3-fluorophenyl hydrogen[({[5,6-bis(3-{[amino(imino)methyl]amino}propoxy)-3-methyl-1-benzothien-2-yl]sulfonyl}amino)methyl]phosphonate;

6-cyanopyridin-3-yl hydrogen[({[5,6-bis(3-aminopropoxy)-3-methyl-1-benzothien-2-yl]sulfonyl}amino)methyl]phosphonate;

6-cyanopyridin-3-yl hydrogen({[(5,6-bis{3-[(iminomethyl)amino]propoxy}-3-methyl-1-benzothien-2-yl)sulfonyl]amino}methyl)phosphonate;

6-cyanopyridin-3-yl hydrogen[({[5,6-bis(3-{[amino(imino)methyl]amino}propoxy)-3-methyl-1-benzothien-2-yl]sulfonyl}amino)methyl]phosphonate;

6-cyanopyridin-3-yl[({[5,6-bis(3-ammoniopropoxy)-3-methyl-1-benzothien-2-yl]sulfonyl}amino)methyl]phosphonate chloride;

6-cyanopyridin-3-yl hydrogen[({[5,6-bis(3-aminopropoxy)-4-fluoro-3-methyl-1-benzothien-2-yl]sulfonyl}amino)methyl]phosphonate;

6-cyanopyridin-3-yl hydrogen[({[5,6-bis(3-aminopropoxy)-7-fluoro-3-methyl-1-benzothien-2-yl]sulfonyl}amino)methyl]phosphonate;

6-cyanopyridin-3-yl hydrogen[({[5,6-bis(3-aminopropoxy)-4,7-difluoro-3-methyl-1-benzothien-2-yl]sulfonyl}amino)methyl]phosphonate;

4-cyano-3-fluorophenyl hydrogen[({[5,6-bis(3-aminopropoxy)-4-fluoro-3-methyl-1-benzothien-2-yl]sulfonyl}amino)methyl]phosphonate;

4-cyano-3-fluorophenyl hydrogen[({[5,6-bis(3-aminopropoxy)-7-fluoro-3-methyl-1-benzothien-2-yl]sulfonyl}amino)methyl]phosphonate;

4-cyano-3-fluorophenyl hydrogen[({[5,6-bis(3-aminopropoxy)-4,7-difluoro-3-methyl-1-benzothien-2-yl]sulfonyl}amino)methyl]phosphonate;

4-cyano-3-fluorophenyl({[(5-{3-[4-(3-ammoniopropyl)-1,4-diazoniabicyclo[2.2.2]oct-1-yl]propoxy}-3-methyl-1-benzothien-2-yl)sulfonyl]amino}methyl)phosphonate dichloride;

4-cyano-3-fluorophenyl({[(5-{3-[4-(3-{[(Z)-iminomethyl]amino}propyl)-1,4-diazoniabicyclo[2.2.2]oct-1-yl]propoxy}-3-methyl-1-benzothien-2-yl)sulfonyl]amino}methyl)phosphonate chloride;

4-cyano-3-fluorophenyl({[(5-{3-[4-(3-{[(Z)-amino(imino)methyl]amino}propyl)-1,4-diazoniabicyclo[2.2.2]oct-1-yl]propoxy}-3-methyl-1-benzothien-2-yl)sulfonyl]amino}methyl)-phosphonate chloride;

6-cyanopyridin-3-yl({[(5-{3-[4-(3-ammoniopropyl)-1,4-diazoniabicyclo[2.2.2]oct-1-yl]propoxy}-3-methyl-1-benzothien-2-yl)sulfonyl]amino}methyl)phosphonate dichloride;

6-cyanopyridin-3-yl({[(5-{3-[4-(3-{[(Z)-iminomethyl]amino}propyl)-1,4-diazoniabicyclo[2.2.2]oct-1-yl]propoxy}-3-methyl-1-benzothien-2-yl)sulfonyl]amino}methyl)phosphonate chloride;

6-cyanopyridin-3-yl({[(5-{3-[4-(3-{[(Z)-amino(imino)methyl]amino}propyl)-1,4-diazoniabicyclo[2.2.2]oct-1-yl]propoxy}-3-methyl-1-benzothien-2-yl)sulfonyl]amino}methyl)phosphonate chloride;

or pharmaceutically acceptable salts thereof.

Other examples are:

4-cyano-3-fluorophenyl hydrogen(5-(3,4-bis(3-aminopropoxy)benzamido)benzo[b]thiophene-2-sulfonamido)methylphosphonate trifluoroacetate;

4-cyano-3-fluorophenyl hydrogen(5-(3,4,5-tris(3-aminopropoxy)benzamido)-benzo[b]thiophene-2-sulfonamido)methylphosphonate trifluoroacetate;

4-cyano-3-fluorophenyl hydrogen(5-(3,5-bis(3-aminopropoxy)benzamido)benzo[b]thiophene-2-sulfonamido)methylphosphonate trifluoroacetate;

6-cyanopyridin-3-yl[({[5,6-bis(3-ammoniopropoxy)-3-methyl-1-benzothien-2-yl]sulfonyl}amino)methyl]phosphonate chloride;

6-cyanopyridin-3-yl[({[5,6-bis(3-ammoniopropoxy)-3-methyl-1-benzothien-2-yl]sulfonyl}amino)methyl]phosphonate trifluoroacetate; and 4-cyano-3-fluorophenyl[({[5,6-bis(3-ammoniopropoxy)-3-methyl-1-benzothien-2-yl]sulfonyl}amino)methyl]phosphonate trifluoroacetate.

Still other examples are:

6-cyanopyridin-3-yl[({[5,6-bis(3-ammoniopropoxy)-3-methyl-1-benzothien-2-yl]sulfonyl}amino)methyl]phosphonate chloride; and 6-cyanopyridin-3-yl[({[5,6-bis(3-ammoniopropoxy)-3-methyl-1-benzothien-2-yl]sulfonyl}amino)methyl]phosphonate trifluoroacetate.

In certain preferred embodiments, the β-lactamase inhibitor is a salt of the compound of Formula I or II, the salt preferably being formed by treating the compound of Formula I or II with a base so as to remove the phosphonate hydrogen atom. Non-limiting examples of bases which may be use to deprotonate the compound of Formula (I) or (II) include sodium hydroxide, potassium hydroxide ammonium hydroxide, sodium bicarbonate, potassium bicarbonate, sodium carbonate, and potassium carbonate. Preferably, the counterion thereby introduced is a pharmaceutically acceptable counterion, including without limitation sodium, magnesium, calcium, or ammonium. Another aspect, the invention provides pharmaceutical compositions comprising a β-lactamase inhibitor of the invention and a pharmaceutically acceptable carrier or diluent. The characteristics of the carrier will depend on the route of administration. As used herein, the term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism. Thus, compositions and methods according to the invention may contain, in addition to the inhibitor, diluents, fillers, salts, buffers, stabilizers, solubilizers, and other materials well known in the art. The pharmaceutical composition of the invention may also contain other active factors and/or agents which enhance the inhibition of β-lactamases and/or DD-peptidases.

As employed herein, the term "pro-drug" refers to pharmacologically acceptable derivatives, e.g., esters and amides, such that the resulting biotransformation product of the derivative is the active drug. Pro-drugs are known in the art and are described generally in, e.g., Goodman and Gilman, "Biotransformation of Drugs", In The Pharmacological Basis of Therapeutics, 8th Ed., McGraw Hill, Int. Ed. 1992, p. 13-15, which is hereby incorporated by reference in its entirety. Compounds of the invention may be formulated by any method well known in the art and may be prepared for administration by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other embodiments, administration may be preferably by the oral route.

The invention also provides methods for inhibiting bacterial growth, such methods comprising administering to a bacterial cell culture, or to a bacterially infected cell culture, tissue, or organism, a β-lactamase inhibitor of Formula (I) or Formula (II) as defined for the first aspect of the invention.

Preferably, the bacteria to be inhibited by administration of a β-lactamase inhibitor of the invention are bacteria that are resistant to β-lactam antibiotics. More preferably, the bacteria to be inhibited are β-lactamase positive strains that are highly resistant to β-lactam antibiotics. The terms "slightly resistant" and "highly resistant" are well-understood by those of ordinary skill in the art (see, e.g., Payne et al., Antimicrobial Agents and Chemotherapy 38:767-772 (1994); Hanaki et al., Antimicrobial Agents and Chemotherapy 30:11.20-11.26 (1995)). Preferably, "highly resistant" bacterial strains are those against which the MIC of methicillin is >100 μg/mL. Preferably, "slightly resistant" bacterial strains are those against which the MIC of methicillin is >25 μg/mL.

The methods according to this aspect of the invention are useful for inhibiting bacterial growth in a variety of contexts. In certain preferred embodiments, the compound of the invention is administered to an experimental cell culture in vitro to prevent the growth of β-lactam resistant bacteria. In certain other preferred embodiments the compound of the invention is administered to an animal, including a human, to prevent the growth of β-lactam resistant bacteria in vivo. The method according to this embodiment of the invention comprises administering a therapeutically effective amount of a β-lactamase inhibitor according to the invention for a therapeutically effective period of time to an animal, including a human. Preferably, the β-lactamase inhibitor is administered in the form of a pharmaceutical composition-according to the second aspect of the invention.

The terms "therapeutically effective amount" and "therapeutically effective period of time" are used to denote known treatments at dosages and for periods of time effective to show a meaningful patient benefit, i.e., healing of conditions associated with bacterial infection, and/or bacterial drug resistance. Preferably, such administration should be parenteral, oral, sublingual, transdermal, topical, intranasal, intratracheal, or intrarectal. When administered systemically, the therapeutic composition is preferably administered at a sufficient dosage to attain a blood level of inhibitor of at least about 100 micrograms/mL, more preferably about 1 milligram/mL, and still more preferably about 10 milligrams/mL. For localized administration, much lower concentrations than this may be effective, and much higher concentrations may be tolerated.

In certain preferred embodiments of the method according to this aspect of the invention, a β-lactamase inhibitor according to the invention is co-administered with an antibiotic. Preferably, such co-administration produces a synergistic effect. As employed herein, the terms "synergy" and "synergistic effect" indicate that the effect produced when two or more drugs are co-administered is greater than would be predicted based on the effect produced when the compounds are administered individually. While not wishing to be bound by theory, the present inventors believe that the β-lactamase inhibitors according to the invention act to prevent degradation of β-lactam antibiotics, thereby enhancing their efficacy and producing a synergistic effect. In particularly preferred embodiments of the invention, therefore, the co-administered antibiotic is a β-lactam antibiotic. For purposes of this invention, the term "co-administered" is used to denote simultaneous or sequential administration.

Synergy may be expressed as a ratio of the minimum inhibitory concentration (MIC) of an antibiotic tested in the absence of a β-lactamase inhibitor to the MIC of the same antibiotic tested in the presence of the β-lactamase inhibitor. A ratio of one (1) indicates that the β-lactamase inhibitor has no effect on antibiotic potency. A ratio greater than one (1) indicates that the β-lactamase inhibitor produces a synergistic effect when co-administered with the antibiotic agent. Preferably the β-lactamase inhibitor produces a synergy ratio of at least about 2, more preferably about 4, and still more preferably about 8. Most preferably, the β-lactamase inhibitor produces a synergy ratio of at least about 16. Alternatively, the synergy effect may be expressed as a factor, again, utilizing a concentration of the BLI to lower the MIC of the antibiotic.

Thus, if the MIC of the antibiotic is 20 μg/mL and a 1.56 concentration of BLI lowers the MIC to 5 μg/mL, the synergy effect is four fold or "4× synergy".

In certain other preferred embodiments, the β-lactamase inhibitor according to the invention may itself have antibiotic activity, and thus potentially can be administered alone or can be co-administered with a β-lactam antibiotic or any other type of antibiotic.

The term "antibiotic" is used herein to describe a compound or composition which decreases the viability of a microorganism, or which inhibits the growth or proliferation of a microorganism. "Inhibits the growth or proliferation" means increasing the generation time by at least 2-fold, preferably at least 10-fold, more preferably at least 100-fold, and most preferably indefinitely, as in total cell death. As used in this disclosure, an antibiotic is further intended to include an antimicrobial, bacteriostatic, or bactericidal agent. Non-limiting examples of antibiotics useful according to this aspect of the invention include penicillins, cephalosporins, carbapenems, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and others. The term β-lactam antibiotic" is used to designate compounds with antibiotic properties containing a β-lactam functionality. Non-limiting examples of β-lactam antibiotics useful according to this aspect of the invention include penicillins, cephalosporins, penems, carbapenems, and monobactams.

Generally, the compounds of the invention can be routinely synthesized using techniques known to those skilled in the art (see U.S. Pat. No. 6,472,406, incorporated herein in its entirety) in conjunction with the teachings herein.

The following examples are intended to further illustrate certain preferred embodiments of the invention, and are not intended to limit the scope of the invention. In Schemes 1 through 4 the abbreviated terms are defined as: Boc=CO₂t-Bu, DMAP=4-dimethylaminopyridine, PMB=para-methoxybenzyl, TEA=triethylamine, DIAD=diisopropylazodicarboxylate, TFA=trifluoroacetic acid, TMSBr=bromotrimethylsilane, R=methyl or ethyl, R₁ is defined, HETAR=heteroaromatic/aromatic, L=linker, n=1-3, X=leaving group, Nuc=nucleophile (all as defined).

SCHEME 1

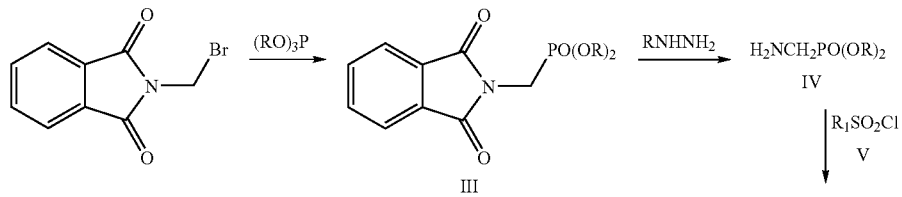

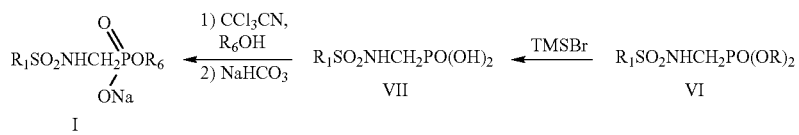

Generally, the compounds of the invention can be routinely synthesized using techniques known to those skilled in the art in conjunction with the teachings herein. The compounds of Formula (I) and (II) can be prepared in certain preferred embodiments according to the general synthetic route depicted in Scheme 1. Thus, Arbusov reaction of bromomethylphthalimide with a phosphite such as triethylphosphite is preferably conducted at elevated temperature, e.g., 145° C., in a solvent such as xylenes to afford the phthalimidomethylphosphonate III. Treatment of III with a hydrazine such as methylhydrazine in an alcoholic solvent such as methanol effects phthalimide cleavage to afford the aminomethylphosphonate IV. Treatment of IV with a sulfonyl chloride of the general formula V in an organic solvent such as methylene chloride, and in the presence of a base such as triethylamine, provides the N-sulfonylaminomethylphosphonate VI. Treatment of VI with a silyl halide such as trimethylsilyl bromide at room temperature in a solvent such as methylene chloride effects cleavage of the phosphonate ester to provide the phosphonic acid VII. In situ activation of VII with trichloroacetonitrile in pyridine, followed by treatment at 100° C. with an aryl or heteroaryl alcohol, such as phenol or substituted phenol, affords an aryl or heteroaryl phosphonate. Treatment with an aqueous base such as sodium bicarbonate then provides the sodium salt I, M=Na⁺, which corresponds to the compound of Formula (I) or (II).

SCHEME 2

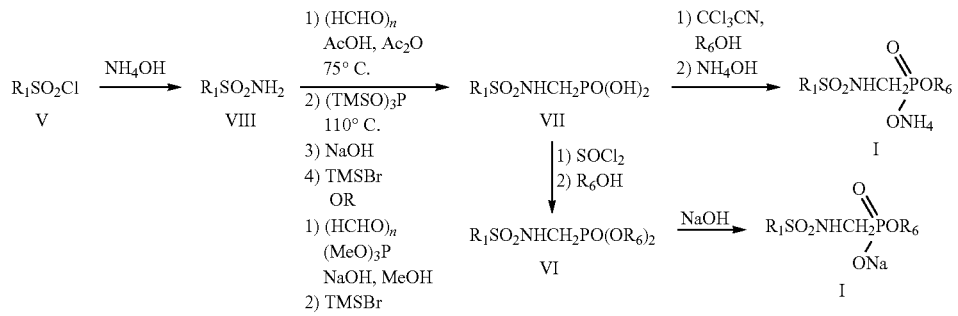

In certain other preferred embodiments, sulfonamidemethylphosphonates of formula I may be prepared according to the procedures illustrated in Scheme 2. Thus, sulfonyl chloride V is treated with ammonium hydroxide to produce the corresponding sulfonamide of formula VIII. Treatment of VIII with paraformaldehyde in the presence of a phosphite such as trimethylphosphite affords the phosphonate diester which in turn upon exposure to a silyl halide such as bromotrimethylsilane (TMSBr) produces the phosphonic acid of formula VII. Alternatively, the Arbusov reaction of VIII maybe performed with paraformaldehyde in the presence of acetic anhydride and a phosphite such as trimethylsilylphosphite to produce a more labile diester which as before readily yields VII. It is further noted, that this alternative often affects the formation of a small amount of N-acetylated by product which is easily hydrolyzed to the desired product by treatment sodium hydroxide during workup. The phosphonic acid VII may be converted to I by treatment with trichloroacetonitrile in pyridine in the presence of an aryl or heteroaryl alcohol, as described above, followed by basification with ammonium hydroxide. Alternatively, treatment of VII with a chlorinating agent such as sulfuryl chloride or thionyl chloride, followed by treatment with an aryl or heteroaryl alcohol, affords the diester VI, which is mono-deprotected by treatment with base to afford I.

SCHEME 3

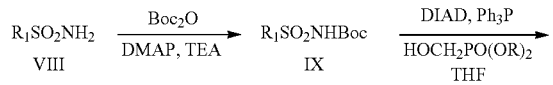

-continued

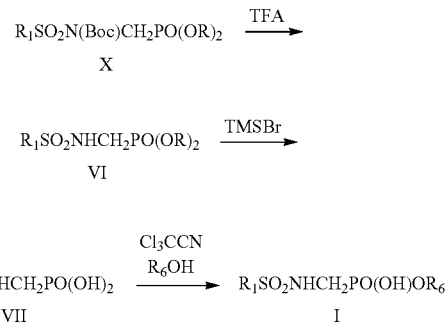

As an alternative to the synthetic process outlined in Scheme 2, sulfonamide VIII may be converted to the products of the invention by the route exhibited in Scheme 3. Thus, VIII is converted to the corresponding N-Boc-derivative IX by exposure to a t-butylcarbonylating agent such as t-butyl-choroformate or di-t-butyl dicarbonate ($Boc_2O$) in the presence of a base such as triethylamine (TEA) and a catalytic amount of 4-N,N-dimethylaminopyridine (DMAP). Mitsunobu reaction of IX with either dimethyl or diethyl-hydroxymethylphosphonate in the presence of a phosphine or a phosphine based resin such as triphenylphosphine and a diazodicarboxylate such as diisopropylazodicarboxylate (DIAD) provides X. Removal of the Boc group of X is accomplished with trifluoroacetic acid to yield the phosphonate intermediate VI. As previously described, VI is converted to the products of the invention I.

SCHEME 4

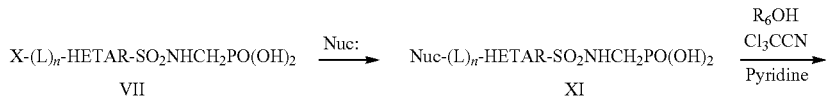

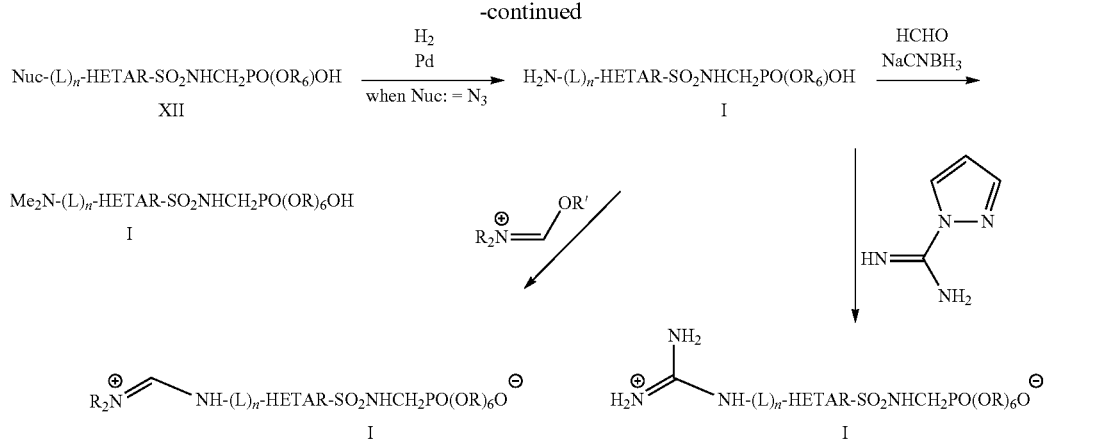

In certain other preferred embodiments, sulfonamidemethylphosphonates of formula I or II may be prepared according to the procedures illustrated in Scheme 4. Intermediate VII is converted to certain products of the invention I by displacement of the leaving group (X) present in VII with nucleophiles (Nuc:). In the instance where the nucleophile does not provide a product of the invention, such as when it is azide, the resulting intermediate is then converted to the products of the invention by conversion to intermediate XI, as previously described, followed by reduction of the azide group with hydrogen gas in the presence of palladium black. Further, such amine products are convertible to other products of the invention by such reactions as amidation, with an amidinating agent such as ethyl formimidate hydrochloride; guanidination, with a guanidinating agent such as 1H-pyrazole-1-carboxamidine; and alkylation, such as with formaldehyde and sodium cyanoborohydride.

In certain other preferred embodiments, sulfonamidomethylphosphonates of Formula I or II are synthesized by more specific or less general chemistry which are exemplified in the experimental section.

Preparative Example 1

Preparation of
1-[(2,2-Diethoxyethyl)Thio]-4-Methylbenzene

To a stirred solution of 4-methylbenzenethiol (25 g, 0.201 mol, 1 eq) in acetone (250 mL) at room temperature was added bromoacetaldehyde diethyl acetal (31.8 mL, 0.211 mol, 1.05 eq) followed by potassium carbonate (30.6 g, 0.221 mol, 1.10 eq). After 48 h the reaction mixture was filtered and the filtrate was concentrated. The residue was dissolved in ethyl acetate, washed with water and brine, dried over sodium sulfate, concentrated and dried under high vacuum to afford crude 1-[(2,2-diethoxyethyl)thio]-4-methylbenzene as an oil, which was used without further purification.

$^1$H NMR (400 MHz, CDCl$_3$) δ (ppm): 7.29 (d, J=8.0 Hz, 2H), 7.08 (d, J=8.0 Hz, 2H), 4.62 (t, J=5.4 Hz, 1H), 3.70-3.50 (m, 4H), 3.10 (d, J=5.4 Hz, 2H), 2.32 (s, 3H), 1.21 (t, J=7.2 Hz, 6H); MS m/z 279 (M+K).

Preparative Example 2

Preparation of
2,5-Dichloro-4-Methylbenzenesulfonic Acid

Oleum (15%, 28 g) was added dropwise to 2,5-dichlorotoluene (20.0 g, 124.0 mmol) while stirring at room temperature. The reaction mixture was stirred for 1 hour until it solidified. A saturated aqueous solution of sodium chloride was slowly added and stirring was continued for 30 min. The precipitate was filtered off and rinsed with brine. The solid was suspended in ethyl acetate, stirred for 20 min, filtered off and dried in vacuo to afford 2,5-dichloro-4-methylbenzenesulfonic acid as a white solid.

$^1$H NMR (400 MHz, DMSO-d$_6$) δ (ppm): 7.77 (s, 1H), 7.39 (s, 1H), 2.30 (s, 3H); MS m/z 239 (M−1) [major isotope].

Preparative Example 3

Preparation of
2,5-Dichloro-4-Methylbenzene-1-Sulfonyl Chloride

To a stirred solution of 2,5-dichloro-4-methylbenzenesulfonic acid (90.0 g, 0.37 mol), prepared in the prior Example, in thionyl chloride (500 mL) under nitrogen was added DMF (0.4 mL) at room temperature. The reaction mixture was heated under reflux, stirring for 4 hours then it was concentrated in vacuo. The residue was dissolved in ethyl acetate and washed with water. The organic layer was dried over sodium sulfate then concentrated to afford 2,5-dichloro-4-methylbenzene-1-sulfonyl chloride as a brown oil.

$^1$H NMR (400 MHz, DMSO-d$_6$) δ (ppm): 7.78 (s, 1H), 7.40 (s, 1H), 2.30 (s, 3H).

Preparative Example 4

Preparation of 2,5-Dichloro-4-Methylbenzenethiol

A solution of 2,5-dichloro-4-methylbenzene-1-sulfonyl chloride (1.0 g, 3.9 mmol, 1 eq), prepared in the prior Example, in anhydrous diethyl ether (10 mL) was added dropwise to a stirred, refluxing suspension of lithium aluminum hydride (0.80 g, 21 mmol, 5.5 eq) in anhydrous diethyl ether (50 mL). The mixture was heated under reflux with stirring for 24 hours, cooled to 0° C. and quenched by the addition of ethyl acetate (20 mL) followed by drop wise addition of methanol (5 mL) and water (40 mL). The mixture was acidified (pH 2) with hydrochloric acid (3N). A further amount of ethyl acetate was added (200 mL) and the mixture was stirred for 15 min then filtered through celite and rinsed with ethyl acetate. The biphasic mixture was transferred to a separatory funnel and the phases were separated. The aqueous phase was extracted twice with ethyl acetate then the combined organic extracts were dried over sodium sulfate, concentrated and dried under high vacuum to afford the title compound 2,5-dichloro-4-methylbenzenethiol as a beige solid.

$^1$H NMR (400 MHz, DMSO-$d_6$) δ (ppm): 7.62 (s, 1H), 7.44 (s, 1H), 5.94 (bs, 1H), 2.24 (s, 3H).

Preparative Example 5

Preparation of O-(2-Chloro-4-Methoxyphenyl) Dimethylthiocarbamate

To a solution of the 2-chloro-4-methoxyphenol (25.4 g, 160.2 mmol), in anhydrous THF (254 mL) was added DBU (24.8 mL, 176.1 mmol) and N,N-dimethylthiocarbamoyl chloride (20.8 g, 168.2 mmol). The mixture was stirred initially at 0° C. and then warmed to room temperature and stirred for an additional 2 hrs. The mixture was diluted with EtOAc and washed with cold 2N HCl, water, 5% aq. NaHCO$_3$ solution and brine. The separated organic phase was dried with Na$_2$SO$_4$, filtered and evaporated to dryness. The resulting residue was purified by silica gel chromatography (230-400 mesh) with 20% EtOAc-hexanes as the eluent to give of O-(2-chloro-4-methoxyphenyl) dimethylthiocarbamate.

$^1$H NMR (400 MHz, CDCl$_3$) δ (ppm): 7.03 (d, J=8.9 Hz, 1H), 6.95 (d, J=2.0 Hz, 1H), 6.80 (dd, J=9.0 Hz, 2.9 Hz, 1H), 3.78 (s, 3H), 3.45 (s, 3H), 3.36 (s, 3H).

Utilizing the foregoing procedure, the following compound was prepared:
O-(2-fluoro-4-methoxyphenyl)dimethylthiocarbamate $^1$H NMR (500 MHz, CDCl$_3$) δ (ppm): 6.99 (t, J=8.7 Hz, 1H), 6.69 (m, 2H), 3.79 (s, 3H), 3.93 (s, 3H), 3.45 (s, 3H), 3.34 (S, 3H).

Preparative Example 6

Preparation of S-(2-Chloro-4-Methoxyphenyl) Dimethylthiocarbamate

A solution of O-(2-chloro-4-methoxyphenyl) dimethylthiocarbamate (36.1 g, 147.3 mmol), in 350 mL of anhydrous diphenyl ether was stirred at reflux (259° C.) for 4 hrs. The reaction mixture was cooled to room temperature and concentrated in vacuo to give viscous oil. The oil was purified by silica gel chromatography (230-400 mesh) with 20% EtOAc-hexanes as the eluent to give S-(2-chloro-4-methoxyphenyl) dimethylthiocarbamate.

$^1$H NMR (400 MHz, CDCl$_3$) δ (ppm): 7.45 (d, J=8.6 Hz, 1H), 7.05 (d, J=2.6 Hz, 1H), 6.79 (dd, J=8.6 Hz, 2.9 Hz, 1H), 3.79 (s, 3H), 3.10 (bs, 3H), 3.08 (bs, 3H).

Utilizing the foregoing procedure, the following compound was prepared:
S-(2-fluoro-4-methoxyphenyl)dimethylthiocarbamate $^1$H NMR (500 MHz, CDCl$_3$) δ (ppm): 7.32 (t, J=8.1 Hz, 1H), 6.71 (s, 1H), 6.69 (s, 1H), 3.79 (s, 3H), 3.07 (s, 3H), 2.99 (bs, 3H).

Preparative Example 7

Preparation of 2-Chloro-4-Methoxythiophenol

To a solution of S-(2-chloro-4-methoxyphenyl)dimethylthiocarbamate (22.8 g, 92.7 mmol) in 520 mL of methanol, under a continuous nitrogen purge via an inlet tube, was added NaOH (12.9 g, 324.5 mmol) and the mixture was stirred at 40° C. for 4 hrs. The reaction was cooled to 0° C. and was carefully acidified to pH 3 with 6N HCl. The reaction was diluted with EtOAc and sequentially washed with water and brine. The separated organic phase was dried with Na$_2$SO$_4$, filtered and evaporated and dried in vacuo to give 2-chloro-4-methoxythiophenol.

$^1$H NMR (600 MHz, CDCl$_3$) δ (ppm): 7.24 (d, J=8.6 Hz, 1H), 6.94 (d, J=2.6 Hz, 1H), 6.71 (dd, J=8.6 Hz, 2.6 Hz, 1H), 3.76 (s, 3H), 3.68 (d, J=2.2 Hz, 1H).

Utilizing the foregoing procedure, the following compound was prepared:
2-fluoro-4-methoxythiophenol $^1$H NMR (500 MHz, CDCl$_3$) δ (ppm): 7.21 (t, J=8.6 Hz, 1H), 6.67-6.62 (m, 2H), 3.78 (s, 3H), 3.35 (s, 1H).

Preparative Example 8

Preparation of 2-Chloro-1-[(2,2-Diethoxy)Thio]-4-Methoxybenzene

To a stirred solution of 2-chloro-4-methoxythiophenol (17.4 g, 92.7 mmol), prepared in the prior Example, dissolved in 300 mL of anhydrous acetone was added K$_2$CO$_3$ (15.1 g, 109.5 mmol) and bromoacetaldehyde diethyl acetal (15.7 mL, 104.6 mmol). The suspension was stirred at room temperature for 18 hrs. The mixture was filtered and the resulting filtrate was concentrated in vacuo. The crude product was purified by silica gel chromatography (230-400 mesh) using 20% EtOAc-hexanes as the eluent to give 2-chloro-1-[(2,2-diethoxyethyl)thio]-4-methoxybenzene, as a yellow oil.

$^1$H NMR (500 MHz, CDCl$_3$) δ (ppm): 7.46 (d, J=8.7 Hz, 1H), 7.00 (d, J=2.8 Hz, 1H), 6.79 (dd, J=8.7 Hz, 2.8 Hz, 1H), 4.65 (t, J=5.8 Hz, 1H), 3.82 (s, 3H) 3.68 (m, 2H), 3.66 (m, 2H), 3.07 (d, J=5.5 Hz, 2H), 1.20 (t, J=7.1 Hz, 6H).

Preparative Example 9

Preparation of 1,4-Dichloro-2-[(2,2-Diethoxy)Thio]-5-Methylbenzene

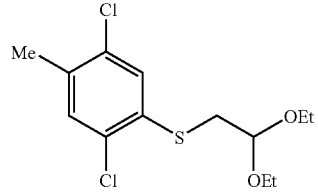 [SMILES: CCOC(CSc1cc(Cl)c(C)cc1Cl)OCC]

To a stirred solution of 2,5-dichloro-4-methylbenzenethiol (4.9 g, 25 mmol, 1 eq) in acetone (300 mL) at room temperature was added bromoacetaldehyde diethyl acetal (3.82 mL, 25.4 mmol, 1.01 eq) followed by potassium carbonate (3.9 g, 28 mmol, 1.1 eq). After 24 h the reaction mixture was filtered and the filtrate was concentrated. The residue was dissolved in ethyl acetate, washed with water and brine, dried over sodium sulfate, concentrated and dried under high vacuum to afford the product as an oil, which was used without further purification in the next step.

Preparative Example 10

Preparation of 1-[(2-Fluoro-4-Methoxyphenyl)Thio]Acetone

To a stirred solution of 2-fluoro-4-methoxythiophenol (4.7 g, 29.7 mmol) in 150 mL of anhydrous acetone was added K$_2$CO$_3$ (8.2 g, 59.5 mmol) and chloroacetone (4.7 mL, 59.4 mmol). The resulting suspension was stirred at room temperature for 18 hrs. The mixture was filtered and the filtrate was concentrated in vacuo. The crude product was purified by silica gel chromatography (230-400 mesh) with 10% EtOAc-hexanes as the eluent to give of product as yellow oil.

$^1$H NMR (500 MHz, CDCl$_3$) δ (ppm): 7.39 (t, J=8.3 Hz, 1H), 6.7 (m, 2H), 3.81 (s, 3H), 3.54 (s, 2H), 2.30 (s, 3H).

Preparative Example 11

Preparation of 1-[(3,4-Dimethoxyphenyl)Thio]Butan-2-One

Following the foregoing procedure, this compound was synthesized by the reaction of 3,4-dimethoxybenzenethiol, 1-bromo-2-butanone and K$_2$CO$_3$ in acetone at room temperature. The reaction mixture was filtered and the filtrate then was partitioned between saturated NaHCO$_3$ and EtOAc, the layers were separated, and the aqueous layer was extracted again with EtOAc. The combined organic layers were dried (MgSO$_4$), filtered, and evaporated in vacuo. The resulting solid was purified by silica gel chromatography (EtOAc/Hexane=1:9) to provide the product.

$^1$H NMR (500 MHz, CDCl$_3$) δ (ppm): 7.00 (dd, 1H), 6.95 (d, 1H), 6.80 (d, 1H), 3.92 (d, 6H), 3.60 (s, 2H), 2.60 (q, 2H), 1.10 (t, 3H).

Utilizing the foregoing procedures, the following compound was prepared:

1-[(2,5-difluoro-3,4-dimethoxyphenyl)thio]butan-2-one $^1$H NMR (500 MHz, CDCl$_3$) δ (ppm): 6.90 (m, 1H), 4.00 (d, 6H), 3.60 (s, 2H), 2.60 (q, 2H), 1.10 (t, 3H).

Preparative Example 12

Preparation of 4-Methoxy-2-Nitro-1-[(Trifluoromethyl)Thio]Benzene

To a solution of commercially available 1-iodo-4-methoxy-2-nitrobenzene (1.75 g, 6.28 mmol) in anhydrous NMP (15 mL) was added trifluoromethylthiocopper (2.1 g, 12.6 mmol). The mixture was heated at 150° C. for 18 hrs, cooled to room temperature, and diluted with EtOAc. The organic phase was washed with cold 2N HCl, dilute aqueous NaHCO$_3$ solution and brine. The separated organic phase was dried with Na$_2$SO$_4$, filtered and evaporated. The resulting crude residue was purified by silica gel chromatography (230-400 mesh) with 10% EtOAc-hexanes as the eluent to give 4-methoxy-2-nitro-1-[(trifluoromethyl)thio]benzene.

$^1$H NMR (500 MHz, CDCl$_3$) δ (ppm): 7.42 (d, J=8.9 Hz, 1H), 7.47 (d, J=2.9 Hz, 1H), 7.18 (dd, J=8.9 Hz, 2.9 Hz, 1H), 3.93 (s, 2H).

Preparative Example 13

Preparation of 4-Methoxy-2-Nitrophenyl Trifluoromethylsulfoxide

To a solution of 4-methoxy-2-nitro-1-[(trifluoromethyl)thio]benzene (1.05 g, 4.15 mmol) in dichloromethane [DCM] (30 mL) was added m-CPBA (1.43 g, 8.3 mmol, 75% technical grade). The mixture was stirred at room temperature for 18 hrs. The mixture was diluted with DCM and washed with 10% aq. Na$_2$S$_2$O$_3$, dilute NaHCO$_3$ solution and brine. The separated organic phase was dried with anhydrous Na$_2$SO$_4$, filtered and evaporated. The resulting residue was purified by silica gel chromatography (230-400 mesh) 25% using EtOAc-hexanes as the eluent to give 4-methoxy-2-nitrophenyl trifluoromethylsulfoxide.

$^1$H NMR (500 MHz, CDCl$_3$) δ (ppm): 8.24 (d, J=8.7 Hz, 1H), 7.89 (d, J=2.5 Hz, 1H), 7.51 (dd, J=8.9 Hz, 2.8 Hz, 1H), 4.03 (s, 3H).

Preparative Example 14

Preparation of 4-Methoxy-2-Nitrophenyl Trifluoromethylsulfone

To a stirred solution of chromium(VI)oxide (20.9 g, 209 mmol) in refluxing acetic acid (225 mL) was added carefully, drop wise over 30 min., a solution of 4-methoxy-2-nitrophenyl trifluoromethylsulfoxide (11.3 g, 41.9 mmol) in acetic acid (25 mL) (CAUTION: reaction may exotherm). The mixture was stirred at 110° C. for 18 hrs. The mixture was cooled to room temperature, diluted with EtOAc, and washed with water and brine. The organic layer was dried with Na$_2$SO$_4$, filtered and evaporated. The resulting residue was purified by silica gel chromatography (230-400 mesh) using 20% EtOAc-hexanes as the eluent to give 4-methoxy-2-nitrophenyl trifluoromethylsulfone.

$^1$H NMR (500 MHz, CDCl$_3$) δ (ppm): 8.12 (d, J=8.7 Hz, 1H), 7.33 (bs, 1H), 7.51 (d, J=9.0 Hz, 1H), 4.04 (s, 3H).

Preparative Example 15

Preparation of 2-Fluoro-4-Methoxyphenyl Trifluoromethylsulfone

To a stirred solution of 4-methoxy-2-nitrophenyl trifluoromethylsulfone (4.5 g, 15.8 mmol) in anhydrous DMSO (200 mL) was added dry KF (1.83 g, 31.6 mmol) and tetraphenylphosphonium bromide (1.65 g, 3.94 mmol). The mixture was stirred at 130° C. for 25 min. The mixture was cooled to room temperature, diluted with EtOAc, and washed with water and brine. The organic layer was dried with Na$_2$SO$_4$, filtered and evaporated. The resulting residue was purified by silica gel chromatography (230-400 mesh) with 15% EtOAc-hexanes as the eluent to give 2-fluoro-4-methoxyphenyl trifluoromethylsulfone.

$^1$H NMR (500 MHz, CDCl$_3$) δ (ppm): 7.86 (t, J=8.1 Hz, 1H), 6.89 (dd, J=2.3 Hz, 1H), 6.78 (dd, J=11.7 Hz, 2.3 Hz, 1H), 3.93 (s, 3H).

Preparative Example 16

Preparation of 2-Fluoro-4-Hydroxyphenyl Trifluoromethylsulfone

A mixture of 2-fluoro-4-methoxyphenyl trifluoromethylsulfone (1.95 g, 7.55 mmol) and pyridine hydrochloride (3.03 g, 26.2 mmol) was combined in a sealed tube and warmed to 160° C. for 3 hrs. The mixture was cooled to room temperature. The resulting solid was dissolved with water and EtOAc with sonication. The organic phase was washed with water and brine. The organic layer was dried with Na$_2$SO$_4$, filtered and evaporated. The resulting residue was purified by silica gel chromatography (230-400 mesh) with 30% EtOAc-hexanes as the eluent to give 2-fluoro-4-hydroxyphenyl trifluoromethylsulfone as a crystalline solid.

$^1$H NMR (500 MHz, CDCl$_3$) δ (ppm): 8.64 (s, 1H), 7.84 (t, J=8.4 Hz, 1H), 6.88 (dd, J=8.9 Hz, 2.3 Hz, 1H), 6.81 (dd, J=11.3 Hz, 2.3 Hz, 1H); $^{19}$F NMR (CDCl$_3$, ppm)-79.6 (ArSO$_2$CF$_3$), −101.9 (ArF).

Preparative Example 17

Preparation of 1-(3-aminopropyl)-4-aza-1-azoniabicyclo[2.2.2]octane trifluoromethanesulfonate A mixture of 1-(3-azidopropyl)-4-aza-1-azoniabicyclo[2.2.2]octane trifluormethanesulfonate (500 mg, 1.6 mmol), prepared according to U.S. Pat. No. 6,399,597B1, and 200 mg of 10% Pd/C in anhydrous MeOH (20 mL) was hydrogenated under a balloon filled with hydrogen gas at room temperature overnight. The reaction mixture was filtered through celite and the celite was washed thrice with MeOH. The filtrate was concentrated and dried to give product which was used as is in the next step.

Preparative Example 18

Preparation of 1-{3-[(2,3-Dimethoxybenzoyl)Amino]Propyl}-4-Aza-1-Azoniabicyclo[2.2.2]Octane Trifluoromethanesulfonate To an stirred solution of 2,3-dimethoxybenzoic acid (0.292 g, 1.6 mmol) in anhydrous DMF (4.8 mL) was added benzotriazole-1-yloxy-tris-(dimethylamino)phosphonium hexafluorophosphate (HATU) (0.608 g, 1.6 mmol) and N,N-diisopropylethylamine (0.557 mL, 3.2 mmol). The mixture was stirred at room temperature for 5 minutes and then 1-(3-aminopropyl)-4-aza-1-azoniabicyclo[2.2.2]octane trifluormethanesulfonate (0.272 g, 1.6 mmol), prepared in the prior Example, was added. The resulting mixture was stirred further overnight and then concentrated in vacuo. The residue was diluted with 5 mL of DMSO/water/acetonitrile (1/2/2) and purified by HPLC using a reversed phase $C_{18}$ column to afford, after lyophilization, 1-{3-[(2,3-dimethoxybenzoyl)amino]propyl}-4-aza-1-azoniabicyclo[2.2.2]octane trifluoromethanesulfonate.
MS m/z 334 (M).

Preparative Example 19

Preparation of 1-{3-[(2,3-Dihydroxybenzoyl)Amino]Propyl}-4-Aza-1-Azoniabicyclo[2.2.2]Octane Trifluoromethanesulfonate To a cold (−78° C.) suspension of 1-{3-[(2,3-dimethoxybenzoyl)amino]propyl}-4-aza-1-azoniabicyclo[2.2.2]octane trifluoromethanesulfonate (65 mg, 0.14 mmol), prepared in the prior Example, in 4 mL of anhydrous dichloromethane (DCM) was added drop wise 1 M $BBr_3$ in DCM (0.87 mL, 0.87 mmol) under nitrogen. The reaction mixture was allowed to warm to room temperature and stirred overnight. The mixture was cooled in a dry ice-acetone bath and quenched with pyridine (0.21 mL, 2.61 mmol). The mixture was concentrated in vacuum. The residue was diluted with 1 mL of DMSO/water/acetonitrile (1/2/2) and purified by HPLC using a reversed phase $C_{18}$ column to afford, after lyophilization, 1-{3-[(2,3-dihydroxybenzoyl)amino]propyl}-4-aza-1-azoniabicyclo[2.2.2]octane trifluoroacetate.
MS m/z 306 (M).

Preparative Example 20

Preparation of 1,1'-propane-1,3-diylbis-4-aza-1-azoniabicyclo[2.2.2]octane bis-triflate To a stirred solution of 1,1'-propane-1,3-diylbis-4-aza-1-azoniabicyclo[2.2.2]octane dibromide (1.12 g, 2.62 mmol), prepared according to N. S. Isaacs, et. al *Tetrahedron*, 1986, 42, 601-607, dissolved in 2 mL of deionized $H_2O$, was added a 2 M aqueous solution of silver triflate (2.62 mL, 5.24 mmol). After stirring for 30 min., the resulting suspension was filtered. The filtrate was lyophilized to give product as a white solid.
MS m/z=134 (M+1)/2.

Preparative Example 21

Preparation of Bis-4-methoxybenzyl(iminodipropane-3,1-diyl)biscarbamate (A) and 4-methoxybenzyl-5-({3-[4-methoxybenzylcarbonyl]amino}pentanoate (B)

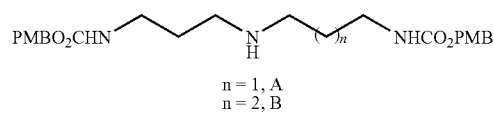

n = 1, A
n = 2, B

The bis para-methoxybenzyl carbamates of N-(3-aminopropyl)propane-1,3-diamine (A) and N-(3-aminopropyl)butane-1,4-diamine (B) were obtained, utilizing the general procedure of Bochet, C. G. *Tetrahedron Letters* 2001, 42, 5227-5229.
A: MS m/z 460 (M+1); B: MS m/z 474 (M+1).

Preparative Example 22

Preparation of 1-Bromo-3,4-Dimethoxy-2-Methylbenzene

To a stirred solution of 1,2-dimethoxy-2-methoxy-3-methylbenzene (4 g, 26.3 mmol) in 35 mL THF at room temperature was added NBS (4.68 g, 26.3 mmol). The reaction mixture was stirred at room temperature overnight. The reaction mixture was partitioned between saturated $NaHCO_3$ and EtOAc, the layers were separated, and the aqueous layer was extracted again with EtOAc. The combined organic layers were dried ($MgSO_4$), filtered, and evaporated in vacuo. The resulting material was purified by silica gel chromatography (30% EtOAc in hexane) to provide the product.
$^1$H NMR (500 MHz, $CDCl_3$) δ (ppm): 7.28 (d, 1H), 6.70 (d, 1H), 3.90 (s, 3H), 3.86 (s, 3H), 2.40 (s, 3H).

Utilizing the foregoing procedure, the following compound was prepared:

1-bromo-4,5-dimethoxy-2-methylbenzene was prepared in 83% yield after purification by silica gel chromatography (30% EtOAc in hexane).
$^1$H NMR (500 MHz, $CDCl_3$) δ (ppm): 7.04 (s, 1H), 6.78 (s, 1H), 3.90 (s, 6H), 2.40 (s, 3H).

Preparative Example 23

Preparation of 3,4-Dimethoxy-2-Methylphenyl Boronic Acid

To a stirred solution of 1-bromo-3,4-dimethoxy-2-methoxy-3-methylbenzene (5 g, 21.6 mmol) in 50 mL THF at −78° C. was added 1.6N n-BuLi (16 mL, 26.0 mmo) drop wise. After addition, the solution was allowed to stir at −78° C. for 10 min. Then, triisopropylborate (6 mL, 26.0 mmol) was added and the mixture was stirred further for 30 min. 2N HCl (50 mL) was added to the reaction mixture and it was stirred at ambient temperature for 4 h. The reaction mixture was partitioned between saturated NaHCO$_3$ and EtOAc, the layers were separated, and the aqueous layer was extracted again with EtOAc. The combined organic layers were dried (MgSO$_4$), filtered, and evaporated in vacuo. The resulting material was purified by silica gel chromatography (40% EtOAc in hexane) to provide the product.

$^1$H NMR (500 MHz, CDCl$_3$) δ (ppm): 8.04 (d, 1H), 6.95 (d, 1H), 4.00 (s, 3H), 3.86 (s, 3H), 2.80 (s, 3H).

Utilizing the foregoing procedure, the following compound was prepared:

4,5-dimethoxy-2-methylphenyl boronic acid was prepared and purified by silica gel chromatography (40% EtOAc in hexane).

$^1$H NMR (500 MHz, CDCl$_3$) δ (ppm): 7.80 (s, 1H), 6.80 (s, 1H), 3.98 (d, 6H), 2.80 (s, 3H).

Preparative Example 24

Preparation of
5-(3,4-Dimethoxyphenyl)Thiophene-2-Sulfonamide

A stirred solution of 5-bromothiophene-2-sulfonamide (2 g, 8.26 mmol) and (3,4-dimethoxyphenyl)boronic acid (1.8 g, 9.90 mmol) in 30 mL DMF at room temperature was purged with N$_2$ gas for 10 mins. To this stirred solution was added (Ph$_3$P)$_4$Pd (1.9 g, 1.65 mmol) and saturated Na$_2$CO$_3$/H$_2$O (2.63 g, 3 mmol). The N$_2$ purge was stopped and the reaction mixture was sealed and heated with a preheated oil bath at 100° C. overnight. The reaction mixture was filtered and the filtrate was partitioned between saturated NaHCO$_3$ and EtOAc, the layers were separated, and the aqueous layer was extracted again with EtOAc. The combined organic layers were dried (MgSO$_4$), filtered, and evaporated in vacuo. The resulting material was purified by silica gel chromatography (40% EtOAc in hexane) to provide the product, as a light yellow solid.

$^1$H NMR (500 MHz, CD$_3$OD) δ (ppm): 7.56 (d, 1H), 7.30 (d, 1H), 7.24 (m, 2H), 7.00 (d, 1H), 3.90 (d, 6H).

Utilizing the foregoing procedure, the following compounds were prepared:

5-(3,4-dimethoxy-2-methylphenyl)thiophene-2-sulfonamide was prepared and purified by silica gel chromatography (40% EtOAc in hexane) to provide the product, as a white solid.

$^1$H NMR (500 MHz, CD$_3$OD) δ (ppm): 7.60 (d, 1H), 7.16 (d, 1H), 7.00 (d, 2H), 7.00 (d, 1H), 6.96 (d, 1H), 3.90 (d, 3H), 3.80 (s, 3H), 2.30 (s, 3H).

5-(4,5-dimethoxy-2-methylphenyl)thiophene-2-sulfonamide was prepared and purified by silica gel chromatography (40% EtOAc in hexane).

$^1$H NMR (500 MHz, CD$_3$OD) δ (ppm): 7.58 (d, 1H), 7.06 (d, 1H), 6.94 (s, 1H), 6.90 (s, 1H), 3.82 (d, 6H), 2.40 (s, 3H).

Preparative Example 25

Preparation of 5-(4-Hydroxyphenyl)-1,3,4-Thiadiazole-2-Sulfonamide

To a stirred solution of thiadiazole derivative (1.2 g, 4.5 mmol) in dichloromethane was added drop wise BBr$_3$ (18 mL, 4 equiv). The resulting mixture was heated at reflux under nitrogen for 2 h and then cooled to room temperature. The organic layer was washed with water, dried over magnesium sulfate, and concentrated. The desired product was purified by silica gel chromatography to afford the product.

$^1$H NMR (400 MHz, CD$_3$OD) δ (ppm): 7.9 (d, 2H), 6.9 (d, 2H); MS m/z 258 (M+1).

Utilizing the foregoing procedure the following compounds were prepared:

5-(4,5-dihydroxy-2-methylphenyl)thiophene-2-sulfonamide was prepared and used as is in the next step.

$^1$H NMR (500 MHz, CD$_3$OD) δ (ppm): 7.60 (d, 1H), 6.96 (d, 1H), 6.82 (s, 1H), 6.70 (d, 1H), 2.26 (s, 3H).

5-(3,4-dihydroxy-2-methylphenyl)thiophene-2-sulfonamide was prepared and used as is for next step.

$^1$H NMR (500 MHz, CD$_3$OD) δ (ppm): 7.60 (d, 1H), 6.96 (d, 1H), 6.80 (s, 1H), 6.70 (d, 1H), 2.24 (s, 3H).

Preparative Example 26

N-[(1E)-(Dimethylamino)Methylene]-5-(4-Hydroxyphenyl)-1,3,4-Thiadiazole-2-Sulfonamide A solution of the sulfonamide product of the prior Example (4.6 g, 18 mmol) and DMF-dimethylacetal (3 mL, 1.2 equiv) in anhydrous DMF (50 mL) was stirred at room temperature and then let stand overnight. The mixture was diluted with ethyl acetate and washed twice with water. The organic extract was dried with magnesium sulfate and evaporated to give a white solid product.

$^1$H NMR (400 MHz, CD$_3$OD) δ (ppm): 8.35 (s, 1H), 7.9 (d, 2H), 6.95 (d, 2H), 3.3 (s, 3H), 3.1 (s, 3H); MS m/z 313 (M+1).

Utilizing this procedure, the following compounds were prepared:

N-[(dimethylamino)methylene]-5-[4-(2-hydroxyethoxy)phenyl]-1,3,4-thiadiazole-2-sulfonamide was prepared.

$^1$H NMR (500 MHz, CDCl$_3$) δ (ppm): 8.38 (s, 1H), 8.00 (d, 2H), 7.15 (d, 2H), 4.20 (t, 2H), 3.94 (t, 2H), 3.35 (s, 6H); MS m/z 357 (M+1).

N-[(dimethylamino)methylene]-5-(3,4-dihydroxyphenyl)-thiophene-2-sulfonamide was prepared and used as is for next step.

$^1$H NMR (500 MHz, CD$_3$OD) δ (ppm): 8.20 (s, 1H), 7.44 (d, 1H), 7.32 (d, 1H), 7.08 (s, 1H), 7.00 (dd, 1H), 6.80 (d, 1H), 3.20 (s, 3H), 2.82 (s, 3H).

N-[(dimethylamino)methylene]-5-(3,4-dihydroxy-2-methylphenyl)thiophene-2-sulfonamide was prepared and used as is for next step.

$^1$H NMR (500 MHz, CD$_3$OD) δ (ppm): 8.20 (s, 1H), 7.50 (d, 1H), 6.92 (d, 1H), 6.72 (d, 1H), 6.70 (d, 1H), 3.20 (s, 3H), 3.10 (s, 3H), 2.22 (s, 3H).

N-[(dimethylamino)methylene]-5-(4,5-dihydroxy-2-methylphenyl)thiophene-2-sulfonamide was prepared and used as is in the next step.

$^1$H NMR (500 MHz, CD$_3$OD) δ (ppm): 8.20 (s, 1H), 7.50 (d, 1H), 6.96 (d, 1H), 6.82 (s, 1H), 6.70 (s, 1H), 3.20 (s, 3H), 3.06 (s, 3H), 2.22 (s, 3H); MS m/z 341 (M+1).

Preparative Example 27

5-[4-(3-Chloropropoxy)Phenyl]-N-[(1E)-(Dimethylamino)Methylene]-1,3,4-Thiadiazole-2-Sulfonamide A mixture of the products of the prior Example (2.6 g, 8.3 mmol), Cs$_2$CO$_3$ (8.1 g, 3 equiv), and 1,3-bromochloropropane (2.8 mL, 4 equiv) in DMF was stirred at room temperature for 16 h. The white inorganic solid was filtered off and washed with EtOAc. The filtrate was washed with water, and dried over magnesium sulfate. Removal of the solvents gave the crude product as an oil.

¹H NMR (400 MHz, CDCl₃) δ (ppm): 8.4 (s, 1H), 7.95 (d, 2H), 7.0 (d, 2H), 4.2 (t, 2H), 3.8 (t, 2H), 3.3 (s, 3H), 3.2 (s, 3H), 2.3 (m, 2H); MS m/z 389 (M+1).

Utilizing the foregoing procedure, the following compounds were prepared:

5-[3,4-bis(3-chloropropoxy)phenyl]-N-[(1E)-(dimethylamino)methylene]thiophene-2-sulfonamide was prepared and used as is for next step.

¹H NMR (500 MHz, CD₃OD) δ (ppm): 8.20 (s, 1H), 7.50 (d, 1H), 7.24 (m, 3H), 7.04 (d, 1H), 4.20 (m, 4H), 3.80 (m, 4H), 3.20 (s, 3H), 3.04 (s, 3H), 2.26 (m, 4H); MS m/z 479 (M⁺).

5-[3,4-bis(3-chloropropoxy)-2-methylphenyl]-N-[(1E)-(dimethylamino)methylene]thiophene-2-sulfonamide was prepared and used as is for next step.

¹H NMR (500 MHz, CD₃OD) δ (ppm): 8.20 (s, 1H), 7.50 (d, 1H), 7.10 (d, 1H), 7.00 (d, 1H), 6.98 (d, 1H), 4.20 (t, 2H), 4.10 (t, 2H), 3.84 (m, 4H), 3.20 (s, 3H), 3.04 (s, 3H), 2.26 (m, 7H).

5-[4,5-bis(3-chloropropoxy)-2-methylphenyl]-N-[(1E)-(dimethylamino)methylene]thiophene-2-sulfonamide was prepared and used as is for next step.

¹H NMR (500 MHz, CD₃OD) δ (ppm): 8.20 (s, 1H), 7.52 (d, 1H), 7.06 (d, 1H), 7.00 (s, 1H), 6.98 (s, 1H), 4.22 (t, 2H), 4.14 (t, 2H), 3.80 (m, 4H), 3.36 (s, 6H), 2.26 (m, 7H).

Preparative Example 28

5-[4-(3-Chloropropoxy)Phenyl]-1,3,4-Thiadiazole-2-Sulfonamide

To a stirred solution of the crude formamidine, prepared in the prior Example, in acetone was added excess of NH₄OH (20%) at room temperature. The resulting mixture was left an additional 10 minutes and the volatiles were evaporated. The residue was dissolved in ethyl acetate, and the organic layer was washed with water, dried and concentrated to give the while solid product.

¹H NMR (400 MHz, acetone-d₆) δ (ppm): 8.05 (d, 2H), 7.2 (d, 2H), 4.3 (t, 2H), 3.9 (t, 2H), 2.3 (m, 2H); MS m/z 334 (M+1).

Utilizing the foregoing procedure, the following compounds were prepared:

5-[4-(2-chloroethoxy)phenyl]-1,3,4-thiadiazole-2-sulfonamide was prepared.

¹H NMR (500 MHz, CD₃OD) δ (ppm): 8.00 (d, 2H), 7.18 (d, 2H), 4.40 (t, 2H), 3.90 (t, 2H); MS m/z 320 (M+1).

5-[3,4-bis(3-chloropropoxy)phenyl]thiophene-2-sulfonamide was prepared and used as is for next step.

¹H NMR (500 MHz, CD₃OD) δ (ppm): 7.68 (d, 1H), 7.08 (d, 1H), 7.04 (m, 2H), 7.00 (d, 1H), 4.20 (m, 4H), 3.80 (m, 4H), 2.22 (m, 4H); MS m/z 424 (M⁺).

5-[3,4-bis(3-chloropropoxy)-2-methylphenyl]thiophene-2-sulfonamide was prepared and used as is for next step. ¹H NMR (500 MHz, CD₃OD) δ (ppm): 7.58 (d, 1H), 7.10 (d, 1H), 6.98 (d, 1H), 6.94 (d, 1H), 4.20 (t, 2H), 4.10 (t, 2H), 3.80 (m, 4H), 2.22 (m, 4H), 2.20 (s, 3H). 5-[4,5-bis(3-chloropropoxy)-2-methylphenyl]thiophene-2-sulfonamide was prepared and used as is for next step.

¹H NMR (500 MHz, CD₃OD) δ (ppm): 7.58 (d, 1H), 7.00 (d, 1H), 6.98 (s, 1H), 6.92 (s, 1H), 4.20 (t, 2H), 4.10 (t, 2H), 3.80 (m, 4H), 2.34 (s, 3H), 2.22 (m, 4H).

Preparative Example 29

Methyl {-4-[5-({[(1E)-(Dimethylamino)Methylene]-Amino}Sulfonyl)-1,3,4-Thiadiazol-2-Yl]Phenoxy}Acetate A mixture of the N-[(1E)-(dimethylamino)methylene]-5-(4-hydroxyphenyl)-1,3,4-thiadiazole-2-sulfonamide (1.72 g, 5.5 mmol), generated in Preparative Example 26, methylbromoacetate (574 uL, 6.1 mmol) and K₂CO₃ in acetone was heated to reflux under N₂ for 3 h. The reaction was monitored by LC-MS. The reaction mixture was cooled to room temperature and filtered through celite. The filtrate was concentrated in vacuo to give product which was used as is in the next step.

¹H NMR (500 MHz, CDCl₃) δ (ppm): 8.40 (s, 1H), 7.96 (d, 2H), 7.00 (d, 2H), 4.75 (s, 2H), 3.84 (s, 3H), 2.24 (s, 3H), 3.18 (s, 3H); MS m/z 385 (M+1).

Preparative Example 30

5-[4-(2-Hydroxyethoxy)Phenyl]1,3,4-Thiadiazole-2-Sulfonamide

To a solution of above material (1.4 g, 3.6 mmol) in 50 mL THF at 0° C. was added 5 mL of MeOH and NaBH₄ (688 mg, 18.2 mmol). The reaction was allowed to stir at room temperature for 6 h and monitored by LC-MS. The reaction mixture was partitioned between 2N HCl and EtOAc, the layers were separated, and the aqueous layer was extracted again with EtOAc. The combined organic layers were washed with H₂O, brine and dried (MgSO₄), filtered, and evaporated in vacuo. The resulting solid was washed by Et₂O and dried in vacuo.

¹H NMR (500 MHz, CDCl₃) δ (ppm): 8.00 (d, 2H), 7.15 (d, 2H), 4.18 (t, 2H), 3.94 (t, 2H); MS m/z 302 (M+1).

Preparative Example 31

5-[4-(2-Chloroethoxy)Phenyl]-N-[(Dimethylamino)Methylene]-1,3,4-Thiadiazole-2-Sulfonamide To a solution of the material (700 mg, 1.97 mmol), prepared in Preparative Example 23, in 20 mL benzene at room temperature was added SOCl₂ (286 uL, 3.94 mmol) and pyridine (319 uL, 3.97 mmol). The reaction was refluxed for 1 h and monitored by LC-MS. The reaction mixture was partitioned between 2N HCl and EtOAc, the layers were separated, and the aqueous layer was extracted again with EtOAc. The combined organic layers were washed with H₂O, brine and dried (MgSO₄), filtered, and evaporated in vacuo to give product in.

¹H NMR (500 MHz, CD₃OD) δ (ppm): 8.38 (s, 1H), 8.00 (d, 2H), 7.15 (d, 2H), 4.38 (t, 2H), 3.90 (t, 2H), 3.35 (s, 6H); MS m/z 375 (M+1).

Preparative Example 32

3,4-Bis(3-Chloropropoxy)Benzenamine

To a stirred solution of 4-nitrobenzene-1,2-diol (14.1 g, 91.0 mmol) in acetone (200 mL) at room temperature was successively added 1-bromo-3-chloropropane (26.86 mL, 273 mmol), K₂CO₃ (37.73 g, 273 mmol) and KI (3.02 g, 18.2 mmol). The reaction mixture was heated to reflux overnight under N₂ and then cooled to rt. The reaction mixture was filtered and the filtrate was concentrated. The residue was dissolved in EtOAc (300 mL) and then the resulting solution was washed with water (80 mL×2) and brine (150 mL). The organic phase was dried over $Na_2SO_4$ and filtered. The filtrate was concentrated and the residue was purified by flash column chromatography (eluent EtOAc/hexanes: from 10:90 to 20:80) to produce an amorphous brownish material.

MS m/z 308 (M+1).

This material was dissolved in AcOH (150 mL) and iron powder (23.4 g, 428.3 mmol) was added. The resulting reaction mixture was stirred at rt overnight under $N_2$ and filtered through a celite pad. The filtrate was concentrated, the residue was diluted with water (100 mL) and made alkaline with a solution of NaOH (50%) to pH=10. The resulting basic solution was extracted with EtOAc (200 mL×3); the combined extracts were washed with water (80 mL) and brine (150 mL). The organic phase was dried over $Na_2SO_4$ and then filtered. The filtrate was concentrated to dryness and the residue was purified by flash column chromatography (eluent EtOAc/hexanes, 30:70) to afford the title compound as pale brown oil. MS m/z 278 (M+1).

Preparative Example 33

Dimethyl 2,2'-(4-Nitro-1,2-Phenylene)Bis(Oxy)Diacetate

To a stirred suspension of 4-nitrocatechol (1.10 g, 7.09 mmol) and potassium carbonate (4.0 g, 29 mmol) in acetone (100 mL) was added methyl bromoacetate (1.3 mL, 2.1 g, 14 mmol,). The mixture was heated to reflux for 3 h, then cooled and concentrated under reduced pressure. The residue was partitioned between water and ethyl acetate, and the combined organic extracts were washed with aqueous sodium hydroxide (1M), saturated ammonium chloride, and brine, dried over magnesium sulfate, and concentrated. The residue was triturated with 1:1 ethyl acetate/hexanes to provide the product as a colorless solid.

$^1$H NMR (400 MHz, DMSO-$d_6$) δ (ppm): 7.88 (dd, J=9.0, 2.7, 1H); 7.74 (d, J=2.7, 1H); 7.14 (d, J=9.0, 1H); 5.02 (s, 2H); 5.00 (s, 2H); 3.70 (s, 3H); 3.69 (s, 3H).

Preparative Example 34

3,4-Bis(2-Chloroethoxy)Aniline

To a stirred suspension of the product from the prior example (7.68 g, 25.7 mmol,) and sodium borohydride (1.15 g, 30.4 mmol) in THF (300 mL) was added methanol (5.0 mL) and the resulting mixture was stirred for 2 h. It was then concentrated, partitioned between ethyl acetate and water, and the combined organic extracts were washed with water, brine, dried over magnesium sulfate, and concentrated. The resulting crude diol was suspended in toluene (100 mL) and pyridine (5 mL), and heated to reflux. Thionyl chloride (5 mL) was then added dropwise, and the suspension was heated under reflux for 1 hour. The toluene was then removed under reduced pressure, the residue was partitioned between ether and water, and the combined organic extracts were washed with water, dried over magnesium sulfate, and concentrated. To this crude dichloride in methanol (200 mL) was added palladium on activated carbon (10%, 0.50 g), and this was stirred under an atmosphere of $H_2$ for 6 h. The mixture was then filtered through celite, concentrated under reduced pressure, and purified by column chromatography (55% ethyl acetate/hexanes) to yield the product as an off-white, crystalline solid.

$^1$H NMR (400 MHz, DMSO-$d_6$) δ (ppm): 6.69 (d, J=8.4, 1H); 6.25 (d, J=2.5, 1H); 6.08 (dd, J=8.4, 2.5, 1H); 4.80 (br s, 2H); 4.14-4.11 (m, 2H); 4.07-4.04 (m, 2H); 3.91-3.87 (m, 2H); 3.81-3.77 (m, 2H);

Preparative Example 35

5,6-Bis(2-Chloroethoxy)Benzo[D]Thiazol-2-Amine

To a suspension of lead thiocyanate (6.6 g, 20.4 mmol) in acetic acid (40 mL) was added bromine (1.2 mL, 3.7 g, 23.4 mmol) dropwise, and the mixture was stirred until the orange color has almost completely faded (10 min). This solution was then filtered into the product of the prior example (3.35 g, 13.5 mmol) in acetic acid (30 mL); the mixture was stirred for 30 min, and then concentrated under reduced pressure. The solid was suspended in ethyl acetate and filtered over suction. The resulting solid was suspended in saturated sodium bicarbonate and extracted repeatedly with ethyl acetate. The combined organic extracts were washed with brine, dried over magnesium sulfate, and concentrated. Column chromatography (ethyl acetate) afforded the product. MS m/z 307 (M).

Utilizing the foregoing procedure, the following compound was prepared:

5,6-Bis(3-chloropropoxy)benzo[d]thiazol-2-amine. Prepared 6.5 g (100% yield), as a pale yellow solid.

MS m/z 335 (M+1).

Preparative Example 36

5,6-Bis(2-Chloroethoxy)Benzo[D]Thiazole 5,6-Bis(2-chloroethoxy)benzo[d]thiazol-2-amine (2.00 g, 6.51 mmol) was stirred in 85% phosphoric acid (50 mL) overnight to partially dissolve. It was then cooled to 0° C., and sodium nitrite (0.60 g, 8.7 mmol) in water (5 mL) was added, and the mixture was stirred for 10 min. This was then poured into hypophosphorous acid (100 mL) at r.t. and left to stand for 18 h. It was then diluted with water and extracted multiple times with ethyl acetate. The combined organic layers were filtered through a short plug of silica (to remove insoluble solids) and concentrated, and the resulting solid was triturated with 1:1 ethyl acetate/hexanes to provide the product as a solid.

$^1$H NMR (400 MHz, $CD_3OD$) δ (ppm): 9.14 (s, 1H); 7.67 (s, 1H); 7.63 (s, 1H); 4.39-4.34 (m, 4H); 3.94-3.90 (m, 4H).

Utilizing the foregoing procedure, the following compound was prepared:

5,6-Bis(3-chloropropoxy)benzo[d]thiazole

The product was purified by flash chromatography on silica gel using 5% EtOAc/DCM as an eluent, followed by trituration with diethyl ether to afford product as a pale yellow solid.

MS m/z 320 (M+1).

Preparative Example 37

5,6-Bis(2-Chloroethoxy)Benzo[D]Thiazole-2-Thiol

To 5,6-bis(2-chloroethoxy)benzo[d]thiazole (2.4 g, 8.2 mmol) in THF (100 mL) was added n-butyllithium (2.5 M in hexanes, 4.1 mL, 10.3 mmol) dropwise, at −78° C. The mixture was stirred for 30 min, then sulfur (1.25 g, 39.0 mmol) suspended in THF (5 mL) was added, and the mixture was stirred for a further 30 min at −78° C. The reaction was quenched with ~1 mL saturated ammonium chloride and concentrated under reduced pressure. The residue was partitioned between aqueous sodium hydroxide (1M) and ethyl acetate, and the combined aqueous layers were acidified with hydrochloric acid (1M), extracted with ethyl acetate, washed with aqueous ammonium chloride, dried over magnesium sulfate, and concentrated. The crude product was triturated with 1:1 dichloromethane/hexanes to provide the product as a colorless solid.

$^1$H NMR (400 MHz, DMSO-d$_6$) δ (ppm): 13.59 (br s, 1H); 7.42 (s, 1H); 6.88 (s, 1H); 4.27-4.21 (m, 4H); 4.00-3.90 (m, 4H).

Utilizing the foregoing procedure, the following compound was prepared:

5,6-Bis(3-chloropropoxy)benzo[d]thiazole-2-thiol

The product was purified by flash column chromatography using 40% EtOAc/DCM as an eluent to produce product as a pale yellow solid.

$^1$H NMR (400 MHz, DMSO-d$_6$) δ (ppm): 13.60 (bs, 1H), 7.40 (s, 1H), 6.86 (s, 1H), 4.06 (q, J=5.9 Hz, 4H), 3.78 (q, J=6.5 Hz, 4H), 2.16 (m, 4H); MS m/z 350 (M−1]).

Preparative Example 38

Diethyl (5,6-Bis(2-Chloroethoxy)Benzo[D]Thiazol-2-Ylthioamino)-Methylphosphonate To 5,6-bis(2-chloroethoxy)benzo[d]thiazole-2-thiol (1.10 g, 3.39 mmol) in DME (10 mL) was added aqueous sodium hydroxide (1.25 M, 5.4 mL, 6.8 mmol) and the mixture was diluted to 25 mL with water. Sodium hypochlorite (12% solution, 2.4 mL, 0.29 g, 3.9 mmol) was diluted with water (25 mL). These two solutions were added simultaneously, dropwise, to a stirred solution of diethyl aminomethylphosphonate oxalate (2.10 g, 8.17 mmol) and aqueous sodium hydroxide (1.25 M, 6.6 mL, 8.2 mmol) in DME (10 mL), at 0° C., over ~10 min. The mixture was stirred for 10 min, and then the DME was removed under reduced pressure. The residue was partitioned between water and ethyl acetate, and the combined organic extracts were washed with saturated ammonium chloride and brine, dried over magnesium sulfate, and concentrated. Column chromatography (ethyl acetate) provided the product.

$^1$H NMR (400 MHz, CD$_3$OD) δ (ppm): 7.56 (s, 1H); 7.38 (s, 1H); 4.35-4.31 (m, 4H); 4.19 (quint, J=6.9, 4H); 3.92-3.87 (m, 4H); 3.56 (d, J=10.4, 2H); 1.35 (t, J=7.0, 6H).

Utilizing the foregoing procedure, the following compound was prepared:

diethyl (5,6-bis(3-chloropropoxy)benzo[d]thiazol-2-ylthioamino)methylphosphonate The product was purified by flash chromatography on silica gel (eluent 75% EtOAc/hexanes to 100% EtOAc) to give product, as a pale brownish yellow oil.

MS m/z 517 (M+1).

Preparative Example 39

General Preparation of Benzothiophenes

Method A. 3-Methyl-5-Methoxy-1-Benzothiophene

To a stirred, freshly prepared solution of 4-methoxybenzenethiol (10 mL, 81.1 mmol) in 200 mL acetone at room temperature was bubbled in nitrogen gas for 10 mins. To this stirred solution was added K$_2$CO$_3$ (11 g, 81.1 mmol) and chloroacetone (6.8 mL, 85.2 mmol). The nitrogen bubbling was stopped and the reaction mixture was stirred overnight at room temperature. The reaction mixture was filtered and the filtrate was partitioned between saturated aqueous NaHCO$_3$ solution and EtOAc. The layers were separated and the aqueous layer was extracted again with EtOAc. The combined organic layers were dried over MgSO$_4$, filtered, and the filtrate evaporated in vacuo. The resulting solid was dissolved in toluene and slowly added to the mixture of PPA (15 g) and toluene at 125° C. in a two-neck round bottom flask fitted with a condenser. The reaction mixture was refluxed overnight and then partitioned between saturated aqueous NaHCO$_3$ solution and EtOAc. The layers were separated and the aqueous layer was extracted again with EtOAc. The combined organic layers were dried (MgSO$_4$), filtered, and evaporated in vacuo. After evaporation of the solvent, the residue was purified by silica gel chromatography (EtOAc/Hexane (1:9) to provide the product as a solid.

$^1$H NMR (400 MHz, CDCl$_3$) δ (ppm): 7.80 (d, 1H), 7.2 (d, 1H), 7.16 (s, 1H), 7.08 (dd, 1H), 3.95 (s, 3H), 2.45 (s, 3H).

Utilizing the foregoing procedure, the following compound was prepared:

7-chloro-5-methoxy-3-methyl-1-benzothiophene was prepared starting with 2-chloro-4-methoxybenzenethiol $^1$H NMR (400 MHz, CDCl$_3$) δ (ppm): 7.15 (s, 1H), 7.08 (s, 1H), 7.05 (s, 1H), 3.90 (s, 3H), 2.40 (s, 3H).

Method B.
3-Methyl-5-Methoxy-7-Fluoro-1-Benzothiophene

A mixture of 1-[(2-fluoro-4-methoxyphenyl)thio]acetone (6.3 g, 29.4 mmol), prepared in Preparative Example 10, anhydrous chlorobenzene (150 mL) and polyphosphoric acid (30.8 g) was vigorously stirred under reflux at 140° C. for 20 min. The mixture was cooled to room temperature and the separated chlorobenzene layer was carefully decanted. The chlorobenzene layer was evaporated and the resulting residue was purified using silica gel chromatography (230-400 mesh) with 5% EtOAc-hexanes to give 7-fluoro-5-methoxy-3-methyl-1-benzothiophene as a colorless oil.

$^1$H NMR (500 MHz, CDCl$_3$) δ (ppm): 7.13 (s, 1H), 6.99 (d, J=2.3 Hz, 1H), 6.78 (dd, J=11.2 Hz, 2.3 Hz, 1H), 3.94 (s, 3H), 2.45 (d, J=1.2 Hz, 1H).

Method C.
Methyl-5-Methoxy-1-Benzothiophen-2-Carboxylate

To a stirred solution of the 2-fluoro-5-methoxybenzaldehyde (10 g, 64.8 mmol) in anhydrous DMSO (300 mL) at room temperature was added methylthioglycolate (13.8 g, 106.1 mmol), followed by triethylamine (45 mL, 324.4 mmol). The solution was warmed to 70° C. and stirred for 16 hrs. The cooled solution was diluted with EtOAc and sequentially washed with cold aqueous 2N HCl, deionized water, saturated aqueous NaHCO$_3$ solution and brine. The separated organic layer was dried over anhydrous Na$_2$SO$_4$, filtered and evaporated. The crude residue was crystallized from ethanol (100 mL) to give product.

$^1$H NMR (500 MHz, CDCl$_3$) δ (ppm): 8.03 (s, 1H), 7.76 (d, J=8.7 Hz, 1H), 7.32 (d, J=2.3 Hz, 1H), 7.16 (dd, J=2.5 Hz, 1H), 3.99 (s, 3H), 3.93 (s, 3H).

Method D. Preparation of
5-Methyl-1-Benzothiophene

A 1 L three-necked round-bottom flask equipped with a reflux condenser, a mechanical stirrer and an addition funnel was charged with polyphosphoric acid (34 g) and anhydrous toluene (105 mL). The mixture was stirred vigorously at 100° C. and a solution of 1-[(2,2-diethoxyethyl)thio]-4-methylbenzene (15 g, 62.4 mmol), prepared in Preparative Example 1, in anhydrous toluene (30 mL) was added drop wise over a 1 h period. The mixture was stirred at 125° C.-130° C. for 18 hours then it was cooled down to room temperature, poured into ice-water and stirring was continued for 30 min. The mixture was filtered through a celite pad, rinsed with ethyl acetate and water, transferred to a separatory funnel and the phases were separated. The organic phase was concentrated. Purification by flash chromatography on silica gel (100% hexane) afforded the product as an off-white solid.

$^1$H NMR (400 MHz, CDCl$_3$) δ (ppm): 7.76 (d, J=8.0 Hz, 1H), 7.62 (s, 1H), 7.40 (d, J=5.6 Hz, 1H), 7.26 (d, J=5.6 Hz, 1H), 7.18 (d, J=8.0 Hz, 1H), 2.49 (s, 3H).

Method E. Preparation of 7-Chloro-5-Methoxy-1-Benzothiophene

A mixture of 2-chloro-1-[(2,2-diethoxyethyl)thio]-4-methoxybenzene (22.7 g, 78.2 mmol) and PPA (100.8 g) in anhydrous toluene (250 mL) was vigorously stirred at reflux (110° C.) for 45 min. The mixture was cooled to 70° C. and water (200 mL) was carefully added over 10 min. After 2 hrs, the mixture was diluted with EtOAc and washed with water and brine. The organic layer was dried with Na$_2$SO$_4$, filtered and evaporated. The resulting residue was purified by silica gel chromatography (230-400 mesh) using 5% EtOAc-hexanes as the eluent to give 7-chloro-5-methoxy-1-benzothiophene.

$^1$H NMR (500 MHz, CDCl$_3$) δ (ppm): 7.52 (d, J=5.5 Hz, 1H), 7.32 (d, J=5.5 Hz, 1H), 7.24 (d, J=2.3 Hz, 1H), 7.08 (d, J=2.3 Hz, 1H), 3.91 (s, 3H).

Utilizing the foregoing procedure, the following compounds were prepared:

3-ethyl-5,6-dimethoxy-1-benzothiophene

Purified by silica gel chromatography (EtOAc/Hexane=1: 9).

$^1$H NMR (500 MHz, CDCl$_3$) δ (ppm): 7.30 (s, 1H), 7.20 (s, 1H), 7.00 (s, 1H), 4.00 (d, 6H), 2.85 (q, 2H), 1.40 (t, 3H).

4,7-Difluoro-5,6-dimethoxy-1-benzothiophene was prepared $^1$H NMR (400 MHz, CDCl$_3$) δ (ppm): 7.4 (m, 2H), 4.05 (s, 3H), 4.01 (s, 3H); MS m/z 231 (M+1).

4,7-Difluoro-5,6-dimethoxy-3-ethyl-1-benzothiophene

Purified by silica gel chromatography (EtOAc/Hexane=1: 9).

$^1$H NMR (500 MHz, CDCl$_3$) δ (ppm): 7.00 (s, 1H), 4.05 (d, 6H), 2.95 (q, 2H), 1.36 (t, 3H).

Method F. Preparation of 4,7-Dichloro-5-Methyl-1-Benzothiophene

A 3 L three-necked round-bottom flask equipped with a reflux condenser, a mechanical stirrer and an addition funnel was charged with polyphosphoric acid (30 g) and anhydrous chlorobenzene (1 L). The mixture was stirred vigorously at 100° C. and a solution of crude product, prepared in Preparative Example 9, (6.1 g) in anhydrous chlorobenzene (30 mL) was added dropwise. The mixture was stirred at 120° C. for 18 hours then it was cooled down to room temperature and stirring was stopped. The chlorobenzene layer was decanted from the black phosphoric acid residue and concentrated. Purification by flash chromatography on silica gel (100% hexane) afforded the title compound as an off-white solid.

$^1$H NMR (400 MHz, DMSO-d$_6$) δ (ppm): 7.98 (dd, J=5.6, 0.6 Hz, 1H), 7.54 (d, J=0.6 Hz, 1H), 7.53 (d, J=5.6 Hz, 1H), 2.46 (s, 3H).

Preparative Example 40

General Preparation of Benzothiophenes

Step A. 5-Methoxy-1-Benzothiophene-2-Carboxylic Acid

A stirred solution of methyl-5-methoxy-1-benzothiophene-2-carboxylate (1.87 g, 8.42 mmol) in 2:1 THF-H$_2$O was treated with 5N aqueous NaOH (4 mL, 20 mmol) at 0° C. The solution was warmed to room temperature and stirred for 2 hrs. The solution was diluted with EtOAc and deionized H$_2$O (V/V, 150 mL each) and the separated aqueous phase was acidified to pH 2.0 with 2N aqueous HCl to form a white solid. The solid was collected and rinsed with water (20 mL) and dried to give product.

$^1$H NMR (500 MHz, d$_6$-acetone) δ (ppm): 8.08 (s, 1H), 7.91 (d, J=9.1 Hz, 1H), 7.54 (d, J=2.3 Hz, 1H), 7.20 (dd, J=2.5 Hz, 1H), 3.91 (s, 3H).

Utilizing the above procedure, that of Preparative Example 29, Method B, and that of Shirley, I. M. *Journal of Fluorine Chemistry,* 1994, 66, 51, the following compound was prepared from 2,6-difluoro-4-methoxybenzaldehyde:

4-fluoro-6-methoxy-1-benzothiophene-2-carboxylic acid $^1$H NMR (CD$_3$OD) δ (ppm): 7.99 (s, 1H), 7.37 (s, 1H), 6.86 (d, J=11.4 Hz, 1H), 3.93 (s, 3H).

Step B. Preparation of 5-Methoxy-1-Benzothiophene

To a stirred solution of 5-methoxy-1-benzothiophene-2-carboxylic acid (1.72 g, 8.26 mmol) in anhydrous quinoline (20 mL) at room temperature was added copper powder (920 mg, 14.4 mmol). The resulting suspension was stirred vigorously at 190° C. for 1.5 hrs. The solution was cooled to room temperature and diluted with EtOAc. The separated organic layer was sequentially washed with cold 2N aqueous HCl, water, saturated aqueous NaHCO$_3$ solution and brine. The organic layer was dried over anhydrous Na$_2$SO$_4$, filtered and evaporated in vacuo. The crude residue was purified by silica gel chromatography, using 20% EtOAc-hexanes as the eluent to give 5-methoxy-1-benzothiophene.

$^1$H NMR (500 MHz, CDCl$_3$) δ (ppm): 7.76 (d, J=8.7 Hz, 1H), 7.47 (d, J=5.5 Hz, 1H), 7.31 (d, J=2.5 Hz, 1H), 7.29 (d, J=5.5 Hz, 1H), 7.04 (dd, J=2.5 Hz, 1H), 3.91 (s, 3H).

Utilizing the above procedure the following compound was prepared:

4,5,7-trifluoro-6-methoxy-1-benzothiophene

It was prepared from the known compound, 4,5,7-trifluoro-6-methoxy-1-benzothiophene-2-carboxylic acid (Siemensmeyer, Karl; Thiemann, Thies; Tashiro, Masashi; Mataka, Shuntaro; Tsuzuki, Hirihisa; Mukumoto, Mamoru; Vill, Volkmar; Gesekus, Gunnar. Ger. Offen. (1998).

$^1$H NMR (CDCl$_3$) δ (ppm): 7.46 (m, 2H), 4.13 (s, 3H).

Step B. Preparation of 4-Fluoro-6-Methoxy-1-Benzothiophene

A mixture of 9.2 g 4-fluoro-6-methoxy-1-benzothiophene-2-carboxylic acid, 9 g of Cu powder and 50 mL of quinoline was heated at 170° C. for 1 h and at 190° C. for 2.5 h. TLC showed little reaction. To the cooled reaction mixture was added 9 g Cu$_2$O powder and 3 g of 2,2'-bipyridyl. The resulting mixture was heated at 180° C. for 1.5 h. The reaction mixture was cooled, and partitioned between EtOAc and ice cold 2N HCl. The insolubles were filtered off through a preformed pad of Celite. The organic layer was separated. The aqueous layer was extracted again with 1:1 hexane-EtOAc. Silica gel flash chromatography gave product.

$^1$H NMR (CDCl$_3$) δ (ppm): 7.36 (d, J=5.5 Hz, 1H), 7.27 (d, 1H), 7.16 (d, J=1.8 Hz, 1H), 6.73 (dd, J=11.4 Hz, 1.4 Hz, 1H), 3.89 (s, 3H).

Preparative Example 41

Method A. 3-Methyl-5-Hydroxybenzothiophene

A mixture of the 3-methyl-5-methoxybenzothiophene (6.5 g, 36.1 mmol), generated in Preparative Example 29, Method A, and pyridine-HCl (10.5 g, 90.25 mmol) was heated to 190° C. under N$_2$ for 3 h. The reaction was monitored by examining worked-up aliquots of the reaction mixture by thin-layer chromatography (TLC) with 20% EtOAc/hexane as eluant. The reaction was cooled in an ice bath and ice-H$_2$O was added. The resulting mixture was extracted with EtOAc. The organic extract was washed with 2 N HCl and brine, dried over MgSO$_4$, filtered, and the filtrate concentrated in vacuo. The resulting residue was purified by silica gel chromatography with 20% EtOAc/hexane as the eluant to afford the desired product.

$^1$H NMR (500 MHz, CDCl$_3$) δ (ppm): 7.60 (d, 1H), 7.12 (s, 1H), 7.10 (d, 1H), 6.85 (dd, 1H), 2.35 (s, 3H).

Utilizing the foregoing procedure, the following compound was prepared:

7-Chloro-5-hydroxy-3-methyl-1-benzothiophene.

$^1$H NMR (400 MHz, CDCl$_3$) δ (ppm): 7.18 (s, 1H), 7.10 (s, 1H), 7.02 (s, 1H), 2.40 (s, 3H).

Method B. 5-Hydroxy-1-Benzothiophene 5-methoxy-1-benzothiophene (6.37 g, 38.8 mmol) was combined with pyridine hydrochloride (13.5 g, 116.4 mmol) in a sealed tube and heated to 190° C. for 3.5 hrs. The reaction was cooled to room temperature and the resulting residue was dissolved in 2:1 EtOAc—H$_2$O with sonication. The organic layer was washed with water, brine, dried over anhydrous Na$_2$SO$_4$, and filtered. The filtrate was evaporated in vacuo. The crude residue was purified by silica gel chromatography using 20% EtOAc-hexanes to give 5-hydroxy-1-benzothiophene.

$^1$H NMR (500 MHz, acetone-d$_6$) δ (ppm): 8.32 (s, 1H), 7.43 (d, J=8.8 Hz, 1H), 7.56 (d, J=5.5 Hz, 1H), 7.28 (d, J=2.3 Hz, 1H), 7.25 (d, J=5.3 Hz, 1H), 6.96 (dd, J=2.3 Hz, 1H).

Utilizing the foregoing procedure, the following compounds were prepared:

1-benzothiophene-5,6-diol

It was prepared in quantitative yield from 5,6-dimethoxy-1-benzothiophene; solidified in ether/hexane.

$^1$H NMR (400 MHz, CDCl$_3$) δ (ppm): 7.3 (s, 1H), 7.25 (s, 1H), 7.2 (d, 1H), 7.15 (d, 1H); MS m/z 167 (M+1).

3-ethyl-1-benzothiophene-5,6-diol

Purified by silica gel chromatography (EtOAc/Hexane=2/3).

$^1$H NMR (500 MHz, CD$_3$OD) δ (ppm): 7.20 (s, 1H), 7.10 (s, 1H), 6.90 (s, 1H), 2.75 (q, 2H), 1.35 (t, 3H).

4,7-difluoro-3-ethyl-1-benzothiophene-5,6-diol $^1$H NMR (500 MHz, CDCl$_3$) δ (ppm): 6.85 (s, 1H), 2.95 (q, 2H), 1.30 (t, 3H); MS m/z 231 (M+1).

7-chloro-5-hydroxy-1-benzothiophene $^1$H NMR (400 MHz, CDCl$_3$) δ (ppm): 7.47 (d, J=5.5 Hz, 1H), 7.22 (d, J=5.5 Hz, 1H), 7.15 (d, J=2.1 Hz, 1H), 6.97 (d, J=2.1 Hz, 1H), 5.07 (bs, 1H).

7-fluoro-5-hydroxy-3-methyl-1-benzothiophene $^1$H NMR (500 MHz, CDCl$_3$) δ (ppm): 7.31 (s, 1H), 6.98 (d, J=2.1 Hz, 1H), 6.72 (dd, J=10.5 Hz, 2.1 Hz, 1H), 5.30 (bs, 1H), 2.39 (d, J=0.7 Hz, 3H).

6-hydroxy-1-benzothiophene.

$^1$H NMR (CDCl$_3$) δ (ppm): 7.72 (d, 1H), 7.36 (s, 1H), 7.29 (m, 2H), 6.96 (d, 1H); MS m/z 151 (M+1).

Method C 4,7-Difluoro-5,6-Dihydroxy-1-Benzothiopene

To a stirred solution of the difluorobenzothiophene derivative (4 g, 17.39 mmol), prepared in the Preparative Example 29, Method E, in dichloromethane at −78° C. under nitrogen was added drop wise BBr$_3$ (41 mL, 2.2 equiv). The resulting mixture was immediately warmed up to room temperature and left overnight, after which time, it was quenched with MeOH. The mixture was washed with water, dried over magnesium sulfate, and concentrated to afford the crude product.

$^1$H NMR (400 MHz, CD$_3$OD) δ (ppm): 7.32 (d, 1H), 7.26 (dd, 1H); MS m/z 203 (M+1).

Utilizing the foregoing procedure, the following compounds were prepared:

4,5,7-trifluoro-1-benzothiophene-6-ol $^1$H NMR (CDCl$_3$) δ (ppm): 7.42 (m).

4-fluoro-6-hydroxy-1-benzothiophene $^1$H NMR (CDCl$_3$) δ (ppm): 7.37 (d, J=5.7 Hz, 1H), 7.27 (d, J=5.5 Hz, 1H), 7.14 (d, J=1.8 Hz, 1H), 6.70 (dd, J=11, 2 Hz, 1H).

5-(3,4-dihydroxyphenyl)thiophene-2-sulfonamide was prepared and used as is in the next step.

$^1$H NMR (500 MHz, CD$_3$OD) δ (ppm): 7.52 (d, 1H), 7.16 (d, 1H), 7.10 (s, 1H), 7.00 (dd, 1H), 6.80 (d, 1H).

5-(3,4-dihydroxy-2-methyl-phenyl)thiophene-2-sulfonamide was prepared and used as is in the next step.

$^1$H NMR (500 MHz, CD$_3$OD) δ (ppm): 7.60 (d, 1H), 6.96 (d, 1H), 6.80 (s, 1H), 6.70 (d, 1H), 2.24 (s, 3H).

Preparative Example 42

3-Methyl-4-Chloro-5-Hydroxy-1-Benzothiophene

To a stirred solution of the 3-methyl-5-hydroxy-1-benzothiophene (2.2 g, 13.1 mmol), prepared in the prior Example, in 75 mL of TFA-CH$_2$Cl$_2$ (2:1) was added 1.2 equivalents of N-chlorosuccinimde (NCS) at room temperature. The reaction mixture was stirred for 10 min under an inert atmosphere of nitrogen. The reaction mixture was partitioned between ethyl acetate and water and the organic phase was separated, washed with sodium bicarbonate and brine, dried over anhydrous MgSO$_4$, filtered, and evaporated. Purification by silica gel chromatography afforded the corresponding 3-methyl-4-chloro-5-hydroxy-1-benzothiophene.

$^1$H NMR (500 MHz, CDCl$_3$) δ (ppm): 7.62 (d, 1H), 7.10 (s, 1H), 7.08 (d, 1H), 2.70 (s, 3H).

Preparative Example 43

4-Chloro-5-Hydroxy-1-Benzothiophene

To a stirred solution of 5-hydroxybenzothiophene (248 mg, 1.65 mmol) in chloroform (0.75 mL) at 0° C. was added glacial acetic acid (0.75 mL), N-chlorosuccinamide (220 mg, 1.65 mmol) and trifluoroacetic acid (20 μL, 0.270 mmol). The solution was allowed to warm to room temperature and was stirred for 2 hrs. The reaction was diluted with EtOAc and washed with H$_2$O, dilute aqueous NaHCO$_3$ solution and brine. The separated organic layer was dried over anhydrous Na$_2$SO$_4$, filtered and evaporated. The resulting residue was purified by silica gel plate layer chromatography (3×1000μ plates) eluting with 40% EtOAc-hexanes to give 5-hydroxy-4-chloro-1-benzothiophene.

$^1$H NMR (600 MHz, CD$_3$OD) δ (ppm): 7.66 (d, J=8.6 Hz 1H), 7.53 (d, J=5.5 Hz, 1H), 7.38 (d, J=5.5 Hz, 1H), 7.09 (d, J=8.6 Hz, 1H), 5.67 (bs, 1H).

Preparative Example 44

Dimethyl 2,2'-[1-Benzothiene-5,6-Diylbis(Oxy)] Diacetate

To a stirred solution of 3.9 g, (23.5 mmol) of 1-benzothiophene-5,6-diol in acetone was added sequentially K$_2$CO$_3$ (13 g, 4 equiv) and then 2-bromomethylacetate (8.9 mL, 4 equiv) and the reaction mixture was heated to reflux over a period of 5 h. The white inorganic solid was filtered off and washed with EtOAc. Removal of the solvents and subsequent chromatography gave the product as an oil.

$^1$H NMR (400 MHz, CDCl$_3$) δ (ppm): 7.4 (s, 1H), 7.38 (d, 1H), 7.33 (s, 1H), 7.24 (d, 1H), 4.56 (s, 4H), 3.75 (s, 6H); MS m/z 333 (M+23), 311 (M+1).

Utilizing the foregoing procedure, the following compounds were prepared:

Dimethyl 2,2'-[(4,7-difluoro-1-benzothiene-5,6-diyl)bis (oxy)]diacetate $^1$H NMR (400 MHz, CDCl$_3$) δ (ppm): 7.42 (d, 1H), 7.38 (dd, 1H), 4.89 (s, 2H), 4.85 (s, 2H), 3.8 (s, 6H); MS m/z 369 (M+23).

dimethyl 2,2'-[(3-methyl-1-benzothiene-5,6-diyl)bis (oxy)]diacetate $^1$H NMR (500 MHz, CDCl$_3$) δ (ppm): 7.34 (s, 1H), 7.19 (s, 1H), 6.99 (s, 1H), 4.81 (d, 4H), 3.82 (d, 6H), 2.39 (s, 3H); MS m/z 325 (M+1).

dimethyl 2,2'-[(3-methyl-4,7-difluoro-1-benzothiene-5,6-diyl)bis(oxy)]diacetate $^1$H NMR (500 MHz, CDCl$_3$) δ (ppm): 6.96 (s, 1H), 4.87 (s, 2H), 4.82 (s, 2H), 3.82 (2s, 6H), 2.52 (s, 3H).

dimethyl 2,2'-[(3-ethyl-4,7-difluoro-1-benzothiene-5,6-diyl)bis(oxy)]diacetate

Purified by silica gel chromatography (EtOAc/Hexane=2/3).

$^1$H NMR (500 MHz, CDCl$_3$) δ (ppm): 7.00 (s, 1H), 4.88 (d, 4H), 3.82 (d, 6H), 3.00 (q, 2H), 2.28 (m, 4H), 1.35 (t, 3H); MS m/z 375 (M+1).

Preparative Example 45

2,2'-[1-Benzothiene-5,6-Diylbis(Oxy)]Diethanol

The bis-ester (6 g, 19.2 mmol), from the prior Example, was reduced with NaBH$_4$ (7.3 g, 10 equiv) in 10% MeOH in THF at room temperature. After 1.5 h the reaction mixture was quenched with water/dilute HCL solution. The aqueous phase was partitioned with ethyl acetate, and subsequent washing of the combined organic layer with brine and concentration provided crude product.

$^1$H NMR (400 MHz, CDCl$_3$) δ (ppm): 7.5 (s, 1H), 7.41 (s, 1H), 7.39 (d, 1H), 7.24 (d, 1H), 4.2 (brm, 4H), 4.0 (brm, 4H); MS m/z 277 (M+1).

Utilizing the foregoing procedure, the following compounds were prepared:

2,2'-[(4,7-Difluoro-1-benzothiene-5,6-diyl)bis(oxy)diethanol

It was prepared in 75% yield.

$^1$H NMR (400 MHz, CDCl$_3$) δ (ppm): 7.46 (d, 1H), 7.43 (dd, 1H), 4.36 (m, 4H), 3.96 (m, 4H); MS m/z 291 (M+1).

2,2'-[(3-methyl-1-benzothiene-5,6-diyl)bis(oxy)diethanol $^1$H NMR (500 MHz, CD$_3$OD) δ (ppm): 7.42 (s, 1H), 7.24 (s, 1H), 7.01 (s, 1H), 4.13 (m, 4H), 3.92 (m, 4H), 2.38 (s, 3H).

2,2'-[(3-methyl-4,7-difluoro-1-benzothiene-5,6-diyl)bis (oxy)diethanol

Purification was accomplished by chromatography (Biotage Horizon system; 25 M column, 0% to 100% EtOAc/hexane over 10 column volume and 100% EtOAc for 2 column volume; flow rate=25 mL/min).

$^1$H NMR (500 MHz, CDCl$_3$) δ (ppm): 6.99 (s, 1H), 4.43 (2t, 4H), 3.88 (m, 4H), 2.59 (s, 3H).

2,2'-[(3-ethyl-4,7-difluoro-1-benzothiene-5,6-diyl)bis (oxy)diethanol $^1$H NMR (500 MHz, CDCl$_3$) δ (ppm): 7.20 (s, 1H), 4.30 (t, 2H), 4.25 (t, 2H), 3.90 (m, 4H), 2.98 (q, 2H), 1.35 (t, 3H); MS m/z 319 (M+1).

Preparative Example 46

Method A.

5,6-Bis(2-Chloroethoxy)-1-Benzothiophene

A solution of the crude diol (3 g, 12.9 mmol) and pyridine (3.3 mL, 3 equiv) in absolute benzene (50 mL) was stirred at 80° C. Thionyl chloride (2.4 mL, 3 equiv) was added to the solution drop wise over 1 h and then left for another 1.5 h. The mixture was cooled to room temperature and saturated copper sulfate solution added. The resulting organic phase was separated, washed twice with water, dried over magnesium sulfate, filtered, and evaporated to give an oily residue, which was purified by silica gel chromatography to afford the corresponding dichloride.

$^1$H NMR (400 MHz, CDCl$_3$) δ (ppm): 7.44 (s, 1H), 7.38 (s, 1H), 7.36 (d, 1H), 7.23 (d, 1H), 4.35 (t, 4H), 3.9 (t, 4H); MS m/z 291 (M+1).

Utilizing the foregoing procedure, the following compound was prepared:

5,6-bis(2-chloroethoxy)-4,7-difluoro-1-benzothiophene $^1$H NMR (400 MHz, CDCl$_3$) δ (ppm) 7.45 (d, 1H), 7.42 (d, 1H), 4.45 (m, 4H), 3.8 (m, 4H); MS m/z 328 (M+1).

Method B.

5,6-Bis(2-Chloroethoxy)-3-Methyl-1-Benzothiophene

To a mixture of the product obtained from Preparative Example 37 (1.9810 g, 7.5 mmol) in CCl$_4$/distilled THF (120 mL/50 mL) was added polymer-supported triphenylphosphine (Aldrich, 12.67 g, 37 mmol). The reaction was heated to 80° C. under nitrogen and refluxed for 19 h. The resin was removed by filtration and the filtrate was concentrated in vacuo. The resulting residue was purified by chromatography using the Isco CombiFlash Companion (40 g column; 0% to 100% EtOAc/hexane over 15 min.; flow rate=40 mL/min; desired product elutes at 30% EtOAc/hexane) to give the product as a pale yellow solid.

$^1$H NMR (500 MHz, CDCl$_3$) δ (ppm): 7.00 (s, 1H), 7.24 (s, 1H), 7.40 (s, 1H), 4.33-4.39 (m, 4H), 3.90 (m, 4H), 2.41 (s, 3H).

Utilizing the foregoing procedure, the following compounds were prepared:

5,6-bis(2-chloroethoxy)-3-methyl-4,7-difluoro-1-benzothiophene

A pale yellow oil after purification by chromatography (Biotage Horizon system; 25 M column, 0% to 70% EtOAc/hexane over 10 column volume; flow rate=25 mL/min).

$^1$H NMR (500 MHz, CDCl$_3$) δ (ppm): 6.95 (s, 1H), 4.38-4.44 (2t, 4H), 3.85 (m, 4H), 2.54 (s, 3H).

5,6-bis(2-chloroethoxy)-3-ethyl-4,7-difluoro-1-benzothiophene

Purified by silica gel chromatography (EtOAc/Hexane=1/9).

$^1$H NMR (500 MHz, CD$_3$OD) δ (ppm): 7.20 (s, 1H), 4.45 (t, 2H), 4.40 (t, 2H), 3.90 (m, 4H), 3.00 (q, 2H), 1.35 (t, 3H).

Preparative Example 47

4-Chloro-5-(2-Chloroethoxy)-3-Methyl-1-Benzothiophene

A mixture of the 3-methyl-4-chloro-5-hydroxy-1-benzothiophene (0.84 g, 4.2 mmol), 1-bromo-2-chloroethane (7 mL, 84.0 mmol), and Cs$_2$CO$_3$ (2.7 g 8.4 mmol) in acetone with 2 drops of water was heated to reflux under N$_2$ for 10 h. The progress of the reaction was monitored by examining worked-up aliquots of the reaction mixture by TLC (5% EtOAc/hexane). Upon completion, the reaction was cooled to room temperature and filtered through celite. The filtrate was concentrated in vacuo and purified by silica gel chromatography with 5% EtOAc/hexane as the eluant to afford the desired product.

$^1$H NMR (500 MHz, CDCl$_3$) δ (ppm): 7.64 (d, 1H), 7.10 (s, 1H), 7.05 (d, 1H), 4.35 (t, 2H), 3.90 (t, 2H), 2.75 (s, 3H).

Preparation of
5,6-Bis(3-Chloropropoxy)-1-Benzothiophene

To a solution of 1-benzothiophene-5,6-diol (3 g, 18.1 mmol) in 35 mL DMF at room temperature was added Cs$_2$CO$_3$ (23 g, 72.4 mmol) and 1-bromo-3-chloropropane (36 mL, 362 mmol). The reaction was allowed to stir at room temperature for 2 h and monitored by TLC. The reaction mixture was partitioned between H$_2$O and EtOAc, the layers were separated, and the aqueous layer was extracted again with EtOAc. The combined organic layers were washed by H$_2$O, brine and dried (MgSO$_4$), filtered, and evaporated in vacuo. The resulting product was used as is.

$^1$H NMR (500 MHz, CDCl$_3$) ppm(δ): 7.40 (s, 1H), 7.36 (m, 2H), 7.24 (d, 1H), 4.26 (t, 4H), 3.84 (t, 4H), 2.40 (m, 4H).

Preparation of 5-(3-Chloropropoxy)-1-Benzothiophene-6-Ol and 6-(3-Chloropropoxy-1-Benzothiophene-5-Ol To a stirred solution of 1-benzothiophene-5,6-diol (0.51 g, 3.1 mmol) in anhydrous DMF (6 mL) was added cesium carbonate (1.2 g, 3.7 mmol) at 0° C. under nitrogen followed by dropwise addition of 1-bromo-3-chloropropane (0.33 mL, 3.4 mmol). After the addition, the reaction was allowed to warm to ambient temperature and stirred for 22 h. The reaction mixture was filtered to remove excess cesium carbonate. The filtrate was partitioned between EtOAc and 2 N HCl/ice. The organic layer was collected, washed with brine, dried over sodium sulfate, and concentrated in vacuo. The residue was purified by chromatography using the Isco CombiFlash Companion (12 g, column, 0% to 100% EtOAc/hexane over 28 column volume; flow rate=30 mL/min; desired product elutes at 48% EtOAc/hexane) to give the product as a 2:1 mixture of regioisomers. Further purification by Chiracel Semi-Prep OD column (flow rate=9 mL/min; 15% EtOH/heptane for 28 min.; 220 nM; 13 injections) separated the regioisomers as white solids.

Major isomer (0.1966 g): $^1$H NMR (500 MHz, CDCl$_3$) δ (ppm): 7.35 (2s, 2H), 7.30 (d, 1H), 7.20 (d, 1H), 4.31 (t, 4H), 3.79 (t, 4H), 2.36 (m, 4H).

Minor isomer (0.0732 g): $^1$H NMR (500 MHz, CDCl$_3$) δ (ppm): 7.41 (s, 2H), 7.28 (s, 1H), 7.28 (d, 1H), 7.21 (d, 1H), 4.32 (t, 4H), 3.79 (t, 4H), 2.36 (m, 4H).

6-(4-Chlorobutoxy)-5-(3-Chloropropoxy)-1-Benzothiophene and 5-(4-Chlorobutoxy-6-(3-Chloropropoxy)-1-Benzothiophene Utilizing the procedure described above, the two isomers, from the previous example, were separately treated with 1-bromo-4-chlorobutane to give the desire products after purification by chromatography using the Isco CombiFlash Companion (4 g, column, 0% to 70% EtOAc/hexane over 40 column volume; flow rate=18 mL/min; desired product elutes at 20% EtOAc/hexane).

Major isomer (0.23 g): $^1$H NMR (500 MHz, CDCl$_3$) δ (ppm): 7.38 (s, 1H), 7.31 (d, 1H), 7.29 (s, 1H), 7.22 (d, 1H), 4.23 (t, 2H), 4.11 (t, 2H), 3.81 (t, 2H), 3.71 (t, 2H), 2.34 (m, 2H), 2.04 (m, 4H).

Minor isomer (0.0838 g): $^1$H NMR (500 MHz, CDCl$_3$) δ (ppm): 7.34 (s, 1H), 7.32 (s, 1H), 7.31 (d, 1H), 7.22 (d, 1H), 4.23 (t, 2H), 4.11 (t, 2H), 3.82 (t, 2H), 3.70 (t, 2H), 2.34 (m, 2H), 2.04 (m, 4H)

Preparation of
5-(2-Chloroethoxy)-3-Methyl-1-Benzothiophene

To an acetone solution (180 mL) of 5-hydroxy-1-benzothiophene (3.56 g, 23.73 mmol) was added cesium carbonate (30.1 g, 92.5 mmol), 1-bromo-2-chloroethane (5.9 mL, 71.2 mmol) and 0.5 mL of deionized water. The suspension was stirred vigorously at 60° C. for 4.0 hrs. The mixture was cooled to room temperature and the white precipitate was removed by filtration. The filtrate was diluted with EtOAc and washed with water and brine. The organic layer was dried over anhydrous Na$_2$SO$_4$, filtered and evaporated in vacuo. The crude residue was purified by silica gel chromatography using a gradient elution with 5% EtOAc-hexanes to 100% EtOAc to give 5-(2-chloroethoxy)-1-benzothiophene.

$^1$H NMR (500 MHz, CDCl$_3$) δ (ppm): 7.95 (d, J=8.7 Hz, 1H), 7.49 (d, J=5.2 Hz, 1H), 7.33 (d, J=2.5 Hz, 1H), 7.29 (d, J=5.2 Hz, 1H), 7.07 (dd, J=2.3 Hz, 8.8 Hz, 1H), 4.34 (t, J=6.0 Hz, 2H), 3.89 (t, J=6.0 Hz, 2H).

Utilizing the above procedure the following compounds were prepared:

5,6-bis(4-chlorobutoxy)-1-benzothiophene and purified using 5% EtOAc/hexane as the chromatography eluant on a short pad silica gel.

$^1$H NMR (500 MHz, CDCl$_3$) δ (ppm): 7.3 (s, 1H), 7.3 (d, 1H), 7.3 (s, 1H), 7.2 (d, 1H), 4.2 (t, 4H), 3.7 (t, 4H), 2.1 (m, 8H).

5,6-bis(3-chloropropoxy)-3-methyl-1-benzothiophene $^1$H NMR (500 MHz, CDCl$_3$) δ (ppm): 7.4 (s, 1H), 7.2 (s, 1H), 7.0 (s, 1H), 4.35 (m, 4H), 3.85 (m, 4H), 2.45 (s, 3H), 2.35 (m, 4H); MS m/z 334 (M+1).

5,6-bis(3-chloropropoxy)-3-ethyl-1-benzothiophene

Purified by silica gel chromatography (EtOAc/Hexane=1/9).

$^1$H NMR (500 MHz, CDCl$_3$) δ (ppm): 7.40 (s, 1H), 7.22 (s, 1H), 7.00 (d, 1H), 4.22 (m, 4H), 3.82 (m, 4H), 2.82 (q, 2H), 2.35 (m, 4H), 1.40 (t, 3H).

5,6-bis(3-chloropropoxy)-4,7-difluoro-1-benzothiophene $^1$H NMR (500 MHz, CDCl$_3$) δ (ppm): 7.42 (m, 2H), 4.35 (m, 4H), 3.85 (m, 4H), 2.35 (m, 4H); MS m/z 357 (M+1).

5,6-bis(3-chloropropoxy)-4,7-difluoro-3-methyl-1-benzothiophene $^1$H NMR (500 MHz, CDCl$_3$) δ (ppm): 6.99 (s, 1H), 4.4 (two t, 4H), 3.85 (m, 4H), 2.6 (s, 3H), 2.25 (m, 4H).

5,6-bis(3-chloropropoxy)-4,7-difluoro-3-ethyl-1-benzothiophene

Purified by silica gel chromatography (EtOAc/Hexane=1/9).

$^1$H NMR (500 MHz, CDCl$_3$) δ (ppm): 7.00 (s, 1H), 4.35 (t, 2H), 4.30 (t, 2H), 3.86 (m, 4H), 3.00 (q, 2H), 2.28 (m, 4H), 1.35 (t, 3H).

6-(2-chloroethoxy)-4,5,7-trifluoro-1-benzothiophene $^1$H NMR (CDCl$_3$) δ (ppm): 7.49 (d, J=5.3 Hz, 1H), 7.45 (dd, 1H), 4.48 (t, J=6.0 Hz, 2H), 3.86 (t, J=6.0 Hz, 2H).

6-(2-chloroethoxy)-4-fluoro-1-benzothiophene $^1$H NMR (CDCl$_3$) δ (ppm): 7.39 (d, J=5.5 Hz, 1H), 7.31 (d, 1H), 7.19 (d, J=1.8 Hz, 1H), 6.79 (dd, 1H), 4.32 (t, J=5.9 Hz, 2H), 3.89 (t, J=5.9 Hz, 2H).

6-(2-chloropropyloxy)-4-fluoro-1-benzothiophene $^1$H NMR (CDCl$_3$) δ (ppm): 7.37 (d, J=5.5 Hz, 1H), 7.29 (d, 1H), 7.16 (d, J=1.8 Hz, 1H), 6.74 (dd, 1H), 4.09 (t, J=6 Hz, 2H), 3.68 (t, J=6 Hz, 2H), 2.04 (m, 4H).

7-Chloro-5-(2-chloroethoxy)-3-methyl-1-benzothiophene $^1$H NMR (400 MHz, CDCl$_3$) δ (ppm): 7.18 (s, 1H), 7.10 (s, 1H), 7.08 (s, 1H), 4.32 (t, 2H), 3.84 (t, 2H), 2.40 (s, 3H).

5-(2-chloroethoxy)-4-chloro1-benzothiophene $^1$H NMR (600 MHz, CDCl$_3$) δ (ppm): 7.72 (d, J=8.7 Hz 1H), 7.55 (d, J=5.5 Hz, 1H), 7.50 (d, J=5.5 Hz, 1H), 7.12 (d, J=8.7 Hz, 1H), 4.39 (t, J=4.8 Hz, 1H), 3.91 (t, J=4.8 Hz, 2H).

7-chloro-5-(2-chloroethoxy)-1-benzothiophene $^1$H NMR (400 MHz, CDCl$_3$) δ (ppm): 7.49 (d, J=5.3 Hz, 1H), 7.26 (d, J=5.3 Hz, 1H), 7.19 (d, J=1.9 Hz, 1H), 7.06 (d, J=1.9 Hz, 1H), 4.25 (t, J=5.9 Hz, 2H), 3.81 (t, J=5.7 Hz, 2H).

5-(2-chloroethoxy)-7-fluoro-3-methyl-1-benzothiophene $^1$H NMR (500 MHz, CDCl$_3$) δ (ppm): 7.31 (s, 1H), 7.01 (d, J=2.0 Hz, 1H), 6.80 (dd, J=12.0 Hz, 2.1 Hz, 1H), 4.34 (t, J=5.7 Hz, 2H), 3.89 (t, J=5.9 Hz, 2H), 2.43 (d, J=0.9 Hz, 3H).

Preparative Example 48

5-(Bromomethyl)-1-Benzothiophene

N-Bromosuccinimide (4.53 g, 25.4 mmol, 1.20 eq) and 1,1'-azobis(cyclohexane-carbonitrile) (260 mg, 1.06 mmol, 0.05 eq) were added to a solution of 5-methyl-1-benzothiophene (3.14 g, 21.2 mmol, 1 eq) in carbon tetrachloride (90 mL) under nitrogen. The reaction mixture was heated under reflux and after 3 h a further amount of 1,1'-azobis(cyclohexane-carbonitrile) (260 mg, 1.06 mmol, 0.05 eq) was added. After an additional 3 h of heating under reflux, the reaction mixture was cooled down to room temperature and filtered. The filtrate was transferred to a separatory funnel, washed with a saturated aqueous solution of sodium bicarbonate, and the organic phase was dried over sodium sulfate, filtered and concentrated. Purification by flash chromatography on silica gel (ethyl acetate/hexane, 2:98 to 4:96) afforded 5-(bromomethyl)-1-benzothiophene.

Preparative Example 49

Preparation of 5-Vinyl-1-Benzothiophene

Triphenylphosphine (1.20 g, 4.58 mmol) and 5-(bromomethyl)-1-benzothiophene (1.00 g, 4.40 mmol) in toluene (50 mL) was heated under reflux for 2 h. The mixture was then cooled and the resulting white crystalline precipitate was isolated by suction filtration, rinsed with a small amount of hexanes, and dried in vacuo. The solid was suspended in aqueous formaldehyde (37%, 20 mL) and aqueous sodium hydroxide (3M, 10 mL) was added dropwise. The resulting mixture was stirred for 3 h at r.t. It was then extracted with hexanes, dried (MgSO$_4$), and concentrated under reduced pressure. Column chromatography of the residue (hexanes) afforded the product.

$^1$H NMR (400 MHz, CDCl$_3$) δ (ppm): 7.83-7.80 (m, 2H); 7.48-7.42 (m, 2H); 7.31 (dd, J=5.2, 0.8, 1H); 6.83 (dd, J=17.0, 11.0, 1H); 5.82 (d, J=17.4, 1H); 5.28 (d, J=11.0, 1H).

Preparative Example 50

Preparation of 4-(1-Benzothien-5-Ylmethyl)Morpholine

To a stirred solution of 5-(bromomethyl)-1-benzothiophene (2.3 g, 10.1 mmol, 1 eq) in dimethylsulfoxide (10 mL) were added morpholine (0.97 mL, 11 mmol, 1.1 eq) and diisopropylethylamine (2.6 mL, 15.2 mmol, 1.5 eq). The solution was stirred at room temperature under nitrogen for 18 h then water (200 mL) was added. The solution was made alkaline (pH 12) with aqueous sodium hydroxide (1N) and the aqueous phase was extracted twice with ethyl acetate. Combined organic phases were washed with brine, dried over sodium sulfate and concentrated. Purification by flash chromatography on silica gel (methanol/dichloromethane, 1:99) afforded 4-(1-benzothien-5-ylmethyl)morpholine.

$^1$H NMR (400 MHz, CDCl$_3$) δ (ppm): 7.84 (d, J=8.0 Hz, 1H), 7.79 (s, 1H), 7.45 (d, J=5.6 Hz, 1H), 7.37 (d, J=8.0 Hz, 1H), 7.32 (d, J=5.6 Hz, 1H), 3.82-3.72 (m, 4H), 3.72-3.63 (bs, 2H), 2.54 (bs, 4H); MS m/z 234 (M+1).

Preparative Example 51

(1-Benzothien-6-Yloxy)(Triisopropyl)Silane

To a cold (0° C.) anhydrous CH$_2$Cl$_2$ solution of 6-hydroxy-1-benzothiophene (8.0 g, 53.25 mmol) was added 2,6-lutidine (7.17 g, 66.56 mmol) and triisopropylsilyl trifluoromethanesulfonate (16.80 g, 54.85 mmol). The mixture was stirred at 0° C. under N$_2$ for 20 minutes. The reaction mixture was quenched with 1 N HCl and extracted with hexane. The organic layer was washed with water, brine, dried over anhydrous Na$_2$SO$_4$, and filtered. The filtrate was evaporated in vacuo. The crude residue was purified by silica gel chromatography using hexanes as the eluent to give product.

$^1$H NMR (CDCl$_3$) δ (ppm): 7.70 (d, 1H), 7.40 (s, 1H), 7.29 (m, 2H), 7.02 (d, 1H), 1.37 (m, 3H), 1.18 (d, 18); MS m/z 307 (M+1).

Preparative Example 52

Method A.
5-Methyl-1-Benzothiophene-2-Sulfonamide

To a solution of 5-methyl-1-benzothiophene (11.8 g, 79.6 mmol, 1 eq) in anhydrous tetrahydrofuran (300 mL) at −78° C. was slowly added n-butyllithium (38.2 mL, 2.5 M solution in hexane, 95.5 mmol, 1.20 eq). The reaction mixture was warmed to −40° C., placed under an atmosphere of SO$_2$ and slowly warmed up to room temperature. The SO$_2$ was allowed to evaporate and the reaction mixture was concentrated. The residue was suspended in dichloromethane (350 mL) and treated with N-chlorosuccinimide (12.2 g, 91.5 mmol, 1.15 eq). After stirring for 1 hour at room temperature, the reaction mixture was filtered through celite and concentrated. The residue was dissolved in acetone (350 mL), treated with ammonium hydroxide (75 mL) for 1 hour, concentrated and dried under high vacuum. The resulting solid was triturated in a mixture of methanol and dichloromethane (10:1), filtered, rinsed with methanol and dried under high vacuum to afford the product as a light pink solid.

$^1$H NMR (400 MHz, DMSO-$d_6$) δ (ppm): 7.92 (d, J=8.4 Hz, 1H), 7.82 (bs, 2H), 7.81 (d, J=0.8 Hz, 1H), 7.78 (t, J=0.8 Hz, 1H), 7.32 (ddd, J=8.4, 1.8, 0.5 Hz, 1H), 2.43 (s, 3H).

Method B. 5-(Morphin-4-Ylmethyl)-1-Benzothiophene-2-Sulfonamide

To a solution of 4-(1-benzothien-5-ylmethyl)morpholine (1.7 g, 7.29 mmol, 1 eq) in anhydrous tetrahydrofuran (36 mL) at −78° C. was slowly added n-butyllithium (3.50 mL, 2.5 M solution in hexane, 8.75 mmol, 1.20 eq). The reaction mixture was allowed to warm to −40° C., placed under $SO_2$ and slowly warmed up to room temperature. The $SO_2$ was removed and the reaction mixture was concentrated. The residue was suspended in dichloromethane (45 mL) and treated with N-chlorosuccinimide (1.12 g, 8.38 mmol, 1.15 eq). After stirring for 1 hour at room temperature, the reaction mixture was filtered through celite and concentrated. The residue was dissolved in acetone (35 mL), treated with ammonium hydroxide (7 mL) for 1 hour and concentrated. The residue was adsorbed on silica gel and purified by flash chromatography on silica gel (methanol/dichloromethane, 6:94). The resulting solid was triturated with dichloromethane, filtered off, rinsed with dichloromethane and dried under high vacuum to afford 5-(morpholin-4-ylmethyl)-1-benzothiophene-2-sulfonamide as a white solid.

$^1$H NMR (400 MHz, DMSO-$d_6$) δ (ppm): 7.98 (d, J=8.4 Hz, 1H), 7.90 (s, 1H), 7.87 (s, 1H), 7.45 (d, J=8.4 Hz, 1H), 3.60-3.55 (m, 6H), 2.40-30 (m, 4H); MS m/z 313 (M+1).

Following the foregoing general procedure, the following compounds were prepared:

4-chloro-5-(2-chloroethoxy)-3-methyl-1-benzothiophene-2-sulfonamide

It was prepared after purification by silica gel chromatography using 30% EtOAc/hexane as the eluant.

$^1$H NMR (500 MHz, $CD_3OD$) δ (ppm): 7.94 (d, 1H), 7.45 (d, 1H), 4.5 (t, 2H), 4.0 (t, 2H), and 3.0 (s, 3H).

7-Chloro-5-(2-chloroethoxy)-3-methyl-benzothiophene-2-sulfonamide

It was prepared and purified using 30% EtOAc/hexane as the chromatography eluant.

$^1$H NMR (400 MHz, $CD_3OD$) δ (ppm): 7.35 (s, 1H), 7.24 (s, 1H), 4.40 (t, 2H), 3.90 (t, 2H), 2.62 (s, 3H).

5,6-Bis(4-chlorobutoxy)-1-benzothiophene-2-sulfonamide

It was prepared and purified using 30% EtOAc/hexane as the chromatography eluant.

$^1$H NMR (500 MHz, $CD_3OD$) δ (ppm): 7.75 (s, 1H), 7.46 (s, 1H), 7.4 (s, 1H), 4.18 (m, 4H), 3.70 (t, 4H), 2.00 (m, 8H).

5,6-Bis(3-chloropropoxy)-1-benzothiophene-2-sulfonamide

It was prepared and purified using 30% EtOAc/hexane as the chromatography eluant.

$^1$H NMR (500 MHz, $CD_3OD$) δ (ppm): 7.75 (s, 1H), 7.42 (s, 1H), 4.20 (m, 4H), 3.82 (t, 4H), 2.30 (m, 4H).

5-(4-chlorobutoxy)-6-(3-chloropropoxy)-1-benzothiophene-2-sulfonamide and
6-(4-chlorobutoxy)-5-(3-chloropropoxy)-1-benzothiophene-2-sulfonamide Purification was accomplished by chromatography using the Isco CombiFlash Companion (4 g, column, 10% to 100% EtOAc/hexane over 30 column volume; flow rate=18 mL/min; desired product elutes at 68% EtOAc/hexane).

Major isomer (0.2066 g): $^1$H NMR (500 MHz, $CDCl_3$) δ (ppm): 7.81 (s, 1H), 7.31 (s, 1H), 7.28 (s, 1H), 5.05 (bs, 2H), 4.27 (t, 2H), 4.13 (t, 2H), 3.85 (t, 2H), 3.73 (t, 2H), 2.39 (m, 2H), 2.08 (m, 4H).

Minor isomer (0.0657 g): $^1$H NMR (500 MHz, $CDCl_3$) δ (ppm): 7.79 (s, 1H), 7.29 (s, 1H), 7.25 (s, 1H), 5.11 (bs, 2H), 4.22 (t, 2H), 4.13 (t, 2H), 3.83 (t, 2H), 3.71 (t, 2H), 2.34 (m, 2H), 2.06 (m, 4H).

5,6-Bis(2-chloroethoxy)-1-benzothiophene-2-sulfonamide $^1$H NMR (400 MHz, $CDCl_3$) δ (ppm): 7.29 (s, 1H), 7.26 (s, 1H), 7.24 (s, 1H), 4.25 (m, 4H), 3.80 (m, 4H); MS m/z 291 (M+1).

5,6-bis(2-chloroethoxy)-4,7-difluoro-1-benzothiophene-2-sulfonamide $^1$H NMR (400 MHz, $CDCl_3$) δ (ppm): 7.85 (m, 1H), 4.4 (m, 4H), 3.80 (m, 4H); MS m/z 407 (M+1).

5,6-bis(2-chloroethoxy)-3-methyl-4,7-difluoro-1-benzothiophene-2-sulfonamide

Purification was accomplished by chromatography using the Biotage Horizon (25 M column, 10% to 100% EtOAc/hexane over 10 column volumes; flow rate=25 mL/min) to give the desired product as a pale yellow solid.

$^1$H NMR (500 MHz, $CD_3OD$) δ (ppm): 4.49 (t, 2H), 4.42 (t, 2H), 3.90 (t, 4H), 2.78 (s, 3H).

5,6-bis(2-chloroethoxy)-3-ethyl-4,7-difluoro-1-benzothiophene-2-sulfonamide

Purified by silica gel chromatography (EtOAc/Hexane=2/3).

$^1$H NMR (500 MHz, $CD_3OD$) δ (ppm): 4.50 (t, 2H), 4.44 (t, 2H), 3.90 (m, 4H), 3.24 (q, 2H), 1.36 (t, 3H).

5,6-bis(2-chloroethoxy)-3-methyl-1-benzothiophene-2-sulfonamide

Purification was accomplished by chromatography using the Isco CombiFlash Companion (12 g, column, 5% to 100% EtOAc/hexane over 12 min.; flow rate=30 mL/min; desired product elutes at 65% EtOAc/hexane).

$^1$H NMR (500 MHz, $CD_3OD$) δ (ppm): 7.49 (s, 1H), 7.40 (s, 1H), 4.37 (m, 4H), 3.91 (m, 4H), 2.61 (s, 3H).

4-chloro-5-(2-chloroethoxy)-1-benzothiophene-2-sulfonamide $^1$H NMR (500 MHz, $d_6$-acetone) δ (ppm): 7.98 (d, J=8.9 Hz 1H), 7.91 (s, 1H), 7.48 (d, J=8.9 Hz, 1H), 7.17 (bs, 2H), 4.52 (t, J=5.2 Hz, 2H), 4.02 (t, J=5.2 Hz, 2H).

7-chloro-5-(2-chloroethoxy)-1-benzothiophene-2-sulfonamide $^1$H NMR (400 MHz, $CDCl_3$) δ (ppm): 7.86 (s, 1H), 7.56 (d, J=2.2 Hz, 1H), 7.29 (d, J=2.2 Hz, 1H), 7.12 (bs, 2H), 4.39 (t, J=5.3 Hz, 2H), 3.94 (t, J=5.1 Hz, 2H).

5-(2-chloroethoxy)-7-fluoro-3-methyl-benzothiophene-2-sulfonamide $^1$H NMR (500 MHz, $d_6$ acetone) δ (ppm): 7.35 (d, J=2.0 Hz, 1H), 7.14 (bs, 2H), 7.06 (dd, J=11.2 Hz, 2.1 Hz, 1H), 4.46 (t, J=5.3 Hz, 2H), 3.98 (t, J=5.0 Hz, 2H), 2.68 (s, 3H).

5,6-bis(3-chloroproxy)-3-methyl-1-benzothiophene-2-sulfonamide $^1$H NMR (500 MHz, $CD_3OD$) δ (ppm): 7.45 (s, 1H), 7.34 (s, 1H), 4.25 (m, 4H), 3.85 (m, 4H), 2.65 (s, 3H); 2.3 (m, 4H); MS m/z 412 (M+1).

5,6-bis(3-chloroproxy)-3-ethyl-1-benzothiophene-2-sulfonamide

Purified by silica gel chromatography (EtOAc/Hexane=2/3).

¹H NMR (500 MHz, CD₃OD) δ (ppm): 7.45 (s, 1H), 7.35 (s, 1H), 4.22 (m, 4H), 3.82 (m, 4H), 3.20 (q, 2H), 2.30 (m, 4H), 1.30 (t, 3H).

5,6-bis(3-chloroproxy)-4,7-difluoro-3-methyl-1-benzothiophene-2-sulfonamide

¹H NMR (500 MHz, CDCl₃) δ (ppm): 4.4 (two t, 4H), 3.85 (m, 4H); 2.8 (s, 3H), 2.3 (m, 4H); MS m/z 448 (M+1).

5,6-bis(3-chloroproxy)-4,7-difluoro-3-ethyl-1-benzothiophene-2-sulfonamide

Purified by silica gel chromatography (EtOAc/Hexane=2/3).

¹H NMR (500 MHz, CD₃OD) δ (ppm): 4.40 (t, 2H), 4.30 (t, 2H), 3.82 (m, 4H), 3.22 (q, 2H), 2.26 (m, 4H), 1.36 (t, 3H).

5,6-bis(3-chloroproxy)-4,7-difluorol-1-benzothiophene-2-sulfonamide

¹H NMR (500 MHz, CD₃OD) δ (ppm): 7.9 (d, 1H), 4.24 (m, 4H), 3.85 (m, 4H); 2.2 (m, 4H); MS m/z 434 (M+1).

6-[(triisopropylsilyl)oxy]-1-benzothiophene-2-sulfonamide

¹H NMR (CDCl₃) δ (ppm): 7.86 (s, 1H), 7.76 (d, 1H), 7.33 (s, 1H), 7.08 (d, 1H), 5.08 (s, 2H), 1.35 (m, 3H), 1.18 (d, 18).

5-vinyl-benzo[b]thiophene-2-sulfonamide

¹H NMR (400 MHz, DMSO-d₆) δ (ppm): 8.03-8.00 (m, 2H); 7.87-7.85 (br s, 3H); 7.67 (dd, J=8.4, 1.8, 1H); 6.83 (dd, J=17.6, 11.0, 1H); 5.93 (d, J=17.6, 1H); 5.33 (d, J=11.0, 1H).

Method C. 4,7-Dichloro-5-Methyl-1-Benzothiophene-2-Sulfonamide

To a stirred solution of diisopropylamine (2.04 mL, 14.6 mmol, 1.30 eq) in anhydrous tetrahydrofuran (50 mL) at 0° C. under nitrogen was slowly added n-butyllithium (6.3 mL, 16 mmol, 1.4 eq). After stirring for 30 min, this solution was transferred via canula onto a stirred solution of 4,7-dichloro-5-methyl-1-benzothiophene (2.43 g, 11.2 mmol, 1 eq) in anhydrous tetrahydrofuran (200 mL) at −78° C. The reaction mixture was allowed to warm up to −40° C., placed under SO₂ and slowly warmed up to room temperature. The SO₂ was removed and the reaction mixture was concentrated. The lithium 4,7-dichloro-5-methyl-1-benzothiophene-2-sulfinate salt was triturated in a mixture of ethyl acetate and hexane, filtered off, rinsed with hexane and dried under high vacuum. The solid was suspended in dichloromethane (200 mL) and treated with N-chlorosuccinimide (1.72 g, 12.9 mmol, 1.15 eq). After stirring for 1 hour at room temperature, the reaction mixture was filtered through celite and concentrated. The residue was dissolved in acetone (150 mL), treated with ammonium hydroxide (15 mL) for 1 hour, concentrated and dried under high vacuum. The resulting solid was triturated in dichloromethane, filtered off, rinsed with dichloromethane and dried under high vacuum to afford the title compound as a beige solid.

¹H NMR (400 MHz, DMSO-d₆) δ (ppm): 8.07 (bs, 2H), 7.90 (s, 1H), 7.74 (s, 1H), 2.49 (s, 3H).

Preparative Example 53

Tert-Butyl [(5-{[(Triisopropylsilyl)Oxy]Methyl}-Thieno[3,2-b]Thien-2-Yl)-Sulfonyl]Carbamate Step A: To a stirred mixture of 5-formylthieno[3,2-b]thiophene-2-sulfonamide (0.57 g, 2.3 mmol), prepared according to Prugh et al., *J. Med. Chem.*, 1991, 34, 1805-1818, in distilled THF (6 mL) at ambient temperature under nitrogen was added triethylamine (0.64 mL, 4.6 mmol), followed by Boc₂O (0.75 g, 3.5 mmol) and a catalytic amount of DMAP. After stirring for 5 h, the reaction became a homogeneous solution. The reaction was quenched with 2 N HCl at 0° C. and extracted with EtOAc. The organic layer was collected, washed with brine, dried with Na₂SO₄, and concentrated in vacuo to give the product which was used as is in the next step.

Step B: The crude residue was dissolved in MeOH/THF (1:1, 6 mL) and cooled to 0° C. To the stirred reaction solution was added NaBH₄ (0.17 g, 4.6 mmol). After stirring for 2 h, the reaction was quenched with cold 2 N HCl, and extracted with EtOAc. The organic layer was collected, washed with brine, dried with Na₂SO₄, and concentrated in vacuo to give the crude product.

¹H NMR (500 MHz, CDCl₃) δ (ppm): 7.99 (s, 1H), 7.72 (bs, 1H), 7.22 (s, 1H), 4.95 (s, 2H), 1.43 (s, 9H).

Step C: To a stirred solution of the crude residue from Step B in anhydrous DMF (6 mL) at 0° C. was added Hunig's base (0.80 mL, 4.6 mmol) and TIPSCl (0.73 mL, 3.5 mmol). After addition of the reagents, the reaction mixture was warmed to ambient temperature and stirred for 5 h. The progress of the reaction was monitored by TLC (40/10/1 CHCl₃/MeOH/conc. NH₄OH). An additional 0.4 mL of Hunig's base and 0.37 mL of TIPSCl was added to the reaction mixture to drive it to completion. The reaction mixture was stirred for another 17.5 h and partitioned between EtOAc and cold 2 N HCl. The organic layer was washed with brine, dried with Na₂SO₄, and concentrated in vacuo.

Purification via chromatography using the Biotage Horizon (25 M cartridge; 0% to 100% EtOAc/hexane over 10 column volumes; flow rate=25 mL/min) provided the desired compound as a pale yellow oil.

¹H NMR (500 MHz, CDCl₃) δ (ppm): 8.00 (s, 1H), 7.47 (bs, 1H), 7.16 (s, 1H), 5.08 (s, 2H), 1.43 (s, 9H), 1.20 (m, 3H), 1.08 (s, 18H).

Preparative Example 54

Tert-Butyl [(5-{[(Triisopropylsilyl)Oxy]Methyl}-Thieno[2,3-b]Thien-2-Yl)-Sulfonyl]Carbamate Step A: Utilizing the procedure described in Example 44, Step A, methyl 5-(aminosulfonyl)thieno[2,3-b]thiophene-2-carboxylate (0.1579 g, 0.57 mmol), prepared according to Prugh et al., *J. Med. Chem.*, 1991, 34, 1805-1818, was converted to the Boc-protected sulfonamide and used without further purification.

¹H NMR (500 MHz, CDCl₃) δ (ppm): 9.11 (bs, 1H), 8.00 (s, 1H), 7.98 (s, 1H), 3.93 (s, 3H), 1.40 (9H).

Step B: To a stirred solution of the product obtained from Step A (0.57 mmol) in anhydrous ether (5 mL) was added a 1 M solution of LAH in ether (1.1 mL, 1.1 mmol) at 0° C. under N₂. The reaction mixture was allowed to stir at 0° C. for 17 h. Another 0.5 mL of LAH was added to the reaction to drive it to completion. After 2 h, the reaction was quenched with 2 N HCl. The resulting mixture was extracted with EtOAc. The organic layer was collected, washed with brine, dried over Na₂SO₄, and concentrated in vacuo. The crude material was used as is in the next reaction.

¹H NMR (500 MHz, CDCl₃) δ (ppm): 7.94 (s, 1H), 7.80 (bs, 1H), 7.20 (s, 1H), 4.97 (s, 2H), 1.46 (9H).

Step C: Utilizing the procedure described in Example 44, Step C, the product obtained from Step B (0.57 mmol) was converted to the desired product.

¹H NMR (500 MHz, CDCl₃) δ (ppm): 8.00 (bs, 1H), 7.91 (s, 1H), 7.10 (s, 1H), 5.03 (s, 2H), 1.46 (9H), 1.20 (m, 3H), 1.13 (s, 18H).

Preparative Example 55

Method A. Tert-Butyl [(5-Methyl-1-Benzothien-2-Yl)-Sulfonyl]Carbamate

To a stirred solution of 5-methyl-1-benzothiophene-2-sulfonamide (2.0 g, 8.8 mmol, 1 eq) in anhydrous dichloromethane (30 mL) at room temperature was added 4-(dimethylamino)pyridine (108 mg, 0.88 mmol, 0.10 eq) followed by triethylamine (1.35 mL, 9.68 mmol, 1.10 eq) and di-tert-butyl dicarbonate (2.02 g, 9.24 mmol, 1.05 eq). After 16 h the reaction mixture was concentrated and a saturated solution of ammonium chloride (50 mL) was added followed by dichloromethane (100 mL). The phases were separated, the aqueous phase was extracted twice with dichloromethane and the combined organic layers were dried over anhydrous sodium sulfate, filtered and concentrated. Purification by flash chromatography on silica gel (ethyl acetate/dichloromethane, 1:1) afforded the product.

$^1$H NMR (400 MHz, DMSO-d$_6$) δ (ppm): 11.95 (bs, 1H), 7.92 (d, J=8.4 Hz, 1H), 7.89 (bs, 1H), 7.79 (s, 1H), 7.33 (d, J=8.4 Hz, 1H), 2.42 (s, 3H), 1.31 (s, 9H).

Method B. Tert-Butyl [(5-Morpholinomethyl)-1-Benzothien-2-Yl)Sulfonyl]Carbamate To a stirred solution of the sulfonamide (1.38 g, 4.42 mmol, 1 eq) in anhydrous dichloromethane (30 mL) at room temperature was added 4-(dimethylamino)pyridine (54 mg, 0.44 mmol, 0.10 eq) followed by triethylamine (0.68 mL, 4.9 mmol, 1.1 eq) and di-tert-butyl dicarbonate (1.17 g, 5.08 mmol, 1.15 eq). After 5 h the reaction mixture was concentrated and the residue was purified by flash chromatography on silica gel (methanol/dichloromethane/ammonium hydroxide, 5:94:1 to 49:49:2) to afford the title compound as a beige solid.

MS m/z 413 (M+1).

Utilizing the foregoing procedures, the following compounds were prepared:

tert-butyl 5-vinylbenzo[b]thiophen-2-ylsulfonylcarbamate

Used crude in the next reaction.

tert-butyl {[4,7-dichloro-5-methyl-1-benzothiophen-2-yl]sulfonyl}carbamate $^1$H NMR (400 MHz, DMSO-d$_6$) δ (ppm): 8.01 (s, 1H), 7.81 (s, 1H), 2.49 (s, 3H), 1.36 (s, 9H).

tert-butyl {[4-chloro-5-(2-chloroethoxy)-3-methyl-1-benzothien-2-yl]sulfonyl}carbamate It was prepared after purification by silica gel chromatography using 5% MeOH/CH$_2$Cl$_2$ as the eluant.

$^1$H NMR (500 MHz, CD$_3$OD) δ (ppm): 8.00 (d, 1H), 7.55 (d, 1H), 4.50 (t, 2H), 4.00 (t, 2H), 3.0 (s, 3H), 1.40 (s, 9H).

tert-butyl [7-chloro-5-(2-chloroethoxy)-3-methyl-1-benzothien-2-yl]sulfonyl carbamate It was prepared after purification by silica gel chromatography using 5% MeOH/CH$_2$Cl$_2$ as the eluant.

$^1$H NMR (500 MHz, CD$_3$OD) δ (ppm): 7.42 (d, 1H), 7.35 (d, 1H), 4.40 (t, 2H), 3.90 (t, 2H), 2.64 (s, 3H), 1.40 (s, 9H).

tert-butyl ({5-[4-(2-chloroethoxy)phenyl]-1,3,4-thiadiazol-2-yl}sulfonyl)carbamate $^1$H NMR (500 MHz, CD$_3$OD) δ (ppm): 8.04 (d, 2H), 7.18 (d, 2H), 4.40 (t, 2H), 3.90 (t, 2H), 1.44 (s, 9H); MS m/z 420 (M+1).

tert-butyl ({5-[4-(3-chloropropoxy)phenyl]}sulfonyl)carbamate

It was prepared as a foam.

$^1$H NMR (400 MHz, CDCl$_3$) δ (ppm): 8.0 (d, 2H), 7.0 (d, 2H), 4.2 (t, 2H), 3.80 (t, 2H), 2.3 (m, 2H), 1.5 (s, 9H).

tert-butyl ({5-[3,4-bis(3-chloropropoxy)phenyl]thiophen-2-yl}sulfonyl)carbamate

It was prepared and purified by silica gel chromatography (5% of MeOH in CH$_2$Cl$_2$).

$^1$H NMR (500 MHz, CD$_3$OD) δ (ppm): 7.70 (d, 1H), 7.32 (d, 1H), 7.04 (m, 2H), 7.00 (d, 1H), 4.20 (m, 4H), 3.80 (m, 4H), 2.22 (m, 4H), 1.42 (s, 9H).

tert-butyl ({5-[3,4-bis(3-chloropropoxy)-2-methylphenyl]thiophen-2-yl}sulfonyl)carbamate It was prepared and purified by silica gel chromatography (5% MeOH in CH$_2$Cl$_2$).

$^1$H NMR (500 MHz, CD$_3$OD) δ (ppm): 7.78 (d, 1H), 7.20 (d, 1H), 7.10 (d, 1H), 7.00 (d, 1H), 4.20 (t, 2H), 4.10 (t, 2H), 3.82 (m, 4H), 2.34 (s, 3H), 2.24 (m, 4H), 1.44 (s, 9H).

tert-butyl ({5-[4,5-bis(3-chloropropoxy)-2-methylphenyl]thiophen-2-yl}sulfonyl)carbamate It was prepared and purified by silica gel chromatography (5% MeOH in CH$_2$Cl$_2$).

$^1$H NMR (500 MHz, CD$_3$OD) δ (ppm): 7.78 (d, 1H), 7.10 (d, 1H), 7.00 (s, 1H), 6.98 (s, 1H), 4.20 (t, 2H), 4.10 (t, 2H), 3.80 (m, 4H), 2.36 (s, 3H), 2.22 (m, 4H), 1.44 (s, 9H).

tert-butyl {[5,6-bis(4-chlorobutoxy)-1-benzothien-2-yl]sulfonyl}carbamate

It was prepared after purification by silica gel chromatography using 5% MeOH/CH$_2$Cl$_2$ as the eluant.

$^1$H NMR (500 MHz, CD$_3$OD) δ (ppm): 8.00 (s, 1H), 7.40 (s, 1H), 7.30 (s, 1H), 7.25 (s, 1H), 4.18 (m, 4H), 3.72 (t, 4H), 2.15 (m, 8H), 1.40 (s, 9H).

tert-butyl {[5,6-bis(3-chloropropoxy)-1-benzothien-2-yl]sulfonyl}carbamate

It was prepared after purification by silica gel chromatography using 5% MeOH/CH$_2$Cl$_2$ as the eluant.

$^1$H NMR (500 MHz, CD$_3$OD) δ (ppm): 7.95 (s, 1H), 7.52 (s, 1H), 7.50 (s, 1H), 4.26 (m, 4H), 3.84 (t, 4H), 2.30 (m, 4H), 1.40 (s, 9H).

tert-butyl {[5,6-bis(3-chloroethoxy)-1-benzothien-2-yl]sulfonyl}carbamate

It was prepared in >90% yield, as a colorless oil.

$^1$H NMR (400 MHz, CDCl$_3$) δ (ppm): 8.0 (s, 1H), 7.8 (s, 1H), 7.4 (s, 1H), 7.35 (s, 1H), 4.4 (m, 4H), 3.90 (m, 4H).

tert-butyl {[5,6-bis(2-chloroethoxy)-4,7-difluoro-1-benzothien-2-yl]sulfonyl}carbamate $^1$H NMR (400 MHz, CDCl$_3$) δ (ppm): 8.1 (d, 1H), 7.8 (s, 1H), 4.5 (t, 2H), 4.45 (t, 2H), 3.85 (m, 4H), 1.5 (s, 9H).

tert-butyl {[5,6-bis(3-chloropropoxy)-3-methyl-1-benzothien-2-yl]sulfonyl}carbamate $^1$H NMR (500 MHz, CD$_3$OD) δ (ppm): 7.5 (brs, 1H), 7.28 (s, 1H), 7.24 (s, 1H), 4.25 (t, 4H), 3.8 (q, 4H); 2.7 (s, 3H), 2.4 (m, 4H), 1.4 (s, 9H).

tert-butyl {[5,6-bis(3-chloropropoxy)-3-ethyl-1-benzothien-2-yl]sulfonyl}carbamate Purified by silica gel chromatography (MeOH/CH$_2$Cl$_2$=0.5/9.5).

$^1$H NMR (500 MHz, CD$_3$OD) δ (ppm): 7.50 (s, 1H), 7.40 (s, 1H), 4.25 (m, 4H), 3.82 (m, 4H), 3.20 (q, 2H), 2.30 (m, 4H), 1.40 (s, 9H), 1.30 (t, 3H).

tert-butyl {[5,6-bis(3-chloropropoxy)-4,7-difluoro-3-methyl-1-benzothien-2-yl]sulfonyl}-carbamate $^1$H NMR (500 MHz, CDCl$_3$) δ (ppm): 4.4 (two t, 4H), 3.82 (m, 4H), 2.85 (s, 3H), 2.3 (m, 4H), 1.5 (s, 9H).

tert-butyl {[5,6-bis(2-chloroethoxy)-4,7-difluoro-3-ethyl-1-benzothien-2-yl]sulfonyl}carbamate $^1$H NMR (500 MHz, CD$_3$OD) δ (ppm): 4.50 (t, 2H), 4.40 (t, 2H), 3.86 (m, 4H), 3.28 (q, 2H), 1.40 (s, 9H), 1.30 (t, 3H).

tert-butyl {[5,6-bis(3-chloropropoxy)-4,7-difluoro-3-ethyl-1-benzothien-2-yl]sulfonyl}carbamate $^1$H NMR (500 MHz, CD$_3$OD) δ (ppm): 4.42 (t, 2H), 4.32 (t, 2H), 3.86 (m, 4H), 3.28 (q, 2H), 2.26 (m, 4H), 1.40 (s, 9H), 1.30 (t, 3H).

tert-butyl {[5,6-bis(3-chloropropoxy)-4,7-difluoro-1-benzothien-2-yl]sulfonyl}carbamate $^1$H NMR (500 MHz, CDCl$_3$) δ (ppm): 8.1 (d, 1H), 8.2 (d, 1H), 4.4 (two t, 4H), 3.82 (t, 4H), 2.25 (m, 4H), 1.5 (s, 9H).

tert-butyl ({6-[triisopropylsilyl)oxy]-1-benzothien-2-yl}sulfonyl)carbamate $^1$H NMR (CDCl$_3$) δ (ppm): 8.02 (s, 1H), 7.77 (d, 1H), 7.39 (s, 1H), 7.33 (s, 1H), 7.07 (d, 1H), 1.46 (s, 9H), 1.32 (m, 3H), 1.15 (d, 18); MS m/z 508 (M+23).

Preparative Example 56

General Methods for Dialkoxyphosphorylmethyl-Sulfonylcarbamates

Method A. Diethyl({(Tert-Butoxycarbonyl)[(5-Methyl-1-Benzothien-2-Yl)Sulfonyl]Amino}Methyl)Phosphonate To a stirred solution of tert-butyl [(5-methyl-1-benzothien-2-yl)sulfonyl]carbamate (2.6 g, 7.9 mmol, 1 eq) in anhydrous tetrahydrofuran (25 mL) at room temperature was added diethyl hydroxymethylphosphonate (1.4 mL, 9.5 mmol, 1.2 eq) followed by triphenylphosphine (2.5 g, 9.5 mmol, 1.2 eq) and diisopropyl azodicarboxylate (2.03 mL, 10.3 mmol, 1.30 eq). After 24 h the reaction mixture was diluted with ethyl acetate (100 mL) and the organic phase was washed with aqueous sodium hydroxide (1N, 100 mL), dried over anhydrous sodium sulfate and concentrated. The residue was purified by flash chromatography on silica gel (ethyl acetate/dichloromethane 8:92 to 1:9), then re-purified by flash chromatography on silica gel (ethyl acetate/hexane: 3:7 to 1:1) followed by drying under high vacuum to afford the product.

$^1$H NMR (400 MHz, DMSO-d$_6$) δ (ppm): 8.22 (d, J=0.6 Hz, 1H), 8.01 (d, J=8.4 Hz, 1H), 7.84 (t, J=0.8 Hz, 1H), 7.41 (ddd, J=8.4, 1.6, 0.5 Hz), 4.21 (d, J=9.6 Hz, 2H), 4.03 (m, 4H), 2.44 (s, 3H), 1.32 (s, 9H), 1.22 (t, J=10.8 Hz, 6H); MS m/z 378 (M+1-Boc).

Method B. Diethyl [((Tert-Butoxycarbonyl){[5-(Morpholin-4-Yl-Methyl)-1-Benzothien-2-Yl]Sulfonyl}Amino)Methyl]Phosphonate To a stirred solution of tert-butyl [(5-morpholinomethyl)-1-benzothien-2-yl)sulfonyl]carbamate (1.57 g, 3.81 mmol, 1 eq) in anhydrous tetrahydrofuran (16 mL) at room temperature was added diethyl hydroxymethylphosphonate (0.68 mL, 4.2 mmol, 1.1 eq) followed by triphenylphosphine (1.2 g, 4.6 mmol, 1.2 eq) and diethyl azodicarboxylate (0.78 mL, 4.9 mmol, 1.3 eq). After 18 h, N,N-dimethylformamide (9 mL) was added followed by further amounts of triphenylphosphine (0.30 g, 1.1 mmol, 0.30 eq) and diethyl azodicarboxylate (0.60 mL, 3.8 mmol, 1.0 eq). The reaction mixture was warmed to 30° C., stirred and additional 24 h then diluted with ethyl acetate (100 mL) and water (100 mL). The organic phase was separated, washed with brine, dried over sodium sulfate and concentrated. The residue was purified by flash chromatography on silica gel (ethyl acetate/dichloromethane: 1:1 to methanol/dichloromethane: 1:9) then dried under high vacuum to afford the title compound.

MS m/z 563 (M+1).

Method C. Preparation of Tert-Butyl (4,7-Dichloro-5-Methyl-1-Benzothien-2-Yl)-Sulfonyl((Dimethoxy Phosphoryl)Methyl)Carbamate To a stirred solution of the carbamate (820 mg, 2.07 mmol, 1 eq) in anhydrous tetrahydrofuran (50 mL) at room temperature was added dimethyl hydroxymethylphosphonate (350 mg, 2.48 mmol, 1.20 eq) followed by triphenylphosphine (1.1 g, 4.1 mmol, 2.0 eq) and diethyl azodicarboxylate (0.70 mL, 4.4 mmol, 2.1 eq). After 48 h the reaction mixture was diluted with ethyl acetate (100 mL) and the organic phase was washed with sodium hydroxide (1N, 100 mL), dried over sodium sulfate and concentrated. The residue was purified by flash chromatography on silica gel (ethyl acetate/dichloromethane: 4:96) then dried under high vacuum to afford the product.

$^1$H NMR (400 MHz, CDCl$_3$) δ (ppm): 8.26 (s, 1H), 7.40 (s, 1H), 4.33 (d, J=9.6 Hz, 2H), 3.83 (s, 3H), 3.80 (s, 3H), 2.52 (s, 3H), 1.49 (s, 9H); MS m/z 540 (M+Na) [(major isotope].

Utilizing the foregoing procedure, the following compound was prepared:

tert-butyl 5-vinyl-1-benzothien-2-yl)-sulfonyl((dimethoxyphosphoryl)methyl)carbamate The product was chromatographed on silica gel (eluent 65% ethyl acetate/hexanes) to afford product, contaminated with some triphenylphosphine oxide, and used as in the next reaction.

Method D. Preparation of Diethyl {[{[5,6-Bis(2-Chloroethoxy)-1-Benzothien-2-Yl]-Sulfonyl}(Tert-Butoxycarbonyl)Amino]Methyl}Phosphonate The N-Boc sulfonamide (2.54 g, 5.4 mmol), triphenylphosphine resin (7.2 g, 3 equiv), and diethyl-hydroxymethylphosphonate (2.5 mL, 3 equiv) were combined and stirred in anhydrous THF. The stirred mixture was cooled to 0° C. and diisopropyl azodicarboxylate (4.3 mL, 3 equiv) was added dropwise over a 0.2 h period. The resulting pale yellow solution was stirred at room temperature overnight. The volatile components were then removed in vacuo and the residue purified by silica gel flash chromatography (EA/Hex=1:2, followed by 3% MeOH/CH$_2$Cl$_2$) to give the product which was contaminated with a small amount of diethyl-hydroxymethylphosphonate).

$^1$H NMR (400 MHz, CDCl$_3$) δ (ppm): 8.0 (s, 1H), 7.35 (s, 1H), 7.3 (s, 1H), 4.3 (m, 4H), 4.25 (d, 2H), 4.1 (m, 4H), 3.85 (m, 4H), 1.4 (s, 9H), 1.3 (t, 6H).

Utilizing the foregoing procedures, the following compounds were prepared:

diethyl[((tert-butoxycarbonyl) {[4-chloro-5-(2-chloroethoxy)-3-methyl-1-benzothien-2-yl]-sulfonyl}amino)methyl]phosphonate It was prepared after purification using 50% EtOAc/hexane as the chromatography eluant.

$^1$H NMR (500 MHz, CD$_3$OD) δ (ppm): 7.84 (d, 1H), 7.42 (d, 1H), 4.40 (m, 4H), 4.20 (t, 4H), 3.90 (t, 2H), 2.90 (s, 3H), 1.40 (t, 6H), 1.38 (s, 9H).

diethyl {[(tert-butoxycarbonyl)({5-[4-(3-chloropropoxy)phenyl]-1,3,4-thiadiazol-2-yl}sulfonyl)-amino]methyl}phosphonate was prepared and purified using [EtOAc/hexane (1:2), followed by 3% MeOH/CH$_2$Cl$_2$], and was slightly contaminated with hydroxymethyl phosphonate.

$^1$H NMR (400 MHz, CDCl$_3$) δ (ppm): 8.0 (d, 2H), 7.0 (d, 2H), 4.4 (d, 2H), 4.2 (m), 3.8 (t, 2H), 2.3 (m, 2H), 1.45 (s, 9H), 1.3 (m); MS m/z 484 (M−100).

diethyl [((tert-butoxycarbonyl){[7-chloro-5-(2-chloroethoxy)-3-methyl-1-benzothien-2-yl]-sulfonyl}amino)methyl]phosphonate It was prepared and purified using 5% MeOH/CH$_2$Cl$_2$ as the chromatography eluant.

$^1$H NMR (500 MHz, CD$_3$OD) δ (ppm): 7.40 (d, 1H), 7.32 (d, 1H), 4.40 (t, 2H), 4.15 (m, 4H), 3.96 (t, 2H), 3.48 (d, 2H), 2.64 (s, 3H), 1.28 (t, 6H), 1.40 (s, 9H); MS m/z 490 (M−100).

diethyl-{[(tert-butoxycarbonyl)({6-[(6-chlorohexyl)oxy]-1-benzothien-2-yl}sulfonyl)amino]-methyl}phosphonate.

$^1$H NMR (CDCl$_3$) δ (ppm): 8.11 (s, 1H), 7.80 (d, 1H), 7.10 (d, 1H), 4.33 (d, 2H), 4.22 (quintet, 4H), 4.10 (t, 2H), 3.60 (t, 2H), 1.88 (m, 4H), 1.46 (s, 9H), 1.37 (t, 6H); MS m/z 598 (M+1).

diethyl-{[(tert-butoxycarbonyl)({5-[4-(3-chloroethoxy)phenyl]-1,3,4-thiadiazol-2-yl}sulfonyl)-amino]methyl}phosphonate $^1$H NMR (500 MHz, CD$_3$OD) δ (ppm): 8.04 (d, 2H), 7.18 (d, 2H), 4.40 (d, 2H), 4.39 (q, 2H), 4.20 (m, 4H), 3.90 (t, 2H), 1.44 (s, 9H), 1.40 (t, 6H); MS m/z 471 (M+1-100).

diethyl-{[(tert-butoxycarbonyl)({5-[3,4-bis(3-chloropropoxy)phenyl]thiophen-2-yl}sulfonyl)-amino]methyl}phosphonate It was prepared and purified by silica gel chromatography (5% MeOH in CH$_2$Cl$_2$).

$^1$H NMR (500 MHz, CD$_3$OD) δ (ppm): 7.80 (d, 1H), 7.60 (d, 1H), 7.30 (m, 2H), 7.08 (d, 1H), 4.30 (d, 2H), 4.20 (m, 8H), 3.80 (m, 4H), 2.22 (m, 4H), 1.42 (s, 9H), 1.36 (m, 6H).

diethyl-{[(tert-butoxycarbonyl)({5-[3,4-bis(3-chloropropoxy)-2-methylphenyl]thiophen-2-yl}-sulfonyl)-amino]methyl}phosphonate It was prepared and purified by silica gel chromatography (5% MeOH in CH$_2$Cl$_2$).

$^1$H NMR (500 MHz, CD$_3$OD) δ (ppm): 7.80 (d, 1H), 7.12 (d, 1H), 7.08 (d, 1H), 6.98 (d, 1H), 4.30 (d, 2H), 4.20 (m, 6H), 4.10 (t, 2H), 3.80 (m, 4H), 2.30 (s, 3H), 2.22 (m, 4H), 1.42 (s, 9H), 1.36 (m, 6H).

diethyl-{[(tert-butoxycarbonyl)({5-[4,5-bis(3-chloropropoxy)-2-methylphenyl]thiophen-2-yl}-sulfonyl)-amino]methyl}phosphonate It was prepared and purified by silica gel chromatography (5% MeOH in CH$_2$Cl$_2$).

$^1$H NMR (500 MHz, CD$_3$OD) δ (ppm): 7.84 (d, 1H), 7.14 (d, 1H), 7.00 (s, 1H), 6.98 (s, 1H), 4.30 (d, 2H), 4.20 (m, 8H), 3.80 (m, 4H), 2.40 (s, 3H), 2.22 (m, 4H), 1.42 (s, 9H), 1.34 (m, 6H).

diethyl-{[{[5,6-bis(4-chlorobutoxy)-1-benzothien-2-yl]sulfonyl}(tert-butoxycarbonyl)amino]-methyl}phosphonate It was prepared and purified using 5% MeOH/CH$_2$Cl$_2$ as the chromatography eluant.

$^1$H NMR (500 MHz, CDCl$_3$) δ (ppm): 8.08 (s, 1H), 7.50 (s, 1H), 7.46 (s, 1H), 4.35 (d, 2H), 4.20 (m, 8H), 3.70 (m, 4H), 2.05 (m, 8H), 1.42 (s, 9H), 1.38 (t, 6H); MS m/z 576 (M−100).

diethyl-{[{[5,6-bis(3-chloropropoxy)-1-benzothien-2-yl]sulfonyl}(tert-butoxycarbonyl)amino]-methyl}phosphonate It was prepared in 89% yield and purified using 5% MeOH/CH$_2$Cl$_2$ as the chromatography eluant.

$^1$H NMR (500 MHz, CDCl$_3$) δ (ppm): 8.08 (s, 1H), 7.32 (s, 1H), 7.30 (s, 1H), 4.30 (d, 2H), 4.20 (m, 8H), 3.82 (t, 4H), 2.38 (m, 4H), 1.42 (s, 9H), 1.38 (t, 6H); MS m/z 548 (M−100).

diethyl {[{[5,6-bis(2-chloroethoxy)-4,7-difluoro-1-benzothien-2-yl]sulfonyl}(tert-butoxycarbonyl)amino]methyl}phosphonate $^1$H NMR (400 MHz, CDCl$_3$) δ (ppm): 8.22 (d, 1H), 4.55 (t, 2H), 4.45 (t, 2H), 4.3 (d, 2H), 4.2 (m, 4H), 1.5 (s, 9H), 1.4 (t, 6H).

diethyl {[{[5,6-bis(2-chloroethoxy)-4,7-difluoro-3-ethyl-1-benzothien-2-yl]sulfonyl}(tert-butoxycarbonyl)amino]methyl}phosphonate Purified by silica gel chromatography (EtOAc/Hexane=3/7).

$^1$H NMR (500 MHz, CD$_3$OD) δ (ppm): 4.58 (t, 2H), 4.44 (t, 2H), 4.40 (d, 2H), 4.25 (m, 4H), 3.90 (m, 4H), 3.14 (q, 2H), 1.40 (m, 15H), 1.30 (t, 3H); MS m/z 585 (M−100).

diethyl {[{[5,6-bis(3-chloropropoxy)-3-methyl-1-benzothien-2-yl]sulfonyl}(tert-butoxycarbonyl)amino]methyl}phosphonate $^1$H NMR (500 MHz, CDCl$_3$) δ (ppm): 7.27 (s, 1H), 7.22 (s, 1H), 4.4 (d, 2H), 4.2 (m, 4H), 3.8 (m, 4H), 2.6 (s, 3H), 2.4 (m, 4H), 1.55 (m, 6H), 1.5 (s, 9H).

diethyl {[{[5,6-bis(3-chloropropoxy)-3-ethyl-1-benzothien-2-yl]-sulfonyl}(tert-butoxycarbonyl)amino]methyl}phosphonate Purified by silica gel chromatography (EtOAc/Hexane=3/7).

$^1$H NMR (500 MHz, CD$_3$OD) δ (ppm): 7.50 (s, 1H), 7.40 (s, 1H), 4.20 (m, 8H), 3.85 (d, 2H), 3.80 (m, 4H), 3.10 (q, 2H), 2.30 (m, 4H), 1.40 (s, 9H), 1.30 (m, 9H); MS m/z 576 (M−100).

diethyl {[{[4,7-difluoro-5,6-bis(3-chloropropoxy)-3-ethyl-1-benzothien-2-yl]sulfonyl}(tert-butoxycarbonyl)amino]methyl}phosphonate Purified by silica gel chromatography (EtOAc/Hexane=3/7).

$^1$H NMR (500 MHz, CD$_3$OD) δ (ppm): 4.40 (t, 2H), 4.30 (t, 2H), 4.30 (m, 8H), 3.85 (d, 2H), 3.82 (m, 4H), 3.14 (q, 2H), 2.42 (m, 4H), 1.40 (s, 9H), 1.35 (m, 9H); MS m/z 712 (M−100).

dimethyl ({(tert-butoxycarbonyl)[(5-{[(triisopropylsilyl)oxy]methyl}-thieno[3,2-b]thien-2-yl)-sulfonyl]amino}methyl)phosphonate Purification using the Biotage Horizon (25 S cartridge; 0% to 100% EtOAc/hexane over 10 column volumes; flow rate=25 mL/min) provided the product as a pale yellow oil which solidified upon standing.

$^1$H NMR (500 MHz, CDCl$_3$) δ (ppm): 8.10 (s, 1H), 7.14 (s, 1H), 5.08 (s, 2H), 4.31 (d, 2H), 3.82 (s, 6H), 1.46 (s, 9H), 1.20 (m, 3H), 1.13 (s, 18H).

Dimethyl ({(tert-butoxycarbonyl)[(5-{[(triisopropylsilyl)oxy]methyl}-thieno[2,3-b]thien-2-yl)-sulfonyl]amino}methyl)phosphonate Purification was accomplished by two silica gel plate chromatographies (1000 micron, with 40/10/1 CHCl$_3$/MeOH/conc. NH$_4$OH, 2× with 50% EtOAc/hexanes).

$^1$H NMR (500 MHz, CDCl$_3$) δ (ppm): 8.03 (s, 1H), 7.11 (s, 1H), 5.05 (s, 2H), 4.32 (d, 2H), 3.82 (d, 6H), 1.48 (s, 9H), 1.20 (m, 3H), 1.14 (s, 18H).

Diethyl-{[(tert-butoxycarbonyl)({6-[(triisopropylsilyl)oxy]-1-benzothien-2-yl}sulfonyl)-amino]methyl}phosphonate $^1$H NMR (CDCl$_3$) δ (ppm): 8.09 (s, 1H), 7.77 (d, 1H), 7.33 (s, 1H), 7.08 (d, 1H), 4.34 (d, 2H), 4.20 (quartet, 4H), 1.45 (s, 9H), 1.36 (t, 6H), 1.32 (m, 3H), 1.16 (d, 18); MS m/z 636 (M+1).

Preparative Example 57

Dimethyl [((Tert-Butoxycarbonyl){[5-(Hydroxymethyl)Thieno[3,2-B]Thien-2-Yl]Sulfonyl}Amino)Methyl]-Phosphonate To a stirred solution of the product obtained from prior Preparative Example (1.4515 g, 2.3 mmol) in THF (15 mL) at 0° C. was added a 1 M solution of TBAF in THF (2.5 mL, 2.5 mmol). After stirring for 10 min., the reaction mixture was complete as indicated by TLC (50% EtOAc/hexane). The reaction was partitioned between EtOAc and saturated aqueous NaHCO$_3$ solution. The organic layer was washed with brine, dried with Na$_2$SO$_4$, and concentrated in vacuo. Purification via chromatography using the Biotage Horizon (25 S cartridge; 0% to 100% EtOAc/hexanes over 10 column volumes; flow rate=25 mL/min) provided the desired compound as a colorless oil which solidified upon standing.

$^1$H NMR (500 MHz, CDCl$_3$) δ (ppm): 8.12 (s, 1H), 7.23 (s, 1H), 4.96 (bd, 2H), 4.31 (d, 2H), 3.82 (s, 6H), 1.45 (s, 9H).

Utilizing the foregoing procedure the following compound was prepared:

Dimethyl [((tert-butoxycarbonyl{[(5-(hydroxymethyl) thieno[2,3-b]thien-2-yl]-sulfonyl}amino)methyl]phosphonate Purification was accomplished by silica gel plate chromatography (1000 micron, 50% EtOAc/hexanes).

$^1$H NMR (500 MHz, CDCl$_3$) δ (ppm): 8.00 (s, 1H), 7.16 (s, 1H), 4.88 (s, 2H), 4.29 (d, 2H), 3.80 (d, 6H), 1.45 (s, 9H).

Preparative Example 58

Dimethyl [((Tert-Butoxycarbonyl){[5-(Chloromethyl)Thieno[3,2-b]Thien-2-Yl]-Sulfonyl}Amino) Methyl]Phosphonate To a stirred solution of the product obtained from the prior Example (0.3859 g, 0.82 mmol) in anhydrous CH$_2$Cl$_2$ (4 mL) at 0° C. under nitrogen was added triethylamine (0.17 mL, 1.2 mmol) followed by MsCl (0.095 mL, 1.2 mmol). After stirring for 1.5 h, added another 0.17 mL of triethylamine and 0.095 mL of MsCl to the reaction mixture to drive it to completion. The reaction mixture was allowed to stir for 22 h at 0° C., and then warmed to 12° C. for 3 h. The reaction mixture was partitioned between EtOAc and 2 N HCl/ice. The organic layer was washed with brine, dried with Na$_2$SO$_4$, and concentrated in vacuo to give a light yellow oil which solidified upon storage at −20° C. for 48 h.

$^1$H NMR (500 MHz, CDCl$_3$) δ (ppm): 8.14 (s, 1H), 7.32 (s, 1H), 4.87 (s, 2H), 4.31 (d, 2H), 3.82 (d, 6H), 1.46 (s, 9H).

Utilizing the foregoing procedure the following compound was prepared:

Dimethyl [((tert-butoxycarbonyl{[(5-(chloromethyl) thieno[2,3-b]-thien-2-yl]-sulfonyl}amino)methyl]phosphonate The crude pale yellow oil was used in the next reaction without further purification.

$^1$H NMR (500 MHz, CDCl$_3$) δ (ppm): 8.05 (s, 1H), 7.29 (s, 1H), 4.83 (s, 2H), 4.30 (d, 2H), 3.80 (d, 6H), 1.45 (s, 9H).

Preparative Example 59

Dimethyl ({(Tert-Butoxycarbonyl)[(5-{[(3-Chloropropyl)Thio]Methyl}Thieno[3,2-B]Thien-2-Yl)-Sulfonyl]Amino}Methyl)Phosphonate To a nitrogen-sparged, stirred solution of the product obtained from the prior Example (0.0759 g, 0.19 mmol) in acetone (1.0 mL) was added Cs$_2$CO$_3$ (0.1913 g, 0.56 mmol) followed by 3-chloropropanethiol (0.020 mL, 0.21 mmol). The reaction mixture was heated to 60° C. and stirred under N$_2$ for 1 h. The reaction mixture was cooled to ambient temperature and partitioned between EtOAc and 2 N HCl/ice. The organic layer was washed with brine, dried over Na$_2$SO$_4$, and concentrated in vacuo. The residue was purified by silica gel plate chromatography (1000 micron, 50% EtOAc/hexane) to give the desired product as a colorless oil.

$^1$H NMR (500 MHz, CDCl$_3$) δ (ppm): 8.10 (s, 1H), 7.20 (s, 1H), 4.33 (d, 2H), 4.02 (s, 2H), 3.82 (d, 6H), 3.64 (t, 2H), 2.77 (t, 2H), 2.05 (m, 2H), 1.45 (s, 9H); MS m/z 564 (M+1).

Preparative Example 60

Preparation of Diethyl [((Tert-Butoxycarbonyl){6-(4-Chlorobutoxy)-1-Benzothien-2-Yl] Sulfonyl}Amino)Methyl]Phosphonate To an anhydrous DMF (1 mL) solution of diethyl-{[(tert-butoxycarbonyl)({6-[(triisopropylsilyl)oxy]-1-benzothien-2-yl}sulfonyl)-amino]methyl}phosphonate (1.0 g, 1.57 mmol) was added 1-bromo-4-chlorobutane (0.81 g, 4.72 mmol) and 1.0 M tetrabutylammonium fluoride (1.88 mL, 1.88 mmol). The mixture was stirred at room temperature overnight. The reaction mixture was diluted with EtOAc, washed twice with water, and then brine. The organic layer was dried over anhydrous Na$_2$SO$_4$ and filtered. The filtrate was evaporated in vacuo. The crude residue was purified by silica gel chromatography using a gradient elution (33% EtOAc-hexanes to 50% EtOAc-hexanes) to give a colorless oil.

$^1$H NMR (CDCl$_3$) δ (ppm): 8.09 (s, 1H), 7.78 (d, 1H), 7.28 (s, 1H), 7.08 (d, 1H), 4.32 (d, 2H), 4.32 (d, 2H), 4.19 (quintet, 4H), 4.12 (m, 2H), 3.66 (m, 2H), 2.04 (m, 4H), 1.45 (s, 9H), 1.36 (t, 6H); MS m/z 570 (M+1).

Preparative Example 61

General Methods for the Sulfonamidomethyl-Phosphonic Acids and Esters

Method A. Preparation of [({[5-(Morpholin-4-Yl-Methyl)-1-Benzothien-2-Yl]-Sulfonyl}Amino)Methyl]Phosphonic Acid To a stirred solution of diethyl [((tert-butoxycarbonyl){[5-(morpholin-4-yl-methyl)-1-benzothien-2-yl] sulfonyl}amino)methyl]phosphonate (1.52 g, 2.70 mmol, 1.0 eq) in anhydrous dichloromethane (20 mL) at room temperature was added bromotrimethylsilane (1.07 mL, 8.10 mmol, 3.0 eq). After 18 h another portion of bromotrimethylsilane (0.80 mL, 6.1 mmol, 2.3 eq) was added and stirring was continued for an additional 5 h. Trifluoroacetic acid (5 mL) was added, the reaction mixture was stirred at room temperature for 2 h then concentrated. The residue was dissolved in methanol, stirred at room temperature for 2 h then methanol was evaporated; the residue was dissolved in ethyl acetate, concentrated and dried under high vacuum to afford the product as a yellow solid which was used for the next step without further purification.

$^1$H NMR (400 MHz, DMSO-d$_6$) δ (ppm): 8.35 (t, J=6.0 Hz, 1H), 8.19 (d, J=8.4 Hz, 1H), 8.12 (s, 1H), 8.06 (s, 1H), 7.64 (dd, J=8.4, 1.6 Hz, 1H), 4.45 (s, 2H), 3.95-3.55 (m, 4H), 3.25-3.05 (m, 4H), 3.00 (dd, J=13.2, 6.0 Hz, 2H); MS m/z 507 (M+1).

Method B. Preparation of [({[5-(2-Chloroethoxy)-1-Benzothien-2-Yl]-Sulfonyl}Amino)Methyl]Phosphonic Acid Step 1. To a stirred solution of 5-(2-chloroethoxy)-1-benzothiophene-2-sulfonamide (1.68 g, 5.76 mmol) in a 3:2 mixture of acetic anhydride (6.8 mL) and glacial acetic acid (4.2 mL) was added para-formaldehyde. The resulting suspension was warmed to 75° C. for 2.5 hrs or until all of the para-formaldehyde was consumed. To the resulting solution, was added trimethylsilylphosphite and the mixture was stirred at 110° C. for 1 hr. The mixture was cooled to room temperature and then concentrated in vacuo to give an overweight oil (2.4 g) which contained a 5:1 mixture of [({[5-(2-chloroethoxy)-1-benzothien-2-yl]sulfonyl}amino)methyl]phosphonic acid anhydride and [({[5-(2-chloroethoxy)-1-benzothien-2-yl]sulfonyl}amino)methyl]phosphonic acid. The mixture was used as is.

$^1$H NMR (500 MHz, CD$_3$OD) δ (ppm): 7.85 (s, 1H), 7.83 (d, J=8.9 Hz, 1H) minor, 7.78 (d, J=8.8 Hz, 1H) major, 7.47 (d, J=2.3 Hz, 1H) minor, 7.46 (d, J=2.3 Hz, 1H) major, 7.19 (dd, J=2.3, 8.8 Hz, 1H) minor, 7.17 (dd, J=2.3, 8.8 Hz, 1H) major 4.32-4.28 (m, 2H), 3.89-3.86 (m, 2H), 3.42 (bd, 2H); MS m/z 386 (M+1).

Step 2. The mixture of products obtained in the prior step was dissolved in anhydrous methylene chloride (20 mL) and stirred at room temperature with trimethylsilyl bromide (1.67 mL, 57.6 mmol) for 18 hrs. The mixture was concentrated in vacuo and the resulting residue was dissolved in methylene chloride-methanol (1:1) and stirred for 1 hr. The solution was concentrated in vacuo and dried in vacuo. The crude residue was triturated with methylene chloride (5 mL) to afford a white solid. The solid was collected, washed with methylene chloride (1 mL) and dried in vacuo to give 1.31 g of residue which was dissolved in 10% aqueous MeCN and purified by high pressure liquid chromatography (HPLC) using a reverse phase C$_{18}$ column to afford after lyophilization 1.27 g of [({[5-(2-chloroethoxy)-1-benzothien-2-yl]sulfonyl}amino)methyl]-phosphonic acid.

$^1$H NMR (500 MHz, CD$_3$OD) δ (ppm): 7.84 (s, 1H), 7.82 (d, J=9.0 Hz, 1H) 7.46 (d, J=2.4 Hz, 1H), 7.19 (dd, J=2.4, 9.0 Hz, 1H), 4.31 (t, J=6.0 Hz, 2H), 3.89 (t, J=6.0 Hz, 2H), 3.25 (d, J=13.5 Hz, 2H); MS m/z 386 (M+1).

Method C. Preparation of [({[4-Chloro-5-(2-Chloro-ethoxy)-1-Benzothien-2-Yl]Sulfonyl}-Amino)Methyl]Phosphonic Acid Step 1. Using step 1 of the prior Example, a 3:1 mixture of [({[4-chloro-5-(2-chloroethoxy)-1-benzothien-2-yl]sulfonyl}amino)-methyl]phosphonic acid anhydride, [({[4-chloro-5-(2-chloroethoxy)-1-benzothien-2-yl]sulfonyl}amino)methyl]phosphonic acid and 10% of N-acetyl byproducts were obtained which was used as is in the next step.

Step 2. Using the crude mixture obtained in the prior step and employing the conditions of step 2 of the prior Example, a mixture of the corresponding phoshonic acids was obtained which was used as is in the next step.

NAc product: $^1$H NMR (500 MHz, CD$_3$OD) δ (ppm): 8.25 (s, 1H), 7.90 (d, J=9.1 Hz, 1H) 7.45 (d, J=8.9 Hz, 1H), 4.43 (t, J=5.3 Hz, 2H), 4.29 (d, J=10.7 Hz, 2H), 3.93 (t, J=5.3 Hz, 2H), 2.45 (s, 3H); MS m/z 461 (M+1).

Step 3. The crude mixture of products obtained in the foregoing step was dissolved in methanol and stirred with potassium carbonate at room temperature for 18 hrs. The suspension was filtered and the resulting filtrate was evaporated. The residue was dissolved in 10% aqueous MeCN and purified by high pressure liquid chromatography (HPLC) using a reverse phase C$_{18}$ column to afford after lyophilization [({[4-chloro-5-(2-chloroethoxy)-1-benzothien-2-yl]sulfonyl}amino)-methyl]phosphonic acid.

$^1$H NMR (500 MHz, CD$_3$OD) δ (ppm): 7.95 (s, 1H), 7.87 (d, J=9.1 Hz, 1H) 7.41 (d, J=8.9 Hz, 1H), 4.42 (t, J=5.3 Hz, 2H), 3.93 (t, J=5.3 Hz, 2H), 3.29 (d, J=13.5 Hz, 2H); MS m/z 420 (M+1).

Using the foregoing procedure, the following compounds were prepared:

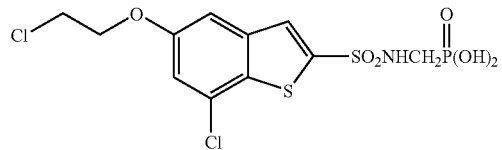

Step 1. A 3:1 mixture of [({[7-chloro-5-(2-chloroethoxy)-1-benzothien-2-yl]sulfonyl}amino)-methyl]phosphonic anhydride, [(acetyl{[7-chloro-5-(2-chloroethoxy)-1-benzothien-2-yl]-sulfonyl}amino)methyl]phosphonic acid and N-acetyl byproducts were obtained. The crude mixture was used as is in the next step.

Step 2. A mixture of [({[7-chloro-5-(2-chloroethoxy)-1-benzothien-2-yl]sulfonyl}amino)-methyl]phosphonic acid and [({[7-chloro-5-(2-chloroethoxy)-1-benzothien-2-yl]-sulfonyl}N-acetylamino)methyl]phosphonic acid (20%) was obtained. The crude mixture was used as is in the next step.

NAc product: $^1$H NMR (600 MHz, CD$_3$OD) δ (ppm): 8.20 (s, 1H), 7.47 (d, J=2.2 Hz, 1H), 7.28 (d, J=2.2 Hz, 1H), 4.30 (t, J=5.4 Hz, 2H), 4.27 (d, J=10.7 Hz, 2H), 3.87 (t, J=5.2 Hz, 2H), 2.43 (s, 3H); MS m/z 463 (M+1).

Step 3. [({[7-chloro-5-(2-chloroethoxy)-1-benzothien-2-yl]sulfonyl}amino)methyl]phosphonic acid was obtained.

$^1$H NMR (600 MHz, CD$_3$OD) δ (ppm): 7.88 (s, 1H), 7.44 (d, J=2.1 Hz, 1H), 7.23 (d, J=2.1 Hz, 2H), 4.30 (t, J=5.4 Hz, 2H), 3.87 (t, J=5.2 Hz, 2H), 3.24 (d, J=13.5 Hz, 2H); MS m/z 421 (M+1).

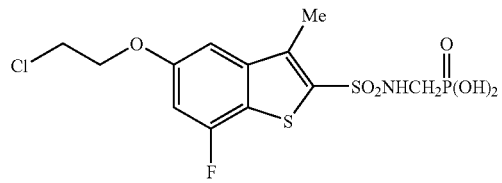

Step 1. A 5:1 mixture of [({[7-fluoro-5-(2-chloroethoxy)-3-methyl-benzothien-2-yl]sulfonyl}-amino)methyl]phosphonic anhydride and [({[7-fluoro-5-(2-chloroethoxy)-3-methyl-benzothien-2-yl]sulfonyl}amino)methyl]phosphonic anhydride, along with the N-acetyl byproducts, were obtained. The crude mixture was used as is in the next step.

Step 2. A mixture of [({[7-fluoro-5-(2-chloroethoxy)-3-methyl-benzothien-2-yl]sulfonyl}-amino)methyl]phosphonic acid and [({[7-fluoro-5-(2-chloroethoxy)-3-methyl-benzothien-2-yl]sulfonyl}N-acetylamino)methyl]phosphonic acid (20%) was obtained. The crude mixture was used as is in the next example.

Step 3. [({[7-fluoro-5-(2-chloroethoxy)-3-methyl-benzothien-2-yl]sulfonyl}amino)methyl]-phosphonic acid was obtained.

$^1$H NMR (500 MHz, CD$_3$OD) δ (ppm): 7.26 (d, J=2.1 Hz, 1H), 7.01 (dd, J=11.2, 2.1 Hz, 1H), 4.36 (t, J=5.3 Hz, 2H), 3.91 (t, J=5.1 Hz, 2H), 3.26 (d, J=13.3 Hz, 2H), 2.67 (s, 3H); MS m/z 418 (M+1).

Method D. Preparation of [({[5,6-Bis(2-Chloroethoxy)-1-Benzothien-2-Yl]Sulfonyl}Amino)Methyl] Phosphonic Acid To a stirred solution of the sulfonamide (0.52 g, 1.39 mmol) in 6 mL of Ac$_2$O/AcOH (2:1) was added paraformaldehyde (51 mg, 1.2 equiv). The reaction mixture was heated at 75° C. until all of the solid was dissolved, and then P(OTMS)$_3$ (0.49 mL, 1.05 equiv) was added. The homogeneous solution was heated at 110° C. for 3 h, then cooled to room temperature, and concentrated. The residue was dissolved in dichloromethane at room temperature and TMSBr (1.8 mL, 8 equiv) was added. The mixture was left overnight and the volatiles were removed by evaporation. The oily residue so obtained was dissolved in MeOH and stirred with 5 equivalents of K$_2$CO$_3$ at room temperature overnight. The mixture was filtered, neutralized with dilute HCl, and purified by HPLC to give the product.

$^1$H NMR (400 MHz, CD$_3$OD) δ (ppm): 7.8 (s, 1H), 7.55 (s, 1H), 7.52 (s, 1H), 4.4 (m, 4H), 3.95 (m, 4H), 3.25 (brd, 2H); MS m/z 464 (M+1).

Utilizing the foregoing procedure, the following compounds were prepared:

[({[6-(4-chlorobutoxy)-5-(3-chloropropoxy)-1-benzothien-2-yl]sulfonyl}amino)methyl]-phosphonic acid The minor isomer, obtained from Preparative Example 43, Method B., (0.0657 g, 0.16 mmol) was elaborated to its corresponding phosphonic acid.

$^1$H NMR (500 MHz, CD$_3$OD) δ (ppm): 7.79 (s, 1H), 7.47 (s, 2H), 4.21 (t, 2H), 4.13 (t, 2H), 3.82 (t, 2H), 3.71 (t, 2H), 3.02 (d, 2H), 2.27 (m, 2H), 2.02 (m, 4H); MS m/z 506 (M).

[({[5,6-bis(2-chloroethoxy)-3-methyl-1-benzothien-2-yl]sulfonyl}amino)methyl]phosphonic acid $^1$H NMR (500 MHz, CD$_3$OD) δ (ppm): 7.52 (s, 1H), 7.43 (s, 1H), 4.39 (m, 4H), 3.92 (m, 4H), 3.03 (d, 2H), 2.65 (s, 3H).

[({[5,6-bis(2-chloroethoxy)-3-methyl-4,7-difluoro-1-benzothien-2-yl]-sulfonyl}amino)methyl]-phosphonic acid $^1$H NMR (500 MHz, CD$_3$OD) δ (ppm): 4.50 (t, 2H), 4.41 (t, 2H), 3.84 (m, 4H), 3.22 (d, 2H), 2.80 (s, 3H); MS m/z 528 (M+1).

Method E. Preparation of [({[5-(Chloromethyl) and 5-(Bromomethyl)Thieno-[3,2-b]Thien-2-Yl]-Sulfonyl}Amino)Methyl]Phosphonic Acids The crude residue from Example 49 (0.0593 g, 0.15 mmol) was dissolved and stirred in CH$_2$Cl$_2$ (1 mL) and treated with TFA (0.5 mL) at ambient temperature. After 1 h, the reaction was concentrated in vacuo. To a stirred solution of the resulting residue in CH$_2$Cl$_2$ (1 mL) was added TMSBr (0.13 mL, 1.0 mmol). The reaction mixture was stoppered and stirred at ambient temperature for 19 h before quenching the reaction with MeOH. The reaction mixture was stirred for 5 minutes, then concentrated in vacuo. Purification was accomplished by triturating the residue with CH$_2$Cl$_2$ (3×), and isolating the resulting insoluble solid by centrifugation.

Cl: $^1$H NMR (500 MHz, CD$_3$OD) δ (ppm): 7.89 (s, 1H), 7.46 (s, 1H), 4.98 (s, 2H), 3.23 (d, 2H); MS m/z 362 (M+1).

Br: $^1$H NMR (500 MHz, CD$_3$OD) δ (ppm): 7.87 (s, 1H), 7.48 (s, 1H), 4.93 (s, 2H), 3.23 (d, 2H); MS m/z 408 (M+1).

Utilizing the foregoing procedure, the following compounds were prepared:

({[(5-{[(3-chloropropyl)thio]methyl}thieno[3,2-b]thien-2-yl)sulfonyl]amino}methyl)phosphonic acid It was prepared as an off-white solid.

$^1$H NMR (500 MHz, CD$_3$OD) δ (ppm): 7.87 (s, 1H), 7.32 (s, 1H), 4.09 (s, 2H), 3.67 (t, 2H), 3.24 (d, 2H), 2.69 (t, 2H), 2.02 (m, 2H); MS m/z 436 (M+1).

[({[5-(chloromethyl)thieno[2,3-b]thien-2-yl]sulfonyl}amino)methyl]phosphonic acid $^1$H NMR (500 MHz, CD$_3$OD) δ (ppm): 7.76 (s, 1H), 7.40 (s, 1H), 4.89 (s, 2H), 3.20 (d, 2H); MS m/z 326 (M−35).

Method F. Preparation of Diethyl {[{[5,6-Bis(2-Chloroethoxy)-1-Benzothien-2-Yl]-Sulfonyl}Amino]Methyl}Phosphonate To a stirred solution of the N-Boc-phosphonate in CH$_2$Cl$_2$ at 0° C. was added drop wise TFA and the mixture was warmed up to room temperature. After 1 h, a saturated, aqueous solution of NaHCO$_3$ was added to quench the excess TFA. The organic layer was separated and the aqueous layer was extracted with ethyl acetate. The organic layers were combined, dried over magnesium sulfate, filtered, and evaporated in vacuo. Purification by silica gel chromatography yielded the product.

$^1$H NMR (400 MHz, CDCl$_3$) δ (ppm): 7.8 (s, 1H), 7.4 (s, 1H), 7.35 (s, 1H), 5.6 (m, 1H), 4.4 (m, 4H), 4.2 (m, 4H), 3.95 (m, 4H), 3.4 (dd, 2H), 1.4 (t, 6H).

Utilizing the foregoing procedure, the following compounds were prepared:

dimethyl [({[5-vinyl-1-benzothien-2-yl]sulfonyl}amino)methyl]phosphonate

Column chromatography (eluent 75% ethyl acetate/hexanes) yielded the product (2.0 g, 5.5 mmol, 66% yield) as a white solid, contaminated with some triphenylphosphine oxide. NOTE: on standing in the solid phase at room temperature, this compound slowly decomposed into an insoluble white (polymeric?) solid. It was therefore stored in ethyl acetate solution at −20° C. and concentrated immediately prior to use.

$^1$H NMR (400 MHz, DMSO-d$_6$) δ (ppm): 8.64 (br s, 1H); 8.08-8.01 (m, 3H) 7.73 (dd, J=8.6, 1.8, 1H); 6.87 (dd, J=17.6, 11.0, 1H); 5.95 (d, J=17.0, 1H); 5.35 (d, J=10.9, 1H); 3.65 (d, J=10.8, 6H); 3.37 (d, J=12.1, 2H).

diethyl [({[6-(4-chlorobutoxy)-1-benzothien-2-yl]sulfonyl}amino)methyl]phosphonate $^1$H NMR (CDCl$_3$) δ (ppm): 7.84 (s, 1H), 7.79 (d, 1H), 7.12 (d, 1H), 5.02 (s, 1H), 4.18 (quartet, 4H), 4.12 (t, 2H), 3.68 (t, 2H), 3.41 (dd, 2H), 2.08 (m, 4H), 1.37 (t, 6H); MS m/z 470 (M+1).

Diethyl [({[5,6-bis(4-chlorobutoxy)-1-benzothien-2-yl]sulfonyl}amino)methyl]phosphonate It was prepared and used as is for next step.

$^1$H NMR (500 MHz, CD$_3$OD) δ (ppm): 7.80 (s, 1H), 7.24 (s, 1H), 7.22 (s, 1H), 4.16 (m, 8H), 3.70 (m, 4H), 3.40 (d, 2H), 2.00 (m, 8H), 1.32 (t, 6H); MS m/z 576 (M).

Diethyl [({[5,6-bis(3-chloropropoxy)-1-benzothien-2-yl]sulfonyl}amino)methyl]phosphonate It was prepared and purified using 5% MeOH/CH$_2$Cl$_2$ as the chromatography eluant.

$^1$H NMR (500 MHz, CD$_3$OD) δ (ppm): 7.82 (s, 1H), 7.32 (s, 1H), 7.30 (s, 1H), 4.24 (q, 4H), 4.18 (m, 4H), 3.82 (t, 4H), 3.20 (d, 2H), 2.30 (m, 4H), 1.32 (t, 6H); MS m/z 548 (M).

diethyl [({[5,6-bis(3-chloropropoxy)-3-ethyl-1-benzothien-2-yl]sulfonyl}amino)methyl]-phosphonate $^1$H NMR (500 MHz, CD$_3$OD) δ (ppm): 7.45 (s, 1H), 7.35 (s, 1H), 4.20 (m, 4H), 4.10 (m, 4H), 3.80 (m, 4H), 3.40 (d, 2H), 3.18 (q, 2H), 2.25 (m, 4H), 1.25 (m, 9H); MS m/z 576 (M).

Diethyl [({[7-chloroethoxy)-3-methyl-1-benzothien-2-yl]sulfonyl}amino)methyl]phosphonate It was prepared and purified using 5% MeOH/CH$_2$Cl$_2$ as the chromatography eluant.

$^1$H NMR (500 MHz, CD$_3$OD) δ (ppm): 7.40 (d, 1H), 7.32 (d, 1H), 4.40 (t, 2H), 4.15 (m, 4H), 3.96 (t, 2H), 3.48 (d, 2H), 2.64 (s, 3H), 1.28 (t, 6H); MS m/z 490 (M).

Diethyl [({[4-chloroethoxy)-3-methyl-1-benzothien-2-yl]sulfonyl}amino)methyl]phosphonate It was prepared crude and used as is in the next step.

$^1$H NMR (500 MHz, CD$_3$OD) δ (ppm): 7.82 (d, 1H), 7.4 (d, 1H), 4.40 (t, 4H), 4.1 (t, 4H), 3.9 (t, 2H), 3.42 (d, 2H), 3.0 (s, 3H), 1.25 (t, 6H).

Diethyl-[({[5,6-bis(3-chloropropoxy)-4,7-difluoro-1-benzothien-2-yl]sulfonyl}amino)methyl]-phosphonate $^1$H NMR (500 MHz, CDCl$_3$) δ (ppm): 7.9 (d, 1H), 7.63 (br m, 1H), 4.35 (two t, 4H), 4.2 (m, 4H), 3.8 (m, 4H), 3.4 (dd, 2H), 2.25 (m, 4H), 1.35 (t, 6H); MS m/z 584 (M+1).

diethyl-[({[5,6-bis(3-chloropropoxy)-4,7-difluoro-3-methyl-1-benzothien-2-yl]-sulfonyl}amino)methyl]phosphonate $^1$H NMR (500 MHz, CDCl$_3$) δ (ppm): 4.35 (m, 4H), 4.2 (m, 4H), 3.8 (m, 4H), 3.4 (brd, 2H), 2.8 (s, 3H), 2.25 (m, 4H), 1.4 (t, 6H); MS m/z 584 (M+1).

diethyl-[({[5,6-bis(2-chloroethoxy)-4,7-difluoro-3-ethyl-1-benzothien-2-yl]-sulfonyl}amino)methyl]phosphonate $^1$H NMR (500 MHz, CD$_3$OD) δ (ppm): 4.54 (t, 2H), 4.42 (t, 2H), 4.18 (m, 4H), 3.90 (m, 4H), 3.50 (d, 2H), 3.25 (q, 2H), 1.30 (m, 9H); MS m/z 584 (M).

diethyl-[({[5,6-bis(3-chloropropoxy)-4,7-difluoro-3-ethyl-1-benzothien-2-yl]-sulfonyl}amino)methyl]phosphonate $^1$H NMR (500 MHz, CD$_3$OD) δ (ppm): 4.40 (t, 2H), 4.30 (t, 2H), 4.20 (m, 8H), 3.88 (m, 4H), 3.50 (d, 2H), 3.25 (q, 2H), 2.28 (m, 4H), 1.30 (m, 9H); MS m/z 612 (M).

Diethyl-{[({5-[4-(2-chloroethoxy)phenyl]-1,3,4-thiadiazol-2-yl}sulfonyl)amino]methyl}-phosphonate $^1$H NMR (500 MHz, CD$_3$OD) δ (ppm): 8.04 (d, 2H), 7.18 (d, 2H), 4.40 (t, 2H), 4.20 (m, 4H), 3.92 (t, 2H), 3.70 (d, 2H), 1.40 (t, 6H); MS m/z 471 (M+1).

Diethyl-{[({5-[4-(3-chloropropoxy)phenyl]-1,3,4-thiadiazol-2-yl}sulfonyl)amino]methyl}-phosphonate $^1$H NMR (400 MHz, CDCl$_3$) δ (ppm): 7.95 (d, 2H), 7.05 (d, 1H), 6.64 (brm, 1H), 4.24 (m, 6H), 3.8 (t, 2H), 3.7 (dd, 2H), 2.35 (m, 2H), 1.4 (t, 6H).

Diethyl-{[({5-[3,4-bis(3-chloropropoxy)phenyl]thiophen-2-yl}sulfonyl)amino]methyl}-phosphonate It was prepared and used as is in the next step.

$^1$H NMR (500 MHz, CD$_3$OD) δ (ppm): 7.60 (d, 1H), 7.35 (d, 1H), 7.28 (m, 2H), 7.08 (d, 1H), 4.20 (m, 8H), 3.80 (m, 4H), 3.40 (d, 2H), 2.22 (m, 4H), 1.36 (m, 6H).

Diethyl-{[({5-[3,4-bis(3-chloropropoxy-2-methylphenyl]thiophen-2-yl}sulfonyl)amino]methyl}-phosphonate It was prepared and used as is in the next step.

$^1$H NMR (500 MHz, CD$_3$OD) δ (ppm): 7.60 (d, 1H), 7.18 (d, 1H), 7.10 (d, 1H), 7.00 (d, 1H), 4.20 (m, 8H), 3.82 (m, 4H), 3.40 (d, 2H), 2.36 (s, 3H), 2.22 (m, 4H), 1.36 (m, 6H).

Diethyl-{[({5-[4,5-bis(3-chloropropoxy-2-methylphenyl]thiophen-2-yl}sulfonyl)amino]methyl}-phosphonate It was prepared and used as is in the next step.

$^1$H NMR (500 MHz, CD$_3$OD) δ (ppm): 7.62 (d, 1H), 7.18 (d, 1H), 7.04 (s, 1H), 6.98 (s, 1H), 4.20 (m, 8H), 3.82 (m, 4H), 3.40 (d, 2H), 2.40 (s, 3H), 2.22 (m, 4H), 1.26 (m, 6H).

Method G. Preparation of Diethyl {[{[4,7-Dichloro-5,6-Bis(2-Chloroethoxy)-1-Benzothien-2-Yl]Sulfonyl}Amino]Methyl}Phosphonate To a stirred solution of diethyl-{[{[5,6-bis(2-chloroethoxy)-1-benzothien-2-yl]sulfonyl}-amino]methyl}phosphonate (3.3 g, 6.33 mmol) in CH$_2$Cl$_2$/HOAc (1:1) at room temperature was added NCS (5.07 g, 4 equiv) and the mixture was heated at 70° C. After 2 h, the reaction mixture was quenched with a saturated, aqueous solution of NaHCO$_3$ and the organic layer was separated, dried, and evaporated to give an oily residue. The residue was purified by silica gel chromatography to afford the product.

$^1$H NMR (400 MHz, CDCl$_3$) δ (ppm): 8.0 (s, 1H), 6.25 (brs, 1H), 4.4 (m, 4H), 4.2 (m, 4H), 3.95 (m, 4H); 3.42 (dd, 2H), 1.4 (m, 6H); MS m/z 590 (M+1).

Method H. Diethyl ({[5-{[(3-Chloropropyl)Sulfonyl]Methyl}-1-Benzothien-2-Yl)Sulfonyl]Amino}Methyl)Phosphonate A solution of oxone (2.6 g, 4.2 mmol, 4.2 eq) in water (10 mL) was added to a solution of diethyl ({[5-{[(3-chloropropyl)thio]methyl}-1-benzothien-2-yl)sulfonyl]amino}methyl)phosphonate (0.70 g, ~70% pure, 1.0 mmol, 1 eq) in methanol (100 mL) and the resulting suspension was stirred rapidly at room temperature for 1 h. The mixture was then concentrated under reduced pressure, and the residue was partitioned between ethyl acetate (60 mL) and water (20 mL), separated, and the aqueous layer was further extracted with ethyl acetate (20 mL). The combined organic extracts were dried over magnesium sulfate, filtered, and concentrated under reduced pressure. The residue was purified by flash column chromatography on silica gel (ethyl acetate) to afford the product.

$^1$H NMR (2:1 CD$_3$OD/D$_2$O) δ (ppm): 7.94 (d, J=1.8, 1H); 7.91 (d, J=8.4, 1H); 7.88 (s, 1H); 7.54 (dd, J=8.4, 1.8, 1H); 5.49 (q, J=4.7, 1H); 4.39 (s, 2H); 4.15 (quint, J=7.0, 2H); 3.67 (t, J=6.1, 2H); 3.40 (dd, J=13.9, 6.1, 2H); 3.10 (d, J=7.4, 2H); 1.33 (t, J=7.1, 3H); MS m/z 518 (M+1).

Method I. Preparation of [({[4,7-Dichloro-5,6-Bis(2-Chloroethoxy)-1-Benzothien-2-Yl]Sulfonyl}Amino)Methyl]Phosphonic Acid To a stirred solution of diethyl-{[{[4,7-dichloro-5,6-bis(2-chloroethoxy)-1-benzothien-2-yl]sulfonyl}-amino]methyl}phosphonate (2 g, 3.38 mmol) in anhydrous dichloromethane at room temperature was added TMSBr (4.4 mL, 10 equiv). The mixture was left overnight and the dichloromethane was evaporated to give an oily residue. The residue was dissolved in MeOH and stirred at room temperature for 30 min. The mixture was evaporated and the residue was triturated with dichloromethane to form a crystalline product which was collected by filtration.

$^1$H NMR (400 MHz, CD$_3$OD) δ (ppm): 8.0 (s, 1H), 4.4 (m, 4H), 4.0 (m, 4H), 3.3 (d, 2H); MS m/z 534 (M+1).

Utilizing the foregoing procedure, the following compounds were prepared:

({[(5-formyl-1-benzothien-2-yl)sulfonyl]amino}methyl)phosphonic acid $^1$H NMR (400 MHz, DMSO-d$_6$) δ (ppm): 10.10 (s, 1H); 8.58 (s, 1H); 8.46-8.42 (m, 1H); 8.30 (d, J=8.6, 1H); 8.19 (s, 1H); 7.98 (d, J=8.6, 1H); 3.02 (dd, J=13.1, 6.3, 2H).

[({[6-(4-chlorobutoxy)-1-benzothien-2yl]sulfonyl}amino)methyl]phosphonic acid $^1$H NMR (CDCl$_3$) δ (ppm): 8.12 (s, 1H), 7.90 (d, 1H), 7.88 (s, 1H), 7.65 (s, 1H), 7.09 (d, 1H), 4.10 (t, 2H), 3.72 (t, 2H), 1.87 (m, 4H); MS m/z 414 (M+1).

[({[4-chloro-5-(2-chloroethoxy)-3-methyl-1-benzothien-2-yl]sulfonyl}amino)methyl]phosphonic acid $^1$H NMR (500 MHz, CD$_3$OD) δ (ppm): 7.80 (d, 1H), 7.38 (d, 1H), 4.40 (t, 2H), 3.30 (d, 2H), 3.00 (s, 3H).

[({[7chloro-5-(2-chloroethoxy)-3-methyl-1-benzothien-2-yl]sulfonyl}amino)methyl]phosphonic acid $^1$H NMR (500 MHz, CD$_3$OD) δ (ppm): 7.40 (d, 1H), 7.30 (d, 1H), 4.40 (t, 2H), 3.90 (t, 2H), 3.30 (d, 2H), 2.70 (s, 3H); MS m/z 434 (M).

[({[5,6-bis(3-chloropropoxy)-1-benzothien-2-yl]sulfonyl}amino)methyl]phosphonic acid It was prepared and used as is in the next step.

MS m/z 492 (M).

[({[5,6-bis(3-chloropropoxy)-3-ethyl-1-benzothien-2-yl]sulfonyl}amino)methyl]phosphonic acid $^1$H NMR (500 MHz, CD$_3$OD) δ (ppm): 7.50 (s, 1H), 7.40 (s, 1H), 4.24 (m, 4H), 3.82 (m, 4H), 3.25 (d, 2H), 3.20 (q, 2H), 2.30 (m, 4H), 1.30 (t, 3H); MS m/z 520 (M).

[({[4,7-difluoro-5,6-bis(2-chloroethoxy)-3-ethyl-1-benzothien-2-yl]sulfonyl}amino)methyl]-phosphonic acid $^1$H NMR (500 MHz, CD$_3$OD) δ (ppm): 4.50 (t, 2H), 4.42 (t, 2H), 3.92 (m, 4H), 3.32 (d, 2H), 3.26 (q, 2H), 1.30 (t, 3H); MS m/z 528 (M).

[({[4,7-difluoro-5,6-bis(3-chloropropoxy)-3-ethyl-1-benzothien-2-yl]sulfonyl}-amino)methyl]-phosphonic acid $^1$H NMR (500 MHz, CD$_3$OD) δ (ppm): 4.40 (t, 2H), 4.30 (t, 2H), 3.82 (m, 4H), 3.30 (d, 2H), 3.22 (q, 2H), 2.25 (m, 4H), 1.30 (t, 3H); MS m/z 557 (M+1).

[({[5,6-bis(4-chlorobutoxy)-1-benzothien-2-yl]sulfonyl}amino)methyl]phosphonic acid It was prepared and used as is in the next step.

$^1$H NMR (500 MHz, CD$_3$OD) δ (ppm): 7.80 (s, 1H), 7.24 (s, 1H), 7.22 (s, 1H), 4.10 (m, 4H), 3.70 (m, 4H), 3.20 (d, 2H), 2.00 (m, 8H); MS m/z 519 (M).

[({[5-(4-chlorobutoxy)-6-(3-chloropropoxy)-1-benzothien-2-yl]sulfonyl}amino)methyl]-phosphonic acid The major isomer obtained from Preparative Example 43, Method B., (0.2066 g, 0.50 mmol) was elaborated to its corresponding phosphonic acid.

{[({5-[4-(3-chloropropoxy)phenyl]-1,3,4-thiadiazol-2-yl}sulfonyl)amino]methyl}phosphonic acid $^1$H NMR (400 MHz, CD$_3$OD) δ (ppm): 7.95 (d, 2H), 7.1 (d, 1H), 4.2 (t, 2H), 3.8 (t, 2H), 3.5 (brs, 2H), 2.25 (m, 2H); MS m/z 428 (M+1).

{[({5-[4-(2-chloroethoxy)phenyl]-1,3,4-thiadiazol-2-yl}sulfonyl)amino]methyl}phosphonic acid $^1$H NMR (500 MHz, CD$_3$OD) δ (ppm): 8.00 (d, 2H), 7.18 (d, 2H), 4.40 (t, 2H), 3.90 (t, 2H), 3.54 (d, 2H); MS m/z 415 (M+1).

{[({5-[3,4-bis(3-chloropropoxy)phenyl]thiophen-2-yl}sulfonyl)amino]methyl}phosphonic acid It was prepared and used as is in the next step.

$^1$H NMR (500 MHz, CD$_3$OD) δ (ppm): 7.60 (d, 1H), 7.35 (d, 1H), 7.24 (m, 2H), 7.04 (d, 1H), 4.20 (m, 4H), 3.80 (m, 4H), 3.20 (d, 2H), 2.22 (m, 4H); MS m/z 518 (M).

{[({5-[3,4-bis(3-chloropropoxy)-2-methylphenyl]thiophen-2-yl}sulfonyl)amino]methyl}-phosphonic acid It was prepared and used as is in the next step.

$^1$H NMR (500 MHz, CD$_3$OD) δ (ppm): 7.60 (d, 1H), 7.20 (d, 1H), 7.10 (d, 1H), 7.00 (d, 1H), 4.20 (t, 2H), 4.10 (t, 2H), 3.80 (m, 4H), 3.24 (d, 2H), 2.36 (s, 3H), 2.22 (m, 4H).

{[({5-[4,5-bis(3-chloropropoxy)-2-methylphenyl]thiophen-2-yl}sulfonyl)amino]methyl}-phosphonic acid It was prepared and used as is in the next step.

$^1$H NMR (500 MHz, CD$_3$OD) δ (ppm): 7.60 (d, 1H), 7.10 (d, 1H), 7.00 (s, 1H), 6.96 (s, 1H), 4.20 (t, 2H), 4.08 (t, 2H), 3.80 (m, 4H), 3.24 (d, 2H), 2.38 (s, 3H), 2.22 (m, 4H); MS m/z 561 (M).

(5,6-bis(2-chloroethoxy)benzo[d]thiazole-2-sulfonamido)methylphosphonic acid $^1$H NMR (400 MHz, DMSO-d$_6$) δ (ppm): 8.78-8.75 (m, 1H); 7.86 (s, 1H); 7.79 (s, 1H); 4.40-4.34 (m, 4H); 4.00-3.96 (m, 4H); 3.22 (dd, J=12.7, 6.3, 2H).

5,6-Bis(3-chloropropoxy)benzo[d]thiazole-2-sulfonamido]methylphosphonic acid

Off-white off solid.

$^1$H NMR (400 MHz, DMSO-d$_6$) δ (ppm): 7.74 (s, 1H), 7.73 (s, 1H), 4.29 (m, 4H), 3.87 (t, J=6.4 Hz, 4H), 3.33 (d, J=12.3 Hz, 2H), 2.33 (m, 4H); MS m/z 491 (M−1).

Method J. Preparation of [({[6-(2-Chloroethoxy)-4,5,7-Trifluoro-1-Benzothien-2-Yl]Sulfonyl}Amino) Methyl]Phosphonic Acid BuLi (1.42 mL, 2.5 M in hexanes) was added dropwise over 7 minutes to a solution of 0.798 g 6-(2-chloroethoxy)-4,5,7-trifluoro-1-benzothiophene (3.23 mmol) in 15 mL anhydrous THF at −78° C. After 5 minutes, a stream of SO$_2$ gas was introduced to the surface of the reaction mixture until it became acidic to wet pH test paper. The reaction mixture was allowed to warm up to ambient temperature under N$_2$ and the solvent was removed. The resulting solid was then treated with 442 mg N-chlorosuccinimide (NCS) in 10 mL CH$_2$Cl$_2$ overnight. The reaction mixture was diluted with hexane, filtered over a pad of celite and concentrated. The residue was treated with 0.71 g diethyl aminomethyl phosphonate oxalate and 1.391 g K$_2$CO$_3$ in 8 mL DMF at 0° C. for 1 h and then at ambient temperature for 1 h. The mixture was diluted with EtOAc, washed with water, 2N HCl and brine. After silica gel flash chromatography, the product was treated with 0.8 mL TMSBr in 3 mL CH$_2$Cl$_2$ for 16 h, and the reaction mixture was concentrated under reduced pressure. The residue was dissolved in MeOH and evaporated, and then repeated. The resulting solid was washed with a CH$_2$Cl$_2$-hexane mixture to give product.

MS m/z 440 (M+1).

Utilizing the above procedure the following compounds were prepared:

[({[6-(2-chloroethoxy)-4-fluoro-1-benzothieny-2-yl]sulfonyl}amino)methyl]phosphonic acid MS m/z 404 (M+1).

[({[6-(2-chloropropoxy)-4-fluoro-1-benzothieny-2-yl]sulfonyl}amino)methyl]phosphonic acid MS m/z 432 (M+1).

Method K. Preparation of Diethyl (5,6-Bis(2-Chloroethoxy)-Benzo[D]Thiazole-2-Sulfonamido)Methylphosphonate To diethyl (5,6-bis(2-chloroethoxy)benzo[d]thiazol-2-ylthioamino)methylphosphonate (0.51 g, 1.0 mmol) in dichloromethane (25 mL) at r.t. was added sodium acetate (0.85 g, 10 mmol) and m-chloroperoxybenzoic acid (0.55 g, 3.2 mmol), and the resulting mixture was stirred for 18 h, then heated to reflux for 1 h. The mixture was cooled to r.t., washed with water, saturated sodium bicarbonate, and brine, dried over magnesium sulfate, and concentrated. Column chromatography (90% ethyl acetate/hexanes) yielded the product as a colorless solid.

$^1$H NMR (400 MHz, CD$_3$OD) δ (ppm): 7.65 (s, 1H); 7.63 (s, 1H); 4.89 (br s, 1H); 4.38-4.35 (m, 4H); 4.14 (quint, J=8.2, 4H); 3.94-3.91 (m, 4H); 3.63 (d, J=11.7, 2H); 1.30 (t, J=7.0, 6H).

Utilizing the foregoing procedure, the following compound was prepared:

diethyl [5,6-bis(3-chloropropoxy)benzo[d]thiazole-2-sulfonamido]methylphosphonate The product was purified by flash column chromatography (eluents 80% EtOAc/DCM to pure AcOEt, then EtOAc/MeOH) to give product as a pale yellow solid.

$^1$H NMR (400 MHz, DMSO-$d_6$) δ (ppm): 7.80 (s, 1H), 7.69 (s, 1H), 4.15-4.20 (m, 4H), 3.99 (m, 4H), 3.81 (t, J=6.5 Hz, 4H), 3.42 (d, J=11.7 Hz, 2H), 2.20 (m, 4H), 1.17 (t, J=7.0 Hz, 6H); MS m/z 547 (M−1).

Preparative Example 62

Preparation of Diethyl {[{[5-(Bromomethyl)-1-Benzothien-2-Yl]-Sulfonyl}(Tert-Butoxycarbonyl)Amino]Methyl}Phosphonate N-Bromosuccinimide (0.59 g, 3.3 mmol, 1.3 eq) and VAZO (0.040 g, 0.16 mmol, 0.07 eq) was added to a solution of diethyl-({(tert-butoxycarbonyl)[(5-methyl-1-benzothien-2-yl)sulfonyl]-amino}methyl)phosphonate (1.15 g, 2.48 mmol, 1 eq) in carbon tetrachloride (55 mL). The resulting suspension was stirred and heated under reflux for 18 hours. It was then cooled and filtered, the solid was rinsed with carbon tetrachloride (5 mL), and the combined filtrates were concentrated under reduced pressure. The residue was purified by flash column chromatography on silica gel (50% ethyl acetate/hexanes) to provide product and dibrominated phosphonate.

MS m/z 456 (M+1-Boc).

Utilizing the foregoing procedure, the following compound was prepared:

dimethyl {[{[5-(bromomethyl)-4,7-dichloro-1-benzothien-2-yl]-sulfonyl}(tert-butoxycarbonyl)-amino]methyl}phosphonate as a 9:2 mixture.

$^1$H NMR (400 MHz, CDCl$_3$) δ (ppm): 8.32 (s, 1H); 7.58 (s, 1H); 4.69 (s, 2H); 4.33 (d, J=9.6, 2H); 3.81 (d, J=11.0, 6H); MS m/z 498 (M+1).

Preparative Example 63

Preparation of Diethyl ({[(5-{[(3-Chloropropyl)Thio]Methyl}-1-Benzothien-2-Yl)Sulfonyl]Amino}Methyl)Phosphonate 3-Chloro-1-propanethiol (0.25 mL, 0.29 g, 2.6 mmol, 1.6 eq) and potassium carbonate (0.51 g, 3.7 mmol, 2.3 eq) were added to a stirred solution of diethyl-({(tert-butoxycarbonyl)[(5-bromomethyl-1-benzothien-2-yl)sulfonyl]-amino}methyl)phosphonate (1.30 g, ~70% pure, 1.64 mmol, 1 eq) in acetone (60 mL). The suspension was stirred at room temperature for 2 h then concentrated under reduced pressure. The residue was partitioned between ethyl acetate (60 mL) and water (40 mL); organic phase was separated, and the aqueous layer was further extracted with ethyl acetate (20 mL). The combined organic extracts were dried over magnesium sulfate, filtered, and concentrated under reduced pressure. To this material was added dichloromethane (20 mL) and trifluoroacetic acid (3 mL, 4.6 g, 40 mmol, 25 eq) and the resulting solution was stirred at room temperature for 18 h, then concentrated under reduced pressure. The residue was purified by flash column chromatography on silica gel (60% ethyl acetate/hexanes) to yield product and dibrominated phosphonate.

MS m/z 486 (M+1).

Utilizing the foregoing procedure, the following compound was prepared:

dimethyl ({[(4,7-dichloro-5-{[(3-chloropropyl)thio]methyl}-1-benzothien-2-yl)sulfonyl]amino}-methyl)phosphonate Preparative Example 64

Dimethyl (5-Formylbenzo[b]Thiophene-2-Sulfonamido)-Methylphosphonate

To a solution of dimethyl (5-vinylbenzo[b]thiophene-2-sulfonamido)methylphosphonate (0.45 g, 1.25 mmol) in THF (75 mL) was added osmium tetroxide (4% in water, 0.1 mL), and sodium periodate (0.70 g, 3.3 mmol) in water (10 mL). This mixture was stirred for 24 h at r.t. and concentrated. The residue was extracted with ethyl acetate; the organic extract was washed with water and brine, dried over magnesium sulfate, and concentrated. Column chromatography (ethyl acetate as an eluent) provided the pure product.

$^1$H NMR (400 MHz, DMSO-$d_6$) δ (ppm): 10.10 (s, 1H); 8.74 (br s, 1H); 8.58 (d, J=1.6, 1H); 8.30 (dd, J=8.4, 0.6, 1H); 8.23 (d. J=0.6, 1H); 7.98 (dd, J=8.4, 1.6, 1H); 3.63 (d, J=10.8, 6H); 3.38 (d, J=12.1, 2H).

Preparative Example 65

Preparation of Hydrogen({[(5-{[(3-Pyridinium-1-Ylpropyl)Thio]Methyl}-1-Benzothien-2-Yl)Sulfonyl]Amino}Methyl)Phosphonate Step A. A solution of diethyl ({[(5-{[(3-chloropropyl)thio]methyl}-1-benzothien-2-yl)-sulfonyl]amino}methyl)phosphonate (0.38 g, ~70% pure, 0.55 mmol), prepared in the prior Example, in pyridine (5 mL) in a pressure vessel was heated in a 140° C. oil bath for 2 hours. The mixture was then cooled to r.t. and transferred to a round-bottomed flask, and the pressure vessel was rinsed with methanol (4×10 mL) to transfer the dark oily residue to the round bottom flask. The combined solution was concentrated under reduced pressure, and the residue was suspended in methanol (25 mL), filtered and the solid was rinsed with methanol (10 mL). The filtrate and washing were combined, concentrated, and the resulting oily material was triturated with ether (10 mL) and dried in vacuo to provide 0.50 g of crude phosphonic acid monoethyl ester [MS m/z 501 (M+1)] contaminated with ethylpyridinium chloride (~1:1).

Step B. To a suspension of the monoethyl ester (0.50 g, ~0.78 mmol, 1 eq), obtained in Step A, in acetonitrile (25 mL) was added bromotrimethylsilane (0.8 mL, 0.9 g, 6 mmol, 8 eq) and the mixture was heated at 60° C. for 3 h, then cooled to room temperature and concentrated under reduced pressure. The residue was suspended in methanol (10 mL), filtered and the solid rinsed with methanol (10 mL). The filtrate and the washing were concentrated, and the residue was triturated with ether and ethyl acetate (both 5 mL). The residue was dried in vacuo to yield 0.60 g of crude product contaminated with ethylpyridinium chloride (~1:1). This crude product was used in the final coupling step.

Reverse phase HPLC (250×21.2 mm Aquasil C18 column, 35%-90% methanol/water linear gradient, 30 min elution time) provided pure product, but the poor solubility of this compound in all solvents tested (DMSO, DMF, MeOH, MeOH-water, pyridine) prevented its use in the final coupling step.

$^1$H NMR (400 MHz, 2:1 CD$_3$OD/D$_2$O) δ (ppm): 8.77 (d, J=5.7, 2H); 8.50 (t, J=7.6, 1H); 7.97 (t, J=7.0, 2H); 7.90 (d, J=8.4, 1H); 7.89 (s, 1H); 7.82 (s, 1H); 7.51 (d, J=8.4, 1H); 4.66 (t, J=6.9, 2H); 3.89 (s, 2H); 3.10 (d, J=13.1, 2H); 2.45 (t, J=7.0, 2H); 2.24 (quint, J=7.0, 2H); MS m/z 473 (M+1).

Utilizing the foregoing procedure, the following compound was prepared:

Hydrogen-({[(4,7-dichloro-5-{[(3-pyridinium-1-ylpropyl)thio]methyl}-1-benzothien-2-yl)-sulfonyl]amino}methyl)phosphonate, contaminated with ethylpyridinium chloride (~1:1). The crude product was used in the final coupling step.

MS m/z 541 (M+1).

Hydrogen-({[(5-{[(3-pyridinium-1-ylpropyl)sulfonyl]methyl}-1-benzothien-2-yl)sulfonyl]-amino}methyl)phosphonate, contaminated with ethylpyridinium chloride (~1:1). The crude product was used in the final coupling step.

MS m/z 505 (M+1).

Preparative Example 66

Method A. Preparation of [({[5,6-Bis(2-Azidoethoxy)-1-Benzothien-2-Yl]-Sulfonyl}Amino)Methyl] Phosphonic Acid A stirred mixture of phosphonic acid (110 mg, 0.24 mmol) and NaN$_3$ (62 mg, 4 equiv) in DMSO was heated at 80° C. for 16 h. The reaction mixture was cooled to room temperature and then purified by reverse phase HPLC to afford the product.

$^1$H NMR (400 MHz, CD$_3$OD) δ (ppm): 7.82 (s, 1H), 7.55 (s, 1H), 7.5 (s, 1H), 4.3 (m, 4H), 3.7 (m, 4H), 3.25 (d, 2H); MS m/z 478 (M+1).

Method B. Preparation of [({[5-(Azidomethyl)Thieno[3,2-b]Thien-2-Yl]-Sulfonyl}Amino)Methyl] Phosphonic Acid To a stirred solution of the product obtained from Preparative Example 52, Method E, (0.0545 g, 0.13 mmol) in DMSO (0.5 Ml) was added NaN$_3$ (0.0135 g, 0.20 mmol). The resulting solution was heated to 90° C. under nitrogen for 1.5 h. The reaction was followed by LC/MS. The crude reaction mixture was purified by reverse-phase HPLC (X-terra Prep MS C18 column, 30×100 mm, 5 micron, flow rate=35 Ml/min, 10/90 CH$_3$CN+0.05% TFA/water+0.05% TFA to 95/5 CH$_3$CN+0.05% TFA/water+0.05% TFA over 20 min. then 95/5 CH$_3$CN+0.05% TFA/water+0.05% TFA for 10 min.) to give a white solid after lyophilization.

$^1$H NMR (500 MHz, CD$_3$OD) δ (ppm): 7.92 (s, 1H), 7.45 (s, 1H), 4.88 (s, 2H), 3.22 (d, 2H); MS m/z 369 (M+1).

Utilizing the foregoing procedures, the following compounds were prepared:

[({[5-(2-azidoethoxy)-4-chloro-3-methyl-1-benzothien-2-yl]sulfonyl}amino)methyl]phosphonic acid $^1$H NMR (500 MHz, CD$_3$OD) δ (ppm): 7.80 (d, 1H), 7.40 (m, 1H), 4.25 (t, 2H), 3.64 (t, 2H), 3.24 (d, 2H), 2.95 (s, 3H); MS m/z 441 (M+1).

[({[5-(2-azidoethoxy)-7-chloro-3-methyl-1-benzothien-2-yl]sulfonyl}amino)methyl]phosphonic acid $^1$H NMR (500 MHz, CD$_3$OD) δ (ppm): 7.40 (d, 1H), 7.30 (d, 1H), 4.30 (t, 2H), 3.66 (t, 2H), 3.22 (d, 2H), 2.70 (s, 3H); MS m/z 441 (M+1).

[({[5-(2-azidoethoxy)-7-fluoro-3-methyl-1-benzothien-2-yl]sulfonyl}amino)methyl]phosphonic acid $^1$H NMR (500 MHz, CD$_3$OD) δ (ppm): 7.26 (d, J=2.1 Hz, 1H), 6.99 (dd, J=11.2, 2.3 Hz, 1H), 4.28 (t, J=4.8 Hz, 2H), 3.66 (t, J=4.6 Hz, 2H), 3.26 (d, J=13.3 Hz, 2H), 2.67 (s, 3H); MS m/z 426 (M+1).

[({[4-chloro-5-(2-azidoethoxy)-1-benzothien-2-yl]sulfonyl}amino)methyl]phosphonic acid $^1$H NMR (500 MHz, CD$_3$OD) δ (ppm): 7.93 (s, 1H), 7.86 (d, J=9.0 Hz, 1H), 7.39 (d, J=8.9 Hz, 1H), 4.31 (t, J=5.6 Hz, 2H), 3.66 (t, J=5.6 Hz, 2H), 3.26 (bd, 2H); MS m/z 428 (M+1).

[({[5-(2-azidoethoxy)-7-chloro-1-benzothien-2-yl]sulfonyl}amino)methyl]phosphonic acid $^1$H NMR (500 MHz, CD$_3$OD) δ (ppm): 7.92 (s, 1H), 7.50 (d, J=2.3 Hz, 1H), 7.27 (d, J=2.3 Hz, 1H), 4.26 (t, J=4.8 Hz, 2H), 3.65 (t, J=4.8 Hz, 2H), 3.28 (d, J=11.9 Hz, 2H); MS m/z 428 (M+1).

{[({5-[4-(2-azidoethoxy)phenyl]-1,3,4-thiadiazol-2-yl}sulfonyl)amino]methyl}phosphonic acid $^1$H NMR (500 MHz, CD$_3$OD) δ (ppm): 8.06 (d, 2H), 7.20 (d, 2H), 4.30 (t, 2H), 3.70 (d, 2H), 3.50 (d, 2H); MS m/z 421 (M+1).

{[({5-[3,4-bis(3-azidopropoxy)phenyl]thiophen-2-yl}sulfonyl)amino]methyl}phosphonic acid It was prepared and purified by reverse phase HPLC.

$^1$H NMR (500 MHz, CD$_3$OD) δ (ppm): 7.60 (d, 1H), 7.38 (d, 1H), 7.24 (m, 2H), 7.04 (d, 1H), 4.20 (m, 4H), 3.60 (m, 4H), 3.10 (d, 2H), 2.10 (m, 4H); MS m/z 532 (M+1).

{[({5-[3,4-bis(3-azidopropoxy)-2-methylphenyl]thiophen-2-yl}sulfonyl)amino]methyl}-phosphonic acid It was prepared and purified by reverse phase HPLC.

$^1$H NMR (500 MHz, CD$_3$OD) δ (ppm): 7.60 (d, 1H), 7.20 (d, 1H), 7.10 (d, 1H), 7.00 (d, 1H), 4.20 (t, 2H), 4.10 (t, 2H), 3.60 (m, 4H), 3.20 (d, 2H), 2.36 (s, 3H), 2.10 (m, 4H); MS m/z 546 (M+1).

{[({5-[4,5-bis(3-azidopropoxy)-2-methylphenyl]thiophen-2-yl}sulfonyl)amino]methyl}-phosphonic acid It was prepared and purified by reverse phase HPLC.

$^1$H NMR (500 MHz, CD$_3$OD) δ (ppm): 7.60 (d, 1H), 7.16 (d, 1H), 7.0 (s, 1H), 6.98 (s, 1H), 4.18 (t, 2H), 4.14 (t, 2H), 3.60 (m, 4H), 3.24 (d, 2H), 2.40 (s, 3H), 2.10 (m, 4H); MS m/z 546 (M+1).

[({[5,6-bis(3-azidopropoxy)-1-benzothien-2-yl]sulfonyl}amino)methyl]phosphonic acid $^1$H NMR (500 MHz, CD$_3$OD) δ (ppm): 7.80 (s, 1H), 7.52 (s, 1H), 7.50 (s, 1H), 4.20 (m, 4H), 3.60 (t, 4H), 3.06 (d, 2H), 2.18 (m, 4H); MS m/z 506 (M+1).

[({[5,6-bis(4-azidobutoxy)-1-benzothien-2-yl]sulfonyl}amino)methyl]phosphonic acid $^1$H NMR (500 MHz, CD$_3$OD) δ (ppm): 7.80 (s, 1H), 7.42 (s, 1H), 7.40 (s, 1H), 4.10 (m, 4H), 3.40 (t, 4H), 3.20 (d, 2H), 1.90 (m, 4H), 1.80 (m, 4H); MS m/z 534 (M+1).

[({[6-(4-azidoobutoxy)-5-(3-azidopropoxy)-1-benzothien-2-yl]sulfonyl}amino)methyl]-phosphonic acid and [({[6-(4-azidobutoxy)-5-(3-azidopropoxy)-1-benzothien-2-yl]-sulfonyl}amino)methyl]phosphonic acid Using the compounds from Preparative Example 52, Methods D and I, the corresponding azides were obtained after purification by reverse-phase HPLC.

Major isomer (0.0639 g): $^1$H NMR (500 MHz, CD$_3$OD) δ (ppm): 7.79 (s, 1H), 7.49 (s, 1H), 7.45 (s, 1H), 4.18 (t, 2H), 4.11 (t, 2H), 3.58 (t, 2H), 3.43 (t, 2H), 3.15 (d, 2H), 2.11 (m, 2H), 1.94 (m, 2H), 1.85 (m, 2H); MS m/z 520 (M+1).

Minor isomer (0.0206 g): $^1$H NMR (500 MHz, CD$_3$OD) δ (ppm): 7.79 (s, 1H), 7.48 (s, 1H), 7.47 (s, 1H), 4.21 (t, 2H), 4.14 (bt, 2H), 3.83 (t, 2H), 3.71 (bt, 2H), 3.19 (d, 2H), 2.28 (m, 2H), 2.00 (m, 4H); MS m/z 520 (M+1).

[({[5,6-bis(2-azidoethoxy)-4,7-dichloro-1-benzothien-2-yl]sulfonyl}amino)methyl]phosphonic acid $^1$H NMR (400 MHz, CD$_3$OD) δ (ppm): 8.0 (s, 1H), 4.35 (m, 4H), 3.7 (m, 4H), 3.1 (d, 2H); MS m/z 546 (M+1).

[({[5,6-bis(2-azidoethoxy)-4,7-difluoro-1-benzothien-2-yl]sulfonyl}amino)methyl]phosphonic acid $^1$H NMR (400 MHz, CD$_3$OD) δ (ppm): 8.0 (d, 1H), 4.45 (t, 2H), 4.4 (t, 2H), 3.7 (m, 4H), 3.3 (d, 2H); MS m/z 514 (M+1).

[({[5,6-bis(2-azidoethoxy)-3-methyl-4,7-difluoro-1-benzothien-2-yl]-sulfonyl}amino)methyl]-phosphonic acid A white solid after purification by reverse-phase HPLC according to conditions described in Example 6 (0.1223 g).

$^1$H NMR (500 MHz, CD$_3$OD) δ (ppm): 4.42 (t, 2H), 4.35 (t, 2H), 3.69 (m, 4H), 3.30 (d, 2H), 2.82 (s, 3H).

[({[5,6-bis(3-azidopropoxy)-4,7-difluoro-1-benzothien-2-yl]sulfonyl}amino)methyl]phosphonic acid $^1$H NMR (500 MHz, CD$_3$OD) δ (ppm): 7.90 (d, 1H), 4.3 (two t, 4H), 3.6 (t, 4H), 3.1 (d, 2H); 2.1 (m, 4H); MS m/z 542 (M+1).

[({[5,6-bis(2-azidoethoxy)-3-methyl-1-benzothien-2-yl]sulfonyl}amino)methyl]phosphonic acid $^1$H NMR (500 MHz, CD$_3$OD) δ (ppm): 7.51 (s, 1H), 7.40 (s, 1H), 4.29 (m, 4H), 3.68 (m, 4H), 3.22 (d, 2H), 2.68 (s, 3H); MS m/z 492 (M+1).

[({[5,6-bis(3-azidopropoxy)-3-methyl-1-benzothien-2-yl]sulfonyl}amino)methyl]phosphonic acid $^1$H NMR (500 MHz, CD$_3$OD) δ (ppm): 7.5 (s, 1H), 7.4 (s, 1H), 4.2 (m, 4H), 3.6 (m, 3.25 (d, 2H), 2.65 (s, 3H), 2.15 (m, 4H); MS m/z 520 (M+1).

[({[5,6-bis(3-azidopropoxy)-3-ethyl-1-benzothien-2-yl]sulfonyl}amino)methyl]phosphonic acid $^1$H NMR (500 MHz, CD$_3$OD) δ (ppm): 7.45 (s, 1H), 7.38 (s, 1H), 4.20 (q, 4H), 3.60 (q, 4H), 3.25 (d, 2H), 3.20 (q, 2H), 2.15 (m, 4H), 1.30 (t, 3H); MS m/z 534 (M+1).

[({[5,6-bis(3-azidopropoxy)-4,7-difluoro-3-methyl-1-benzothien-2-yl]-sulfonyl}amino)methyl]-phosphonic acid $^1$H NMR (500 MHz, CD$_3$OD) δ (ppm): 4.3 (two t, 4H), 3.6 (m, 4H), 3.3 (d, 2H); 2.8 (s, 3H), 2.1 (m, 4H); MS m/z 556 (M+1).

[({[5,6-bis(2-azidoethoxy)-4,7-difluoro-3-ethyl-1-benzothien-2-yl]sulfonyl}amino)methyl]-phosphonic acid $^1$H NMR (500 MHz, CD$_3$OD) δ (ppm): 4.42 (t, 2H), 4.38 (t, 2H), 3.70 (m, 4H), 3.30 (d, 2H), 3.26 (m, 2H), 1.38 (t, 3H); MS m/z 452 (M+1).

[({[5,6-bis(3-azidopropoxy)-4,7-difluoro-3-ethyl-1-benzothien-2-yl]sulfonyl}amino)methyl]-phosphonic acid $^1$H NMR (500 MHz, CD$_3$OD) δ (ppm): 4.30 (t, 2H), 4.20 (t, 2H), 3.60 (m, 4H), 3.30 (d, 2H), 3.26 (m, 2H), 2.05 (m, 4H), 1.30 (t, 3H); MS m/z 570 (M+1).

[({[5-(2-azidoethoxy)-1-benzothien-2-yl]sulfonyl}amino)methyl]phosphonic acid $^1$H NMR (500 MHz, CD$_3$OD) δ (ppm): 7.88 (s, 1H), 7.87 (d, J=8.7 Hz, 1H) 7.52 (d, J=2.5 Hz, 1H), 7.23 (dd, J=8.7, 2.5 Hz, 1H), 4.28 (t, J=4.5 Hz, 2H), 3.68 (t, J=4.5 Hz, 2H), 3.28 (d, J=12.5 Hz, 2H); MS m/z 393 (M+1).

[({[6-(6-azidohexyloxy)-1-benzothien-2-yl]sulfonyl}amino)methyl]phosphonic acid $^1$H NMR (CDCl$_3$) δ (ppm): 8.11 (s, 1H), 7.85 (dd, 1H), 7.64 (d, 1H), 7.10 (d, 1H), 4.08 (t, 2H), 3.37 (t, 2H), 2.98 (dd, 2H), 1.78 (m, 2H), 1.59 (m, 2H), 1.47 (m, 4H); MS m/z 371 (M+23), 897 (2M+1).

[({[6-(2-azidoethoxy)-4,5,7-trifluoro-1-benzothien-2-yl]sulfonyl}amino)methyl]phosphonic acid MS m/z 447 (M+1).

Hydrogen-{[({6-[2-(4-aza-1-azoniabicyclo[2.2.2]oct-1-yl)ethoxy]-4,5,7-trifluoro-1-benzothien-2-yl}sulfonyl)amino]methyl}phosphonate It was prepared using DABCO and [({[6-(2-chloroethoxy)-4,5,7-trifluoro-1-benzothieny-2-yl]sulfonyl}amino)methyl]phosphonic acid prepared in Preparative Example 51, Method J.

MS m/z 516 (M).

{[({6-[4-(pyridine-4-ylthio)butoxy]-1-benzothien-2-yl}sulfonyl)amino]methyl}phosphonic acid

[({[6-(4-chlorobutoxy)-1-benzothien-2yl]sulfonyl}amino)methyl]phosphonic acid,

It was prepared in Preparative Example 52, Method I, tetrabutylammonium iodide, and 4-mercaptopyridine in DMF at 60° C. overnight gave product.

MS m/z 489 (M+1).

({[(5-{[(3-azidopropyl)thio]methyl}thieno[3,2-b]thien-2-yl)sulfonyl]amino}methyl)phosphonic acid $^1$H NMR (500 MHz, CD$_3$OD) δ (ppm): 7.85 (s, 1H), 7.30 (s, 1H), 4.07 (s, 2H), 3.41 (t, 2H), 3.21 (d, 2H), 2.61 (t, 2H), 1.84 (m, 2H); MS m/z 443 (M+1).

[({[5-(azidomethyl)thieno[2,3-b]thien-2-yl]sulfonyl}amino)methyl]phosphonic acid Purification was accomplished by using HPLC conditions described above with a YMC-ODSA column (30×100 mm; 10 micron).

$^1$H NMR (500 MHz, CD$_3$OD) δ (ppm): 7.80 (s, 1H), 7.37 (s, 1H), 4.63 (s, 2H), 3.20 (d, 2H); MS m/z 369 (M+1).

(5,6-Bis(2-azidoethoxy)benzo[d]thiazole-2-sulfonamido)methylphosphonic acid was purified by reverse phase HPLC (250×21.2 mm Aquasil C18 column, 40-70% methanol/water linear gradient, 30 min. elution time; elutes −20 min.) to product as a white solid.

$^1$H NMR (400 MHz, DMSO-d$_6$) δ (ppm): 7.83 (s, 1H); 7.77 (s, 1H); 4.28-4.22 (m, 4H); 3.69-3.64 (m, 4H); 3.16 (d, J=13.1, 2H).

(5,6-bis(3-azidopropoxy)benzo[d]thiazole-2-sulfonamido)methylphosphonic acid

Purified by preparative HPLC (Thermo, Aquasil C18, 240× 21.2 mm, 5 μm; eluting with a gradient MeOH/H$_2$O 10/90 to 95/5, both containing 0.05% HCO$_2$H, over 30 min) to afford title compound as a white solid.

$^1$H NMR (400 MHz, CD$_3$OD) δ (ppm): 7.67 (s, 1H), 7.63 (s, 1H), 4.20 (m, 4H), 3.58 (m, 4H), 3.24 (d, J=13.3 Hz, 2H), 2.12 (m, 4H); MS m/z 505 (M−1).

Preparative Example 67

Preparation of Ammonium 4-Cyano-3-Fluorophenyl [({[5-(Azidomethyl)-Thieno[3,2-b]Thien-2-Yl] Sulfonyl}Amino)Methyl]Phosphonate To the product from the prior Preparative Example (0.0476 g, 0.13 mmol) in anhydrous pyridine/DMF (0.5 mL/0.050 mL) was added 2-fluoro-4-hydroxybenzonitrile (0.018 g, 0.13 mmol) followed by trichloroacetonitrile (0.091 mL, 0.90 mmol). The reaction was conducted in a sealed tube and heated to 105° C. for 4.5 h. The reaction was concentrated in vacuo and purified by silica gel plate chromatography (1000 micron, 40/10/1 CHCl$_3$/MeOH/conc. NH$_4$OH). The product was further triturated with CH$_2$Cl$_2$ (3×) and the desired insoluble solid was collected by centrifugation.

$^1$H NMR (500 MHz, CD$_3$OD) δ (ppm): 7.84 (s, 1H), 7.50 (t, 1H), 7.39 (s, 1H), 7.14 (dd, 1H), 7.06 (dd, 1H), 4.69 (s, 2H), 3.24 (d, 2H).

Utilizing the foregoing procedure the follow compounds were prepared:

Ammonium 4-cyano-3-fluorophenyl({[(5-{[(3-azidopropyl)thio]methyl}thieno-[3,2-b]thien-2-yl)sulfonyl] amino}methyl)phosphonate It was prepared as a tan solid.

$^1$H NMR (500 MHz, CD$_3$OD) δ (ppm): 7.79 (s, 1H), 7.52 (t, 1H), 7.28 (s, 1H), 7.16 (dd, 1H), 7.14 (dd, 1H), 4.08 (s, 2H), 3.40 (t, 2H), 3.22 (d, 2H), 2.62 (t, 2H), 1.84 (m, 2H).

Ammonium 4-cyano-3-fluorophenyl[({[5-(aminomethyl) thieno-[2,3-b]thien-2-yl)sulfonyl}amino)methyl]phosphonate ¹H NMR (500 MHz, CD₃OD) δ (ppm): 7.74 (s, 1H), 7.51 (t, 1H), 7.32 (s, 1H), 7.16 (dd, 1H), 7.14 (dd, 1H), 4.65 (s, 2H), 3.26 (d, 2H); MS m/z 488 (M+1).

4-cyano-3-fluorophenyl hydrogen {[({5-[4-(2-azidoethoxy)phenyl]-1,3,4-thiadiazol-2-yl}-sulfonyl)amino] methyl}phosphonate MS m/z 540 (M+1).

4-cyano-3-fluorophenyl hydrogen {[({5-[3,4-bis(3-azidopropoxy)phenyl]-thophen-2-yl}-sulfonyl)amino] methyl}phosphonate MS m/z 623 (M−28).

4-cyano-3-fluorophenyl hydrogen {[({5-[3,4-bis(3-azidopropoxy)-2-methylphenyl]thophen-2-yl}sulfonyl)amino] methyl}phosphonate It was prepared and used as is in the next step.
MS m/z 637 (M−28).

4-cyano-3-fluorophenyl hydrogen {[({5-[4,5-bis(3-azidopropoxy)-2-methylphenyl]thophen-2-yl}sulfonyl)amino] methyl}phosphonate It was prepared and used as is in the next step.
MS m/z 637 (M−28).

4-cyano-3-fluorophenyl hydrogen[({[5-(2-azidoethoxy)-1-benzothien-2-yl]sulfonyl}-amino)methyl]phosphonate ¹H NMR (500 MHz, CD₃OD) δ (ppm): 7.83 (s, 1H), 7.80 (d, J=8.7 Hz, 1H) 7.57 (d, J=8.3 Hz, 1H), 7.45 (d, J=2.3 Hz, 1H), 7.11-7.20 (m, 2H), 4.26 (t, J=4.6 Hz, 2H), 3.66 (t, J=4.6 Hz, 2H); MS m/z 512 (M+1).

4-cyano-3-fluorophenyl hydrogen[({[5-(2-azidoethoxy)-3-chloro-1-benzothien-2-yl]-sulfonyl}amino)methyl]phosphonate ¹H NMR (600 MHz, CD₃OD) δ (ppm): 7.85 (s, 1H), 7.80 (d, J=8.8 Hz, 1H), 7.48 (t, J=7.8 Hz, 1H), 7.36 (d, J=8.9 Hz, 1H), 7.07 (dd, J=10.8 Hz, 2.4 Hz, 1H), 7.04 (dd, J=8.9 Hz, 1.2 Hz, 1H), 4.37 (t, d=4.9 Hz, 2H), 3.85 (t, J=4.7 Hz, 2H), 3.47 (d, J=10.6 Hz, 2H); MS m/z 547 (M+1).

4-cyano-3-fluorophenyl hydrogen[({[5-(2-azidoethoxy)-7-chloro-1-benzothien-2-yl]sulfonyl}-amino)methyl]phosphonate MS m/z 546 (M+1).

4-cyano-3-fluorophenyl hydrogen[({[5-(2-azidoethoxy)-7-fluoro-3-methyl-1-benzothien-2-yl]-sulfonyl}amino)methyl]phosphonate MS m/z 430 (M+1).

4-cyano-3-fluorophenyl hydrogen[({[6-(6-azidohexyloxy)-1-benzothien-2-yl]-sulfonyl}amino)methyl]phosphonate MS m/z 540 (M−28+1).

4-Cyano-3-fluorophenyl hydrogen[({[5,6-bis(3-azidopropoxy)-1-benzothien-2-yl]sulfonyl}-amino)methyl]phosphonate It was prepared and purified by reverse phase HPLC.
¹H NMR (500 MHz, CD₃OD) δ (ppm): 7.79 (s, 1H), 7.60 (m, 1H), 7.44 (s, 1H), 7.40 (s, 1H), 7.15 (m, 2H), 4.20 (m, 4H), 3.60 (m, 4H), 3.44 (d, 2H), 2.16 (m, 4H); MS m/z 597 (M−27).

4-cyano-3-fluorophenyl hydrogen[({[5,6-bis(3-azidopropoxy)-3-ethyl-1-benzothien-2-yl]-sulfonyl}amino)methyl] phosphonate MS m/z 625 (M−27).

4-cyano-3-fluorophenyl hydrogen[({[4,7-difluoro-5,6-bis (2-azidoethoxy)-3-ethyl-1-benzothien-2-yl]sulfonyl}amino) methyl]phosphonate MS m/z 633 (M−27).

4-cyano-3-fluorophenyl hydrogen[({[4,7-difluoro-5,6-bis (3-azidopropoxy)-3-ethyl-1-benzothien-2-yl] sulfonyl}amino)methyl]phosphonate MS m/z 661 (M−27).

4-Cyano-3-fluorophenyl hydrogen[({[5,6-bis(4-azidobutoxy)-1-benzothien-2-yl]sulfonyl}-amino)methyl]phosphonate It was prepared and used as is in the next step.
MS m/z 625 (M+1).

4-cyano-3-fluorophenyl hydrogen[({[6-(4-azidobutoxy)-5-(3-azidopropoxy)-1-benzothien-2-yl]sulfonyl}amino)methyl]phosphonate and 4-cyano-3-fluorophenyl hydrogen [({[6-(4-azidobutoxy)-5-(3-azidopropoxy)-1-benzothien-2-yl]sulfonyl}amino)methyl]phosphonate The products obtained from Preparative Example 56, Method B., were coupled with 2-fluoro-4-hydroxybenzonitrile. The desired products were obtained after purification by silica gel plate chromatography (1000 micron, 40/10/1 CHCl₃/MeOH/conc. NH₄OH).

Major isomer (0.0263 g): ¹H NMR (500 MHz, CD₃OD) δ (ppm): 7.71 (s, 1H), 7.43 (s, 1H), 7.43 (t, 1H), 7.37 (s, 1H), 7.10 (dd, 1H), 7.03 (dd, 1H), 4.20 (t, 2H), 4.11 (t, 2H), 3.59 (t, 2H), 3.44 (t, 2H), 3.26 (d, 2H), 2.11 (m, 2H), 1.94 (m, 2H), 1.85 (m, 2H); MS m/z 639 (M+1).

Minor isomer (0.0088 g): ¹H NMR (500 MHz, CD₃OD) δ (ppm): 7.72 (s, 1H), 7.43 (s, 1H), 7.43 (t, 1H), 7.40 (s, 1H), 7.10 (dd, 1H), 7.03 (dd, 1H), 4.16 (m, 4H), 3.59 (t, 2H), 3.45 (t, 2H), 3.25 (d, 2H), 2.11 (m, 2H), 1.95 (m, 2H), 1.85 (m, 2H).

4-cyano-3-fluorophenyl hydrogen(5,6-bis(2-azidoethoxy) benzo-[d]thiazole-2-sulfonamido)methylphosphonate The product was partially purified by reverse phase HPLC (250×21.2 mm Aquasil C18 column, 45%-90% methanol/water linear gradient, 30 min. elution time; elutes ~15 min.) and was contaminated with large amounts of un-reacted 2-fluoro-4-hydroxybenzonitrile. It was used as is for the next transformation.

4-cyano-3-fluorophenyl hydrogen(5,6-bis(2-azidopropoxy)-benzo[d]thiazole-2-sulfonamido)methylphosphonate Purification by flash chromatography on silica gel (MeOH/NH₄OH/CHCl₃: 20/1/79) to afforded the title compound as a pale yellow solid.

MS m/z 624 (M−1).

4-cyano-3-fluorophenyl hydrogen {[({6-[4-(pyridin-4-ylthio)butoxy]-1-benzothien-2-yl}-sulfonyl)amino] methyl}phosphonate.

MS m/z 608 (M+1).

Utilizing the foregoing procedure and substituting 2-trifluoromethyl-4-hydroxybenzonitrile for 2-fluoro-4-hydroxybenzonitrile, the following compounds were prepared:

4-cyano-3-(trifluoromethyl)phenyl hydrogen[({[5-(2-azidoethoxy)-1-benzothien-2-yl]-sulfonyl}amino) methyl]phosphonate ¹H NMR (600 MHz, CD₃OD) δ (ppm): 7.79 (s, 1H), 7.76 (d, J=8.8 Hz, 1H), 7.71 (d, J=8.5 Hz, 1H), 7.67 (bs, 1H), 7.44 (d, J=9.0 Hz, 1H), 7.42 (d, J=2.3 Hz, 1H), 7.15 (dd, J=8.8 Hz, 2.3 Hz, 1H), 4.23 (t, J=4.9 Hz, 2H), 3.62 (t, J=4.9 Hz, 2H); MS m/z 562 (M+1).

4-cyano-3-(trifluoromethyl)phenyl hydrogen[({[5-(2-azidoethoxy)-7-chloro-1-benzothien-2-yl]-sulfonyl}amino) methyl]phosphonate MS m/z 597 (M+).

3-fluoro-4-(trifluoromethyl)phenyl hydrogen[({[5-(2-azidoethoxy)-7-fluoro-1-benzothien-2-yl]-sulfonyl}amino)methyl]phosphonate MS m/z 581 (M+1).

4-cyano-3-fluorophenyl hydrogen[({[6-(2-azidoethoxy)-4,5,7-trifluoro-1-benzothien-2-yl]-sulfonyl}amino)methyl] phosphonate MS m/z 538 (M−N₂+1).

4-cyano-3-(trifluoromethy)1phenyl hydrogen[({[5,6-bis-(3-azidopropoxy)-1-benzothien-2-yl]-sulfonyl}amino)methyl]phosphonate MS m/z 647 (M$^+$–27).

Utilizing the foregoing procedure and 2-fluoro-4-hydroxyphenyl-trifluoromethylsulfone, prepared in Preparative Example 15, as the coupling partner, the following compounds were prepared:

3-fluoro-4-[(trifluoromethyl)sulfonyl]phenyl hydrogen [({[5,6-bis(2-azidoethoxy)-4,7-dichloro-1-benzothien-2-yl]sulfonyl}amino)methyl]phosphonate MS m/z 744 (M$^+$–28).

3-fluoro-4-[(trifluoromethyl)sulfonyl]phenyl hydrogen [({[5,6-bis(2-azidoethoxy)-1-benzothien-2-yl]sulfonyl}amino)methyl]phosphonate It was prepared and used as is in the next step.

3-fluoro-4-[(trifluoromethyl)sulfonyl]phenyl hydrogen [({[5-(azidoethoxy)-7-chloro-1-benzothien-2-yl]sulfonyl}amino)methyl]phosphonate MS m/z 654 (M+1).

3-fluoro-4-[(trifluoromethyl)sulfonyl]phenyl hydrogen [({[5-(azidoethoxy)-7-fluoro-3-methyl-1-benzothien-2-yl]sulfonyl}amino)methyl]phosphonate MS m/z 636 (M+1).

Utilizing the foregoing procedure and 2-cyano-5-hydroxypyridine as the coupling partner, the following compounds were prepared:

6-cyanopyridin-3-yl hydrogen[({[5,6-bis(2-azidoethoxy)-1-benzothien-2-yl]sulfonyl}-amino)methyl]phosphonate $^1$H NMR (500 MHz, CD$_3$OD) δ (ppm): 8.50 (s, 1H), 7.80 (m, 2H), 7.46 (m 3H), 4.26 (t, 4H), 3.64 (t, 4H), 3.25 (d, 2H); MS m/z 579 (M$^+$).

6-cyanopyridin-3-yl hydrogen[({[5-(2-azidoethoxy)-1-benzothien-2-yl]sulfonyl}amino)methyl]phoshonate MS m/z 495 (M+1).

Utilizing the foregoing procedure and 6-(methylsulfonyl)pyridine-3-ol as the coupling partner, the following compound was prepared:

4-methylsulfonyl-3-pyridyl[({[5-(2-azidoethoxy)-1-benzothien-2-yl]sulfonyl}amino) methyl]phosphonate MS m/z 548 (M+1).

Preparative Example 68

Preparation of 2-[({[(4-Cyano-3-Fluorophenoxy)(Hydroxy)Phosphoryl]-Methyl}Amino)Sulfonyl]-1-Benzothiophene-5-Carboxylic Acid A solution of ({[(5-formyl-1-benzothien-2-yl)sulfonyl]amino}methyl)phosphonic acid (0.22 g, 0.66 mmol), trichloroacetonitrile (1.0 mL, 10 mmol) and 2-fluoro-4-hydroxybenzonitrile (0.18 g, 1.3 mmol) in anhydrous pyridine (10 mL) was heated at 120° C. for 2.5 h in a pressure bottle. The reaction mixture was then concentrated and the residue triturated with ether and ethyl acetate, and dissolved in 50% aqueous acetone (25 mL). To this solution were added 2-methyl-2-butene (5 mL), sodium chlorite (0.020 g, 0.22 mmol) and potassium dihydrogen phosphate (0.020 g, 0.15 mmol) in water (1 mL). The mixture was stirred for 30 min then concentrated. The residue was purified by reverse phase HPLC (250×21.2 mm Aquasil C18 column, 30%-70% methanol/water linear gradient, 30 min elution time, elutes ~16 min) to yield the product as an amorphous white solid.

$^1$H NMR (400 MHz, CD$_3$OD) δ (ppm): 8.50 (s, 1H); 8.02 (dd, J=8.4, 1.4, 1H); 7.92 (d, J=8.8, 1H); 7.91 (s, 1H); 7.39 (t, J=8.2, 1H); 7.04-6.96 (m, 2H). [CH$_2$ peak hidden underneath residual methanol peak at ~3.2 ppm].

Preparative Example 69

Di-Tert-Butyl 2,2'-(2-(N-(((4-Cyano-3-Fluorophenoxy)(Hydroxy)-Phosphoryl)Methyl)Sulfamoyl)-Benzo[B]Thiophene-5-Carboxamido)Bis(Ethane-2,1-Diyl)Dicarbamate To a solution of the carboxylic acid product of the prior example (7.0 mg, 0.015 mmol), di-tert-butyl 2,2'-azanediylbis(ethane-2,1-diyl)dicarbamate (50 mg, 0.16 mmol) and DIPEA (0.15 mL, 0.86 mmol) in dry DMF (2 mL) at 0° C. was added HATU (31 mg, 0.082 mmol), and the resulting mixture was stirred at r.t. for 24 h. 50% aqueous methanol (1.5 mL) was added, and the mixture was purified by reverse phase HPLC (250×21.2 mm Aquasil C18 column, 40%-75% methanol/water linear gradient, 30 min elution time, elutes ~23 min) to yield the product contaminated with some starting amine, as an amorphous white solid.

MS m/z 754 (M).

Preparative Example 70

Preparation of 4-Cyano-3-Fluorophenyl Hydrogen [({[5-(2-Iodoethoxy)-1-Benzothien-2-Yl]Sulfonyl}Amino)Methyl]Phosphonate To a stirred solution of 4-cyano-3-fluorophenyl hydrogen [({[5-(2-chloroethoxy)-1-benzothien-2-yl]sulfonyl}amino)methyl]phosphonate (56 mg, 0.111 mmol), in acetone (4 mL) was added sodium iodide (498 mg, 3.32 mmol). The suspension was stirred at 60° C. for 72 hrs. The reaction was cooled to room temperature and concentrated in vacuo. The resulting residue was dissolved in 10% MeCN—H$_2$O and purified by HPLC. After lyophilization product was obtained.

$^1$H NMR (500 MHz, CD$_3$OD) δ (ppm): 7.81 (s, 1H), 7.79 (d, J=9.6 Hz, 1H) 7.54 (t, J=8.0 Hz, 1H), 7.42 (dd, J=2.5, 8.9 Hz, 1H), 7.19 (dd, J=2.3, 8.9 Hz, 1H), 7.13 (dd, J=2.1, 11 Hz, 1H), 7.09 (dd, d=1.8, 8.7 Hz, 1H) 4.36 (t, J=6.4 Hz, 2H), 3.54 (t, J=6.4 Hz, 2H), 3.37 (d, J=12.8 Hz, 2H); MS m/z 597 (M+1).

Utilizing the foregoing procedure, the following compound was prepared:

4-cyano-3-fluorophenyl hydrogen[({[4,5,7-trifluoro-6-(2-iodoethoxy)-1-benzothien-2-yl]-sulfonyl}amino)methyl]phosphonate MS m/z 651 (M+1).

Preparative Example 71

Preparation of 4-Cyano-3-Fluorophenyl Hydrogen {[({5-[(Bromoacetyl)Amino]-1-Benzothien-2-Yl}Sulfonyl)Amino]-Methyl}Phosphonate To a stirred suspension of 4-cyano-3-fluorophenyl hydrogen({[(5-amino-1-benzothien-2-yl)sulfonyl]amino}methyl)phosphonate (19 mg, 0.04 mmol), prepared in Example 4, in anhydrous CH$_2$Cl$_2$ (10 mL) at 0° C. under nitrogen were added diisopropylethylamine (38 μL, 0.22 mmol) and bromoacetyl chloride (18 μL, 0.22 mmol), respectively. The reaction mixture was stirred for 1 h, quenched by addition of methanol and water, shaken for 2 h at room temperature, and concentrated. The residue was purified twice by preparative HPLC (Thermo, Aquasil C18, 250×21.2 mm, 5 μm; eluted with a linear gradient of MeOH/H$_2$O: 10/90→95/5 and 5/95→95/5 [both containing 0.05% HCO₂H], over 45 min), to afford the product as a white solid.

¹H NMR (400 MHz, DMSO-d₆) δ (ppm): 10.67 (s, 1H), ABX system ($\delta_A$=8.04, $\delta_B$=7.65, $\delta_X$=8.35, $J_{AB}$=8.8 Hz, $J_{BX}$=1.9 Hz, $J_{AX}$=0 Hz, 3H), 8.04-7.96 (m, 2H), 7.73 (t, J=8.3 Hz, 1H), 7.32 (dd, J=11.7, 2.0 Hz, 1H), 7.13 (d, J=8.4 Hz, 1H), 4.12 (s, 2H), 3.06 (dd, J=12.7, 5.9 Hz, 2H); MS m/z 560.0-561.8 (M−1).

Example 1

Preparation of 4-Cyano-3-Fluorophenyl-[({[5-(2-Pyridiniumethoxy)-1-Benzothien-2-Yl]Sulfonyl}Amino)Methyl]-Phosphonate

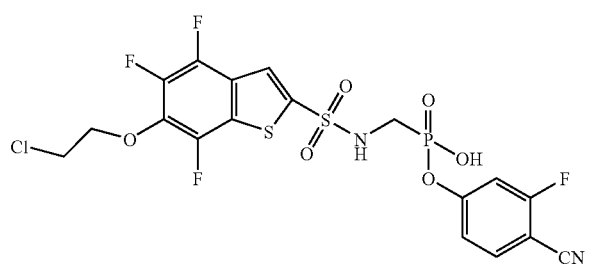 [SMILES: N#Cc1ccc(OP(=O)(O)CNS(=O)(=O)c2cc3c(F)c(F)c(OCCCl)c(F)c3s2)cc1F]

[({[5-(2-chloroethoxy)-1-benzothien-2-yl]sulfonyl}amino)methyl]phosphonic acid (60 mg, 0.156 mmol) was combined with 2-fluoro-4-hydroxybenzonitrile (21.4 mg, 0.156 mmol), trichloroacetonitrile (156 µL, 1.56 mmol) and anhydrous pyridine (1.0 mL) in a sealed tube. The mixture was placed in an oil bath and stirred at 110° C. for 3.5 hrs. The mixture was cooled to room temperature and concentrated in vacuo. The resulting residue was dissolved in 10% MeCN—H₂O and purified by HPLC using a reverse phase C₁₈ column to afford, after lyophilization 4-cyano-3-fluorophenyl hydrogen[({[5-(2-chloroethoxy)-1-benzothien-2-yl]sulfonyl}amino)methyl]phosphonate (A) and the desired product, 4-cyano-3-fluorophenyl[({[5-(2-pyridiniumethoxy)-1-benzothien-2-yl]sulfonyl}amino)methyl]phosphonate (B).

A: ¹H NMR (500 MHz, CD₃OD) δ (ppm): 7.82-7.80 (m, 2H), 7.59 (t, J=8.0 Hz, 1H) 7.44 (d, J=2.3 Hz, 1H), 7.21 (dd, J=8.9, 2.3 Hz, 1H), 7.17 (d, J=10.7 Hz, 1H), 7.11 (d, J=8.5 Hz, 1H), 4.34 (t, J=5.5 Hz, 2H), 3.92 (t, J=5.5 Hz, 2H), 3.43 (bd, 2H); MS m/z 505 (M+1).

B: ¹H NMR (500 MHz, CD₃OD) δ (ppm): 9.16 (d, J=5.8 Hz, 1H), 8.69 (t, J=11.0 Hz), 8.21 (t, J=12.9 Hz, 1H), 7.80 (d, J=9.0 Hz, 1H), 7.74 (s, 1H) 7.41 (d, J=2.5 Hz, 1H), 7.32 (t, J=8.3 Hz, 1H), 7.17 (dd, J=2.5, 8.3 Hz, 1H), 7.03-6.97 (m, 2H), 5.16 (t, J=4.4 Hz, 2H), 4.64 (t, J=4.8 Hz, 2H); MS m/z 549 (M+1).

Utilizing the foregoing procedure, the following compounds were prepared:

4-cyano-3-fluorophenyl hydrogen[({[6-(2-chloroethoxy)-4,5,7-trifluoro-1-benzothien-2-yl]sulfonyl}amino)methyl]phosphonate It was prepared by substituting [({[6-(2-chloroethoxy)-4,5,7-trifluoro-1-benzothien-2-yl]sulfonyl}amino)methyl]phosphonic acid for [({[5-(2-chloroethoxy)-1-benzothien-2-yl]sulfonyl}amino)methyl]phosphonic acid.

¹H NMR (DMSO-d₆) δ (ppm): 8.02 (d, J=3.2 Hz, 1H), 7.65 (t, J=8.5 Hz, 1H), 7.24 (dd, 1H), 7.08 (dd, 1H), 4.55 (t, 2H), 3.97 (t, 2H), 3.00 (d, J=12.6 Hz, 2H).

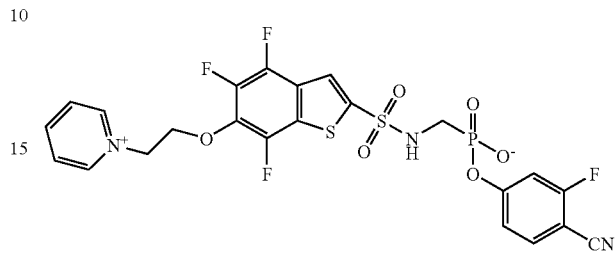

4-cyano-3-fluorophenyl-[({[6-(2-pyridiniumethoxy)-4,5,7-trifluoro-1-benzothien-2-yl]-sulfonyl}amino)methyl]phosphonate ¹H NMR (DMSO-d₆) δ (ppm): 9.15 (d, J=5.6 Hz, 2H), 8.67 (t, J=7.8 Hz, 1H), 8.22 (t, J=7.1 Hz, 2H), 8.12 (broad s, 1H), 7.96 (d, J=3.2 Hz, 1H), 7.58 (t, J=8.4 Hz, 1H), 7.17 (dd, 1H), 7.02 (dd, 1H), 5.08 (t, 2H), 4.79 (t, 2H), 2.93 (dd, 2H).

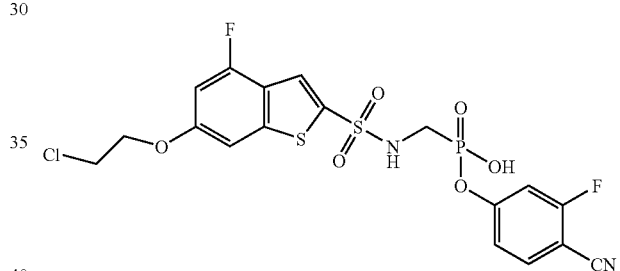

4-cyano-3-fluorophenyl hydrogen[({[6-(2-chloroethoxy)-4-fluoro-1-benzothien-2-yl]-sulfonyl}amino)methyl]phosphonate MS m/z 523 (M+1).

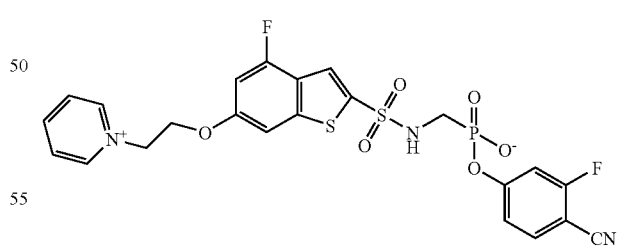

4-cyano-3-fluorophenyl-[({[6-(2-pyridiniumethoxy)-4-fluoro-1-benzothien-2-yl]-sulfonyl}amino)methyl]phosphonate ¹H NMR (CD₃OD) δ (ppm): 9.10 (d, J=5.8 Hz, 2H), 8.63 (t, J=7.8 Hz, 1H), 8.16 (t, J=7.2 Hz, 2H), 7.59 (s, 1H), 7.29 (t, J=8.3 Hz, 1H), 7.17 (d, J=1.7 Hz, 1H), 6.97 (m, 2H), 6.79 (dd, 1H), 5.11 (t, 2H), 4.60 (t, 2H), 3.22 (d, 2H).

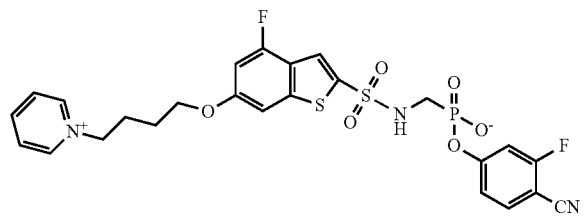 [SMILES: N#Cc1ccc(OP(=O)([O-])CNS(=O)(=O)c2cc3c(F)cc(OCCCC[n+]4ccccc4)cc3s2)cc1F]

4-cyano-3-fluorophenyl-[({[6-(4-pyridiniumbutoxy)-4-fluoro-1-benzothien-2-yl]-sulfonyl}amino)methyl]phosphonate $^1$H NMR (CD$_3$OD) δ (ppm): 9.06 (d, J=5.5 Hz, 2H), 8.62 (t, J=7.7 Hz, 1H), 8.16 (t, J=6.6 Hz, 2H), 7.72 (s, 1H), 7.42 (t, J=8.2 Hz, 1H), 7.18 (s, 1H), 7.05 (m, 2H), 6.79 (d, J=11.4 Hz, 1H), 4.78 (t, 2H), 4.15 (t, 2H), 3.32 (d, 2H), 2.28 (m, 2H), 1.96 (m, 2H).

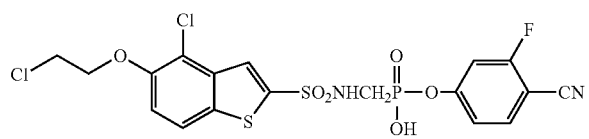

4-cyano-3-fluorophenyl hydrogen[({[4-chloro-5-(2-chloroethoxy)-1-benzothien-2-yl]sulfonyl}-amino)methyl]phosphonate MS m/z 540 (M+1).

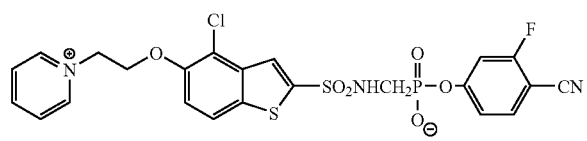

4-cyano-3-fluorophenyl[({[5-(2-pyridinium-1-ylethoxy)-4-chloro-1-benzothien-2-yl]-sulfonyl}amino)methyl]phosphonate $^1$H NMR (500 MHz, CD$_3$OD) δ (ppm): 9.16 (d, J=5.4 Hz, 2H), 8.69 (t, J=7.8 Hz, 1H), 8.22 (t, J=6.9 Hz, 2H), 7.78 (d, J=8.9 Hz, 1H), 7.67 (s, 1H), 7.32 (d, J=6.9 Hz, 1H), 7.18 (t, J=8.0 Hz, 1H), 6.94 (m, 2H), 5.19 (t, J=4.6 Hz, 2H), 4.69 (t, J=4.6 Hz, 2H); MS m/z 581 (M).

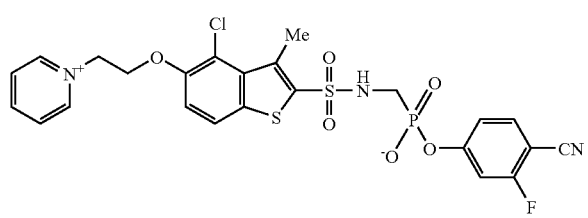

4-cyano-3-fluorophenyl-[({[4-chloro-3-methyl-5-(2-pyridinium-1-ylethoxy)-1-benzothien-2-yl]sulfonyl}amino)methyl]phosphonate was prepared after reverse phase HPLC purification.

$^1$H NMR (500 MHz, CD$_3$OD) δ (ppm): 9.20 (d, 2H), 8.70 (t, 1H), 8.20 (t, 1H), 7.78 (d, 1H), 7.58 (t, 1H), 7.36 (d, 1H), 7.16 (t, 1H), 6.82 (d, 1H), 6.70 (m, 1H), 5.20 (t, 2H), 4.70 (t, 2H), 3.35 (d, 2H), 2.80 (s, 3H); MS m/z 596 (M+1).

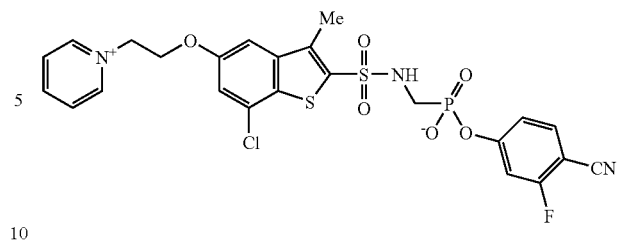

4-cyano-3-fluorophenyl-[({[7-chloro-3-methyl-5-(2-pyridinium-1-ylethoxy)-1-benzothien-2-yl]-sulfonyl}amino)methyl]phosphonate $^1$H NMR (500 MHz, CD$_3$OD) δ (ppm): 7.40 (d, 1H), 7.30 (d, 1H), 4.40 (t, 2H), 3.90 (t, 2H), 3.30 (d, 2H), 2.70 (s, 3H); MS m/z 434 (M).

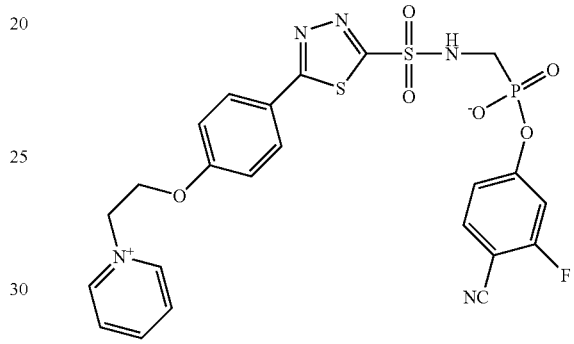

4-cyano-3-fluorophenyl-{[({5-[4-(2-pyridinium-1-ylethoxy)phenyl]-1,3,4-thiadiazol-2-yl}-sulfonyl)amino]methyl}phosphonate $^1$H NMR (500 MHz, CD$_3$OD) δ (ppm): 9.16 (bs, 2H), 8.68 (bs, 1H), 8.20 (bs, 2H), 7.90 (bs, 2H), 7.56 (bs, 1H), 7.10 (bs, 4H), 5.20 (bs, 2H), 4.70 (bs, 2H), 3.50 (bs, 2H); MS m/z 577 (M+1).

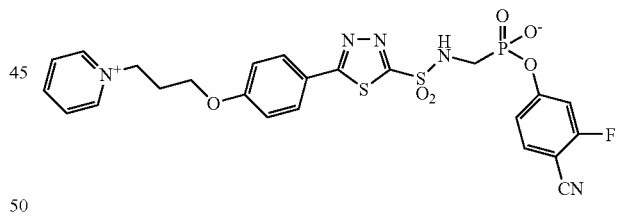

4-cyano-3-fluorophenyl-{[({5-[4-(3-pyridinium-1-ylpropoxy)phenyl]-1,3,4-thiadiazol-2-yl}sulfonyl)amino]methyl}phosphonate was prepared.

$^1$H NMR (400 MHz, CD$_3$OD) δ (ppm): peaks are broad due to the presence of rotamers; MS m/z 590 (M+1).

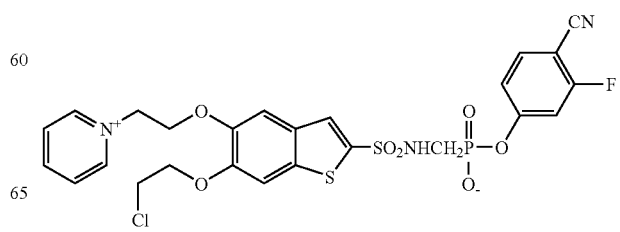

-continued

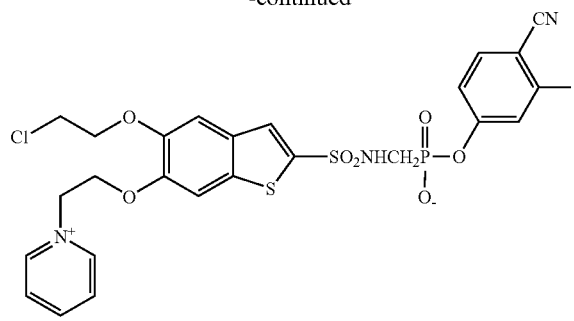

4-cyano-3-fluorophenyl-[({[5-(2-pyridinium-1-ylethoxy)-6-(2-chloroethoxy)-1-benzothien-2-yl]-sulfonyl}amino)methyl]phosphonate and 4-cyano-3-fluorophenyl-[({[6-(2-pyridinium-1-ylethoxy)-5-(2-chloroethoxy)-1-benzothien-2-yl]-sulfonyl}amino)methyl] phosphonate, two regio isomeric products, were prepared which were contaminated with some of the starting phenol.

MS m/z 626 (M+1).

Using the foregoing procedure and substituting 2-trifluoromethyl-4-hydroxybenzonitrile for 2-fluoro-4-hydroxybenzonitrile, the following compounds were prepared:

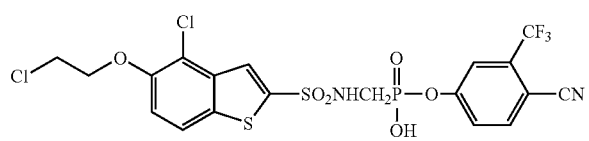

4-cyano-3-(trifluoromethyl)phenyl hydrogen[({[4-chloro-5-(2-chloroethoxy)-1-benzothien-2-yl]sulfonyl}-amino)methyl]phosphonate

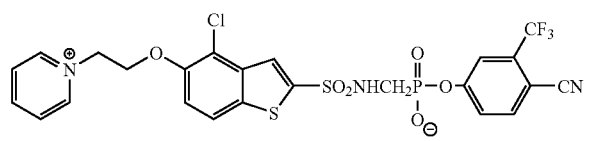

4-cyano-3-(trifluoromethyl)phenyl[({[5-(2-pyridinium-1-ylethoxy)-1-benzothien-2-yl]sulfonyl}amino)methyl]phosphonate ¹H NMR (500 MHz, CD₃OD) δ (ppm): 9.16 (d, J=5.7 Hz, 2H), 8.69 (t, J=7.8 Hz, 1H), 8.22 (t, J=6.6 Hz, 2H), 7.77 (d, J=8.9 Hz, 1H), 7.67 (s, 1H), 7.56 (d, J=2.1 Hz, 1H), 7.48 (d, J=8.4 Hz, 1H), 7.32 (m, 2H), 5.18 (t, J=4.7 Hz, 2H), 4.77 (t, J=4.7 Hz, 2H); MS m/z 632 (M).

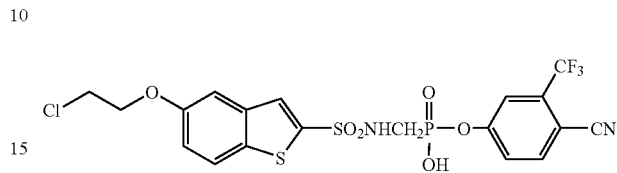

4-cyano-3-(trifluoromethyl)phenyl-[({[5-(2-chloroethoxy)-1-benzothien-2-yl]-sulfonyl}amino)methyl]phosphonate MS m/z 556 ([M+1).

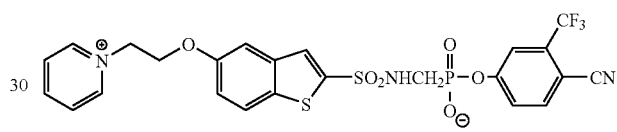

4-cyano-3-(trifluoromethyl)phenyl-[({[5-(2-pyridinium-1-ylethoxy)-1-benzothien-2-yl]-sulfonyl}amino)methyl] phosphonate ¹H NMR (500 MHz, CD₃OD) δ (ppm): 9.12 (d, J=5.5 Hz, 1H), 8.64 (t, J=7.8 Hz, 1H), 8.16 (t, J=7.8 Hz, 2H), 7.75 (d, J=8.9 Hz, 1H), 7.72 (s, 1H), 7.60 (bs, 1H), 7.55 (d, J=8.7 Hz, 1H) 7.36 (bs, 2H), 7.12 (dd, J=8.7 Hz, 2.3 Hz, 1H), 5.12 (t, J=4.8 Hz, 2H) 4.59 (t, d=4.8 Hz, 2H), 3.26 (d, J=11.3 Hz, 2H); MS m/z 597 (M).

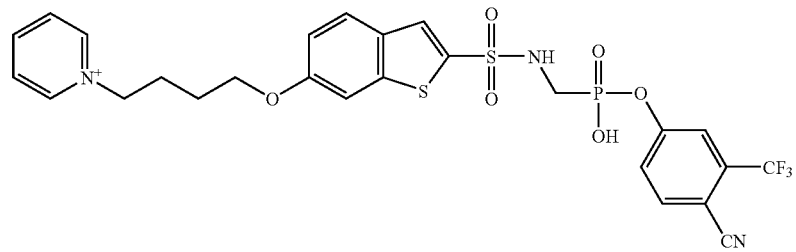 [SMILES: N#Cc1ccc(OP(=O)(O)CNS(=O)(=O)c2cc3ccc(OCCCC[n+]4ccccc4)cc3s2)cc1C(F)(F)F]

4-cyano-3-(trifluoromethyl)phenyl-[({[6-(4-pyridinium-1-ylbutoxy)-1-benzothien-2-yl]-sulfonyl}amino)methyl] phosphonate ¹H NMR (d₆-DMSO) δ (ppm): 9.14 (d, 2H), 8.62 (t, 1H), 8.19 (t, 2H), 7.86 (d, 1H), 7.82 (d, 2H), 7.68 (s, 2H), 7.59 (s, 1H), 7.48 (d, 1H), 7.08 (d, 1H), 4.71 (t, 2H), 4.14 (t, 2H), 2.98 (dd, 2H), 2.12 (quintet, 2H), 1.80 (quintet, 1H); MS m/z 626 (M).

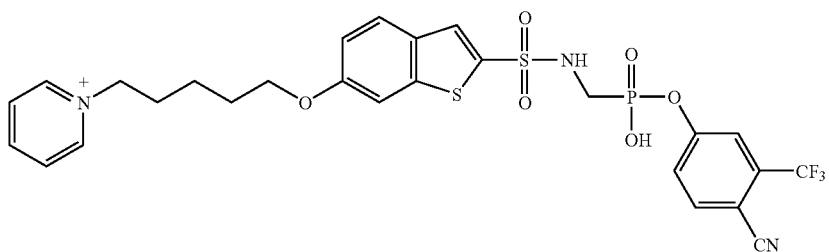

4-cyano-3-(trifluoromethyl)phenyl-[({[6-(5-pyridinium-1-ylpentoxy)-1-benzothien-2-yl]-sulfonyl}amino)methyl]phosphonate $^1$H NMR (d$_6$-DMSO) δ (ppm): 9.12 (d, 2H), 8.61 (t, 1H), 8.18 (t, 2H), 7.91 (d, 1H), 7.76 (s, 1H), 7.72 (s, 1H), 7.59 (s, 1H), 7.48 (d, 1H), 7.04 (d, 1H), 4.64 (t, 2H), 4.08 (t, 2H), 2.95 (dd, 2H), 2.02 (quintet, 2H), 1.82 (quintet, 2H), 1.45 (quintet, 2H); MS m/z 640 (M).

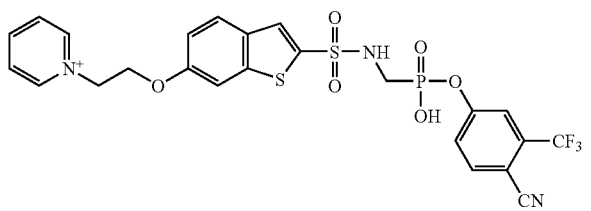 [SMILES: N#Cc1ccc(OP(=O)(O)CNS(=O)(=O)c2cc3ccc(OCC[n+]4ccccc4)cc3s2)cc1C(F)(F)F]

4-cyano-3-(trifluoromethyl)phenyl-[({[6-(2-pyridinium-1-ylethoxy)-1-benzothien-2-yl]sulfonyl}-amino)methyl]phosphonate $^1$H NMR (d$_6$-DMSO) δ (ppm): 9.16 (d, 2H), 8.64 (t, 1H), 8.10 (t, 2H), 7.89 (d, 1H), 7.86 (s, 1H), 7.83 (s, 1H), 7.80 (s, 1H), 7.73 (s, 1H), 7.62 (s, 1H), 7.48 (d, 1H), 7.05 (d, 1H), 5.09 (t, 2H), 4.01 (t, 2H); MS m/z 598 (M).

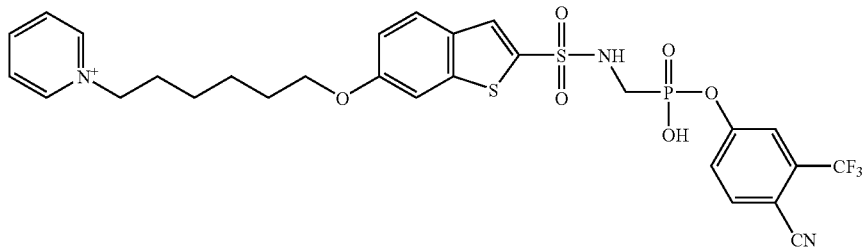 [SMILES: N#Cc1ccc(OP(=O)(O)CNS(=O)(=O)c2cc3ccc(OCCCCCC[n+]4ccccc4)cc3s2)cc1C(F)(F)F]

4-cyano-3-(trifluoromethyl)phenyl-[({[6-(6-pyridinium-1-ylhexoxy)-1-benzothien-2-yl]-sulfonyl}amino)methyl]phosphonate.

$^1$H NMR (d$_6$-DMSO) δ (ppm): 9.09 (d, 2H), 8.60 (t, 1H), 8.17 (t, 2H), 7.93 (d, 1H), 7.84 (s, 1H), 7.75 (s, 1H), 7.64 (s, 1H), 7.58 (s, 1H), 7.50 (d, 1H), 7.08 (d, 1H) 4.62 (t, 2H), 4.03 (t, 2H), 3.02 (dd, 2H), 1.98 (quintet, 2H), 1.75 (quintet, 2H), 1.48 (quintet, 2H), 1.39 (quintet, 2H); MS m/z 654 (M).

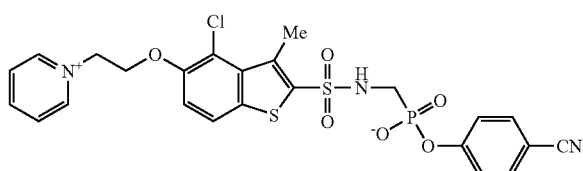

4-cyano-3-(trifluoromethyl)phenyl-[({[4-chloro-3-methyl-5-(2-pyridinium-1-ylethoxy)-1-benzothien-2-yl]sulfonyl}amino)methyl]phosphonate was prepared after reverse phase HPLC purification.

$^1$H NMR (500 MHz, CD$_3$OD) δ (ppm): 9.18 (d, 2H), 8.70 (t, 1H), 8.20 (t, 2H), 7.70 (d, 1H), 7.42 (d, 1H), 7.40 (d, 1H), 7.24 (d, 1H), 7.20 (d, 1H), 5.20 (t, 2H), 4.60 (t, 2H), 3.30 (d, 2H), 2.80 (s, 3H); MS m/z 646 (M+1).

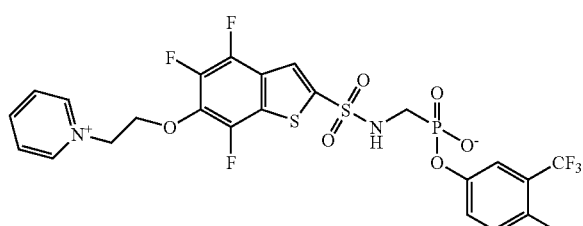

4-cyano-3-(trifluoromethyl)phenyl-[({[4,5,7-trifluoro-6-(2-pyridinium-1-ylethoxy)-1-benzothien-2-yl]sulfonyl}amino)methyl]phosphonate ¹H NMR (DMSO-d₆) δ (ppm): 9.17 (d, J=5.5 Hz, 2H), 8.69 (t, J=7.8 Hz, 1H), 8.24 (t, J=7.1 Hz, 2H), 8.28 (broad s, 1H), 7.99 (d, J=3.2 Hz, 1H), 7.88 (t, J=8.4 Hz, 1H), 7.67 (d, J=2.0 Hz, 1H), 7.47 (dd, 1H), 5.10 (t, 2H), 4.80 (t, 2H), 3.03 (dd, 2H).

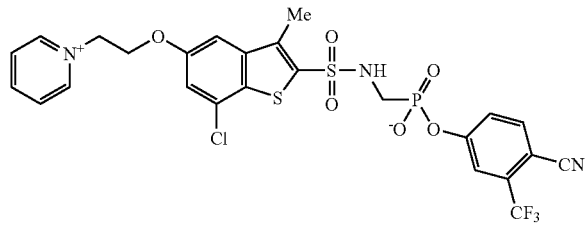

4-cyano-3-(trifluoromethyl)phenyl-[({[7-chloro-3-methyl-5-(2-pyridinium-1-ylethoxy)-1-benzothien-2-yl]sulfonyl}amino)methyl]phosphonate ¹H NMR (500 MHz, CD₃OD) δ (ppm): 9.10 (d, 2H), 8.64 (t, 1H), 8.20 (t, 2H), 7.46 (d, 1H), 7.40 (d, 1H), 7.24 (d, 1H), 7.16 (s, 1H), 7.08 (s, 1H), 5.18 (t, 2H), 4.60 (t, 2H), 3.10 (d, 2H), 2.50 (s, 3H); MS m/z 646 (M).

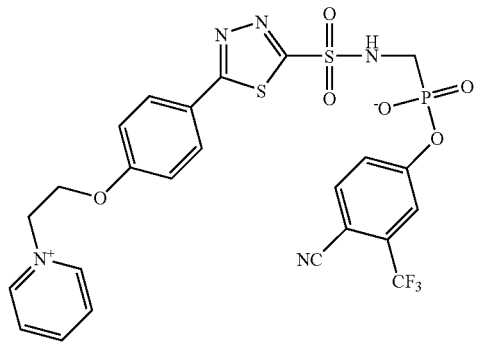

4-cyano-3-(trifluoromethyl)phenyl-{[({5-[4-(2-pyridinium-1-ylethoxy)phenyl]-1,3,4-thiadiazol-2-yl}sulfonyl)amino]methyl}phosphonate ¹H NMR (500 MHz, CD₃OD) δ (ppm): 9.20 (d, 2H), 8.64 (t, 1H), 8.20 (t, 2H), 7.90 (t, 3H), 7.80 (s, 1H), 7.56 (d, 1H), 7.14 (d, 2H), 5.10 (t, 2H), 4.62 (t, 2H), 3.20 (d, 2H); MS m/z 627 (M+1).

Example 2

Preparation of Ammonium 4-Cyano-3-Fluorophenyl [({[5-(Morpholin-4-Yl-Methyl)-1-Benzothien-2-Yl]Sulfonyl}Amino)Methyl]Phosphonate

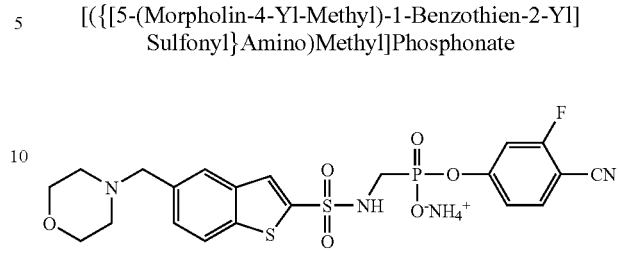

In a sealed tube under nitrogen was placed a solution of [({[5-(morpholin-4-yl-methyl)-1-benzothien-2-yl]sulfonyl}amino)methyl]phosphonic acid (300 mg, 0.74 mmol, 1 eq) trichloroacetonitrile (0.70 mL, 7.0 mmol, 9.4 eq) and 2-fluoro-4-hydroxybenzonitrile (132 mg, 0.960 mmol, 1.3 eq) in anhydrous pyridine (4.2 mL). The tube was sealed and the reaction mixture was heated at 100° C. for 2.5 h. The reaction mixture was concentrated and the residue was purified by flash chromatography on silica gel (methanol/dichloromethane/ammonium hydroxide: 10:89:1). The resulting solid was triturated with methanol for 18 h, filtered, rinsed with methanol and dried to afford the title compound as a beige solid.

¹H NMR (400 MHz, CD₃OD+D₂O+droplet of NH₄OH) δ (ppm): 7.89 (d, J=8.4 Hz, 1H), 7.87-7.84 (m, 2H), 7.53 (d, J=8.4 Hz, 1H), 7.41 (t, J=8.4 Hz, 1H), 7.02-6.96 (m, 2H), 3.73 (t, J=4.4 Hz, 4H), 3.71 (s, 2H), 3.36-3.27 (m, 2H), 2.53 (m, 4H); MS m/z 526 (M+1).

Example 3

Preparation of 4-Cyano-3-Fluorophenyl-({[(4,7-Dichloro-5-{[(3-(Pyridinium-1-Ylpropyl)Thio]Methyl}-1-Benzothien-2-Yl)Sulfonyl]Amino}Methyl) Phosphonate

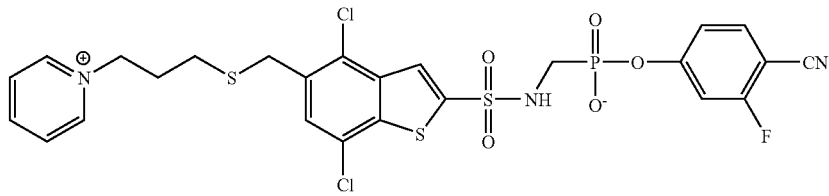 [SMILES: N#Cc1ccc(OP(=O)([O-])CNS(=O)(=O)c2cc3c(Cl)c(CSCCC[n+]4ccccc4)cc(Cl)c3s2)cc1F]

Crude hydrogen({[(4,7-dichloro-5-{[(3-pyridinium-1-ylpropyl)thio]methyl}-1-benzothien-2-yl)-sulfonyl]amino}methyl)phosphonate (0.25 g, ~0.37 mmol, 1 eq), prepared in Preparative Example 56, in dry DMF (15 mL) was added, in 3 mL portions, to a solution of 2-fluoro-4-hydroxybenzonitrile (0.15 g, 1.1 mmol, 3.0 eq) and trichloroacetonitrile (1.0 mL, 1.4 g, 9.7 mmol, 26 eq) in pyridine (30 mL), at 120° C., in a pressure flask. Between the additions of each portion, the flask was sealed and the mixture was stirred and heated for 15 min. When the addition was complete, the dark solution was heated for a further 4 h then cooled to room temperature. The reaction mixture was then transferred to a round bottomed flask and concentrated under reduced pressure. The residue was purified by reverse phase HPLC (250× 21.2 mm Aquasil C18 column, 45%-90% methanol/water linear gradient, 30 min elution time) to yield the product as an amorphous white solid.

¹H NMR (400 MHz, DMSO-d₆) δ (ppm): 9.07 (d, J=5.5, 2H); 8.63 (t, J=7.8, 1H); 8.17 (t, J=7.2, 2H); 7.98 (s, 1H); 7.80 (s, 1H); 7.60 (t, J=8.4, 1H); 7.25 (d, J=11.5, 1H); 7.04 (d, J=7.04, 1H); 4.69 (t, J=6.8, 2H); 4.05 (s, 2H); 3.02 (d, J=12.7, 2H); ~2.5 (2H, under DMSO peak?); 2.28 (quint, J=6.8, 2H); MS m/z 660 (M+1).

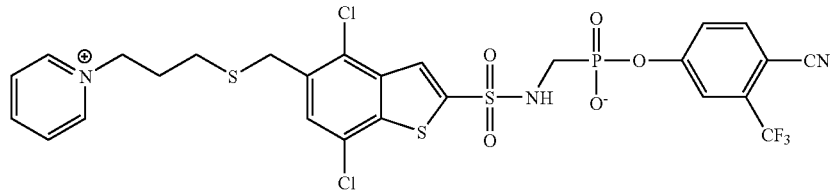 [SMILES: N#Cc1ccc(OP(=O)([O-])CNS(=O)(=O)c2cc3c(Cl)c(CSCCC[n+]4ccccc4)cc(Cl)c3s2)cc1C(F)(F)F]

Utilizing the foregoing procedure and substituting 4-cyano-3-trifluoromethylphenol, 4-cyano-3-(trifluoromethyl)phenyl-({[(4,7-dichloro-5-{[(3-(pyridinium-1-ylpropyl)thio]methyl}-1-benzothien-2-yl)sulfonyl]amino}methyl)phosphonate was prepared after purification by reverse phase HPLC (250×21.2 mm Aquasil C18 column, 40%-90% methanol/water linear gradient, 30 min elution time, then 70%-95% methanol/water linear gradient, 30 min elution time), followed by trituration with ethyl acetate as an amorphous yellow solid.

¹H NMR (400 MHz, CD₃OD) δ (ppm): 8.92 (d, J=5.7, 2H); 8.56 (t, J=7.8, 1H); 8.05 (t, J=7.0, 2H); 7.95 (s, 1H); 7.70 (d, J=8.4, 1H); 7.64 (s, 1H); 7.62 (s, 1H); 7.42 (d, J=8.0, 1H); 4.71 (t, J=7.1, 2H); 4.02 (s, 2H); 3.36 (d, J=12.5, 2H); 2.59 (t, J=7.0, 1H); 2.33 (quint, J=7.0, 2H); MS m/z 710 (M+1).

Example 4

Preparation of 4-Cyano-3-Fluorophenyl Hydrogen [({[5-(Aminomethyl)-Thieno[3,2-b]Thien-2-Yl]Sulfonyl}Amino)Methyl]Phosphonate

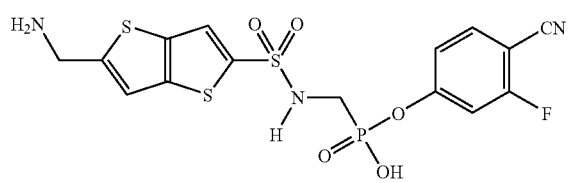 [SMILES: N#Cc1ccc(OP(=O)(O)CNS(=O)(=O)c2cc3sc(CN)cc3s2)cc1F]

To a stirred solution of the product obtained from Preparative Example 56, Method B, (0.0346 g) in DMF/iPrOH (0.2 mL/2 mL) was added Pd black (0.0046 g). The reaction mixture was stirred under an atmosphere of hydrogen at ambient temperature for 16 h. The reaction mixture was filtered through a microfilter (Millex-SV; 5 microns; 25 mm) and the filtrate was concentrated in vacuo. The resulting residue was purified by reverse-phase HPLC (X-terra Prep MS C18 column, 19×100 mm, 5 micron, flow rate=20 mL/min, 0/100 CH₃CN+0.05% TFA/water+0.05% TFA to 70/30 CH₃CN+0.05% TFA/water+0.05% TFA over 30 min. then 100% CH₃CN+0.05% TFA for 5 min.) to give a yellow solid after lyophilization.

¹H NMR (500 MHz, CD₃OD) δ (ppm): 7.88 (s, 1H), 7.53-7.56 (m, 2H), 7.17 (dd, 1H), 7.12 (dd, 1H), 4.48 (s, 2H), 3.24 (d, 2H); MS m/z 445 (M+1).

Utilizing the foregoing procedure, the following compounds were prepared:

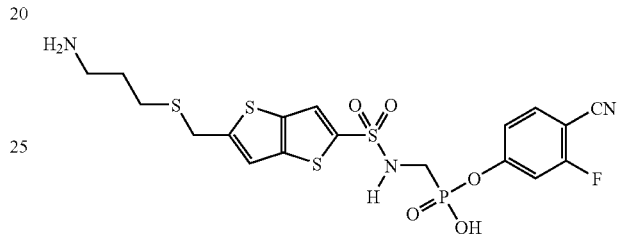

4-cyano-3-fluorophenyl hydrogen({[(5-{[(3-aminopropyl)thio]methyl}thieno[3,2-b]thien-2-yl)sulfonyl]amino}methyl)phosphonate was prepared as a white solid using MeOH as the solvent for the reduction.

¹H NMR (500 MHz, CD₃OD) δ (ppm): 7.79 (s, 1H), 7.52 (t, 1H), 7.28 (s, 1H), 7.13 (dd, 1H), 7.06 (dd, 1H), 4.10 (s, 2H), 3.23 (d, 2H), 3.00 (t, 2H), 2.64 (t, 2H), 1.92 (m, 2H); MS m/z 537 (M+1).

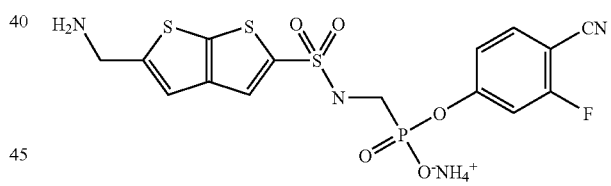

Ammonium-4-cyano-3-fluorophenyl-[({[5-(aminomethyl)thieno[2,3-b]thien-2-yl)sulfonyl}-amino)methyl]phosphonate was prepared using MeOH as the reduction solvent. Purification was accomplished by silica gel plate chromatography (1000 micron plate; 40/10/1 CHCl₃/MeOH/conc. NH₄OH) to give a cream-colored solid.

¹H NMR (500 MHz, CD₃OD+d₆-DMSO) δ (ppm): 7.76 (s, 1H), 7.54 (t, 1H), 7.44 (s, 1H), 7.15 (dd, 1H), 7.08 (dd, 1H), 4.39 (s, 2H), 3.21 (d, 2H); MS m/z 462 (M+1).

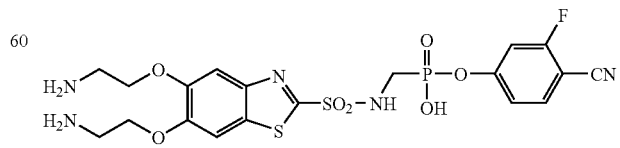

4-cyano-3-fluorophenyl hydrogen(5,6-bis(2-aminoethoxy)benzo[d]thiazole-2-sulfonamido)-methylphosphonate Purified by reverse phase HPLC (250×21.2 mm Aquasil C18 column, 20%-60% methanol/water linear gradient, 30 min. elution time; elutes ~15 min.) to give the product over two steps as a colorless solid.

¹H NMR (400 MHz, CD₃OD) δ (ppm): 7.69 (s, 1H); 7.63 (s, 1H); 7.42 (t, J=8.6, 1H); 7.08-7.04 (m, 2H); 4.63 (br s, 4H); 4.40-4.36 (m, 4H); 4.45 (d, J=13.1, 2H); MS m/z 546 (M).

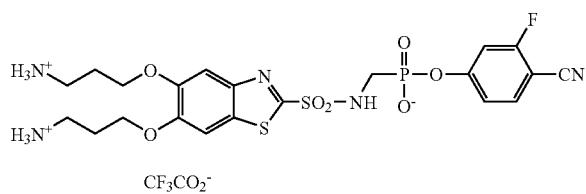

4-cyano-3-fluorophenyl hydrogen(5,6-bis(2-ammoniopropoxy)benzo[d]thiazole-2-sulfonamido)methylphosphonate trifluoroacetate The residue was dissolved in a few drops of TFA, diluted with MeOH (2 mL) and purified by preparative HPLC (Thermo, Aquasil C18, 240×21.2 mm, 5 μm; gradient MeOH/H₂O: 10/90 to 95/5, both containing 0.05% HCO₂H over 30 min) twice to afford the title compound as a white solid.

¹H NMR (400 MHz, CD₃OD) δ (ppm): 8.07 (s, 1H), 7.47 (s, 1H), 7.42 (s, 1H), 7.35 (dd, J=8.0, 8.4 Hz, 1H), 7.02 (m, 2H), 4.24 (m, 4H), 3.46 (d, J=12.7 Hz, 2H), 3.25 (m, 4H), 2.26 (m, 4H); MS m/z 572 (M−1).

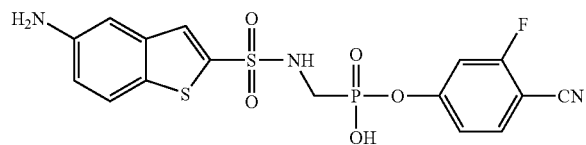 [SMILES: N#Cc1ccc(OP(=O)(O)CNS(=O)(=O)c2cc3cc(N)ccc3s2)cc1F]

4-cyano-3-fluorophenyl hydrogen({[(5-amino-1-benzothien-2-yl)sulfonyl]amino}methyl)-phosphonate prepared as a pale pink solid.

¹H NMR (400 MHz, DMSO-d₆) δ (ppm): 7.99-7.91 (m, 1H), 7.82-7.76 (m, 2H), 7.72 (dd, J=8.3 Hz, 1H), 7.32-7.25 (m, 2H), 7.09 (dd, J=8.4, 2.0 Hz, 1H), 7.03 (d, J=8.4 Hz, 1H), 3.04 (dd, J=12.5, 5.9 Hz, 2H).

Example 5

Preparation of 4-Cyano-3-Fluorophenyl[({[5,6-Bis(2-Ammonioethoxy)-1-Benzothien-2-Yl]Sulfonyl}Amino)Methyl]Phosphonate Trifluoroacetate

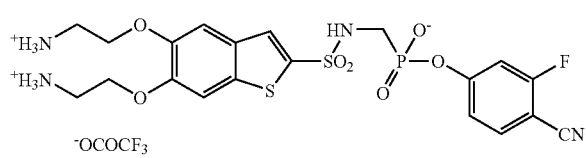

A mixture consisting of [({[5,6-bis(2-azidoethoxy)-1-benzothien-2-yl]sulfonyl}amino)methyl]-phosphonic acid (187 mg, 0.39 mmol), prepared in Preparative Example 56, phenol (70 mg, 1.3 equiv), trichloroacetonitrile (0.4 mL, 10 equiv), anhydrous pyridine (3 mL) and 10% of DMF (0.3 mL) was stirred in a sealed tube for 6 h at 105° C. After the reaction was complete, pyridine was evaporated in vacuum to give an oily residue. To a solution of the crude adduct in MeOH was added palladium black (19 mg, 10%). The resulting mixture was stirred under 40 psi of hydrogen gas overnight. The resulting dark yellow solution was filtered and the organic layer was evaporated to give an oil, which was purified by reverse phase HPLC to afford the diamine.

¹H NMR (400 MHz, CD₃OD) δ (ppm): 7.8 (s, 1H), 7.6 (br t, 1H), 7.45 (s, 1H), 7.4 (s, 1H), 7.2 (m, 2H), 4.3 (m, 4H), 3.7 (m, 4H), 3.5 (d, 2H); MS m/z 545 (M+1).

Utilizing the foregoing procedures, the following compounds were prepared:

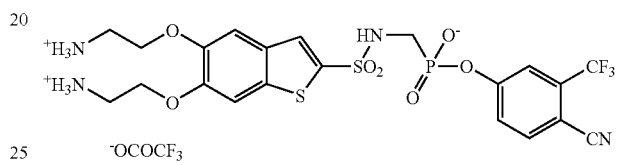

4-cyano-3-(trifluoromethyl)phenyl[({[5,6-bis(2-ammonioethoxy)-1-benzothien-2-yl]-sulfonyl}amino)methyl] phosphonate trifluoroacetate ¹H NMR (400 MHz, DMSO-d₆) δ (ppm): 7.9 (d, 1H), 7.8 (d, 1H), 7.75 (s, 1H), 7.7 (s, 1H), 7.55 (s, 1H), 7.5 (dd, 1H), 4.2 (m, 4H), 3.3 (m, 4H), 2.9 (d, 2H); MS m/z 595 (M+1).

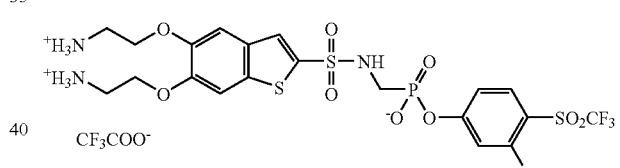

3-fluoro-4-[(trifluoromethyl)sulfonyl]phenyl-[({[5,6-bis(2-ammonioethoxy)-1-benzothien-2-yl]-sulfonyl}amino)methyl]phosphonate trifluoroacetate ¹H NMR (500 MHz, CD₃OD) δ (ppm): 7.75 (s, 1H), 7.70 (t, 1H), 7.55 (s, 1H), 7.46 (s 1H), 7.19 (m, 2H), 4.36 (t, 4H), 3.44 (t, 4H), 3.25 (d, 2H); MS m/z 652 (M+1).

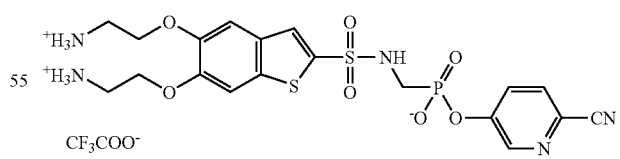

6-cyanopyridin-2-yl-[({[5,6-bis(2-ammonioethoxy)-1-benzothien-2-yl]sulfonyl}amino)-methyl]-phosphonate trifluoroacetate ¹H NMR (500 MHz, CD₃OD) δ (ppm): 8.30 (d, 1H), 7.70 (m, 2H), 7.60 (d, 1H), 7.56 (s 1H), 7.46 (s, 1H), 4.40 (m, 4H), 3.44 (m, 4H), 3.25 (d, 2H); MS m/z 528 (M+1).

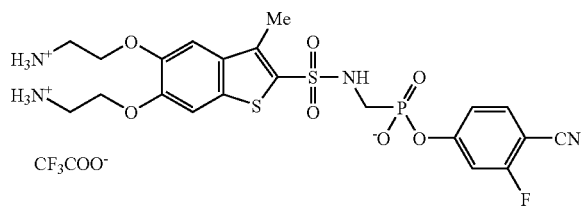

4-cyano-3-fluorophenyl[({[5,6-bis(2-ammonioethoxy)-3-methyl-1-benzothien-2-yl]sulfonyl}-amino)methyl]phosphonate trifluoroacetate $^1$H NMR (500 MHz, CD$_3$OD) δ (ppm): 7.50 (s, 1H), 7.33 (s, 1H), 7.31 (t, 1H), 6.94 (m, 2H), 4.39 (m, 4H), 3.49 (t, 4H), 3.28 (d, 2H), 2.56 (s, 3H); MS m/z 559 (M+1).

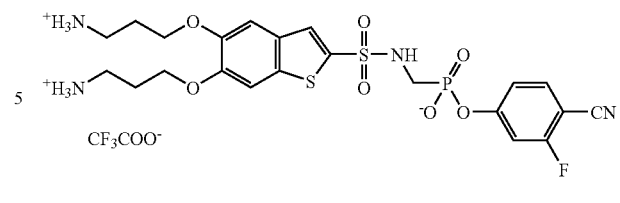

4-cyano-3-fluorophenyl[({[5,6-bis(3-ammoniopropoxy)-1-benzothien-2-yl]sulfonyl}amino)-methyl]phosphonate trifluoroacetate $^1$H NMR (500 MHz, CD$_3$OD) δ (ppm): 7.62 (s, 1H), 7.40 (s, 1H), 7.32 (s, 1H), 7.30 (m, 1H), 7.00 (m, 2H), 4.24 (m, 4H), 3.30 (d, 2H), 3.2 (m, 4H), 2.24 (m, 4H); MS m/z 573 (M+1).

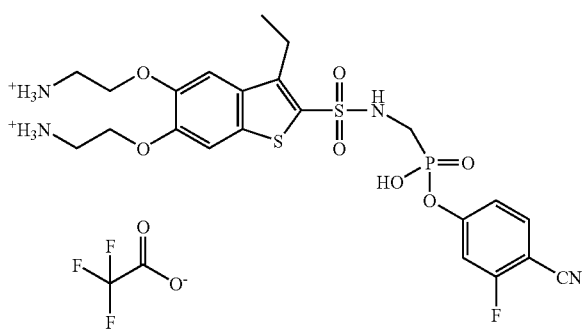 [SMILES: CCc1c(S(=O)(=O)NCP(=O)(O)Oc2ccc(C#N)c(F)c2)sc2cc(OCC[NH3+])c(OCC[NH3+])cc12 ; O=C([O-])C(F)(F)F]

4-cyano-3-fluorophenyl[({[5,6-bis(2-ammonioethoxy)-3-ethyl-1-benzothien-2-yl]sulfonyl}-amino)methyl]phosphonate trifluoroacetate $^1$H NMR (500 MHz, CD$_3$OD) δ (ppm): 7.54 (s, 1H), 7.38 (s, 1H), 7.36 (m, 1H), 6.98 (m, 2H), 4.20 (m, 4H), 3.50 (m, 4H), 3.30 (d, 2H), 3.10 (q, 2H), 1.25 (t, 3H); MS m/z 573 (M+1).

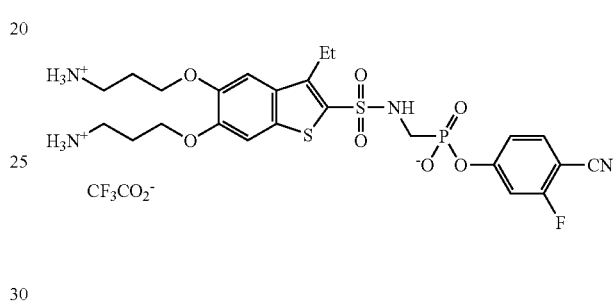

4-cyano-3-fluorophenyl[({[5,6-bis(3-ammoniopropoxy)-3-ethyl-1-benzothien-2-yl]-sulfonyl}amino)methyl]phosphonate trifluoroacetate $^1$H NMR (500 MHz, CD$_3$OD) δ (ppm): 7.40 (s, 1H), 7.26 (m, 1H), 7.20 (s, 1H), 6.90 (m, 2H), 4.26 (m, 4H), 3.30 (d, 2H), 3.26 (m, 4H), 3.05 (d, 2H), 3.20 (q, 2H), 2.25 (m, 4H), 1.25 (t, 3H); MS m/z 601 (M+1).

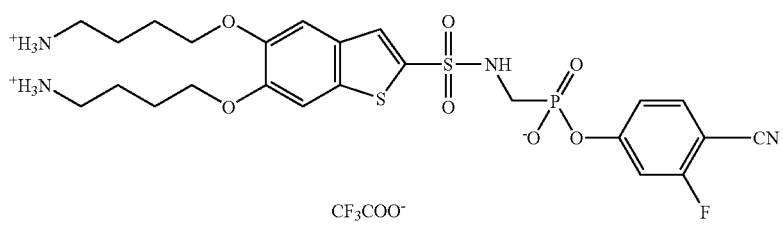

4-cyano-3-fluorophenyl[({[5,6-bis(4-ammoniobutoxy)-1-benzothien-2-yl]sulfonyl}amino)-methyl]phosphonate trifluoroacetate $^1$H NMR (500 MHz, CD$_3$OD) δ (ppm): 7.70 (s, 1H), 7.42 (s, 1H), 7.40 (m, 2H), 7.00 (m, 2H), 4.20 (m, 4H), 3.30 (d, 2H), 3.15 (m, 4H), 2.00 (m, 8H); MS m/z 601 (M+1).

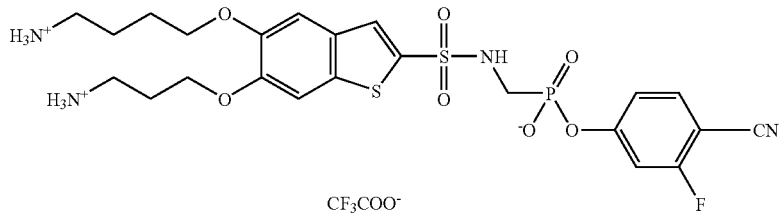

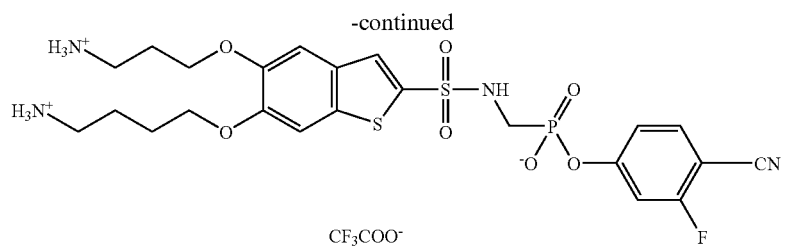

4-cyano-3-fluorophenyl hydrogen[({[6-(4-ammoniobutoxy)-5-(3-ammoniopropoxy)-1-benzothien-2-yl]sulfonyl}amino)methyl]phosphonate and 4-cyano-3-fluorophenyl hydrogen [({[5-(4-ammoniobutoxy)-6-(3-ammoniopropoxy)-1-benzothien-2-yl]sulfonyl}amino)methyl]phosphonate The products obtained from Preparative Example 57 were converted to the products.

Major isomer: $^1$H NMR (500 MHz, CD$_3$OD) δ (ppm): 7.62 (s, 1H), 7.38 (s, 1H), 7.32 (t, 1H), 7.32 (s, 1H), 7.01 (m, 2H), 4.28 (t, 2H), 4.12 (t, 2H), 3.26 (m, 4H), 3.07 (t, 2H), 2.26 (m, 2H), 1.97 (m, 2H), 1.91 (m, 2H).

Minor isomer: $^1$H NMR (500 MHz, CD$_3$OD) δ (ppm): 7.65 (s, 1H), 7.44 (s, 1H), 7.37 (s, 1H), 7.33 (t, 1H), 7.00 (m, 2H), 4.26 (t, 2H), 4.19 (t, 2H), 3.27 (t, 2H), 3.25 (d, 2H), 3.07 (t, 2H), 2.24 (m, 2H), 1.99 (m, 2H), 1.90 (m, 2H).

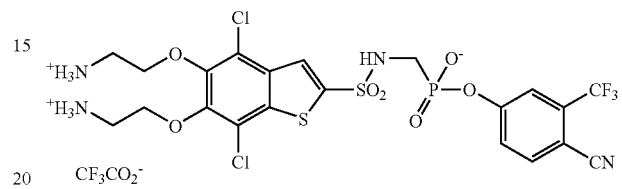

4-cyano-3-(trifluoromethyl)phenyl[({[5,6-bis(2-ammonioethoxy)-4,7-dichloro-1-benzothien-2-yl]sulfonyl}amino)methyl]phosphonate trifluoroacetate $^1$H NMR (400 MHz, CD$_3$OD) δ (ppm): 7.9 (s, 1H), 7.8 (d, 1H), 7.65 (s, 1H), 7.5 (d, 1H), 4.4 (m, 4H), 3.42 (m, 4H), 3.3 (d, 2H); MS m/z 663 (M+1).

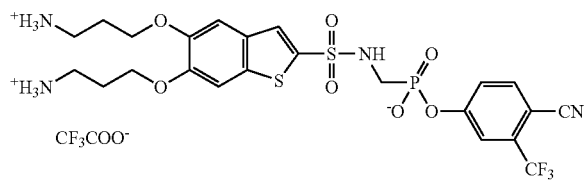

4-cyano-3-(trifluoromethyl)phenyl[({[5,6-bis(3-ammoniopropoxy)-1-benzothien-2-yl]sulfonyl}-amino)methyl]phosphonate trifluoroacetate $^1$H NMR (500 MHz, CD$_3$OD) δ (ppm): 7.62 (m, 3H), 7.40 (m, 2H), 7.38 (s, 1H), 4.24 (m, 4H), 3.32 (d, 2H), 3.26 (m, 4H), 2.26 (m, 4H); MS m/z 623 (M+1).

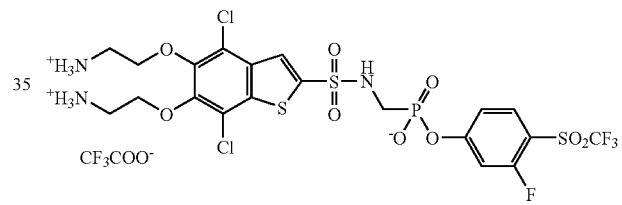

3-fluoro-4-[(trifluoromethyl)sulfonyl]phenyl-[({[5,6-bis(2-ammonioethoxy)-4,7-dichloro-1-benzothien-2-yl]sulfonyl}amino)methyl]phosphonate trifluoroacetate $^1$H NMR (500 MHz, CD$_3$OD) δ (ppm): 8.00 (s, 1H), 7.85 (m, 1H), 7.40 (m, 1H), 7.25 (m, 1H), 4.40 (t, 4H), 3.50 (t, 4H), 3.35 (d, 2H); MS m/z 720 (M).

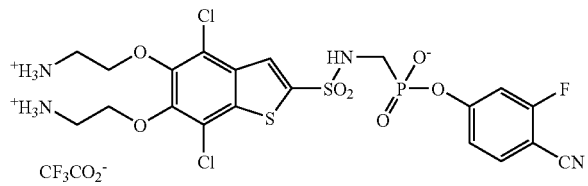 [SMILES: "CF3CO2-" ; N#Cc1ccc(OP(=O)([O-])CNS(=O)(=O)c2cc3c(Cl)c(OCC[NH3+])c(OCC[NH3+])c(Cl)c3s2)cc1F]

4-cyano-3-fluorophenyl[({[5,6-bis(2-ammonioethoxy)-4,7-dichloro-1-benzothien-2-yl]sulfonyl}-amino)methyl]phosphonate trifluoroacetate $^1$H NMR (400 MHz, CD$_3$OD) δ (ppm): 7.9 (s, 1H), 7.4 (t, 1H), 7.05 (d, 1H), 7.0 (d, 1H), 4.4 (m, 4H), 3.42 (m, 4H), 3.3 (d, 2H); MS m/z 613 (M+1).

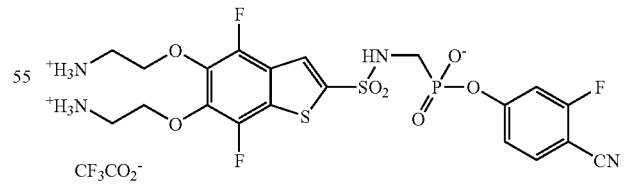

4-cyano-3-fluorophenyl[({[5,6-bis(2-ammonioethoxy)-4,7-difluoro-1-benzothien-2-yl]sulfonyl}-amino)methyl]phosphonate trifluoroacetate $^1$H NMR (400 MHz, CD$_3$OD) δ (ppm): 7.85 (brs, 1H), 7.5 (brt, 1H), 7.1 (m, 1H), 4.5 (two brd, 4H), 3.4 (m, 4H), 3.3 (d, 2H, hidden); MS m/z 581 (M+1).

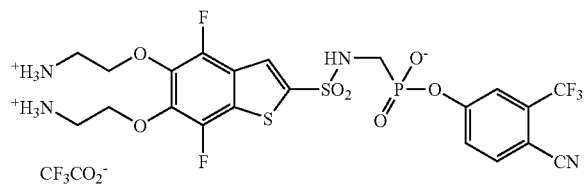 [SMILES: "CF3CO2-" ; N#Cc1ccc(OP(=O)([O-])CNS(=O)(=O)c2cc3c(Cl)c(OCC[NH3+])c(OCC[NH3+])c(Cl)c3s2)cc1C(F)(F)F]

4-cyano-3-(trifluoromethyl)phenyl[({[5,6-bis(2-ammonioethoxy)-4,7-difluoro-1-benzothien-2-yl]sulfonyl}amino)methyl]phosphonate trifluoroacetate $^1$H NMR (400 MHz, CD$_3$OD) δ (ppm): 7.9 (d, 1H), 7.8 (d, 1H), 7.75 (brs, 1H), 7.55 (d, 1H), 4.55 (t, 2H), 4.45 (t, 2H), 3.3 (d, 2H, hidden); MS m/z 631 (M+1).

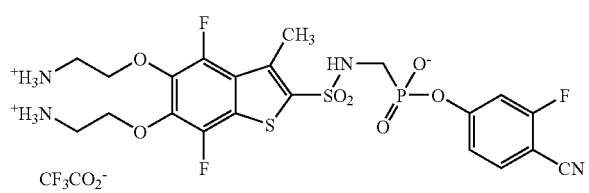 [SMILES: "CF3CO2-" ; Cc1c(S(=O)(=O)NCP(=O)([O-])Oc2ccc(C#N)c(F)c2)sc2c(F)c(OCC[NH3+])c(OCC[NH3+])c(F)c12]

4-cyano-3-fluorophenyl[({[5,6-bis(2-ammonioethoxy)-3-methyl-4,7-difluoro-1-benzothien-2-yl]sulfonyl}amino)methyl]phosphonate trifluoroacetate $^1$H NMR (500 MHz, CD$_3$OD) δ (ppm): 7.49 (t, 1H), 6.99-7.08 (m, 2H), 4.50 (t, 2H), 4.41 (t, 2H), 3.42 (m, 4H), 3.32 (d, 2H), 2.72 (s, 3H); MS m/z 595 (M+1).

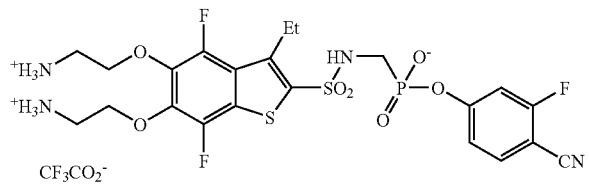 [SMILES: "CF3CO2-" ; CCc1c(S(=O)(=O)NCP(=O)([O-])Oc2ccc(C#N)c(F)c2)sc2c(F)c(OCC[NH3+])c(OCC[NH3+])c(F)c12]

4-cyano-3-fluorophenyl[({[5,6-bis(2-ammonioethoxy)-3-ethyl-4,7-difluoro-1-benzothien-2-yl]sulfonyl}amino)methyl]phosphonate trifluoroacetate $^1$H NMR (500 MHz, CD$_3$OD) δ (ppm): 7.50 (t, 1H), 7.05 (d, 1H), 7.00 (d, 1H), 4.50 (t, 2H), 4.40 (t, 2H), 3.40 (m, 4H), 3.30 (d, 2H), 3.20 (q, 2H), 1.25 (t, 3H); MS m/z 609 (M+1).

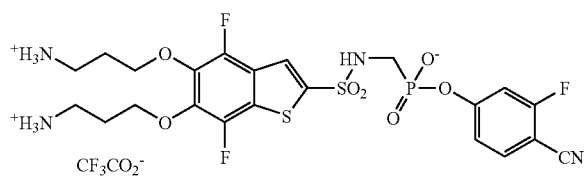

4-cyano-3-fluorophenyl[({[5,6-bis(3-ammoniopropoxy)-4,7-difluoro-1-benzothien-2-yl]sulfonyl}amino)methyl]phosphonate trifluoroacetate $^1$H NMR (500 MHz, CD$_3$OD) δ (ppm): 7.8 (brs, 1H), 7.5 (t, 1H), 7.1 (m, 2H), 4.4 (two t, 4H), 3.3 (d, 2H, hidden), 3.25 (m, 4H), 2.2 (m, 4H); MS m/z 609 (M+1).

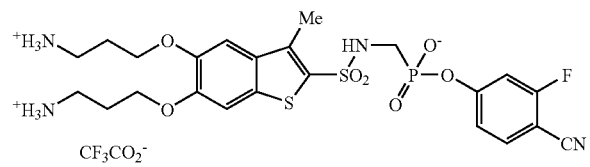

4-cyano-3-fluorophenyl[({[5,6-bis(3-ammoniopropoxy)-3-methyl-1-benzothien-2-yl]-sulfonyl}amino)methyl]phosphonate trifluoroacetate $^1$H NMR (500 MHz, CD$_3$OD) δ (ppm): 7.4 (s, 1H), 7.3 (t, 1H), 7.2 (s, 1H), 6.92 (s, 1H), 6.9 (dd, 1H), 4.3 (m, 4H), 2.5 (s, 3H), 2.3 (m, 4H); MS m/z 587 (M+1).

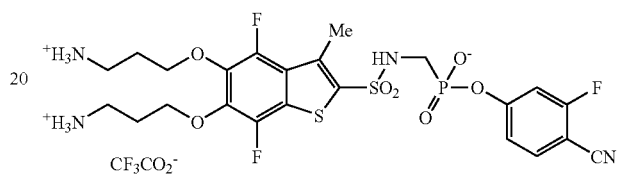

4-cyano-3-fluorophenyl[({[5,6-bis(3-ammoniopropoxy)-4,7-difluoro-3-methyl-1-benzothien-2-yl]sulfonyl}amino)methyl]phosphonate trifluoroacetate $^1$H NMR (500 MHz, CD$_3$OD) δ (ppm): 7.45 (t, 1H), 7.15 (dd, 1H), 6.95 (d, 1H), 4.4 (two t, 4H), 3.53 (d, 2H, hidden), 3.25 (m, 4H), 2.7 (s, 3H), 2.2 (m, 4H); MS m/z 623 (M+1).

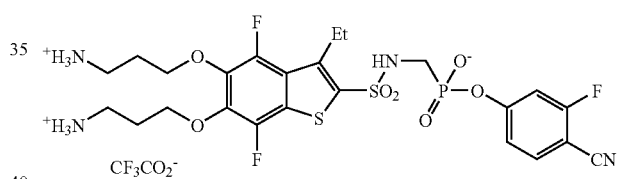

4-cyano-3-fluorophenyl[({[5,6-bis(3-ammoniopropoxy)-4,7-difluoro-3-ethyl-1-benzothien-2-yl]-sulfonyl}amino)methyl]phosphonate trifluoroacetate $^1$H NMR (500 MHz, CD$_3$OD) δ (ppm): 7.50 (t, 1H), 7.05 (d, 1H), 7.00 (d, 1H), 4.42 (t, 2H), 4.38 (t, 2H), 3.40 (d, 2H), 3.26 (m, 4H), 3.20 (q, 2H), 2.20 (m, 4H), 1.25 (t, 3H); MS m/z 637 (M+1).

Example 6

Utilizing the foregoing hydrogenation procedures, the following compounds were prepared:

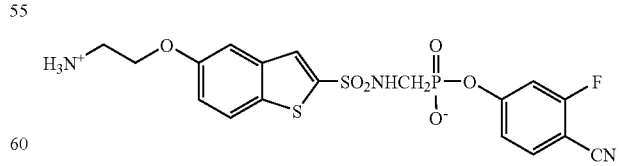

4-cyano-3-fluorophenyl-[({[5-(2-ammonioethoxy)-1-benzothien-2-yl]sulfonyl}amino)methyl]-phosphonate $^1$H NMR (500 MHz, CD$_3$OD) δ (ppm): 7.81 (d, J=8.9 Hz, 1H), 7.76 (s, 1H) 7.44 (d, J=2.4 Hz, 1H), 7.39 (t, J=8.1 Hz, 1H), 7.24 (dd, J=8.9, 2.4 Hz, 1H), 7.07 (dd, J=11.1 Hz, 1.9 Hz, 1H), 6.99 (dd, J=8.6 Hz, 1.9 Hz, 1H) 4.31 (t, J=4.9 Hz, 2H), 3.41 (t, J=4.8 Hz, 2H), 3.26 (d, J=12.5 Hz, 2H); MS m/z 486 (M+1).

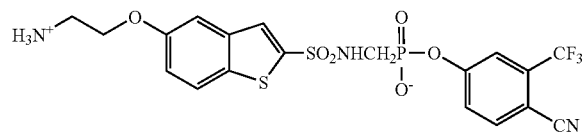

4-cyano-3-(trifluoromethyl)phenyl-[({[5-(2-ammonioethoxy)-1-benzothien-2-yl]sulfonyl}amino) methyl]phosphonate ¹H NMR (600 MHz, CD₃OD) δ (ppm): 7.79 (d, J=9.1 Hz, 1H), 7.77 (s, 1H), 7.65 (m, 2H), 7.44 (d, J=2.5 Hz, 1H), 7.40 (dd, J=8.5 Hz, 1.6 Hz, 1H), 7.21 (dd, J=8.9 Hz, 2.4 Hz, 1H), 4.28 (t, J=5.1 Hz, 2H), 3.40 (t, J=4.8 Hz, 2H), 3.25 (d, J=12.8 Hz, 2H); MS m/z 536 (M).

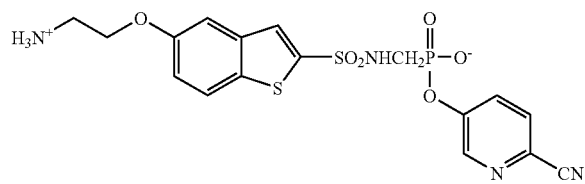

6-cyanopyridin-3-yl-[({[5-(2-ammonioethoxy)-1-benzothien-2-yl]sulfonyl}amino)methyl]phosphonate ¹H NMR (500 MHz, CD₃OD) δ (ppm): 8.4 (d, 1H), 7.83 (d, 1H), 7.81 (s, 1H), 7.7 (dd, 1H), 7.6 (d, 1H), 7.5 (d, 1H), 7.3 (dd, 1H), 4.3 (t, 2H), 3.4 (t, 2H), 3.25 (d, 2H); MS m/z 469 (M).

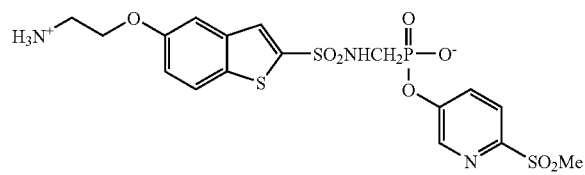

6-methylsulfonylpyridin-3-yl-[({[5-(2-ammonioethoxy)-1-benzothien-2-yl]sulfonyl}amino) methyl]phosphonate ¹H NMR (600 MHz, CD₃OD) δ (ppm): 8.42 (d, 1H), 7.85 (d, 1H), 7.8 (m, 2H), 7.64 (dd, 1H), 7.40 (d, 1H), 7.21 (dd, 1H), 4.28 (t, 2H), 3.40 (t, 2H), 3.18 (s, 3H); MS m/z 521 (M+1).

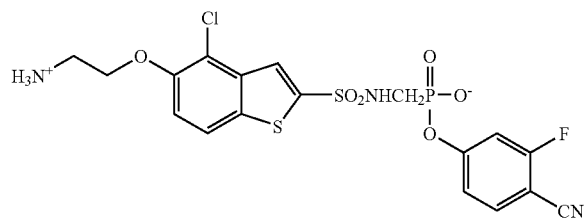

4-cyano-3-fluorophenyl-[({[5-(2-ammonioethoxy)-4-chloro-1-benzothien-2-yl]sulfonyl}amino) methyl]phosphonate ¹H NMR (500 MHz, CD₃OD) δ (ppm): 7.88 (d, J=8.8 Hz, 1H), 7.85 (s, 1H), 7.57 (t, J=7.9 Hz, 1H), 7.43 (d, J=8.8 Hz, 1H), 7.05 (m, 2H), 4.49 (t, d=4.8 Hz, 2H), 3.59 (t, J=4.9 Hz, 2H); MS m/z 519 (M).

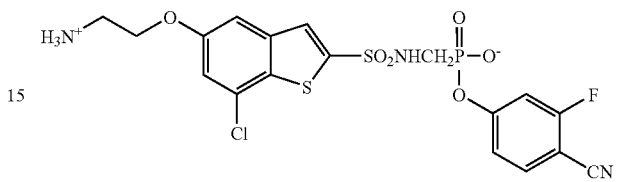

4-cyano-3-fluorophenyl-[({[5-(2-ammonioethoxy)-7-chloro-1-benzothien-2-yl]sulfonyl}amino) methyl]phoshonate ¹H NMR (500 MHz, CD₃OD) δ (ppm): 7.83 (s, 1H), 7.45 (d, J=2.1 Hz, 1H), 7.40 (t, J=8.3 Hz, 1H), 7.33 (d, J=2.5 Hz, 1H), 7.05 (dd, J=13.3 Hz, 1.7 Hz, 1H), 7.02 (dd, J=8.3 Hz, 2.1 Hz, 1H), 4.33 (t, J=4.5 Hz, 2H), 3.41 (t, J=4.3 Hz, 2H); MS m/z 519 (M).

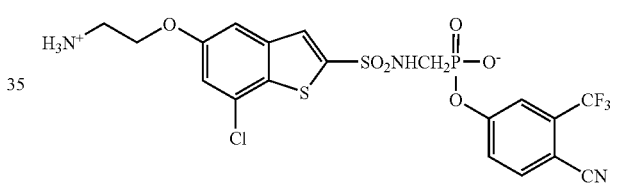

4-cyano-3-(trifluoromethyl)phenyl-[({[5-(2-ammonioethoxy)-7-chloro-1-benzothien-2-yl]-sulfonyl}amino)methyl] phoshonate ¹H NMR (500 MHz, CD₃OD) δ (ppm): 7.85 (s, 1H), 7.69 (d, J=8.5 Hz, 1H), 7.65 (bs, 1H), 7.43 (m, 2H), 7.32 (d, J=2.0 Hz, 1H), 4.31 (t, J=4.8 Hz, 2H), 3.41 (t, J=4.6 Hz, 2H); MS m/z 571 (M).

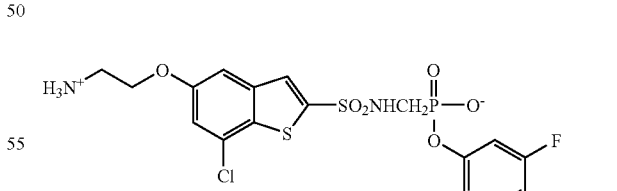

3-fluoro-4-[(trifluoromethyl)sulfonyl]phenyl-[({[5-(2-ammonioethoxy)-7-chloro-1-benzothien-2-yl] sulfonyl}amino)methyl]phosphonate ¹H NMR (500 MHz, CD₃OD) δ (ppm): 7.88 (s, 1H), 7.77 (t, J=8.75 Hz, 1H), 7.46 (d, J=2.1 Hz, 1H), 7.31 (d, J=2.1 Hz, 1H), 7.21 (d, J=10.7 Hz, 2H), 4.32 (t, J=5.4 Hz, 2H), 3.43 (t, J=5.7 Hz, 2H), 3.35 (d, J=12.9 Hz, 2H); MS m/z 627 (M).

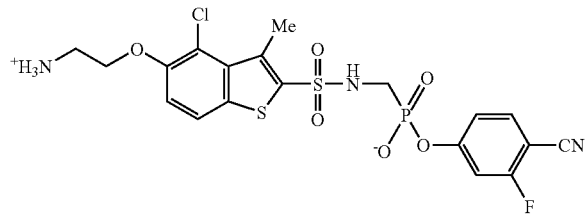

4-cyano-3-fluorophenyl-[({[5-(2-ammonioethoxy)-4-chloro-3-methyl-1-benzothien-2-yl]sulfonyl}amino)methyl]phosphonate was prepared in two steps. After the first step, the crude product [MS m/z 560 (M+1)] was used in the second step.

$^1$H NMR (500 MHz, CD$_3$OD) δ (ppm): 7.80 (d, 1H), 7.40 (m, 1H), 7.35 (t, 1H), 6.95 (m, 2H), 4.40 (t, 2H), 3.50 (t, 2H), 3.38 (d, 2H), 2.95 (s, 3H); MS m/z 534 (M+1).

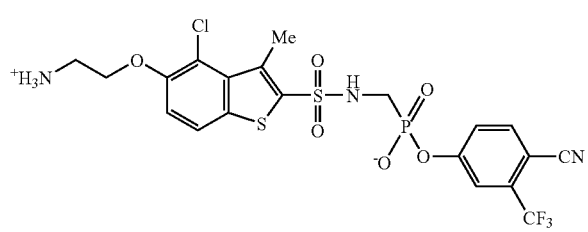

4-cyano-3-(trifluoromethyl)phenyl-[({[5-(2-ammonioethoxy)-4-chloro-3-methyl-1-benzothien-2-yl]sulfonyl}amino)methyl]phosphonate was prepared in two steps in 10% overall yield. The first reaction was monitored by LC-MS and the crude product was used as is.

$^1$H NMR (500 MHz, CD$_3$OD) δ (ppm): 7.80 (d, 1H), 7.60 (m, 1H), 7.55 (t, 1H), 7.30 (m, 2H), 4.40 (t, 2H), 3.50 (t, 2H), 3.38 (d, 2H), 2.95 (s, 3H); MS m/z 584 (M+1).

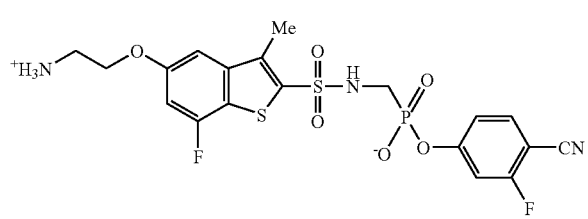

4-cyano-3-fluorophenyl-[({[5-(2-ammonioethoxy)-7-fluoro-3-methyl-1-benzothien-2-yl]sulfonyl}-amino)methyl]phosphonate $^1$H NMR (500 MHz, CD$_3$OD) δ (ppm): 7.28 (d, J=2.1 Hz, 1H), 7.16 (dd, J=11.2, 2.3 Hz, 1H), 7.05 (dd, J=11.1, 2.1 Hz, 1H), 6.96 (m, 2H) 4.35 (t, J=5.1 Hz, 2H), 3.43 (t, J=5.1 Hz, 2H), 2.58 (s, 3H); MS m/z 518 (M).

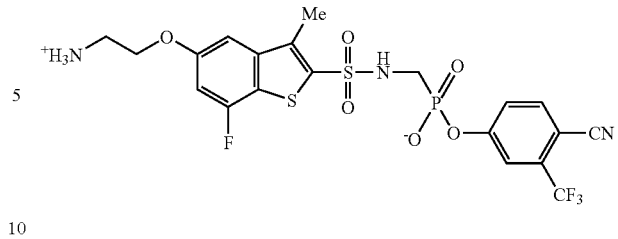

3-fluoro-4-(trifluoromethyl)phenyl-[({[5-(2-ammonioethoxy)-7-fluoro-3-methyl-1-benzothien-2-yl]sulfonyl}amino)methyl]phosphonate $^1$H NMR (500 MHz, CD$_3$OD) δ (ppm): 7.64 (d, J=8.4 Hz, 1H), 7.58 (d, J=1.8 Hz, 1H), 7.36 (dd, J=8.4 Hz, 1.8 Hz, 1H), 7.15 (d, J=1.8 Hz, 1H) 7.01 (dd, J=10.8 Hz, 1.8 Hz, 1H), 4.32 (t, J=5.1 Hz, 2H), 3.40 (t, J=5.0 Hz, 2H); MS m/z 568 (M).

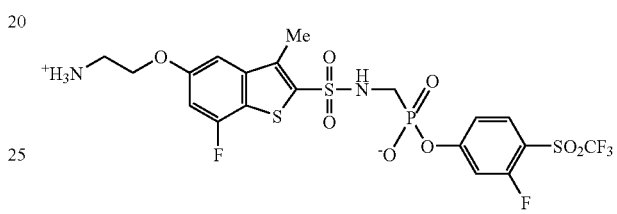

3-fluoro-4-[(trifluoromethyl)sulfonyl]phenyl-[({[5-(2-ammonioethoxy)-7-fluoro-3-methyl-1-benzothien-2-yl]sulfonyl}amino)methyl]phosphonate $^1$H NMR (600 MHz, CD$_3$OD) δ (ppm): 7.70 (t, J=8.4 Hz, 1H), 7.16 (d, J=2.4 Hz, 1H), 7.09 (m, 2H), 7.02 (dd, J=10.8 Hz, 2.4 Hz, 1H) 7.01 (dd, J=10.8 Hz, 1.8 Hz, 1H), 4.33 (t, J=4.8 Hz, 2H), 3.42 (t, J=4.8 Hz, 2H) 3.35 (d, J=12.6 Hz, 2H), 2.60 (s, 3H); MS m/z 625 (M).

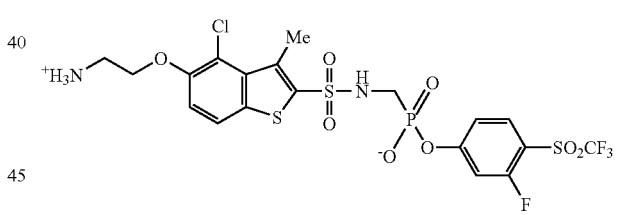

4-cyano-3-[(trifluoromethyl)sulfonyl]-phenyl-[({[5-(2-ammonioethoxy)-4-chloro-3-methyl-1-benzothien-2-yl]sulfonyl}amino)methyl]phosphonate was prepared in two steps in 8% overall yield. The first reaction was monitored by LC-MS and the crude product was used as is.

$^1$H NMR (500 MHz, CD$_3$OD) δ (ppm): 7.75 (d, 1H), 7.60 (t, 1H), 7.35 (d, 1H), 7.05 (m, 2H), 4.40 (t, 2H), 3.40 (t, 2H), 3.35 (d, 2H), 2.95 (s, 3H); MS m/z 641 (M+1).

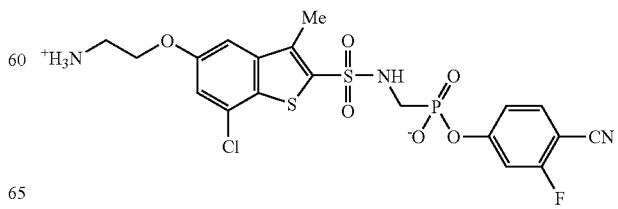

4-cyano-3-fluorophenyl-[({[5-(2-ammonioethoxy)-7-chloro-3-methyl-1-benzothien-2-yl]sulfonyl}amino)methyl]phosphonate ¹H NMR (500 MHz, CD₃OD) δ (ppm): 7.50 (t, 1H), 7.30 (m, 2H), 6.90 (m, 1H), 6.70 (m 1H), 4.38 (t, 2H), 3.42 (t, 2H), 3.35 (d, 2H), 2.60 (s, 3H); MS m/z 534 (M+1).

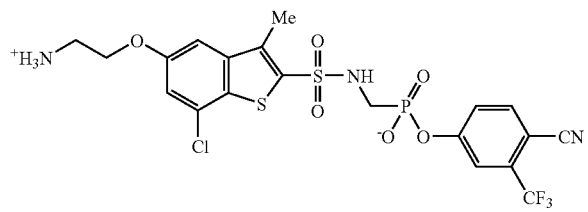

4-cyano-3-(trifluoromethyl)phenyl-[({[5-(2-ammonioethoxy)-7-chloro-3-methyl-1-benzothien-2-yl]sulfonyl}amino)methyl]phosphonate ¹H NMR (500 MHz, CD₃OD) δ (ppm): 7.60 (d, 1H), 7.55 (s, 1H), 7.34 (m, 3H), 4.32 (t, 2H), 3.42 (t, 2H), 3.30 (d, 2H), 2.60 (s, 3H); MS m/z 584 (M+1).

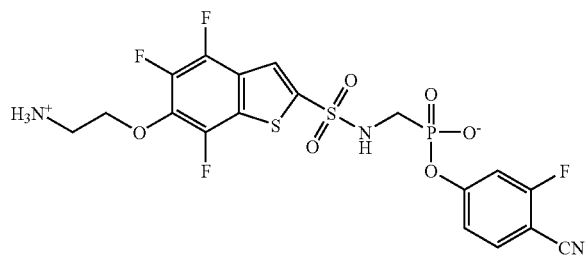 [SMILES: N#Cc1ccc(OP(=O)([O-])CNS(=O)(=O)c2cc3c(F)c(F)c(OCC[NH3+])c(F)c3s2)cc1F]

4-cyano-3-fluorophenyl-[({[6-(2-ammonioethoxy)-4,5,7-trifluoro-1-benzothien-2-yl]sulfonyl}-amino)methyl]phosphonate.

¹H NMR (DMSO-d₆) δ (ppm): 8.03 (d, J=3.0 Hz, 1H), 7.65 (t, 1H), 7.23 (d, J=11.9 Hz, 1H), 7.08 (d, J=8.5 Hz, 1H), 4.47 (t, 2H), 3.29 (2H), 3.01 (d, J=12.6 Hz, 2H); MS m/z 540 (M+1).

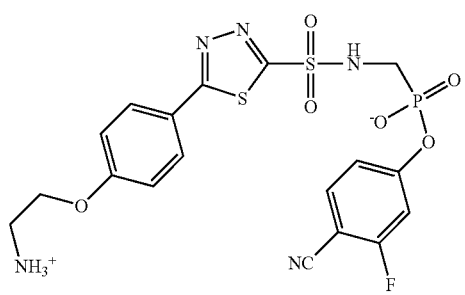

4-cyano-3-fluorophenyl-{[({5-[4-(2-ammonioethoxy)phenyl]-1,3,4-thiadiazol-2-yl}sulfonyl)-amino]methyl}phosphonate was prepared in 11% overall yield after purification by reverse phase HPLC.

¹H NMR (500 MHz, CD₃OD) δ (ppm): 8.00 (d, 1H), 7.60 (t, 1H), 7.20 (m, 3H), 6.70 (m, 2H), 4.20 (t, 2H), 3.44 (t, 2H), 3.32 (d, 2H); MS m/z 540 (M+1).

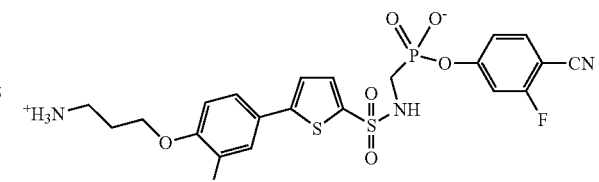

4-cyano-3-fluorophenyl-{[({5-[3,4-bis(3-ammoniopropoxy)phenyl]thiophen-2-yl}sulfonyl)-amino]methyl}phosphonate trifluoroacetate ¹H NMR (500 MHz, CD₃OD) δ (ppm): 7.50 (m, 2H), 7.24 (m, 3H), 7.10 (m, 3H), 4.20 (m, 4H), 3.20 (m, 6H), 2.20 (m, 4H); MS m/z 598 (M+1).

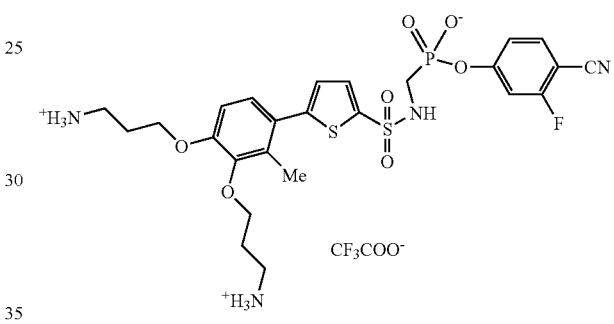

4-cyano-3-fluorophenyl-{[({5-[3,4-bis(3-ammoniopropoxy)-2-methylphenyl]thiophen-2-yl}sulfonyl)amino]methyl}phosphonate trifluoroacetate ¹H NMR (500 MHz, CD₃OD) δ (ppm): 7.60 (t, 1H), 7.52 (d, 1H), 7.20 (m, 2H), 7.08 (d, 1H), 6.98 (d, 1H), 6.96 (d, 1H), 4.20 (t, 2H), 4.06 (t, 2H), 3.20 (m, 6H), 2.22 (s, 3H), 2.20 (m, 4H); MS m/z 613 (M+1).

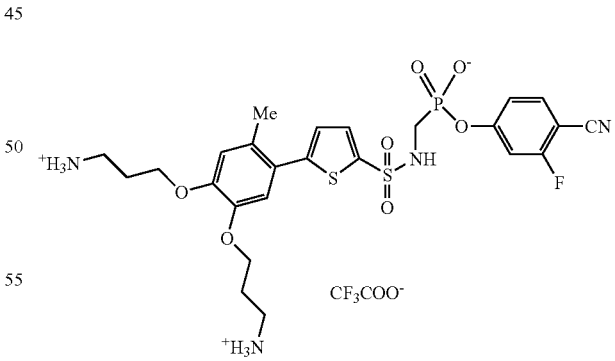

4-cyano-3-fluorophenyl-{[({5-[4,5-bis(3-ammoniopropoxy)-2-methylphenyl]thiophen-2-yl}-sulfonyl)amino]methyl}phosphonate ¹H NMR (500 MHz, CD₃OD) δ (ppm): 7.60 (m, 2H), 7.20 (m, 2H), 7.10 (d, 1H), 7.00 (d, 2H), 4.22 (t, 2H), 4.20 (t, 2H), 3.22 (d, 2H), 3.20 (m, 4H), 2.38 (s, 3H), 2.20 (m, 4H); MS m/z 613 (M+1).

Example 7

Preparation of 4-Cyano-3-Fluorophenyl-[({[6-(2-Ammonioethoxy)-5-(2-{[2,3-Bis(Benxyloxy)Benzoyl]Amino}Ethoxy)-1-1Benzothien-2-Yl]-Sulfonyl}Amino)Methyl]Phosponate and 4-Cyano-3-Fluorophenyl-[({[5-(2-Ammonioethoxy)-6-(2-{[2,3-Bis(Benxyloxy)Benzoyl]Amino}Ethoxy)-1-1Benzothien-2-Yl]-Sulfonyl}Amino)Methyl]Phosponate

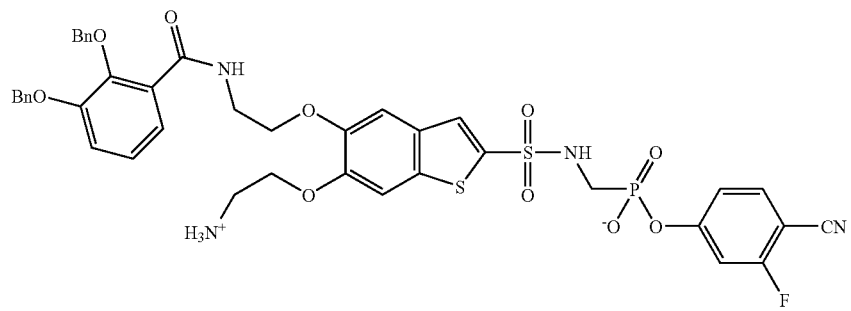

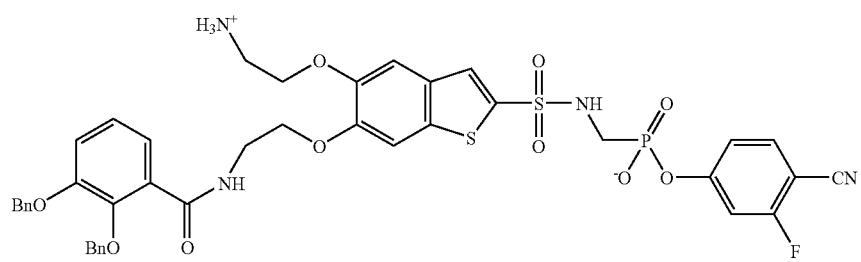

To a solution of 4-cyano-3-fluorophenyl[({[5,6-bis(2-ammonioethoxy)-1-benzothien-2-yl]sulfonyl}amino)methyl] phosphonate (72 mg, 0.12 mmol) in 2 mL of DMF at 0° C. was added a mixture of 2,3-bis(benzyloxy)benzoic acid, HATU and DIEA in DMF. The reaction was allowed to stir at 0° C. for 1 h and the progress monitored by LC-MS. The reaction mixture was neutralized with TFA, purified by reverse phase HPLC and lyophilized overnight to give the product mixture.

$^1$H NMR (500 MHz, CD$_3$OD) δ (ppm): 7.75 (d, 1H), 7.50-7.30 (m, 10H), 7.22-7.06 (m, 8H), 5.20 (s, 2H), 5.02 (s, 2H), 4.20 (m, 4H), 3.86 (m, 2H), 3.36 (d, 2H), 3.26 (m, 2H); MS m/z 861 (M+1).

Utilizing the foregoing procedure, the following compounds were prepared:

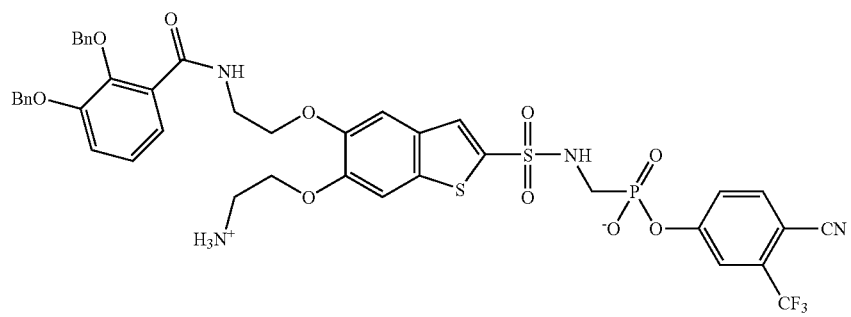

-continued

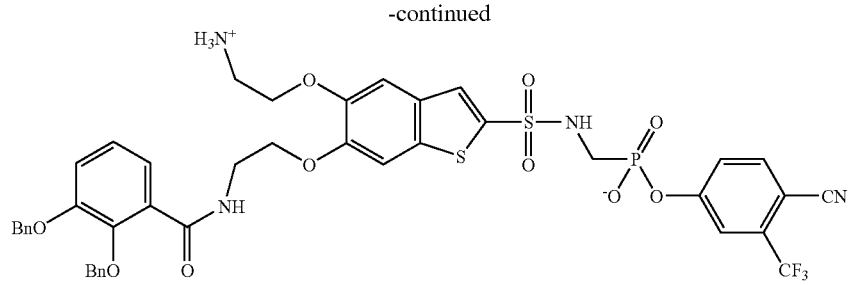

4-cyano-3-(trifluoromethyl)phenyl-[({[6-(2-ammonioethoxy)-5-(2-{[3,4-bis(benzyloxy)benzoyl]-amino}ethoxy)-1-benzothien-2-yl]sulfonyl}amino)methyl]phosphonate and 4-cyano-3-(trifluoromethyl)phenyl-[({[5-(2-ammonioethoxy)-6-(2-{[3,4-bis(benzyloxy)benzoyl]amino}ethoxy)-1-benzothien-2-yl]sulfonyl}amino)methyl]phosphonate ¹H NMR (500 MHz, CD₃OD) δ (ppm): 7.70 (m, 4H), 7.54 (m, 2H), 7.44 (m, 6H), 7.35 (m, 5H), 7.10 (d, 2H), 5.50 (s, 2H), 5.22 (s, 2H), 5.18 (s, 2H), 4.30 (m, 4H), 3.90 (m, 2H), 3.32 (d, 2H), 3.26 (m, 2H); MS m/z 911 (M+1).

Example 8

Preparation of 4-Cyano-3-Fluorophenyl({[6-(2-Ammonioethoxy)-5-{2-[(2,3-Dihydroxybenzoyl)Amino]Ethoxy-1-Benzothien-2-Yl}Sulfonyl]-Amino}Methylphosphonate and 4-Cyano-3-Fluorophenyl({[5-(2-Ammonioethoxy)-6-{2-[(2,3-Dihydroxybenzoyl)Amino]Ethoxy-1-Benzothien-2-Yl}Sulfonyl]Amino}Methylphosphonate

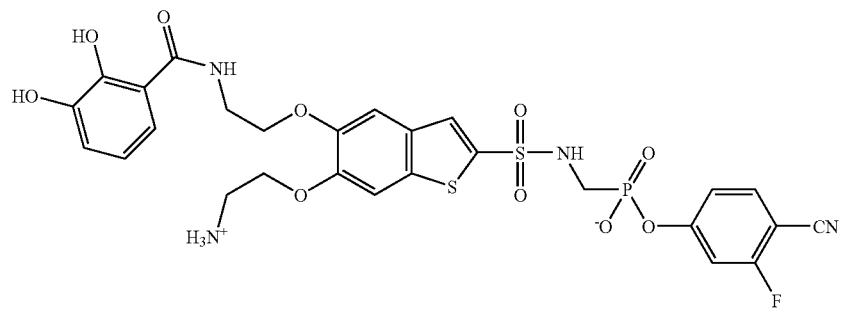

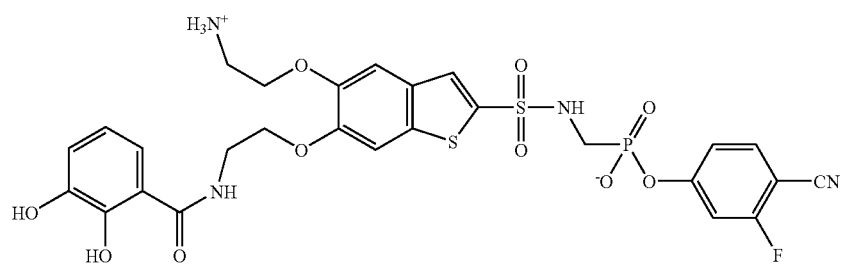

To a solution of the product mixture of the prior Example (6 mg) in 5 mL MeOH at room temperature was added 1 mg of Pd black. The mixture was stirred under a balloon of hydrogen gas overnight and the progress of the reaction monitored by LC-MS. The reaction mixture was neutralized with TFA and filtered. The filtrate was purified by reverse phase HPLC and lyophilized overnight to give the product mixture.

¹H NMR (500 MHz, CD₃OD) δ (ppm): 7.74 (d, 1H), 7.60 (s, 1H), 7.54 (d, 1H), 7.50 (s, 1H), 7.25 (d, 1H), 7.20 (m, 2H), 6.96 (d, 1H), 6.75 (t, 1H), 4.35 (m, 4H), 3.95 (m, 2H), 3.30 (d, 2H), 3.26 (m, 2H); MS m/z 681 (M+1).

Utilizing the foregoing procedure, the following compound was prepared:

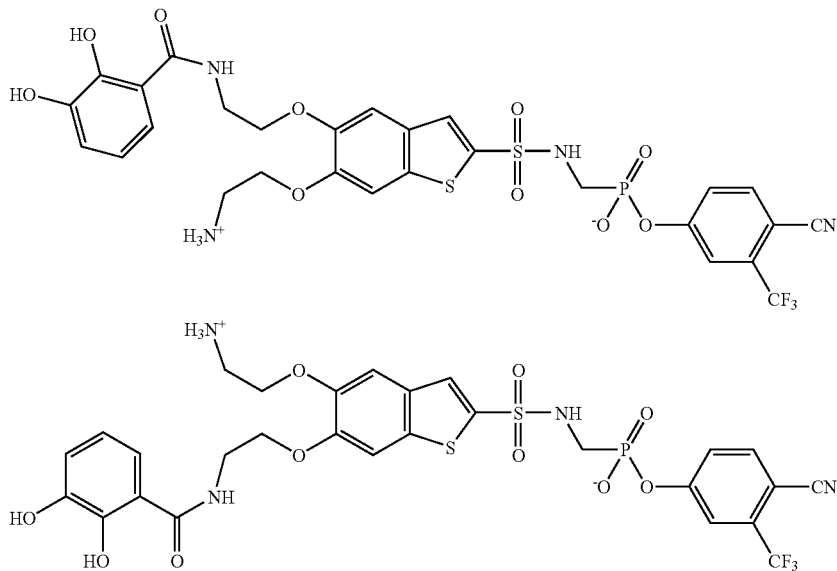

4-cyano-3-(trifluoromethyl)phenyl-({[(6-(2-ammonioethoxy)-5-{2-[(3,4-dihydroxybenzoyl)-amino]ethoxy}-1-benzothien-2-yl)sulfonyl]amino}methyl)phosphonate and 4-cyano-3-(trifluoromethyl)phenyl-({[(5-(2-ammonioethoxy)-6-{2-[(3,4-dihydroxybenzoyl)amino]ethoxy}-1-benzothien-2-yl)sulfonyl]amino}methyl)phosphonate $^1$H NMR (500 MHz, CD$_3$OD) ☐ ppm): 7.70 (m, 3H), 7.50 (m, 3H), 7.30 (s, 1H), 7.20 (d, 1H), 6.80 (d, 1H), 4.30 (m, 4H), 3.90 (m, 2H), 3.32 (d, 2H), 3.26 (m, 2H); MS m/z 731 (M+1).

Example 9

Preparation of 4-Cyano-3-Fluorophenyl {[({5-[2-Dimethylammonio-Ethoxy]-1-Benzothien-2-Yl}Sulfonyl)Amino]Methyl}Phosphonate

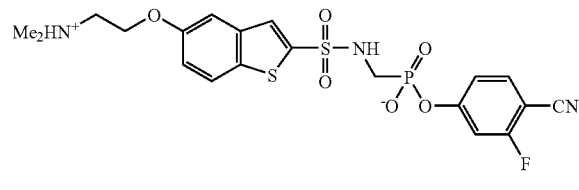

A solution of 4-cyano-3-fluorophenyl-[({[5-(2-ammonioethoxy)-1-benzothien-2-yl]sulfonyl}-amino)methyl]phosphonate (13.1 mg, 0.027 mmol), 37% aq. formaldehyde (4.1 µL, 0.054 mmol) and NaCNBH$_3$ (54 µL, 1.0M THF) in 2:1 THF-MeOH was stirred at room temperature for 18 hrs. The reaction was concentrated in vacuo and dissolved in 10% aq. MeCN. The solution was purified by HPLC. After lyophilization the product was obtained.

$^1$H NMR (500 MHz, CD$_3$OD) δ (ppm): 7.87 (d, J=8.9 Hz, 1H), 7.79 (s, 1H) 7.51 (d, J=2.1 Hz, 1H), 7.21 (t, J=8.1 Hz, 1H), 7.14 (dd, J=8.5, 2.1 Hz, 1H), 7.01 (m, 2H), 4.45 (t, J=5.0 Hz, 2H), 3.67 (t, J=4.8 Hz, 2H), 3.04 (s, 6H); MS m/z 513 (M+1).

Example 10

Preparation of 4-Cyano-3-(Trifluoromethyl)Phenyl-({[(5-{2-[(Iminiomethyl)Amino]Ethoxy}-1-Benzothien-2-Yl) Sulfonyl]-Amino}Methyl)Phosphonate Trifluoroacetate

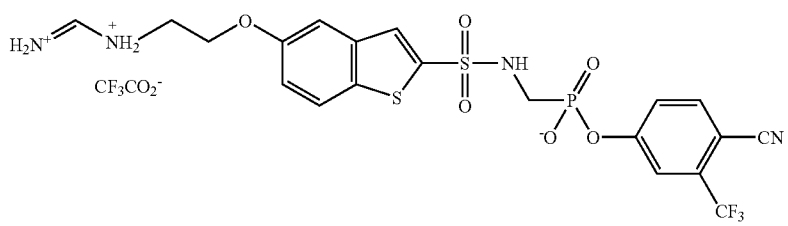

To a stirred solution of the 4-cyano-3-trifluoromethylphenyl-[({[5-(2-ammonioethoxy)-1-benzothien-2-yl]sulfonyl}amino)methyl]phosphonate (8 mg, 0.0149 mmol) in 5:1 H$_2$O-MeCN at 0° C. was added ethyl formimidate hydrochloride (16 mg, 0.149 mmol) followed by 5N aq. NaOH (20 μL, 0.10 mmol); (pH~8.5). After 45 min., the crude mixture was purified by HPLC on a $C_{18}$ reverse phase column. After lyophilization, 3.6 mg of was obtained as a 3:1 mixture of geometric isomers.

$^1$H NMR (500 MHz, CD$_3$OD) δ (ppm): 8.02 (s, 1H), 7.9 (s, 1H), 7.77-7.82 (m, 4H), 7.65-7.68 (m, 4H), 7.41-7.45 (m, 4H), 7.16 (dd, J=8.5 Hz, 2.3 Hz, 2H). 4.28 (t, J=4.7 Hz, 2H), 4.22 (t, J=4.8 Hz, 2H), 3.81 (t, J=4.7 Hz, 2H), 3.77 (t, J=4.8 Hz, 2H), 3.37 (m, 4H), 3.27 (d, J=12.8 Hz, 4H); MS m/z 563 (M).

Example 11

Preparation of 4-Cyano-3-Fluorophenyl[({[5-(2-{[(Dimethyliminio)-Methyl]Amino}Ethoxy)-1-Benzothien-2-Yl]Sulfonyl}Amino)Methyl]-Phosphonate

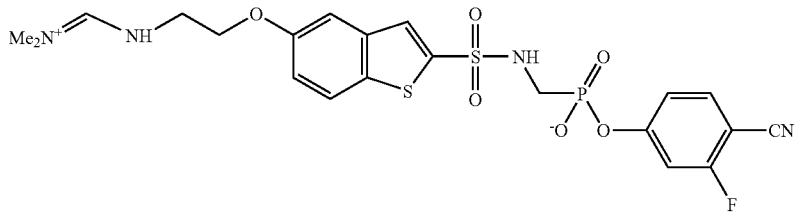

A solution of 4-cyano-3-fluorophenyl-[({[5-(2-ammonioethoxy)-1-benzothien-2-yl]sulfonyl}-amino)methyl]phosphonate (12.1 mg, 0.025 mmol), 1.0 N aq. NaOH (30 μL, 0.03 mmol) and N,N-dimethylformamide dimethylacetal (6.6 μL, 0.050 mmol) was stirred at 0° C. for 1 hr. The solution was warmed to room temperature and stirred for 4 hrs. The reaction was concentrated in vacuo and reconstituted with 10% aq. MeCN. The resulting solution was purified by HPLC. After lyophilization product was obtained.

$^1$H NMR (600 MHz, CD$_3$OD) δ (ppm): 8.58 (bt, 1H), 8.12 (s, 1H) 7.74 (d, J=8.9 Hz, 1H), 7.71 (s, 1H), 7.36 (d, J=2.1 Hz, 1H), 7.30 (t, J=8.3, 1H), 7.18 (dd, J=8.9 Hz, 1.9 Hz, 1H), 7.01 (dd, J=11.1 Hz, 1.9 Hz, 1H), 6.99 (dd, J=8.6 Hz, 1.9 Hz, 1H), 4.23 (t, J=4.6 Hz, 2H), 3.85 (t, J=4.6 Hz, 2H) 3.07 (s, 6H); MS m/z 541 (M+1).

Example 12

Preparation of 4-Cyano-3-Fluorophenyl Hydrogen [({[5,6-Bis(3-{[Amino(Iminio)Methyl]Amino}Propoxy)-4,7-Difluoro-1-Benzothien-2-Yl]Sulfonyl}Amino)Methyl]Phosphonate Trifluoroacetate

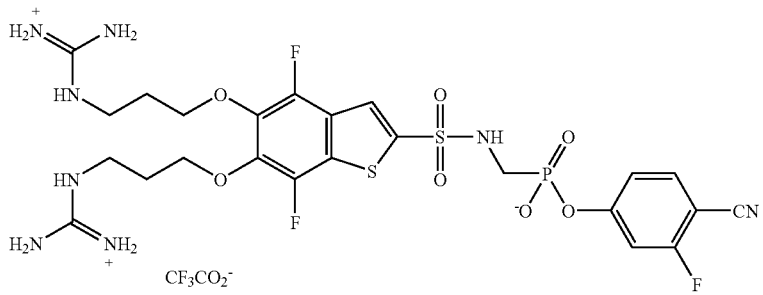

To 4-cyano-3-fluorophenyl[({[5,6-bis(3-ammoniopropoxy)-4,7-difluoro-1-benzothien-2-yl]-sulfonyl}amino)methyl]phosphonate trifluoroacetate (35 mg, 0.05 mmol) and 1H-pyrazole-1-carboxamidine (30 mg, 4 equiv.) in dry DMF (1 mL) was added diisopropylethylamine (0.087 mL, 10 equiv.), and the reaction mixture was stirred at room temperature for 6 h. The resulting mixture was subject to the HPLC purification using reverse phase column to afford the product (33 mg, 82%).

¹H NMR (500 MHz, CD₃OD) δ (ppm): 7.86 (brd, 1H), 7.52 (m, 2H), 7.08 (m, 2H), 4.3 (two t, 4H), 3.5 (m, 4H), 3.32 (d, 2H, hidden), 2.12 (m, 4H); MS m/z 693 (M+1).

Utilizing the foregoing procedure, the following compounds were prepared:

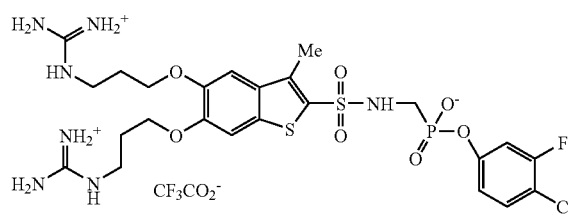

4-cyano-3-fluorophenyl[({[5,6-bis(3-{[amino(iminio) methyl]amino}propoxy)-3-methyl-1-benzothien-2-yl] sulfonyl}amino)methyl]phosphonate trifluoroacetate ¹H NMR (500 MHz, CD₃OD) δ (ppm): 7.52 (m, 1H), 7.4 (s, 1H), 7.3 (t, 1H), 7.22 (s, 1H), 6.92 (m, 2H), 4.22 (m, 4H), 3.48 (m, 4H), 3.28 (d, 2H), 2.54 (s, 3H), 2.16 (m, 4H); MS m/z 671 (M+1).

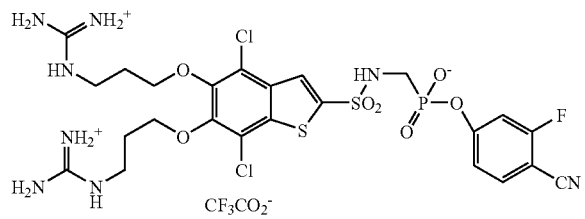

4-cyano-3-fluorophenyl[({[5,6-bis(3-{[amino(iminio) methyl]amino}propoxy)-4,7-dichloro-1-benzothien-2-yl] sulfonyl}amino)methyl]phosphonate trifluoroacetate ¹H NMR (500 MHz, CD₃OD) δ (ppm): 7.88 (s, 1H), 7.46 (s, 1H), 7.3 (t, 2H), 7.04 (m, 2H), 4.26 (two t, 4H), 3.54 (m, 4H), 3.34 (d, 2H, hidden), 2.16 (m, 4H); MS m/z 726 (M+1).

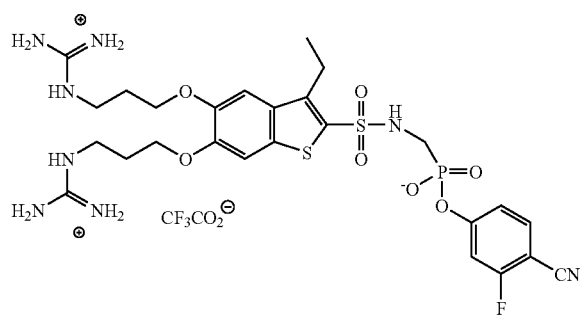

4-cyano-3-fluorophenyl[({[5,6-bis(3-{[amino(iminio) methyl]amino}propoxy)-3-ethyl-1-benzothien-2-yl] sulfonyl}amino)methyl]phosphonate trifluoroacetate ¹H NMR (500 MHz, CD₃OD) δ (ppm): 7.48 (t, 1H), 7.06 (d, 1H), 7.00 (d, 1H), 4.38 (q, 2H), 4.30 (q, 2H), 3.48 (m, 4H), 3.36 (d, 2H), 3.20 (q, 2H), 2.10 (m, 4H), 1.28 (t, 3H); MS m/z 721 (M+1).

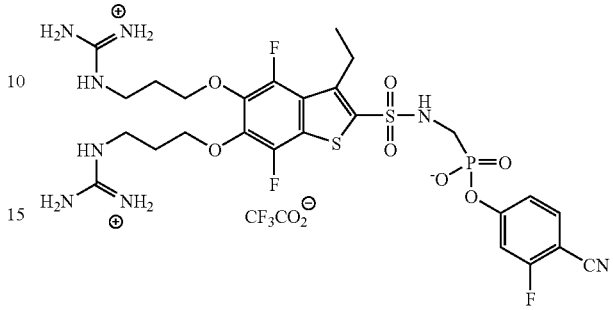

4-cyano-3-fluorophenyl[({[5,6-bis(3-{[amino(iminio) methyl]amino}propoxy)-4,7-fluoro-3-ethyl-1-benzothien-2-yl]sulfonyl}amino)methyl]phosphonate trifluoroacetate ¹H NMR (500 MHz, CD₃OD) δ (ppm): 7.42 (s, 1H), 7.38 (q, 1H), 7.24 (s, 1H), 6.98 (m, 2H), 4.22 (m, 4H), 3.46 (m, 4H), 3.30 (d, 2H), 3.10 (q, 2H), 2.20 (m, 4H), 1.25 (t, 3H); MS m/z 685 (M+1).

Example 13

Preparation of 4-Cyano-3-Fluorophenyl-{[({5-(2-(4-Aza-1-Azoniabicyclo[2.2.2]Oct-1-Yl)Ethoxy)-1-Benzothien-2-Yl}Sulfonyl)-Amino] Methyl}Phosphonate

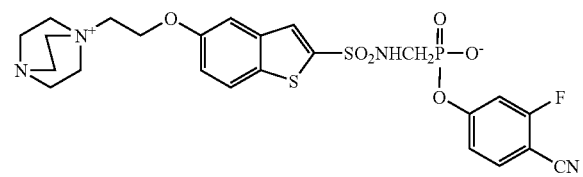

To a stirred solution of 4-cyano-3-fluorophenyl hydrogen [({[5-(2-chloroethoxy)-1-benzothien-2-yl]sulfonyl}amino) methyl]phosphonate (10 mg, 0.0198 mmol) in 0.5 mL of anhydrous MeCN was added 1-4-diazabicyclo[2.2.2]octane (44 mg, 0.396 mmol) and potassium iodide (0.32 mg, 0.019 mmol). The mixture was stirred at 80° C. for 32 hrs. The cooled reaction mixture was diluted with 1.5 mL of water and then purified by HPLC. After lyophilization product was obtained.

¹H NMR (500 MHz, CD₃OD) δ (ppm): 7.83 (s, 1H), 7.73 (s, 1H) 7.45 (d, J=2.5 Hz, 1H), 7.33 (t, J=8.3 Hz, 1H), 7.24 (dd, J=2.5, 8.5 Hz, 1H), 7.05 (dd, J=1.8, 10.9 Hz, 1H), 6.98 (dd, d=1.2, 8.5 Hz, 1H) 4.60 (bt, 2H), 3.85 (t, J=4.3 Hz, 1H), 3.62 (t, J=7.3 Hz, 6H), 3.24 (m, 8H); MS m/z 582 (M+1).

Utilizing the foregoing procedure, the following compound was prepared:

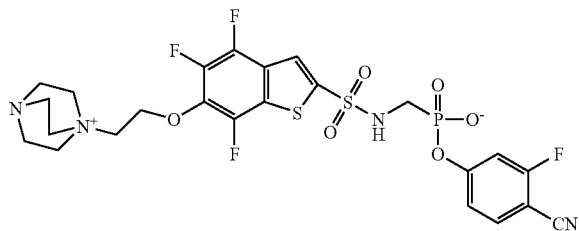 [SMILES: N#Cc1ccc(OP(=O)([O-])CNS(=O)(=O)c2cc3c(F)c(F)c(OCC[N+]45CCN(CC4)CC5)c(F)c3s2)cc1F]

4-cyano-3-fluorophenyl-{[({6-(2-(4-aza-1-azoniabicyclo[2.2.2]oct-1-yl)ethoxy)-4,5,7-trifluoro-1-benzothien-2-yl}sulfonyl)amino]methyl}phosphonate $^1$H NMR (DMSO-d$_6$) δ (ppm): 8.08 (d, J=2.7 Hz, 1H), 7.77 (t, J=8.2 Hz, 1H), 7.27 (d, J=11.0 Hz, 1H), 7.14 (d, J=8.9 Hz, 1H); MS m/z 635 (M+1).

Example 14

Preparation of 4-Cyano-3-(Trifluoromethyl)Phenyl-[({[5-(2-(4-Methyl-1,4-Diazoniabicyclo[2.2.2]Oct-1-Yl)Ethoxy)-1-Benzothien-2-Yl]Sulfonyl}-Amino)Methyl]-Phosphonate Trifluoroacetate

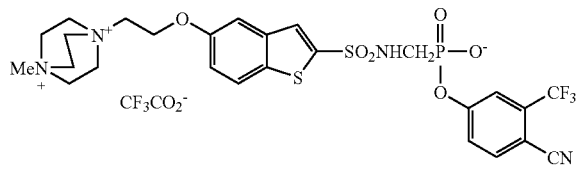

To a stirred solution of 4-cyano-3-(trifluoromethyl)phenyl hydrogen[({[5-(2-chloroethoxy)-1-benzothien-2-yl]sulfonyl}amino)methyl]phosphonate (16 mg, 0.029 mmol) in 1.0 mL of anhydrous DMF at room temperature was added (1-methyl)-1,4-diazabicyclo[2.2.2]octane (73 mg, 0.289 mmol) [prepared according to *J. Chem. Soc. Perkin Trans.* 1988, 1219] and tetrabutylammonium iodide, (10.8 mg, 0.029 mmol). The mixture was stirred at 60° C. for 36 hrs. The solution was cooled to room temperature, diluted with 3 mL of H$_2$O, and purified by HPLC. After lyophilization product was obtained.

$^1$H NMR (600 MHz, CD$_3$OD) δ (ppm): 7.81 (d, J=8.0 Hz, 1H), 7.69 (m, 2H), 7.58 (d, J=8.4 Hz, 1H), 7.45 (d, J=2.1 Hz, 1H), 7.37 (d, J=8.2 Hz, 1H), 7.25 (dd, J=8.9 Hz, 2.2 Hz, 1H), 4.67 (bs, 2H), 4.23 (m, 6H), 4.18 (bs, 2H), 4.08 (m, 6H), 3.42 (s, 3H), 3.26 (d, J=11.3 Hz, 2H); MS m/z 646 (M).

Example 15

Preparation of 4-Cyano-3-Fluorophenyl-({[(5-{2-[4-(3-Azidopropyl)-1,4-Diazoniabicylco-[2.2.2}Oct-1-Yl]Ethoxy}-1-Benzothien-2-Yl)Sulfonyl]-Amino}Methyl)Phosphonate Iodide Trifluoromethanesulfonate

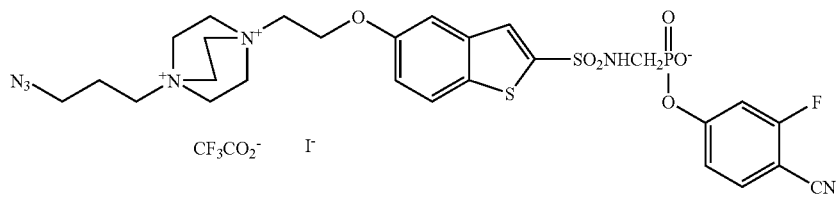

A solution of 4-cyano-3-fluorophenyl hydrogen[({[5-(2-iodoethoxy)-1-benzothien-2-yl]sulfonyl}amino)methyl]phosphonate (10.4 mg, 0.0174 mmol) and 3-azidopropyl)-1,4-diazabicyclo[2.2.2]octane (32 mg, 0.087 mmol), prepared according to U.S. Pat. No. 6,399,597B1, in 1 mL of anhydrous DMF was stirred at 50° C. for 72 hrs. The crude mixture which contained the product, MS m/z 665 (M+1), was used as is in the next reaction.

Utilizing the foregoing procedure, the following compounds were prepared:

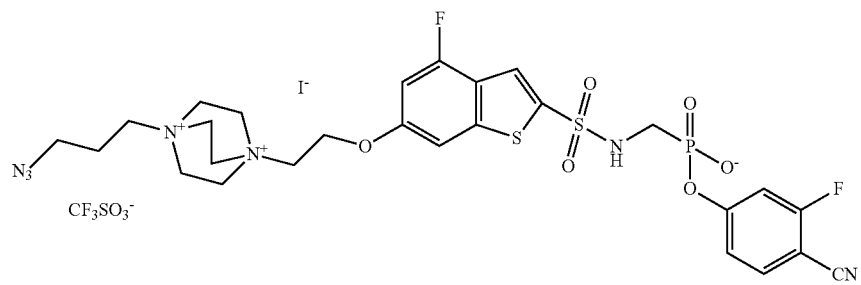

4-cyano-3-fluorophenyl-({[(6-{2-[4-(3-azidopropyl)-1,4-diazoniabicylco[2.2.2]oct-1-yl]ethoxy}-4-fluoro-1-benzothien-2-yl)sulfonyl]amino}methyl)phosphonate iodide trifluoromethanesulfonate ¹H NMR (CD₃OD) δ (ppm): 7.65 (s, 1H), 7.41 (t, J=8.1 Hz, 1H), 7.33 (s, 1H), 7.06 (m, 2H), 6.97 (d, J=5.6 Hz, 1H), 4.71 (br s, 2H), 4.27 (br s, 6H), 4.21 (br s, 2H), 4.10 (br s, 6H), 3.73 (br t, 2H), 3.57 (t, J=6.1 Hz, 2H), 3.28 (d, 2H), 2.14 (m, 2H).

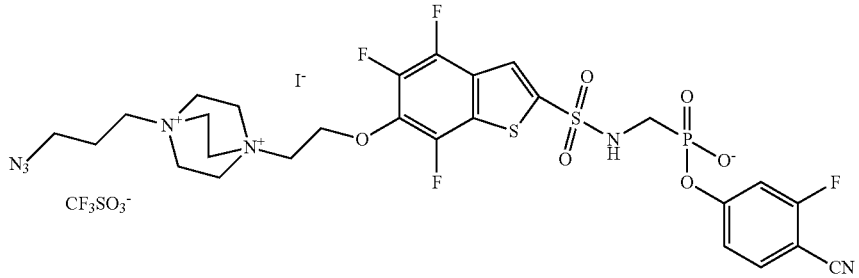

4-cyano-3-fluorophenyl-({[(6-{2-[4-(3-azidopropyl)-1,4-diazoniabicylco[2.2.2]oct-1-yl]ethoxy}-4,5,7-trifluoro-1-benzothien-2-yl)sulfonyl]amino}methyl)phosphonate iodide trifluoromethanesulfonate
MS m/z 718 (M).

Example 16

Preparation of 4-Cyano-3-Fluorophenyl Hydrogen [({[5-(2-{Bis[3-({[(4-Methoxybenzyl)Oxy]-Carbonyl}Amino)Propyl]Amino}Ethoxy)-1-Benzothien-2-Yl]Sulfonyl}Amino)Methyl]-Phosphonate

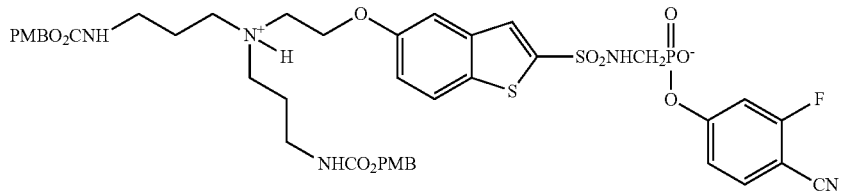

A solution of 4-cyano-3-fluorophenyl-hydrogen-[({[5-(2-iodoethoxy)-1-benzothien-2-yl]-sulfonyl}amino)methyl] phosphonate (30 mg, 0.0503 mmol) in 0.5 mL of anhydrous DMF was combined with the bis-4-methoxybenzyl (iminodipropane-3,1-diyl)biscarbamate (118 mg, 0.252 mmol), prepared in Preparative Example 20, and stirred at 60° C. for 6 hrs. The solution was cooled to room temperature and purified by HPLC. Lyophilization afforded product.

¹H NMR (500 MHz, CD₃OD) δ (ppm): 7.82 (s, 1H), 7.80 (d, 1H), 7.5 (t, 1H), 7.4 (d, 1H), 7.28 (d, 2H), 7.18 (dd, 1H), 7.15 (dd, 1H), 7.08 (dd, 1H), 6.9 (d, 2H), 5.0 (s, 4H), 4.38 (t, 2H), 3.8 (s, 6H), 3.5 (t, 2H), 3.4 (d, 2H), 3.2 (m, 4H), 2.9 (m, 4H), 1.8 (m, 4H); MS m/z 929 (M+1).

Utilizing the foregoing procedure, the following compounds were prepared:

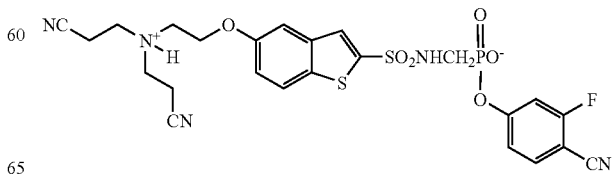

4-cyano-3-fluorophenyl hydrogen[({[5-{2-[bis(2-cyanoethyl)amino]ethoxy}-1-benzothien-2-yl]-sulfonyl}amino)methyl]phosphonate was prepared from 4-cyano-3-fluorophenyl hydrogen[({[5-(2-iodoethoxy)-1-benzothien-2-yl]sulfonyl}amino)methyl]phosphonate and 3,3'-iminopropionitrile at 80° C. for 7 hrs.

$^1$H NMR (500 MHz, CD$_3$OD) δ (ppm): 7.8 (m, 2H), 7.4 (m, 2H), 7.2 (dd, 1H), 7.15 (dd, 1H), 7.0 (dd, 1H), 4.2 (t, 2H), 3.15 (t, 2H), 3.1 (t, 4H), 2.6 (t, 4H); MS m/z 592 (M+1).

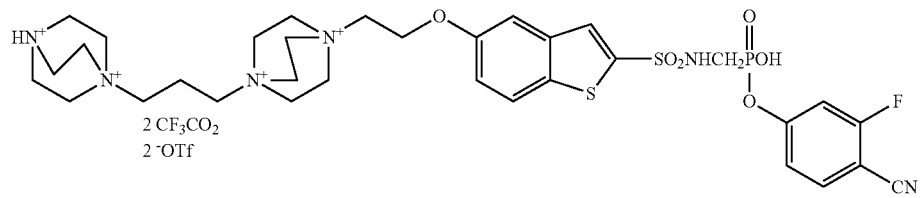

4-cyano-3-fluorophenyl[({[5-(2-{4-[3-(1,4-diazoniabicyclo[2.2.2]oct-1-yl)propyl]-1,4-diazoniabicyclo[2.2.2]oct-1-yl}ethoxy)-1-benzothien-2-yl]sulfonyl}amino)methyl]phosphonate bis-trifluoroacetate bis-triflate was prepared from 4-cyano-3-fluorophenyl hydrogen[({[5-(2-iodoethoxy)-1-benzothien-2-yl]sulfonyl}amino)methyl]phosphonate and 1,1'-propane-1,3-diylbis(4-aza-1-azoniabicyclo[2.2.2]octane bis-triflate after heating at 60° C. for 6 hrs in a sealed tube.

$^1$H NMR (500 MHz, CD$_3$OD) δ (ppm): 7.8 (d, 1H), 7.6 (s, 1H), 7.4 (d, 1H), 7.45 (t, 1H), 7.2 (d, 1H), 7.1 (d, 1H), 6.9 (d, 1H), 4.65 (bs, 2H), 4.25 (m, 6H), 4.18 (m, 8H), 3.6 (m, 2H), 3.4 (m, 6H), 3.2 (m, 8H), 2.4 (m, 2H); MS m/z 367 (M+1)/2.

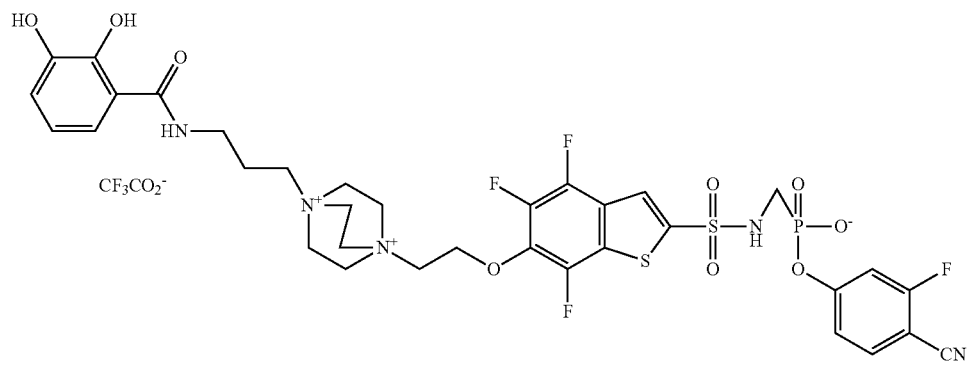

4-cyano-3-fluorophenyl-{[({6-[2-(4-{3-[(2,3-dihydroxybenzoyl)amino]propyl}-1,4-diazoniabicyclo-[2.2.2]oct-1-yl)ethoxy]-4,5,7-trifluoro-1-benzothien-2-yl}sulfonyl)-amino]methyl}phosphonate trifluoroacetate.

$^1$H NMR (CD$_3$OD) δ (ppm): 7.94 (s, 1H), 7.51 (t, 1H), 7.25 (d, 1H), 7.10 (m, 2H), 6.98 (d, 1H), 6.77 (t, 1H), 4.24 (m, 8), 4.20 (m, 2), 4.09 (m, 8), 3.55 (m, 2), 2.24 (m, 2H); MS m/z 828 (M−1).

Utilizing the foregoing procedure, and substituting 4-cyano-3-fluorophenyl hydrogen[({[5-(3-chloropropoxy)-1-benzothien-2-yl]sulfonyl}amino)methyl]phosphonate for 4-cyano-3-fluoro-phenyl hydrogen[({[5-(2-iodoethoxy)-1-benzothien-2-yl]-sulfonyl}amino)methyl]phosphonate the following compound was prepared:

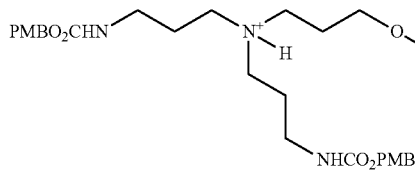
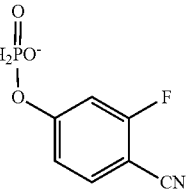

4-cyano-3-fluorophenyl hydrogen[({[5-(3-{bis[3-({[(4-methoxybenzyl)oxy]carbonyl}amino)-propyl]amino}propoxy)-1-benzothien-2-yl]-sulfonyl}amino)methyl]phosphonate $^1$H NMR (600 MHz, CD$_3$OD) δ (ppm): 7.74 (d, 1H), 7.71 (s, 1H), 7.39 (m, 2H), 7.3 (d, 4H), 7.2 (d, 1H), 7.15 (d, 1H), 7.0 (d, 1H), 6.9 (d, 4H), 5.0 (s, 4H), 4.2 (t, 2H), 3.8 (s, 6H), 3.4 (t, 2H), 3.3 (d, 2H), 3.25 (m, 8H), 2.2 (m, 2H), 1.9 (m, 4H); MS m/z 943 (M+1).

Utilizing the foregoing procedure, and substituting 4-cyano-3-fluorophenyl hydrogen[({[5-(3-chloropropoxy)-1-benzothien-2-yl]sulfonyl}amino)methyl]phosphonate for 4-cyano-3-fluoro-phenyl hydrogen[({[5-(2-iodoethoxy)-1-benzothien-2-yl]-sulfonyl}amino)methyl]phosphonate and 4-methoxybenzyl-5-({3-[(4-methoxybenzylcarbonyl)amino]pentanoate for bis-4-methoxy-benzyl (iminodipropane-3,1-diyl)biscarbamate the following compound was prepared:

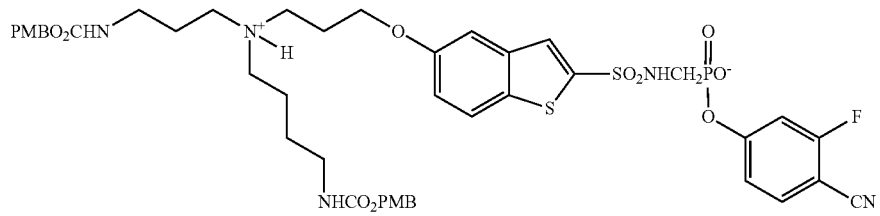

4-cyano-3-fluorophenyl hydrogen[({[5-(3-{[4-({[(4-methoxybenzyl)oxy]carbonyl}amino)-butyl][3-({[(4-methoxybenzyl)oxy]carbonyl}amino)propyl]amino}propoxy)-1-benzothien-2-yl]-sulfonyl}amino)methyl]phosphonate $^1$H NMR (600 MHz, CD$_3$OD) δ (ppm): 7.74 (d, 1H), 7.72 (s, 1H), 7.30 (m, 2H), 7.21 (t, 4H), 7.2 (d, 1H), 7.0 (dd, 1H), 6.95 (dd, 1H), 6.8 (t, 4H), 4.98 (s, 2H), 4.96 (s, 2H), 4.13 (t, 2H), 3.74 (s, 6H), 3.4 (t, 2H), 3.25 (d, 2H), 3.2 (m, 8H), 2.2 (bs, 2H), 1.95 (bs, 2H), 1.7 (bs, 2H), 1.6 (bs, 2H); MS m/z 957 (M+1).

Utilizing the foregoing procedure, and substituting 4-cyano-3-fluorophenyl hydrogen[({[5-(3-chloropropoxy)-3-methyl-1-benzothien-2-yl]sulfonyl}amino)methyl]phosphonate for 4-cyano-3-fluorophenyl hydrogen[({[5-(2-iodoethoxy)-1-benzothien-2-yl]sulfonyl}amino)methyl]-phosphonate the following compound was prepared:

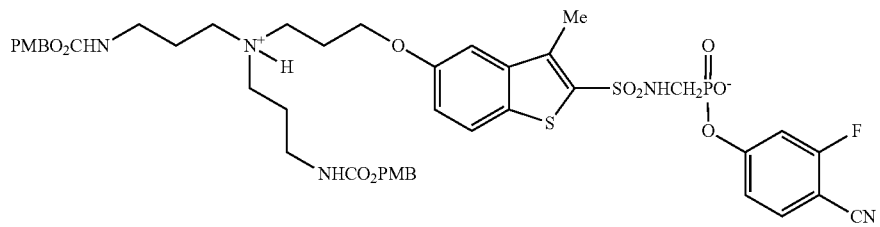

4-cyano-3-fluorophenyl hydrogen[({[5-(3-{bis[3-({[(4-methoxybenzyl)oxy]carbonyl}amino)-propyl]amino}propoxy)-3-methyl-1-benzothien-2-yl]-sulfonyl}amino)methyl]phosphonate $^1$H NMR (600 MHz, CD$_3$OD) δ (ppm): 7.65 (d, 1H), 7.25 (m, 6H), 7.18 (d, 1H), 6.8 (m, 6H), 5.0 (s, 4H), 4.2 (t, 2H), 3.7 (s, 6H), 3.4 (t, 2H), 3.2 (m, 8H), 2.5 (s, 3H), 2.2 (bs, 2H), 1.9 (s, 4H); MS m/z 957 (M+1).

Utilizing the foregoing procedure, and substituting 4-cyano-3-fluorophenyl hydrogen[({[5-(3-chloropropoxy)-3-methyl-1-benzothien-2-yl]sulfonyl}amino)methyl]phosphonate for 4-cyano-3-fluoro-phenyl-hydrogen-[({[5-(2-iodoethoxy)-1-benzothien-2-yl]sulfonyl}amino)methyl]-phosphonate and 4-methoxybenzyl-5-({3-[(4-methoxybenzylcarbonyl)amino]pentanoate for bis-4-methoxy-benzyl (iminodipropane-3,1-diyl)biscarbamate the following compound was prepared:

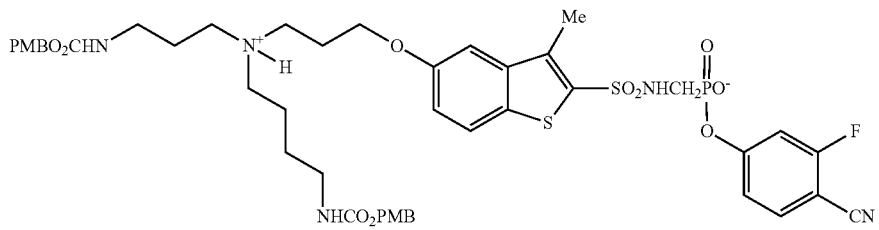

4-cyano-3-fluorophenyl hydrogen[({[5-(3-{[4-({[(4-methoxybenzyl)oxy]carbonyl}-amino)butyl][3-({[(4-methoxybenzyl)oxy]carbonyl}amino)propyl]amino}propoxy)-3-methyl-1-benzothien-2-yl]-sulfonyl}amino)methyl]phosphonate $^1$H NMR (600 MHz, CD$_3$OD) δ (ppm): 7.6 (d, 1H), 7.2 (m, 6H), 7.18 (d, 1H), 6.8 (m, 6H), 4.95 (s, 1H), 4.93 (s, 1H), 4.2 (t, 2H), 3.78 (s, 6H), 3.40 (m, 2H), 3.2 (m, 8H), 2.2 (bs, 2H), 1.95 (bs, 2H), 1.8 (bs, 2H), 1.6 (bs, 2H); MS m/z 971 (M+1).

Example 17

Preparation of N'2',N'2'-Bis{2-[(Tert-Butoxycarbonyl)Amino]Ethyl}-N-{2-[({[(4-Cyano-3-Fluorophenoxy)(Hydroxy)Phosphoryl]Methyl}Amino)Sulfonyl]-1-Benzothien-5-Yl}Glycinamide

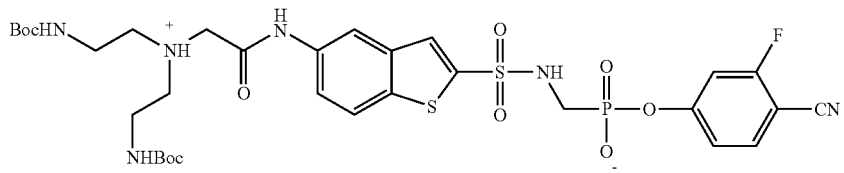 [SMILES: CC(C)(C)OC(=O)NCCN(CCNC(=O)OC(C)(C)C)CC(=O)Nc1ccc2sc(S(=O)(=O)NCP(=O)(O)Oc3ccc(C#N)c(F)c3)cc2c1]

To a stirred solution of di-tert-butyl (iminodiethane-2,1-diyl)biscarbamate (7.2 mg, 0.02 mmol, crude, from Preparative Example 39) in DMSO (500 μL) at room temperature under nitrogen were added 4-cyano-3-fluorophenyl hydrogen {[({5-[(bromoacetyl)amino]-1-benzothien-2-yl}sulfonyl)amino]-methyl}phosphonate (6.7 mg, 0.01 mmol), from Preparative Example 61, and diisopropylethylamine (10 μL, 0.06 mmol), respectively. The reaction mixture was heated at 60° C. for 45 min, cooled to room temperature and purified by preparative HPLC (Thermo, Aquasil C18, 250×21.2 mm, 5 μm; eluent MeOH/H$_2$O [both containing 0.05% HCO$_2$H], linear gradient 20/80→95/5 over 45 min), to afford the product as a white film.

MS m/z 783 (M−1).

Example 18

Preparation of 4-Cyano-3-Fluorophenyl Hydrogen [({[5-{2-[Bis(3-Ammoniopropoxy)Amino]Ethoxy}-1-Benzothien-2-Yl]-Sulfonyl}Amino)Methyl]Phosphonate Bis-Trifluoroacetate

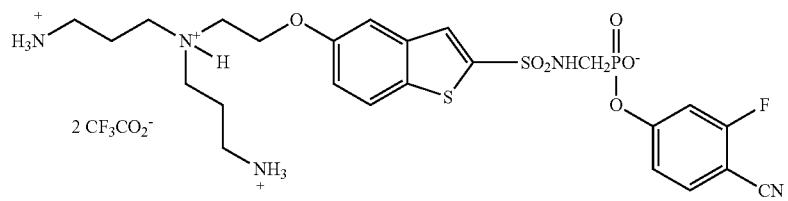

To a solution of the product of Example 15 (19 mg, 0.0205 mmol), in anhydrous dichloromethane (1.5 mL) at room temperature was added TFA (300 μL, 3.89 mmol). After stirring for 10 min., the mixture was concentrated in vacuo. The crude residue was purified by HPLC. Lyophilization gave product.

$^1$H NMR (600 MHz, CD$_3$OD) δ (ppm): 7.8 (d, 1H), 7.6 (s, 1H), 7.4 (d, 1H), 7.35 (t, 1H), 7.2 (dd, 1H), 7.0 (dd, 1H), 6.95 (dd, 1H), 4.4 (bs, 2H), 3.6 (bs, 2H), 3.4 (bs, 4H), 3.2 (d, 2H), 3.1 (t, 4H), 2.2 (bs, 4H); MS m/z 601 (M).

Utilizing the foregoing procedure the following compounds were prepared:

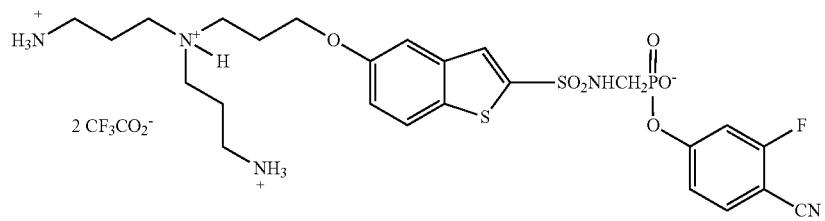

4-cyano-3-fluorophenyl hydrogen({[(5-{3-[bis(3-aminopropyl)amino]propoxy}-1-benzothien-2-yl)sulfonyl]amino}methyl)phosphonate bis-trifluoroacetate $^1$H NMR (600 MHz, CD$_3$OD) δ (ppm): 7.72 (d, 1H), 7.65 (s, 1H), 7.30 (t, 1H), 7.26 (d, 1H), 7.1 (dd, 1H), 7.0 (d, 1H), 6.9 (dd, 1H), 4.2 (t, 2H), 3.4 (bs, 2H), 3.35 (bs, 4H), 3.0 (t, 4H), 2.3 (m, 2H), 2.2 (m, 4H); MS m/z 616 (M).

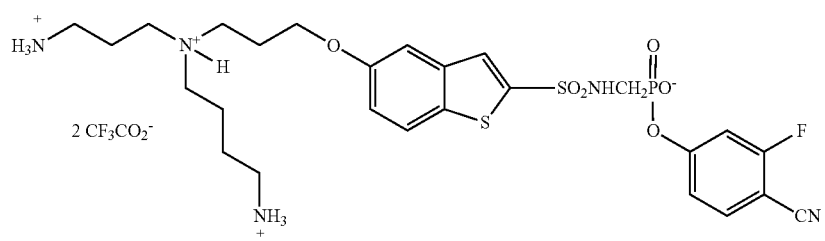

4-cyano-3-fluorophenyl hydrogen({[(5-{3-[(4-aminobutyl)-(3-aminopropyl)amino]propoxy}-1-benzothien-2-yl)sulfonyl]amino}methyl)phosphonate bis-trifluoroacetate $^1$H NMR (500 MHz, CD$_3$OD) δ (ppm): 7.73 (d, 1H), 7.69 (s, 1H), 7.39 (t, 1H), 7.28 (s, 1H), 7.14 (d, 1H), 7.1 (d, 1H), 7.0 (d, 1H), 4.2 (t, 2H), 3.5 (t, 2H), 3.4 (t, 2H), 3.3 (d, 2H), 3.12 (t, 2H), 3.0 (t, 4H), 2.32 (m, 2H), 2.22 (m, 2H), 1.9 (m, 2H), 1.8 (m, 2H); MS m/z 630 (M).

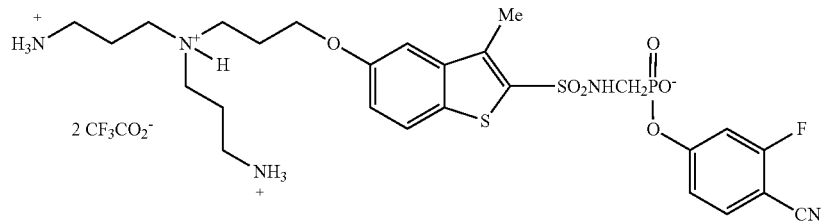

4-cyano-3-fluorophenyl hydrogen({[(5-{3-[bis(3-aminopropyl)amino]propoxy}-3-methyl-1-benzothien-2-yl)sulfonyl]amino}methyl)phosphonate bis-trifluoroacetate $^1$H NMR (600 MHz, CD$_3$OD) δ (ppm): 7.6 (d, 1H), 7.25 (t, 1H), 7.09 (m, 2H), 6.91 (dd, 1H), 6.89 (dd, 1H), 4.2 (t, 2H), 3.4 (t, 2H), 3.05 (t, 8H), 2.4 (s, 3H), 2.3 (bs, 2H), 2.15 (bs, 4H); MS m/z 630 (M).

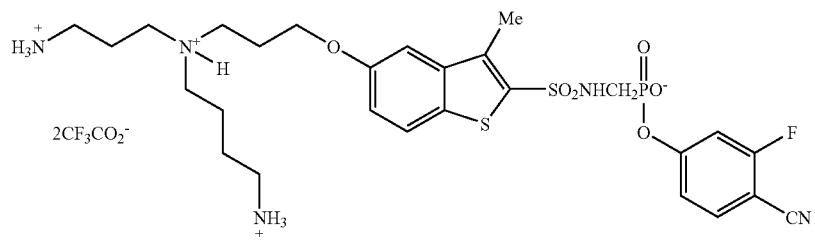

4-cyano-3-fluorophenyl hydrogen({[(5-{3-[(4-aminobutyl)-(3-aminopropyl)amino]propoxy}-3-methyl-1-benzothien-2-yl)sulfonyl]amino}methyl)phosphonate bis-trifluoroacetate $^1$H NMR (600 MHz, CD$_3$OD) δ (ppm): 7.6 (d, 1H), 7.25 (t, 1H), 7.18 (m, 2H), 6.95 (dd, 1H), 6.90 (dd, 1H), 4.2 (t, 2H), 3.48 (t, 2H), 3.35 (d, 2H), 3.15 (t, 2H), 3.0 (t, 2H), 2.4 (s, 3H), 2.3 (m, 4H), 2.19 (m, 2H), 1.95 (m, 2H), 1.8 (m, 2H); MS m/z 643 (M).

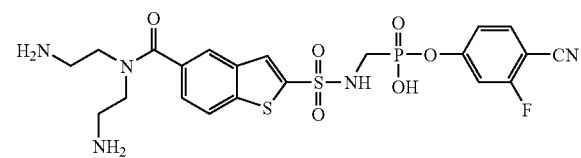 [SMILES: N#Cc1ccc(OP(=O)(O)CNS(=O)(=O)c2cc3cc(C(=O)N(CCN)CCN)ccc3s2)cc1F]

4-cyano-3-fluorophenyl hydrogen(5-(bis(2-aminoethyl)carbamoyl)benzo[b]thiophene-2-sulfonamido)methylphosphonate The product was purified by dissolving the reaction residue in 40% aqueous methanol (3 mL) and applying it to a reverse phase HPLC 250×21.2 mm Aquasil C18 column, and eluting with a 20%-55% methanol/water linear gradient (30 min elution time, elutes ~20 min) to yield the product as an amorphous white solid.

$^1$H NMR (400 MHz, CD$_3$OD) δ (ppm): 8.10-8.08 (m, 2H); 7.99 (s, 1H); 7.64-7.55 (m, 2H); 7.21 (d, J=11.0, 1H); 7.11 (d, J=8.4, 1H); 3.87 (br s, 2H); 3.64 (br s, 2H); 3.26 (d, J=12.5, 2H); 3.06 (br s, 2H); MS m/z 554 (M).

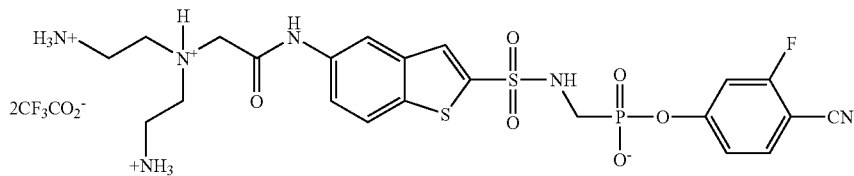

N'2',N'2'-bis(2-aminoethyl)-N-{2-[({[(4-cyano-3-fluorophenoxy)(hydroxy)phosphoryl]-methyl}amino)sulfonyl]-1-benzothien-5-yl}glycinamide bis(trifluoroacetate) (salt)

The product was purified by preparative HPLC (Thermo, Aquasil C18, 250×21.2 mm, 5 μm; eluent MeOH/H₂O [both containing 0.05% HCO₂H], linear gradient 20/80→95/5 over 45 min). The desired fractions were concentrated, suspended in AcOEt containing traces of TFA/MeOH, the solid material was collected by filtration, rinsed with AcOEt, and dried under high vacuum to afford the product over 2 steps) as a white solid.

¹H NMR (400 MHz, DMSO-d₆) δ (ppm): 10.08 (bs, 1H), 8.27 (d, J=1.8 Hz, 1H), 7.98 (d, J=8.6 Hz, 1H), 7.91 (s, 1H), 7.88-7.44 (m, 10H), 7.23 (dd, J=11.9, 2.2 Hz, 1H), 7.03 (dd, J=8.7, 2.1 Hz, 1H), 4H (are overlapped by water signals), 3.00-2.78 (m, 8H); MS m/z 583 (M−1).

Example 19

Utilizing the reduction protocol found in Example 5, the following compounds were prepared:

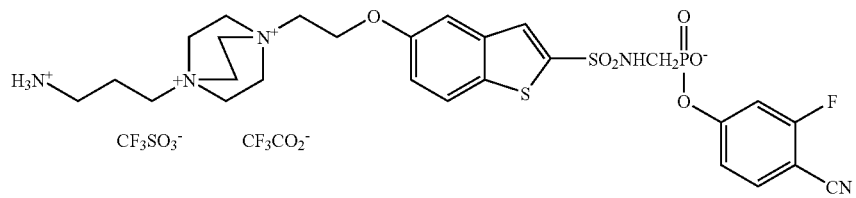

4-cyano-3-fluorophenyl-({[(5-{2-[4-(3-ammoniopropyl)-1,4-diazoniabicylco[2.2.2]oct-1-yl]-ethoxy}-1-benzothien-2-yl)sulfonyl]amino}methyl)phosphonate trifluoroacetate trifluoromethanesulfonate ¹H NMR (600 MHz, CD₃OD) δ (ppm): 7.77 (d, J=9.2 Hz 1H), 7.56 (s, 1H) 7.41 (d, J=1.5 Hz, 1H), 7.33 (t, J=7.9 Hz, 1H), 7.23 (d, J=2.2 Hz, 1H), 7.05 (dd, J=8.9 Hz, 2.7 Hz, 1H), 6.95 (d, J=8.7 Hz, 1H), 4.79 (t, J=7.0 2H), 4.27 (bs, 6H), 4.21 (t, J=7.0 Hz, 2H), 4.17 (bs, 6H) 3.75 (m, 2H), 3.24 (d, J=10.2 Hz, 2H), 3.17 (m, 2H), 2.27 (m, 2H); MS m/z 641 (M⁺).

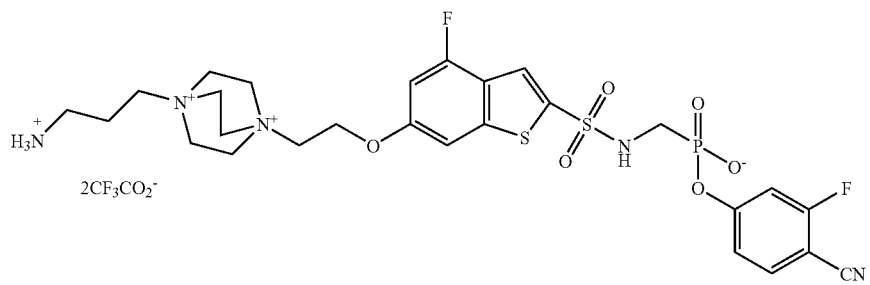 [SMILES: N#Cc1ccc(OP(=O)([O-])CNS(=O)(=O)c2cc3c(F)cc(OCC[N+]45CC[N+](CCCN)(CC4)CC5)cc3s2)cc1F]

4-cyano-3-fluorophenyl-({[(6-{2-[4-(3-ammoniopropyl)-1,4-diazoniabicyclo[2.2.2]oct-1-yl]-ethoxy}-4-fluoro-1-benzothien-2-yl)sulfonyl]amino}methyl)phosphonate bis-trifluoroacetate ¹H NMR (CD₃OD) δ (ppm): 7.45 (m, 1H), 7.08 (m, 2H), 6.96 (m, 1H); MS m/z 692 (M).

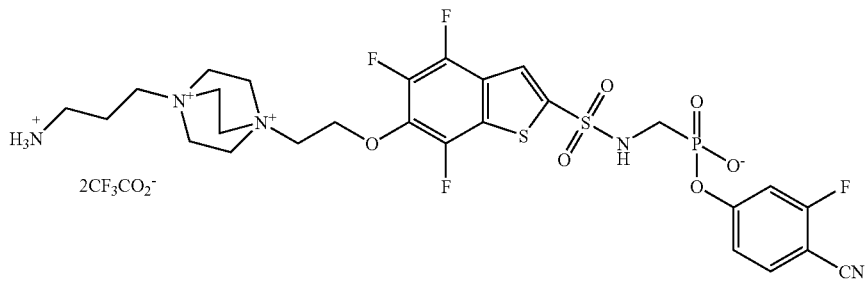 [SMILES: N#Cc1ccc(OP(=O)([O-])CNS(=O)(=O)c2cc3c(F)c(F)c(OCC[N+]45CC[N+](CCCN)(CC4)CC5)c(F)c3s2)cc1F]

4-cyano-3-fluorophenyl-({[(6-{2-[4-(3-ammoniopropyl)-1,4-diazoniabicyclo[2.2.2]oct-1-yl]-ethoxy}-4,5,7-trifluoro-1-benzothien-2-yl)sulfonyl]amino}methyl)phosphonate bis-trifluoroacetate MS m/z 692 (M).

Example 20

Preparation of 4-{[4-({2-[({(4-Cyano-3-Fluorophenoxy)(Hydroxyl)-Phosphoryl]Methyl}Amino)Sulfonyl]-1-Benzothien-6-Yl}-Oxy)Butyl]Thio}-1-Methylpyridinium

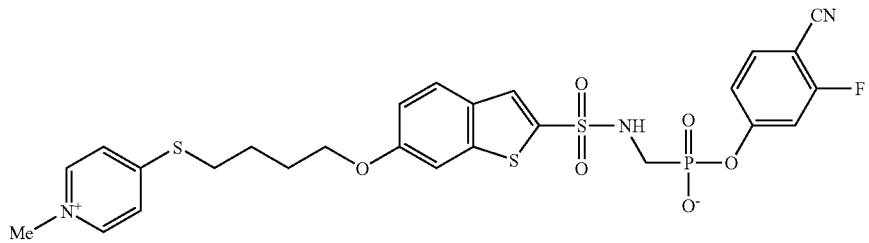 [SMILES: C[n+]1ccc(SCCCCOc2ccc3cc(S(=O)(=O)NCP(=O)([O-])Oc4ccc(C#N)c(F)c4)sc3c2)cc1]

To a stirred solution of 4-cyano-3-fluorophenyl hydrogen {[({6-[4-(pyridin-4-ylthio)butoxy]-1-benzothien-2-yl}sulfonyl)amino]methyl}phosphonate (0.013 g, 0.021 mmol) in anhydrous DMSO (0.126 mL) was added iodomethane (0.003 mg, 0.021 mmol) and N,N-diisopropylethylamine (0.0027 g, 0.021 mmol). The mixture was stirred at room temperature for 2 hrs. The resulting mixture was purified by HPLC using a reversed phase $C_{18}$ column to afford, after lyophilization, product.

$^1$H NMR (CD$_3$OD) δ (ppm): 8.47 (d, 2H), 7.84 (d, 2H), 7.78 (m, 2H), 7.41 (t, 2H), 7.05 (m, 3H), 4.23 (s, 3H), 4.19 (t, 2H), 3.38 (t, 2H), 3.29 (d, 2H), 2.05 (m, 4H); MS m/z 622 (M).

Example 21

Preparation of 4-Cyano-3-Fluorophenyl Hydrogen {[({5-[(Aminoacetyl)Amino]-1-Benzothien-2-Yl}-Sulfonyl)Amino]Methyl}Phosphonate To a stirred solution of 4-cyano-3-fluorophenyl hydrogen {[({5-[(bromoacetyl)amino]-1-benzothien-2-yl}sulfonyl)amino]methyl}phosphonate, prepared in Preparative Example 61, (3 mg, 0.005 mmol) in 2 mL of methanol/water (1:1) at room temperature under nitrogen was added an aqueous solution of NH$_4$OH (2 mL, 30%). The reaction mixture was stirred overnight, concentrated under reduced pressure, and the residue was purified twice by preparative HPLC (Thermo, Aquasil C18, 250×21.2 mm, 5 μm; eluent MeOH/H$_2$O [both containing 0.05% HCO$_2$H], linear gradient 5/95→95/5 over 45 min), to afford the product as a white film.

$^1$H NMR (400 MHz, MeOH-d$_4$) δ (ppm): 8.51 (bs, 1H), ABX system (δ$_A$=7.88, δ$_B$=7.61, δ$_X$=8.29, J$_{AB}$=8.8 Hz, J$_{BX}$=1.8 Hz, J$_{AX}$=0 Hz, 3H), 7.80 (s, 1H), 7.39 (dd, J=8.1 Hz, 1H), 7.07 (dd, J=11.1, 2.0 Hz, 1H), 7.00 (d, J=8.6 Hz, 1H), 4.66 (bs, 2H), 3.89 (s, 2H), 3.31 (d, J=13.1 Hz, 2H).

Utilizing this procedure, the following compound was prepared:

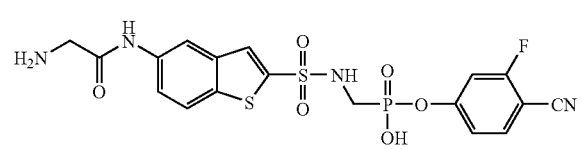 [SMILES: N#Cc1ccc(OP(=O)(O)CNS(=O)(=O)c2cc3cc(NC(=O)CN)ccc3s2)cc1F]
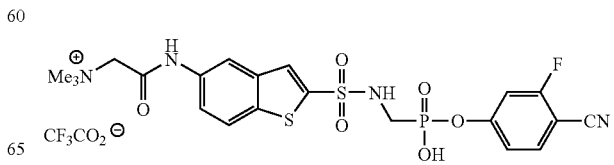

2-(2-(N-(((4-cyano-3-fluorophenoxy)(hydroxy)phosphoryl)methyl)sulfamoyl)benzo[b]thiophen-5-ylamino)-N,N,N-trimethyl-2-oxoethanaminium 2,2,2-trifluoroacetate $^1$H NMR (400 MHz, DMSO-$d_6$) δ (ppm): 10.78 (s, 1H), ABX system ($δ_A$=8.01, $δ_B$=7.58, $δ_X$=8.27, $J_{AB}$=8.8 Hz, $J_{BX}$=2.0 Hz, $J_{AX}$=0 Hz, 3H), 8.09-8.01 (m, 1H), 7.95 (s, 1H), 7.65 (dd, J=8.3 Hz, 1H), 7.24 (dd, J=11.5, 1.9 Hz, 1H), 7.07 (dd, J=8.4, 1.8 Hz, 1H), 4.35 (s, 2H), 3.30 (s, 9H), 3.11-3.02 (m, 2H).

Example 22

Preparation of 4-Cyano-3-Fluorophenyl Hydrogen [5-(2-{[(8-Hydroxyquinolin-5-Yl)Methyl]-(Methyl)Amino}Acetamido)-Benzo[B]Thiophene-2-Sulfonamido]Methyl Phosphonate

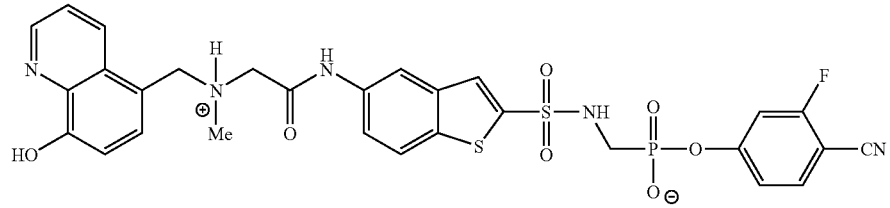 [SMILES: C[NH+](CC(=O)Nc1ccc2sc(S(=O)(=O)NCP(=O)([O-])Oc3ccc(C#N)c(F)c3)cc2c1)Cc1ccc(O)c2ncccc12]

Step 1: To a stirred solution of 2-(N-{[8-(methoxymethoxy)quinolin-5-yl]methyl}-N-methylamino)acetic acid, from Preparative Example 40, (50 mg, 0.17 mmol) in anhydrous DMF (1.5 mL) at 0° C. under nitrogen were added DIPEA (33 μL, 0.19 mmol) and HATU reagent (79 mg, 0.21 mmol). After 15 min, a solution of 4-cyano-3-fluorophenyl hydrogen ({[(5-amino-1-benzothien-2-yl)sulfonyl]amino}methyl)phosphonate (19 mg, 0.04 mmol), prepared in Example 4, (50 mg, 0.11 mmol), DIPEA (60 μL, 0.34 mmol) in anhydrous DMF (1.3 mL) was added drop wise. The reaction mixture was allowed to warm to room temperature over 2 h, and stirred for 2 more hrs. Then another portion of HATU reagent (80 mg, 0.21 mmol) was added. The reaction mixture was stirred for 2.5 h, purified by preparative HPLC (Thermo, aquasil C18, 250×21.2 mm, 5 μm; eluent MeOH/H$_2$O [both containing 0.05% HCO$_2$H], linear gradient 20/80→95/5 over 30 min), to afford 4-cyano-3-fluorophenyl-hydrogen-{5-[2-({[8-(methoxymethoxy)quinolin-5-yl]methyl}(methyl)amino)acetamido]benzo[b]thiophene-2-sulfonamido}methylphosphonate as an off-white solid.

MS m/z 711 (M–1).

Step 2: To a stirred solution of 20 mg of the product from the previous step in anhydrous methanol (2 mL) at room temperature under nitrogen was added a methanolic solution of 3N HCl (430 μL). The reaction mixture was stirred for 2.5 h, quenched with water, and concentrated under reduced pressure. The crude residue was dissolved in MeOH/H$_2$O (containing traces of TFA) and purified twice by preparative HPLC (Thermo, Aquasil C18, 250×21.2 mm, 5 μm; eluent MeOH/H$_2$O [both containing 0.05% HCO$_2$H], linear gradient 30/70→95/5 over 30 min), to afford the product as a pale green-yellowish sticky film.

$^1$H NMR (400 MHz, MeOH-$d_4$) δ (ppm): 9.39 (d, J=8.0 Hz, 1H), 9.05 (d, J=4.1 Hz, 1H), 8.21 (s, 1H), 8.12-7.97 (m, 1H), 7.91 (d, J=8.2 Hz, 1H), 7.88 (d, J=8.8 Hz, 1H), 7.78 (s, 1H), 7.54 (d J=8.4 Hz, 1H), 7.40-7.26 (m, 2H), 7.05 (d, J=10.4 Hz, 1H), 6.94 (d, J=8.0 Hz, 1H), 4.33 (s, 2H), 2 CH$_2$ are covered by methanol signals, 2.98 (s, 3H).

The un-reacted starting material was recovered after the first HPLC purification and was purified again by preparative HPLC (Thermo, Aquasil C18, 250×21.2 mm, 5 μm; eluent MeOH/H$_2$O [both containing 0.05% HCO$_2$H], linear gradient 30/70→85/15 over 30 min), to afford the pure product (TFA salt) of step 1, as a pale yellow sticky solid.

$^1$H NMR (400 MHz, MeOH-$d_4$+TFA) δ (ppm): 9.85 (d, J=8.6 Hz, 1H), 9.25 (d, J=5.1 Hz, 1H), 8.38 (dd, J=8.6, 5.5 Hz, 1H), 8.18-8.15 (m, 2H), 7.87 (d, J=8.8 Hz, 1H), 7.84 (d, J=8.2 Hz, 1H), 7.77 (s, 1H), 7.52 (dd J=8.8, 2.0 Hz, 1H), 7.36 (t J=8.2 Hz, 1H), 7.05 (d, J=10.6 Hz, 1H), 6.96 (d, J=8.4 Hz, 1H), 5.59 (s, 2H), 4.42 (s, 2H), 3.52 (s, 3H), 3.38 (bd, J=11.6 Hz, 2H), signal of the one of CH$_2$ groups is overlapped by signal of methanol, 3.05 (s, 3H).

Utilizing the foregoing procedure, the following compounds were prepared:

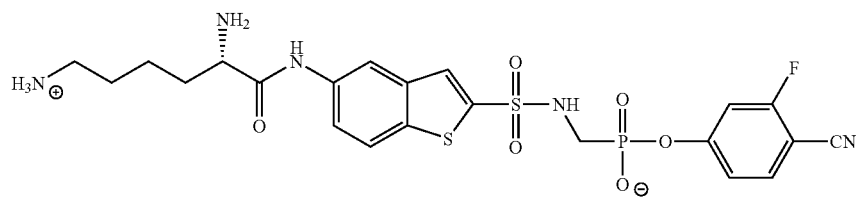 [SMILES: N#Cc1ccc(OP(=O)([O-])CNS(=O)(=O)c2cc3cc(NC(=O)[C@@H](N)CCCC[NH3+])ccc3s2)cc1F]

4-cyano-3-fluorophenyl hydrogen[5-((S)-2,6-diaminohexanamido)benzo[b]thiophene-2-sulfonamido]methylphosphonate was prepared using Boc-Lys(Boc)OH followed by deprotection with wet TFA.

$^1$H NMR (400 MHz, DMSO-$d_6$) δ (ppm): ABX system $δ_A$=7.95, $δ_B$=7.65, $δ_X$=8.32, $J_{AB}$=8.8 Hz, $J_{BX}$=1.8 Hz, $J_{AX}$=0 Hz, 3H), 8.17-8.11 (m, 1H), 7.90 (s, 1H), 7.59 (dd, J=8.3 Hz, 1H), 7.24 (dd, J=12.0, 2.2 Hz, 1H), 7.03 (dd, J=8.6, 1.8 Hz, 1H), 3.48-3.42 (m, 1H), 2.88 (d, J=13.1 Hz, 2H), 2.77 (t, J=7.4 Hz, 2H), 1.80-1.31 (m, 6H).

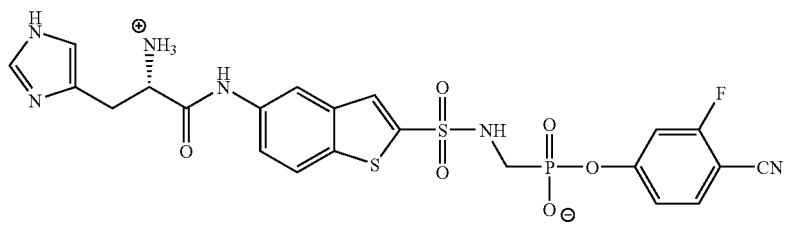 [SMILES: N#Cc1ccc(OP(=O)([O-])CNS(=O)(=O)c2cc3cc(NC(=O)[C@@H]([NH3+])Cc4c[nH]cn4)ccc3s2)cc1F]

4-cyano-3-fluorophenyl-hydrogen-{5-[(S)-2-amino-3-(1H-imidazol-4-yl)propanamido]-benzo[b]thiophene-2-sulfonamido}methylphosphonate was prepared from Boc-His-OH followed by deprotection with wet TFA.

$^1$H NMR (400 MHz, MeOH-d$_4$) δ (ppm): 8.48-8.34 (m, xNH), ABX system ($δ_A$=7.89, $δ_B$=7.59, $δ_X$=8.28, $J_{AB}$=8.8 Hz, $J_{BX}$=2.1 Hz, $J_{AX}$=0 Hz, 3H), 7.82 (s, 1H), 7.78 (s, 1H), 7.42 (t, J=8.1 Hz, 1H), 7.09 (dd, J=11.2, 1.8 Hz, 1H), 7.06 (s, 1H), 7.03 (d, J=8.6 Hz, 1H), 4.24 (dd, J=7.9, 5.8 Hz, 1H), 3.31 (d, J=13.2 Hz, 2H), 3.21 (d, J=8.0 Hz, 1H), 3.17 (d, J=6.0 Hz, 1H).

Utilizing the foregoing procedure described throughout the specification, the following additional compounds were prepared:

Example 23

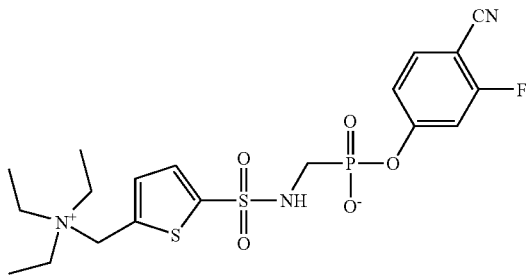 [SMILES: CC[N+](CC)(CC)Cc1ccc(S(=O)(=O)NCP(=O)([O-])Oc2ccc(C#N)c(F)c2)s1]

4-cyano-3-fluorophenyl(5-((triethylammonio)methyl)thiophene-2-sulfonamido) methylphosphonate
(CD3OD) δ (ppm): 7.78-7.72 (m, 2H); 7.53 (s, 1H); 7.35-7.25 (m, 2H); 4.85 (s, 2H); 3.43 (br s, 6H); 3.32 (d, J=13.1, 2H); 1.52 (br s, 9H). LRMS (+ve Scan): 490.1 (calc) 490.1 (found)

Example 24

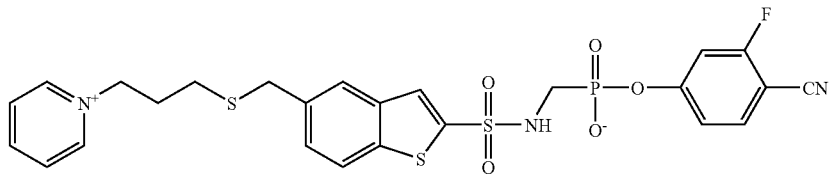 [SMILES: N#Cc1ccc(OP(=O)([O-])CNS(=O)(=O)c2cc3cc(CSCCC[n+]4ccccc4)ccc3s2)cc1F]

4-cyano-3-fluorophenyl(5-((3-(pyridinium-1-yl)propylthio)methyl)benzo[b]thiophene-2-sulfonamido)methylphosphonate
(2:1 MeOD/D2O) δ (ppm): 8.81 (d, J=5.4, 2H); 8.52-8.48 (m, 1H); 7.98 (t, J=7.4, 2H); 7.86 (d, J=8.4, 1H); 7.82 (s, 1H); 7.78 (s, 1H); 7.51 (d, J=8.4, 1H); 7.44 (t, J=8.6, 1H); 7.08-7.00 (m, 2H); 4.67 (t, J=7.0, 2H); 3.90 (s, 2H); 3.28 (d, J=13.1, 2H); 2.48 (t, J=7.0, 2H); 2.25 (quint, J=7.0, 2H). LRMS: 592.1 (calc) 592.2 (found)

Example 25

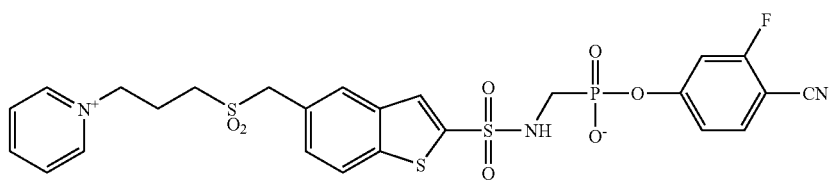 [SMILES: N#Cc1ccc(OP(=O)([O-])CNS(=O)(=O)c2cc3cc(CS(=O)(=O)CCC[n+]4ccccc4)ccc3s2)cc1F]

4-cyano-3-fluorophenyl(5-((3-(pyridinium-1-yl)propyl-sulfonyl)methyl)benzo[b]thiophene-2-sulfonamido)methylphosphonate
LRMS: 624.1 (calc) 624.2 (found)

Example 26

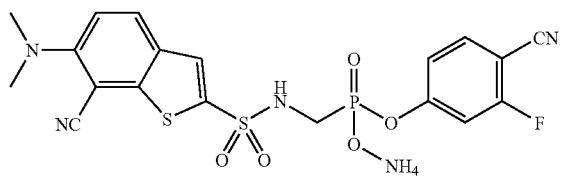

4-cyano-3-fluorophenylaminooxy((7-cyano-6-(dimethy-lamino)benzo[b]thiophene-2-sulfonamido)methyl)phosphinate $^1$H NMR (400 MHz, DMSO-d$_6$) δ (ppm): 7.90 (d, J=9.2 Hz, 1H), 7.76 (s, 1H), 7.53 (t, J=8.4 Hz, 1H), 7.17 (dd, J=12.0, 1.6 Hz, 1H), 7.10 (d, J=9.2 Hz, 1H), 7.01 (dd, J=8.4, 1.6 Hz, 1H), 7.20-7.04 (m, 4H), 3.23 (s, 6H), 2.86 (d, J=12.8 Hz, 2H).

Example 27

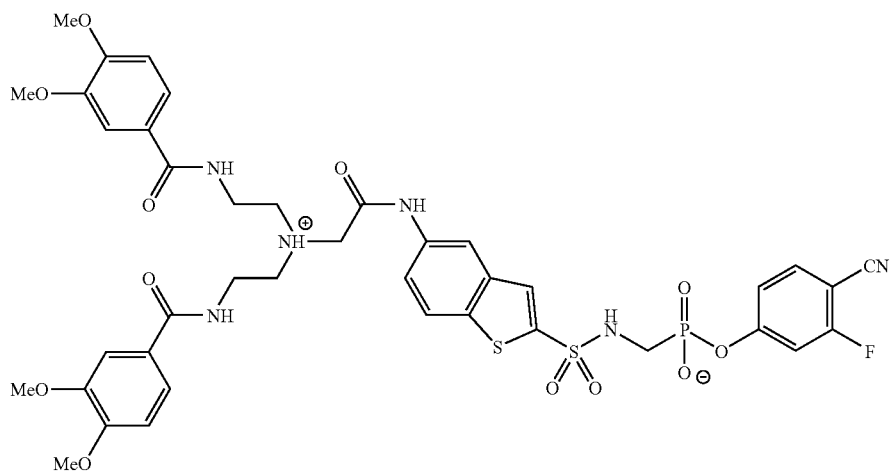 [SMILES: COc1ccc(C(=O)NCC[NH+](CCNC(=O)c2ccc(OC)c(OC)c2)CC(=O)Nc2ccc3sc(S(=O)(=O)NCP(=O)([O-])Oc4ccc(C#N)c(F)c4)cc3c2)cc1OC]

4-cyano-3-fluorophenyl hydrogen(5-(2-(bis(2-(3,4-dimethoxybenzamido)ethyl)-amino)acetamido)-benzo[b]thiophene-2-sulfonamido)methylphosphonate $^1$H NMR (400 MHz, MeOH-d$_4$) δ (ppm): 8.24-8.02 (m, 1H), 7.84 (bd, J=8.8 Hz, 1H), 7.65 (bs, 1H), 7.59 (bd, J=8.6 Hz, 1H), 7.49-7.30 (m, 5H), 7.07 (bd, J=11.2 Hz, 1H), 6.97 (bd, J=8.2 Hz, 1H), 6.92 (bd, J=7.2 Hz, 1H), 4.60-4.20 (m, 2H), 4.00-3.60 (m, 20H), one CH$_2$ is masked by MeOH. MS (m/z): 912.7 [M+H]$^+$.

Example 28

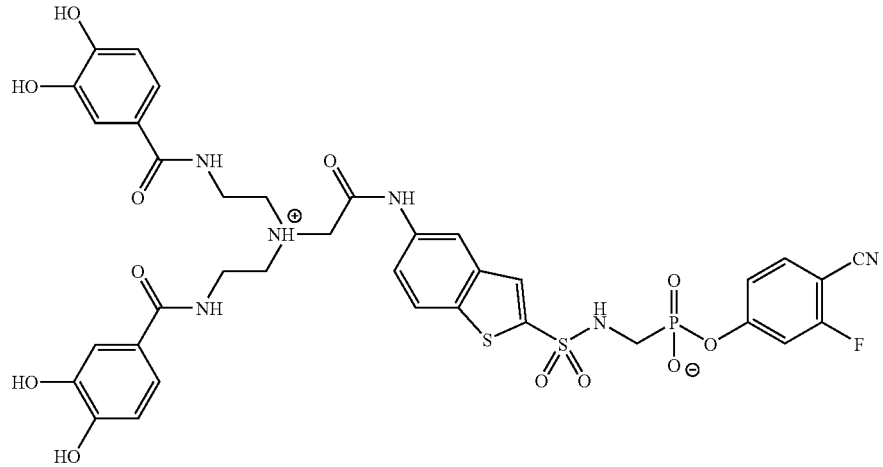 [SMILES: N#Cc1ccc(OP(=O)([O-])CNS(=O)(=O)c2cc3cc(NC(=O)C[NH+](CCNC(=O)c4ccc(O)c(O)c4)CCNC(=O)c4ccc(O)c(O)c4)ccc3s2)cc1F]

4-cyano-3-fluorophenyl hydrogen(5-(2-(bis(2-(3,4-dihydroxybenzamido)ethyl)-amino)acetamido)-benzo[b]thiophene-2-sulfonamido)methylphosphonate $^1$H NMR (400 MHz, MeOH-d$_4$) δ (ppm): 7.65 (d, J=8.8 Hz, 1H), 7.60 (bd, J=9.1 Hz, 1H), 7.56-7.48 (m, 2H), 7.45 (t, J=8.2 Hz, 1H), ABX system (J$_A$=6.72, J$_B$=7.17, J$_X$=7.29, J$_{AB}$=8.3 Hz, J$_{BX}$=2.1 Hz, J$_{AX}$=0 Hz, 6H), 7.20-7.14 (m, 1H masked by B), 7.06 (dd, J=8.4, 1.9 Hz, 1H), 4.75-4.56 (m, 2H), 3.64-3.56 (m, 4H), one CH$_2$ is masked by MeOH, 3.02-2.87 (m, 4H). MS (m/z): 854.9 [M−H]$^+$.

Example 29

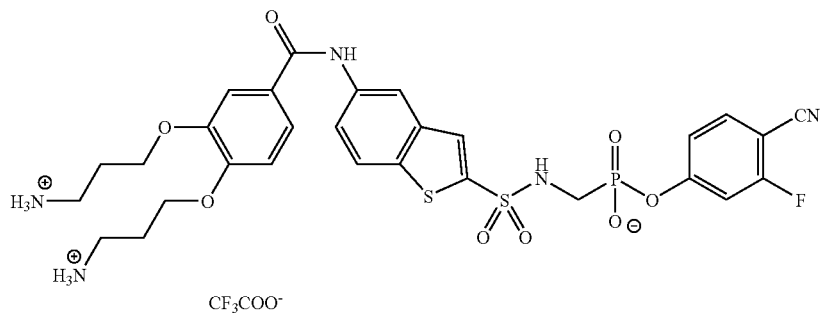

2,2,2-trifluoroacetic acid compound with 4-cyano-3-fluorophenyl hydrogen(5-(3,4-bis(3-aminopropoxy)benzamido)benzo[b]thiophene-2-sulfonamido)methylphosphonate (1:1)

$^1$H NMR (400 MHz, MeOH-d$_4$) δ (ppm): 8.42-8.20 (m, 2H), 7.83 (d, J=8.6 Hz, 1H), 7.72 (dd, J=8.9, 1.6 Hz, 1H), 7.70-7.56 (m, 3H), 7.44 (t, J=8.2 Hz, 1H), 7.11 (d, J=11.2 Hz, 1H), 7.06 (d, J=8.4 Hz, 1H), 7.01 (d, J=8.6 Hz, 1H), 4.30-4.16 (m, 4H), 3.27 (d, J=12.7 Hz, 2H), 3.26-3.16 (m, 4H), 2.30-2.14 (m, 4H). MS (m/z): 692.1 [M+H]$^+$.

Example 30

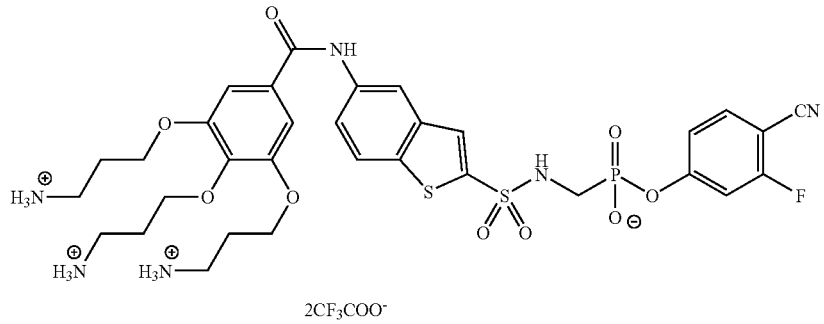

2,2,2-trifluoroacetic acid compound with 4-cyano-3-fluorophenyl hydrogen(5-(3,4,5-tris(3-aminopropoxy)benzamido)-benzo[b]thiophene-2-sulfonamido)methylphosphonate (2:1)

$^1$H NMR (400 MHz, MeOH-d$_4$) δ (ppm): 8.29 (s, 1H), 7.84 (d, J=8.8 Hz, 1H), 7.76-7.68 (m, 2H), 7.43-7.32 (m, 3H), 7.06 (bd, J=10.8 Hz, 1H), 6.96 (d, J=8.4 Hz, 1H), 4.35-4.13 (m, 6H), one CH$_2$ is masked by MeOH, 3.35-3.10 (m, 6H), 2.35-2.15 (m, 6H). MS (m/z): 765.1 [+H]$^+$.

Example 31

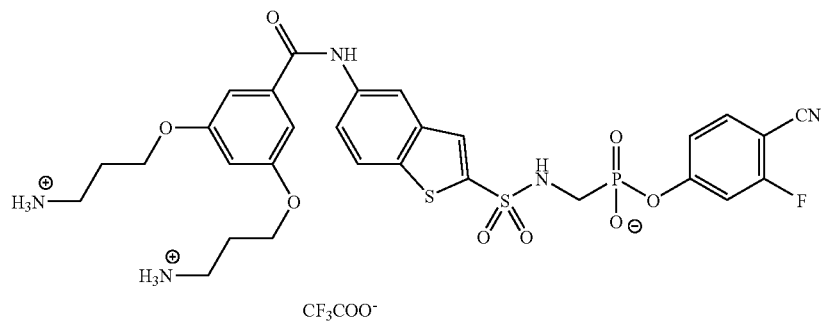

CF₃COO⁻

2,2,2-trifluoroacetic acid compound with 4-cyano-3-fluorophenyl hydrogen(5-(3,5-bis(3-aminopropoxy)benzamido) benzo[b]thiophene-2-sulfonamido)methylphosphonate (1:1)

¹H NMR (400 MHz, MeOH-d₄) δ (ppm): 8.29 (s, 1H), 7.84 (d, J=8.8 Hz, 1H), 7.78-7.70 (m, 2H), 7.39 (t, J=8.1 Hz, 1H), 7.18 (d, J=2.0 Hz, 2H), 7.07 (dd, J=11.0, 1.9 Hz, 1H), 6.97 (dd, J=8.6, 1.8 Hz, 1H), 6.75 (t, J=1.9 Hz, 1H), 4.19 (t, J=5.7 Hz, 4H), 3.27 (d, J=13.1 Hz, 2H), 3.18 (t, J=7.2 Hz, 4H), 2.18 (quintuplet, J=6.4 Hz, 4H). MS (m/z): 690.0 [M−H]⁺.

Example 32

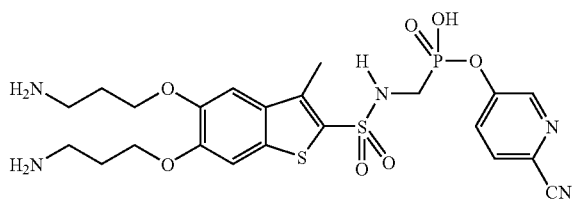 [SMILES: Cc1c(S(=O)(=O)NCP(=O)(O)Oc2ccc(C#N)nc2)sc2cc(OCCCN)c(OCCCN)cc12]

6-cyanopyridin-3-yl hydrogen[({[5,6-bis(3-aminopropoxy)-3-methyl-1-benzothien-2-yl]sulfonyl}amino)methyl]phosphonate The title compound can be made employing a similar procedure described in Example 33 below.

Example 33

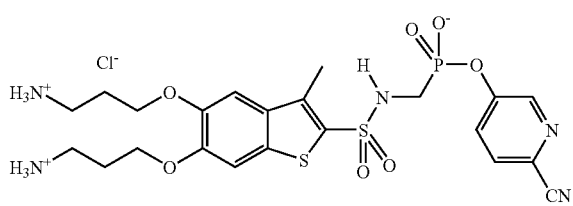 [SMILES: Cc1c(S(=O)(=O)NCP(=O)([O-])Oc2ccc(C#N)nc2)sc2cc(OCCC[NH3+])c(OCCC[NH3+])cc12 ; [Cl-]]

6-cyanopyridin-3-yl[({[5,6-bis(3-ammoniopropoxy)-3-methyl-1-benzothien-2-yl]sulfonyl}amino)methyl]phosphonate chloride Step 1: Preparation of 5-hydroxypyridine-2-carbonitrile

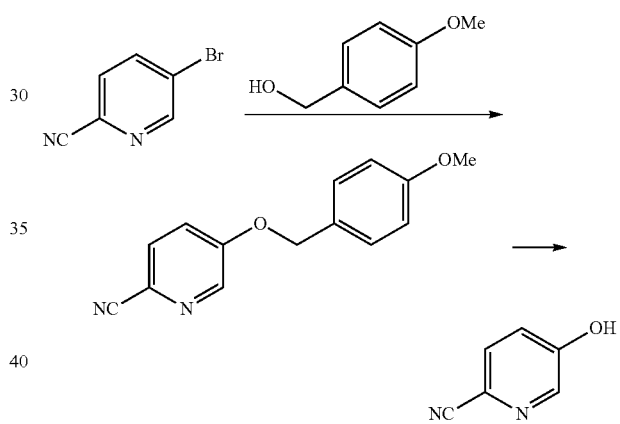

To a solution of 4-methoxybenzyl alcohol (8.3 mL, 66.6 mmol) in DMF (100 mL) was added sodium hydride (3.2 g, 79 mmole) in portions. After gas evolution ceased, 5-bromo-2-cyano-pyridine (10.17 g, 55.6 mmol) was added as a solid. The reaction mixture was stirred at 70° C. under nitrogen for 1 h. The reaction mixture was partitioned between ethyl acetate and cold water. The organic layer was washed with brine, dried over sodium sulfate, and concentrated in vacuo to give an orange solid. The solid was triturated with hexanes to remove less polar impurities. The resulting solid was then dissolved in EtOAc and treated with charcoal. The mixture was filtered and the collected charcoal washed with EtOAc and acetone. The filtrate was concentrated in vacuo to give 5-(4-methoxybenzyloxy)-2-cyano-pyridine (10.6 g) as an off-white solid which became purple upon standing.

To a solution of the above pyridine (10.49 g, 43.7 mmol) in dichloromethane (50 mL) was added triisopropylsilane (0.9 mL, 4.37 mmol) at room temperature under nitrogen. The reaction mixture was stirred for 2 h, at which point TLC (30% EtOAc/Hex) showed reaction complete. The reaction was concentrated in vacuo and the dark oil residue was purified by Isco combiFlash chromatography to give the title compound as a pale yellow solid (5.1 g). ¹H NMR (400 MHz, CD₃OD) δ (ppm) 8.22 (s, 1H), 7.72 (d, 1H), 7.3 (dd, 1H)

Step 2

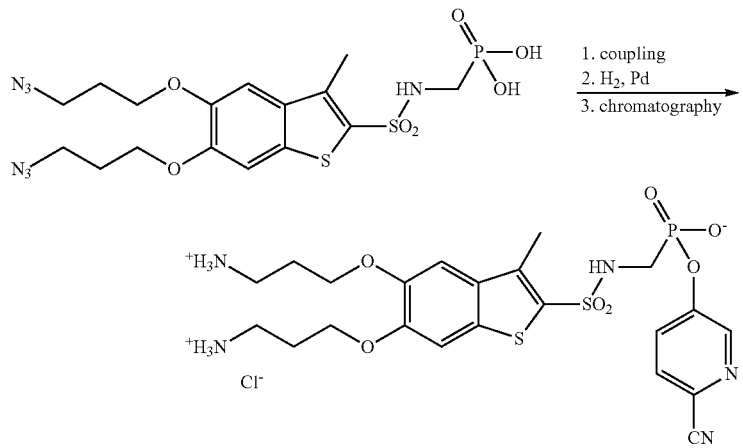

A reaction mixture consisting of [({[5,6-bis(3-azidopropoxy)-3-methyl-1-benzothien-2-yl]sulfonyl}amino)methyl]phosphonic acid (10 g, 19.2 mmol), 5-hydroxypyridine-2-carbonitrile (3.5 g, 1.5 equiv), trichloroacetonitrile (10 equiv), anhydrous DMF (4 mL) and anhydrous pyridine (20 mL) was stirred in a sealed tube for 4 h at 105° C. (note: this was done in batches with the products of the individual batches combined for purification). The reaction was monitored by LC-MS. After the reaction was complete, the reaction mixture was cooled to room temperature, and concentrated under vacuum to afford a brownish oil. To the solution of this crude product in methanol (50 mL) was added palladium black (500 mg). The resulting mixture was shaken under 40 psi of hydrogen for 6 h. The resulting dark yellow solution was filtered, and the filtrate was evaporated to give an oil, which was purified by reverse phase HPLC to afford the trifluoroacetate salt of the title compound (3.8 g, >95% purity). The trifluoroacetate salt (7 g, combined product of several batches) was converted to the corresponding chloride salt by ion-exchange chromatography on a Bio-Rad AG1-X2 resin to afford the title compound as an off-white solid (4 g) after lyophilization. $^{1}$H NMR (500 MHz, DMSO-d6) δ (ppm) 8.34 (s, 1H), 7.74 (d, 1H), 7.66 (dd, 1H), 7.55 (s, 1H), 7.23 (s, 1H), 4.17 (m, 4H), 2.98 (m, 4H), 2.88 (d, 2H), 2.5 (s, 3H), 2.05 (m, 4H); MS m/z 570 (M+1).

Example 34

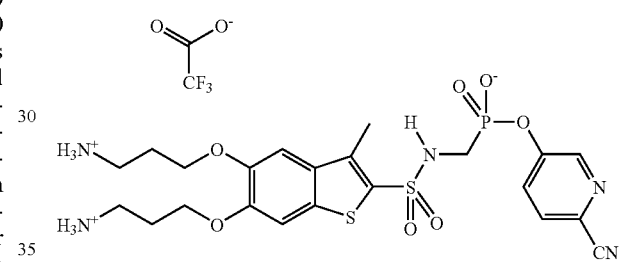

6-cyanopyridin-3-yl[({[5,6-bis(3-ammoniopropoxy)-3-methyl-1-benzothien-2-yl]sulfonyl}amino)methyl]phosphonate trifluoroacetate The title compound is made in accordance with Example 33.

Example 35

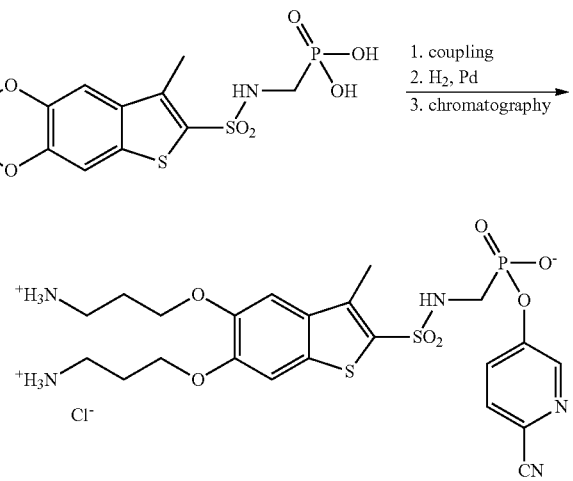

4-cyano-3-fluorophenyl[({[5,6-bis(3-ammoniopropoxy)-3-methyl-1-benzothien-2-yl]sulfonyl}amino)-methyl]phosphonate chloride The title compound was prepared from [({[5,6-bis(3-azidopropoxy)-3-methyl-1-benzothien-2-yl]sulfonyl}amino)methyl]phosphonic acid and 4-cyano-3-fluorophenol using the procedure outlined above for 6-cyanopyridin-3-yl[({[5,6-bis(3-ammoniopropoxy)-3-methyl-1-benzothien-2-yl]sulfonyl}amino)methyl]phosphonate chloride. $^1$H NMR (500 MHz, CD$_3$OD) δ (ppm): 7.4 (s, 1H), 7.28 (t, 1H), 7.19 (s, 1H), 6.92 (brs, 1H), 6.9 (d, 1H), 4.3 (m, 4H), 3.34 (d, 2H hidden), 3.27 (m, 4H), 2.54 (s, 3H), 2.28 (m, 4H); MS m/z 587 (M+1).

Example 36

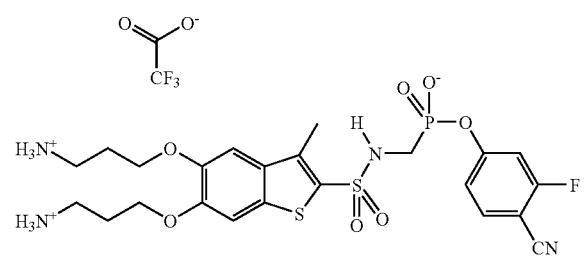 [SMILES: Cc1c(S(=O)(=O)NCP(=O)([O-])Oc2ccc(C#N)c(F)c2)sc2cc(OCCC[NH3+])c(OCCC[NH3+])cc12 ; O=C([O-])C(F)(F)F]

4-cyano-3-fluorophenyl[({[5,6-bis(3-ammoniopropoxy)-3-methyl-1-benzothien-2-yl]sulfonyl}amino)methyl]phosphonate trifluoroacetate The title compound was made in accordance with Example 29.

Biological Assays:

Enzyme Activity: Determination of IC$_{50}$.

The Class A and C enzyme activities were measured in the presence of the test inhibitor in spectrophotometric assay against the commercially available substrate, nitrocefin, while the Class D enzyme activity was determined with CCF$_2$/FA™ (Invitrogen) as substrate in a fluorometric assay. The enzymes, TEM-1, Amp C(P. aeruginosa.), Amp C (A. baumannii), P99, and Oxa-40, as well as both substrates, were dissolved in 100 mM KH$_2$PO$_4$ buffer (pH 7). For the spectrophotometric assay, the buffer also contains 0.005% BSA and for the fluorometric assay, it also contains 0.005% tween-20. The test inhibitor was dissolved in DMSO and diluted 1:20 in the assay, resulting in a final concentration range of 50 uM to 0.0002 uM. In a 96-well microplate, the test inhibitor was incubated with the beta-lactamase enzyme for 40 minutes at ambient temperature, the substrate solution was added, and the incubation continued for another 40 minutes. The spectrophotomertric reaction was quenched by the addition of 2.5 N acetic acid and the absorbance at 492 nm was measured. The fluorometric assay reaction was quenched with 0.3% SDS, and the fluorescense measured at excitation 400 nm, emission 460 nm. The IC 50 was determined from semi logarithmic plots of enzyme inhibition versus inhibitor concentration, with a curve generated using a 4-parameter fit. Representative results using the test inhibitors of the invention showing the inhibition of Class A, C, and D beta-lactamases are shown in Table 1.

TABLE 1

Beta-lactamase Inhibitory Activity of Sulfonamidomethylphosphonate Derivatives

HETAR-SO$_2$NHCH$_2$P(=O)(O$^-$)-O-[3-F,4-CN-phenyl]   IC$_{50}$ (μM)

| Cmpd. | HETAR | Tem-1[a] | Amp C[b] | Amp C[c] | P-99[d] | Oxa-40[e] |
|---|---|---|---|---|---|---|
| 1 | H$_3$N$^+$-CH$_2$CH$_2$-O-(2-methylbenzothiophen-5-yl) | 0.6 | 0.02 | — | 0.003 | 0.5 |
| 2 | pyridinium-CH$_2$CH$_2$-O-(2-methylbenzothiophen-5-yl) | 0.8 | 0.02 | — | 0.002 | 0.4 |
| 3 | DABCO$^+$-CH$_2$CH$_2$-O-(2-methylbenzothiophen-5-yl) | 0.8 | 0.02 | — | 0.002 | 0.5 |

TABLE 1-continued

Beta-lactamase Inhibitory Activity of Sulfonamidomethylphosphonate Derivatives

HETAR-SO₂NHCH₂P(=O)(O⁻)-O-[3-fluoro-4-cyanophenyl]

IC$_{50}$ (μM)

| Cmpd. | HETAR | Tem-1[a] | Amp C[b] | Amp C[c] | P-99[d] | Oxa-40[e] |
|---|---|---|---|---|---|---|
| 4 | pyridinium-CH₂CH₂-O-(4,5,7-trifluoro-2-methylbenzothiophen-6-yl), CF₃CO₂⁻ | 0.2 | 0.008 | — | 0.0006 | 0.2 |
| 5 | pyridinium-(CH₂)₄-O-(4-fluoro-2-methylbenzothiophen-6-yl), CF₃CO₂⁻ | 0.2 | 0.006 | — | 0.0005 | 0.2 |
| 6 | pyridinium-(CH₂)₃-S-CH₂-(2-methylbenzothiophen-5-yl) | 0.4 | 0.03 | — | 0.003 | 0.2 |
| 7 | 1-methyl-4-pyridinium-S-(CH₂)₄-O-(2-methylbenzothiophen-6-yl) | 0.4 | 0.04 | — | 0.08 | 0.1 |
| 8 | Me₂HN⁺-CH₂CH₂-O-(2-methylbenzothiophen-5-yl) | 0.7 | 0.02 | — | 0.002 | 0.5 |
| 9 | pyridinium-(CH₂)₃-O-phenyl-(5-methyl-1,3,4-thiadiazol-2-yl) | 0.7 | 0.04 | — | 0.004 | 0.4 |
| 10 | H₃N⁺(CH₂)₃-N⁺(DABCO)-CH₂CH₂-O-(2-methylbenzothiophen-5-yl), 2 CF₃CO₂⁻ | 2.0 | 0.05 | — | 0.006 | 0.3 |
| 11 | Me₂N-C(=N⁺H)-NH-CH₂CH₂-O-(2-methylbenzothiophen-5-yl) | 1.0 | 0.04 | — | 0.003 | 0.8 |

TABLE 1-continued

Beta-lactamase Inhibitory Activity of Sulfonamidomethylphosphonate Derivatives

HETAR-SO₂NHCH₂P(=O)(O⁻)-O-[3-F-4-CN-phenyl]   IC$_{50}$ (μM)

| Cmpd. | HETAR | Tem-1[a] | Amp C[b] | Amp C[c] | P-99[d] | Oxa-40[e] |
|---|---|---|---|---|---|---|
| 12 | H₃N⁺-CH₂CH₂-O-, H₃N⁺-CH₂CH₂-O- on benzothiophene, 2-methyl; CF₃CO₂⁻ | 1.9 | 0.06 | — | 0.003 | 0.5 |
| 13 | pyridinium-CH₂CH₂-O- on 4-Cl-2,3-dimethylbenzothiophene | 0.9 | 0.04 | — | 0.002 | 0.8 |
| 14 | H₃N⁺-CH₂CH₂-O-, H₃N⁺-CH₂CH₂-O- on 4,7-dichloro-2-methylbenzothiophene; CF₃CO₂⁻ | 0.6 | 0.01 | — | 0.0004 | 0.1 |
| 15 | H₃N⁺-CH₂CH₂-O- on 7-chloro-2,3-dimethylbenzothiophene | 2.9 | 0.01 | — | 0.001 | 2.6 |
| 16 | H₃N⁺-CH₂CH₂-O-, H₃N⁺-CH₂CH₂-O- on 4,7-difluoro-2-methylbenzothiophene; CF₃CO₂⁻ | 0.2 | 0.004 | 0.02 | 0.0003 | 0.3 |
| 17 | H₃N⁺-CH₂- on 5-methylthieno[3,2-b]thiophene | 0.9 | 0.03 | — | 0.002 | 0.4 |
| 18 | H₃N⁺-CH₂- on 5-methylthieno[2,3-b]thiophene | 1.5 | 0.06 | 0.4 | 0.005 | 0.6 |
| 19 | [H₃N(CH₂)₂]₂NH⁺-CH₂-C(=O)-NH- on 2-methylbenzothiophene; 2 CF₃CO₂⁻ | 1.0 | 0.02 | 0.02 | 0.002 | 1.1 |

TABLE 1-continued
Beta-lactamase Inhibitory Activity of Sulfonamidomethylphosphonate Derivatives
HETAR-SO$_2$NHCH$_2$P(=O)(O$^-$)-O-[3-F-4-CN-C$_6$H$_3$]
IC$_{50}$ (μM)
| Cmpd. | HETAR | Tem-1[a] | Amp C[b] | Amp C[c] | P-99[d] | Oxa-40[e] |
|---|---|---|---|---|---|---|
| 20 | 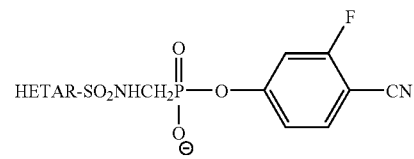 | 0.8 | 0.03 | 0.07 | 0.003 | 0.2 |
| 21 | 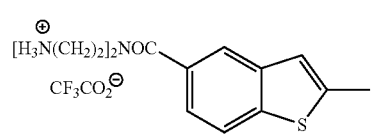 | 1.4 | 0.04 | 0.1 | 0.003 | 0.6 |
| 22 | 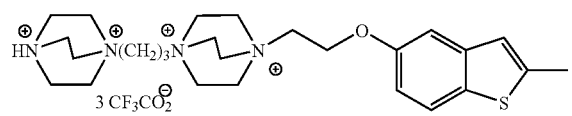 | 0.8 | 0.03 | 0.05 | 0.002 | 0.1 |
| 23 | 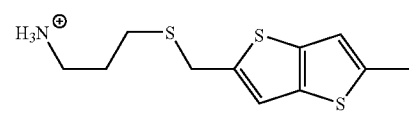 | 0.6 | 0.008 | 0.07 | 0.0004 | 0.6 |
| 24 | 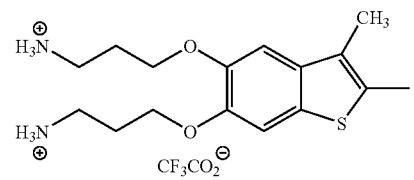 | 0.6 | 0.01 | 0.03 | 0.002 | 0.2 |
| 25 | 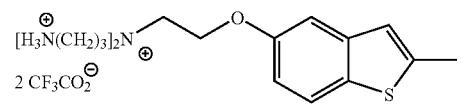 | 1.3 | 0.06 | 0.1 | 0.004 | 0.1 |
| 26 | 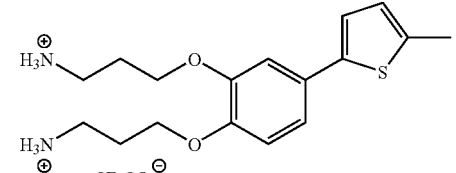 | 0.6 | 0.04 | 0.04 | 0.0007 | 0.2 |
| 27 | 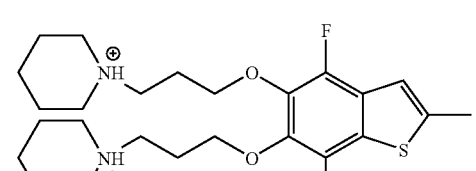 | 0.3 | 0.02 | 0.03 | 0.004 | 0.3 |

TABLE 1-continued

Beta-lactamase Inhibitory Activity of Sulfonamidomethylphosphonate Derivatives

HETAR-SO₂NHCH₂P(=O)(O⁻)—O—[3-F-4-CN-phenyl]

IC$_{50}$ (μM)

| Cmpd. | HETAR | Tem-1[a] | Amp C[b] | Amp C[c] | P-99[d] | Oxa-40[e] |
|---|---|---|---|---|---|---|
| 28 | (structure) | 0.3 | 0.003 | 0.02 | 0.0003 | 0.7 |
| 29 | (structure) | 2.3 | 0.02 | 0.1 | 0.004 | 0.7 |
| 30 | (structure) | 0.9 | 0.03 | 0.04 | 0.005 | 0.2 |
| 31 | (structure) | 0.6 | 0.007 | 0.08 | — | 1.0 |
| 32 | (structure) | 1.0 | 0.02 | 0.02 | 0.002 | 1.1 |
| 33 | (structure) | 0.7 | 0.02 | 0.09 | — | 1.6 |

[a] Class A beta-lactamase from *E. coli*
[b] Class C beta-lactamase from *Ps. aeruginosa*, CL 5701
[c] Class C beta-lactamase from *A. baumanii*, CLB 21648
[d] Class C beta-lactamase from *E. cloacae*, MB 2646
[e] Class D beta-lactamase from *A. baumanii*, CL 6188

Synergy Assay Protocol:

The assay determines the concentration of a β-lactamase inhibitor required to reduce the MIC of a β-lactam antibiotic by one-half, one-quarter, one-eighth, one-sixteenth and one-thirty-second against strains of bacteria normally resistant to the antibiotic in question. This is accomplished by titrating the inhibitor (BLI=beta-lactamase inhibitor) in a serial dilution across a microtiter plate while at the same time titrating the antibiotic (AB) in a serial dilution down the microtiter plate and then inoculating the plate with the bacterial strain in question and allowing the bacteria to grow up overnight. Each well in this microplate checkerboard contains a different combination of concentrations of the inhibitor and the antibiotic allowing a full determination of any synergy between the two.

Bacterial Strain/Antibiotic Combinations:

CL 5701 (*Pseudomonas aeruginosa*; Pa AmpC)/Imipenem
MB 2646 (*Enterobacter cloacae*; P99)/Ceftazidime
CL 5513 (*Klebsiella pneumoniae*; SHV-5)/Ceftazidime
CL 6188 (*Acinetobacter baumanii*; Oxa40)/Imipenem
CL 6569 (*Klebsiella pneumoniae*; KPC-2)/Imipenem
CL 5761 (*Klebsiella pneumoniae*; KPC-3)/Imipenem
CLB 21648 (*Acinetobacter baumanii*; Ab AmpC)/Imipenem General Checkerboard Method:
1. All wells in rows B-H of MIC 2000 microtiter plates are filled with 100 μL of MHBII+1% DMSO (dimethyl sulfoxide).
2. All wells in row A of MIC 2000 microtiter plates are filled with 100 μL of 2×MHBII+2% DMSO.
3. 100 μL of 4× the final antibiotic concentration wanted is added to well A1 of the MIC 2000 plates.
4. 100 μL of 2× the final antibiotic concentration wanted is added to wells A2-A12 of the MIC 2000 plates.
5. 100 μL is serially diluted from row A to row G of each MIC 2000 plate.
6. 100 μL is removed from each well in row G of each MIC 2000 plate.
7. 100 μL of 2× the final inhibitor concentration wanted (in MHBII+1% DMSO) is added to all wells in column 1 of the microtiter plates.
8. 100 μL is serially diluted from column 1 to column 11 of each MIC 2000 plate.
9. 100 μL is removed from each well in column 11 of each MIC 2000 plate.
10. Plates are then inoculated with an overnight growth (in TSB) of the strain to be tested using an MIC 2000 inoculator.
11. Plates are left at 37° C. for about 20 hours and scored for growth by eye.

Media (all are Sterilized by Autoclaving Prior to any Addition of DMSO):

MHBII+1% DMSO

| Mueller Hinton Broth type II cation adjusted (BBL ™) | 4.4 g |
| DMSO | 2.0 mL |
| Distilled water | 198.0 mL |

2×MHBII+2% DMSO

| Mueller Hinton Broth type II cation adjusted (BBL ™) | 8.8 g |
| DMSO | 4.0 mL |
| Distilled water | 196.0 mL |

1.02×MHBII

| Mueller Hinton Broth type II cation adjusted (BBL ™) | 4.4 g |
| Distilled water | 198.0 mL |

1.1×MHBII+1% DMSO

| Mueller Hinton Broth type II cation adjusted (BBL ™) | 4.4 g |
| DMSO | 2.0 mL |
| Distilled water | 178.0 mL |

TSB

Trypticase Soy Broth (BBL™) prepared as directed on bottle.

Antibiotic Preparation:

Imipenem stocks are prepared at about 1280 μg/ml in 10 mM MOPS pH 7.0
  They are stored at −80° C. in aliquots (the powder at −20° C.).
  The true concentration is determined with hydroxylamine.
  Dilutions are also prepared in 10 mM MOPS with a one day use.

Ceftazidime stocks are prepared at 10,240 μg/ml in Sorensen Buffer pH 7.0
  They are stored at −20° C.
  Dilutions are also prepared in Sorensen Buffer pH 7.0.

Sorensen Buffer
  1/15 M $Na_2HPO_4$ 61.1 mL
  1/15 M $KH_2PO_4$ 38.9 mL

Concentration of Antibiotics Used with Each Strain:

| Strain | Antibiotic | Final Top Concentration | 4X Concentration | 2X Concentration |
| --- | --- | --- | --- | --- |
| CL 5701 | Imipenem | 40 μg/ml | 160 μg/ml | 80 μg/ml |
| MB 2646 | Ceftazidime | 256 μg/ml | 1024 μg/ml | 512 μg/ml |
| CL 5513 | Ceftazidime | 256 μg/ml | 1024 μg/ml | 512 μg/ml |
| CL 6188 | Imipenem | 256 μg/ml | 1024 μg/ml | 512 μg/ml |
| CL 6569 | Imipenem | 256 μg/ml | 1024 μg/ml | 512 μg/ml |
| CL 5761 | Imipenem | 16 μg/ml | 64 μg/ml | 32 μg/ml |
| CLB 21648 | Imipenem | 32 μg/ml | 128 μg/ml | 64 μg/ml |

Inhibitor Preparation:

Test inhibitors are dissolved in 100% DMSO.
  They are diluted (1:100) into 1.02×MHBII for a final concentration of MHBII+1% DMSO.
  They are delivered usually either as 20 mM or 25.6 mg/ml in 100% DMSO and are tested at a final top concentration of either 100 μM or 128 μg/ml, but added to the plates as 2× these concentrations (i.e. 200 μM or 256 μg/ml) in MHBII+1% DMSO.

Sulbactam is tested as a control inhibitor.
  Stocks are prepared as 2560 μg/ml in sterile distilled water and stored at −20° C.
  It is diluted to the appropriate concentration for each strain in 1.1×MHBII+1% DMSO. This concentration is 2× the final top concentration at which it is tested.

| | Sulbactam Concentration | |
| --- | --- | --- |
| Strain | Final | 2X |
| CL 5701 | 128 μg/ml | 256 μg/ml |
| MB 2646 | 128 μg/ml | 256 μg/ml |
| CL 5513 | 128 μg/ml | 256 μg/ml |
| CL 6188 | 32 μg/ml | 64 μg/ml |
| CL 6569 | 128 μg/ml | 256 μg/ml |
| CL 5761 | 128 μg/ml | 256 μg/ml |
| CLB 21648 | 8 μg/ml | 16 μg/ml |

Inocula for BLI Checkerboards:
Brain Heart Infusion (BHI) Slants are good for 1 month at 4° C.
  A single colony from a fresh streak (from a frozen vial) onto a BHI plate is used to make the slants.
Strains are grown in 2 ml of TSB in a snap cap 14 ml tube for 18 hrs at 37° C. at 220 rpm.
After 18 hrs tubes are placed on ice until ready to use.
Inocula are based on absorbance of a 1:10 dilution in TSB.
  400 µL of overnight growth is added to 39.6 ml of 0.85% saline if the absorbance is as follows (using a Beckman DU-600) set at $\lambda$ 600:

| Strain | Expected Absorbance |
|---|---|
| CL 5701 | 0.66 |
| MB 2646 | 0.62 |
| CL 5513 | 0.66 |
| CL 6188 | 0.70 |
| CL 6569 | 0.66 |
| CL 5761 | 0.66 |
| CLB 21648 | 0.70 |

If absorbance is not close to the expected value than the following correction is made. All corrections are made at 100 µL increments. This is determined by multiplying the absorbance desired by 400 and dividing by the absorbance obtained and rounding to the closest 100 µL increment.
For Example:
if CL 6188 absorbance is 0.8023 then:

$$\frac{(0.7) \times (400)}{(0.8023)} = 340$$

Therefore, add 300 µL overnight culture to 39.7 ml of 0.85% saline
Reading of Plates:
Plates are scored for growth in each well. End points (MICs) where there is no growth in each row are determined and the concentrations of AB and the test BLI at each of these growth negative wells are then used to determine levels of synergy. Below is a checkerboard scoring/data grid. The final concentration of the antibiotic in each row is shown down the side of the checkerboard diagram and the final concentration of the inhibitor in each column is shown across the top of the checkerboard diagram.
Plate #1 CL5701 (*Pseudomonas*) MHBII+1% DMSO Imipenem vs. Test BLI β-Lactamase Inhibitor-Serum Reversal Slice (BLI-SRS) Assay Protocol:
This assay determines the effect of serum on the activity of a test β-lactamase inhibitor (BLI). Typical results are shown in Table 2. This is accomplished by measuring the concentration required to reduce the MIC of a β-lactam antibiotic to one quarter (4× synergy) against strains of bacteria normally resistant to the antibiotic in question, in the presence and absence of 50% mouse or human serum. The concentration of antibiotic used, one-quarter the MIC, is not antibacterial on its own and will only give an inhibition of bacterial growth if the BLI is synergistic. In essence, this concentration, ¼ the MIC or 4× synergy, is one row or one "slice" from a full checkerboard in which each well in the microplate checkerboard contains a different combination of concentrations of the inhibitor and the antibiotic allowing a full determination of any synergy between the two. This allows for a more rapid and sample-sparing alternative to a full checkerboard. The inhibitor is titrated in a serial dilution across a microtiter plate in the presence of (final) one-quarter of the MIC concentration of the antibiotic, preparing the plates in duplicate and adding an equal volume of serum to one plate for a final 50% concentration while adding water to the other, and then inoculating each plate with the bacterial strain in question and allowing the bacteria to grow up overnight. The 4× synergy concentration of the BLI on the plate containing no serum is compared to the 4× synergy concentration of the BLI on the plate containing serum to determine the fold reversal of synergy in the presence of serum.
Bacterial Strain/Antibiotic Combinations:
CL 5701 (*Pseudomonas aeruginosa*; Pa AmpC)/Imipenem
CL 6188 (*Acinetobacter baumanii*; Oxa40)/Imipenem
General "Slice" Method:
  1. All wells in column 1 of MIC 2000 microtiter plates are filled with 50 µL of MIC concentration of antibiotic in 2×MHBII containing no DMSO.
  2. All wells in columns 2 to 12 of MIC 2000 microtiter plates are filled with 50 µL of one-half MIC concentration of antibiotic in 2×MHBII+2% DMSO.
  3. 50 µL of 2× the final concentration of BLI is added to one well in column one of each of the duplicate plates, same row, for example, well C1.
  4. 50 µL is serially diluted from column 1 to column 11 of each MIC 2000 plate.
  5. 50 µL is removed from each well in column 11 of each MIC 2000 plate.
  6. 50 µL of sterile distilled water is added to all wells in the no serum (control) plate.

| | Test BLI | 1 | 2 | 3 | 4 | 5 | 6 | 7 | 8 | 9 | 10 | 11 | 12 |
|---|---|---|---|---|---|---|---|---|---|---|---|---|---|
| Imipenem | Conc (per ml) | 100 µM | 50 | 25 | 12.5 | 6.25 | 3.125 | 1.563 | 0.782 | 0.391 | 0.196 | 0.098 | 0 |
| A | 40 µg | | | | | | | | | | | | |
| B | 20 | | | | | | | | | | | | |
| C | 10 | | | | | | | | | | | | |
| D | 5 | | | | | | | | | | | | |
| E | 2.5 | | | | | | | | | | | | |
| F | 1.25 | | | | | | | | | | | | |
| G | 0.625 | | | | | | | | | | | | |
| H | 0 | | | | | | | | | | | | GC |

7. 50 μL of sterile prepared mouse or human serum is added to all wells in the plus serum plate.

8. Plates are then inoculated with an overnight growth (in TSB) of the strain to be tested using an MIC 2000 inoculator.

9. Plates are left at 37° C. for exactly 18 hours and scored for growth by eye.

10. Results are reported as the concentration of BLI able to give 4× synergy (the lowest concentration of BLI that gives no growth in the well), both with and without serum, and the fold differential between these two numbers (fold serum reversal).

TABLE 2

Synergy of Imipenem by Sulfonamidomethylphosphonate Derivatives Against *Ps. aeruginosa*, CL 5701, and the Effect of Serum on the Synergy

HETAR-SO$_2$NHCH$_2$P(=O)(O$^-$)-O-C$_6$H$_3$(F)-CN

Serum Added

| Cmpd. | HETAR | Conc. (μM) to achieve 4X synergy$^a$ | Mouse | Human |
|---|---|---|---|---|
| 1* | 4,7-dichloro-2-methylbenzothiophene | 12.5 | 64 | >64 |
| 2* | 4,7-dichloro-5,6-dihydroxy-2-methylbenzothiophene | 1.56 | >512 | >512 |
| 3 | 4,7-dichloro-5,6-bis(2-aminoethoxy)-2-methylbenzothiophene bis(trifluoroacetate) | 1.56 | 25 | 12.5 |
| 4* | 7-chloro-2,3-dimethylbenzothiophene | 25 | >200 | >200 |
| 5* | 7-chloro-3-ethyl-2-methylbenzothiophene | 25 | >200 | >200 |

TABLE 2-continued

Synergy of Imipenem by Sulfonamidomethylphosphonate
Derivatives Against *Ps. aeruginosa*, CL 5701,
and the Effect of Serum on the Synergy HETAR-SO₂NHCH₂P(=O)(O⁻)-O-[3-fluoro-4-cyanophenyl]

Serum Added

| Cmpd. | HETAR | Conc. (μM) to achieve 4X synergy[a] | Mouse | Human |
|---|---|---|---|---|
| 6 | [structure: 3-methyl-2-methyl-7-chloro-5-(2-aminoethoxy)benzothiophene] | 6.25 | 12.5 | — |
| 7* | [structure: 4,7-difluoro-2-methylbenzothiophene] | 25 | >200 | >200 |
| 8* | [structure: 4,7-difluoro-5,6-dimethoxy-2-methylbenzothiophene] | 25 | 200 | — |
| 9 | [structure: 4,7-difluoro-5,6-bis(3-aminopropoxy)-2-methylbenzothiophene, CF₃CO₂⁻] | 1.56 | 12.5 | — |
| 10* | [structure: 5,6-bis(2-chloroethoxy)-2-methylbenzothiophene] | 100 | >200 | >200 |
| 11 | [structure: 5,6-bis(2-aminoethoxy)-2-methylbenzothiophene, CF₃CO₂⁻] | 1.56 | 3.13 | 3.13 |
| 12* | [structure: 2-(3,4-dihydroxyphenyl)-5-methylthiazole] | 1.56 | 50 | 200 |

TABLE 2-continued

Synergy of Imipenem by Sulfonamidomethylphosphonate
Derivatives Against *Ps. aeruginosa*, CL 5701,
and the Effect of Serum on the Synergy HETAR-SO$_2$NHCH$_2$P(=O)(O$^-$)-O-[3-fluoro-4-cyanophenyl]

| Cmpd. | HETAR | Conc. (μM) to achieve 4X synergy[a] | Serum Added Mouse | Human |
|---|---|---|---|---|
| 13* | 3,4-dihydroxyphenyl-(5-methylthiophen-2-yl) | 1.56 | 100 | — |
| 14* | 2,3-dihydroxyphenyl-(5-methylthiophen-2-yl) | 12.5 | >200 | — |
| 15 | bis(3-aminopropoxy)phenyl-(5-methylthiophen-2-yl) · CF$_3$CO$_2^-$ | 12.5 | 50 | — |
| 16 | (aminomethyl)-methyl-thienothiophene | 3.13 | 12.5 | — |
| 17 | bis(3-aminopropoxy)-2-methylbenzothiazole · CF$_3$CO$_2^-$ | 12.5 | 25 | — |
| 18 | pyridinium-ethoxy-2-methylbenzothiophene | 12.5 | 25 | 25 |
| 19 | aminopiperazinyl-propoxy-2-methylbenzothiophene · CF$_3$CO$_2^-$ | 50 | 200 | — |

TABLE 2-continued
Synergy of Imipenem by Sulfonamidomethylphosphonate
Derivatives Against *Ps. aeruginosa*, CL 5701,
and the Effect of Serum on the Synergy
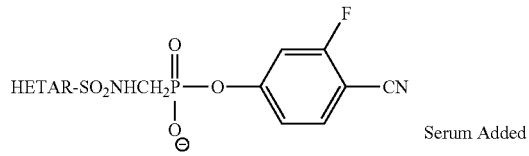
Serum Added
| Cmpd. | HETAR | Conc. (μM) to achieve 4X synergy[a] | Mouse | Human |
|---|---|---|---|---|
| 20 | | 25 | 50 | — |
| 21 | | 50 | 200 | 100 |
| 22 | | 25 | 50 | 50 |
| 23 | | 6.25 | 6.25 | — |
| 24 | | 12.5 | 6.25 | — |
| 25 | | 12.5 | 6.25 | — |
| 26 | | 25 | 12.5 | — |
| 27 | | 6.25 | 25 | — |

TABLE 2-continued

Synergy of Imipenem by Sulfonamidomethylphosphonate Derivatives Against *Ps. aeruginosa*, CL 5701, and the Effect of Serum on the Synergy HETAR-SO$_2$NHCH$_2$P(=O)(O$^-$)-O-[phenyl with F and CN]

Serum Added

| Cmpd. | HETAR | Conc. (µM) to achieve 4X synergy[a] | Mouse | Human |
|---|---|---|---|---|
| 28 | 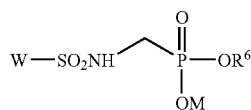 | 3.13 | 12.5 | — |
| 29 | 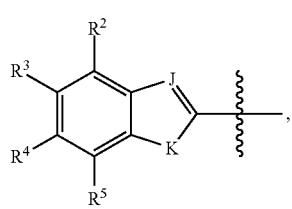 | 3.13 | 25 | — |

*Comparative compounds in U.S. Pat. No. 6,884,791, Apr. 26, 2005, and cross references therein.
[a]Imipenem MIC = 20 µg/mL.

What is claimed is:

1. A compound of Formula I:

Formula I

W—SO$_2$NH—CH$_2$—P(=O)(OM)—OR$^6$ or a pharmaceutically acceptable salt thereof, wherein:
W represents:

[structure with R$^2$, R$^3$, R$^4$, R$^5$, J, K fused bicyclic], wherein
R$^3$ independently represents fluorine, cyano, —O-ethyl, —O-propyl, —O-isopropyl, —O-butyl, —O-tert-butyl, —O-isobutyl, —O-pentyl, —O-hexyl, C$_{1-6}$alkyl, —X$_m$—Y$_m$—Z*$_m$—R$^8$ or —X$_m$—Y$_m$—Z*$_m$-Q$^+$; R$^4$ independently represents hydrogen, halogen, cyano, —OR$^1$, C$_{1-6}$ alkyl, —X$_m$—Y$_m$—Z*$_m$—R$^8$, or —X$_m$—Y$_m$—Z*$_m$-Q$^+$; and R$^8$ represents hydrogen, halo, N(R$^c$)$_2$, —C(O)R$^5$, NR$^c$C(NH)NH$_2$, NR$^c$C(NH)H, (CH$_2$)$_n$C$_{5-10}$heterocyclyl, or (CH$_2$)$_n$C$_{5-10}$ aryl, said heterocyclyl and aryl optionally substituted;

or
R$^3$ independently represents hydrogen, halogen, cyano, —OR$^1$, C$_{1-6}$ alkyl, —X$_m$—Y$_m$—Z*$_m$—R$^8$, or —X$_m$—Y$_m$—Z*$_m$-Q$^+$; R$^4$ independently represents fluorine, cyano, —O-propyl, —O-isopropyl, —O-butyl, —O-tert-butyl, —O-isobutyl, —O-pentyl, —O-hexyl, C$_{1-6}$alkyl, —X$_m$—Y$_m$—Z*$_m$—R$^8$ or —X$_m$—Y$_m$—Z*$_m$-Q$^+$; and R$^8$ represents, halo, N(R$^c$)$_2$, —C(O)R$^5$, NR$^c$C(NH)NH$_2$, NR$^c$C(NH)H, (CH$_2$)$_n$C$_{5-10}$ heterocyclyl, or (CH$_2$)$_n$C$_{5-10}$ aryl, said heterocyclyl and aryl optionally substituted;

or W represents

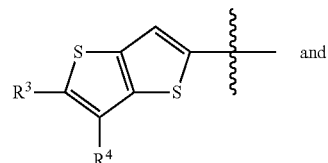 and

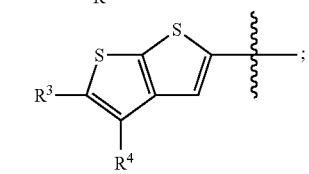;

wherein
R$^3$ and R$^4$ independently represent hydrogen, halogen, cyano, —OR$^1$, C$_{1-6}$ alkyl, —X$_m$—Y$_m$—Z*$_m$—R$^8$, or —X$_m$—Y$_m$—Z*$_m$-Q$^+$; and R$^8$ represents hydrogen, halo, N(R$^c$)$_2$, —C(O)R$^5$, NR$^c$C(NH)NH$_2$, NR$^c$C(NH)H, (CH$_2$)$_n$C$_{5-10}$ heterocyclyl, or (CH$_2$)$_n$C$_{5-10}$ aryl, said heterocyclyl and aryl optionally substituted;

or W represents

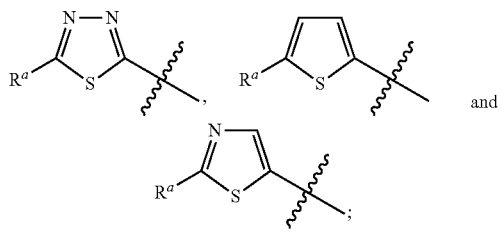

, and

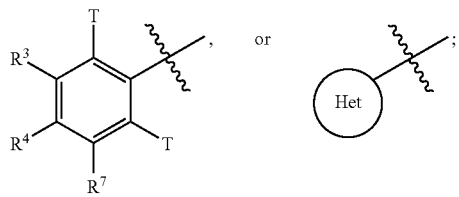

;

$R^a$ represents: $(CH_2)_n R^{aa}$;
$R^{aa}$ represents:

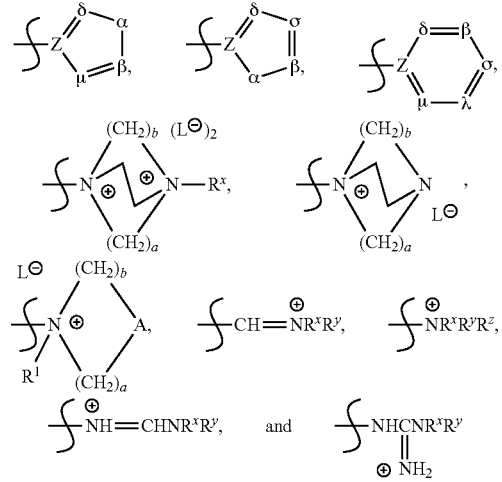

wherein
$R^3$ in $R^{aa}$ independently represents halogen, cyano, —$OR^1$, $C_{1-6}$ alkyl, —$X_m$—$Y_m$—$Z^*_m$—$R^8$, or —$X_m$—$Y_m$—$Z^*_m$-$Q^+$; $R^4$ in Raa independently represents hydrogen, halogen, cyano, —$OR^1$, $C_{1-6}$ alkyl, —$X_m$—$Y_m$—$Z^*_m$—$R^8$, or —$X_m$—$Y_m$—$Z^*_m$-$Q^+$;
$R^7$-independently represents hydrogen, halogen, cyano, —$OR^1$, $C_{1-6}$ alkyl, —$X_m$—$Y_m$—$Z^*_m$—$R^8$, or —$X_m$—$Y_m$—$Z^*_m$-$Q^+$; and $R^8$ represents hydrogen, halo, $N(R^c)_2$, —$C(O)R^5$, $NR^cC(NH)NH_2$, $NR^cC(NH)H$, $(CH_2)_nC_{5-10}$ heterocyclyl, or $(CH_2)_nC_{5-10}$ aryl, said heterocyclyl and aryl optionally substituted; or
$R^3$ in $R^{aa}$ independently represents hydrogen, halogen, cyano, —$OR^1$, $C_{1-6}$ alkyl, —$X_m$—$Y_m$—$Z^*_m$—$R^8$, or —$X_m$—$Y_m$—$Z^*_m$-$Q^+$; $R^4$ in Raa independently represents halogen, cyano, —O-ethyl, —O-propyl, —O-isopropyl, —O-butyl, —O-tert-butyl, —O-isobutyl, —O-pentyl, —O-hexyl, $C_{1-6}$ alkyl, —$X_m$—$Y_m$—$Z^*_m$—$R^8$, or —$X_m$—$Y_m$—$Z^*_m$-$Q^+$;
$R^7$ independently represents hydrogen, halogen, cyano, —$OR^1$, $C_{1-6}$ alkyl, —$X_m$—$Y_m$—$Z^*_m$—$R^8$, or —$X_m$—$Y_m$—$Z^*_m$-$Q^+$; and $R^8$ represents halo, $N(R^c)_2$, —$C(O)R^5$, $NR^cC(NH)NH_2$, $NR^cC(NH)H$, or $(CH_2)_nC_{5-10}$ heterocyclyl, said heterocyclyl optionally substituted;
provided at least one of $R^3$, $R^4$, and $R^7$ is —$X_m$—$Y_m$—$Z^*_m$Q+;
J represents N or $CR^1$;
K represents O, S, or $NR^1$;
Het represents a 5-6 membered nitrogen containing heterocycle substituted with 0 to 4 groups of $R^2$;
T represents hydrogen, halogen, $OR^1$, or $C_{1-6}$ alkyl;
$R^1$ independently represents hydrogen, or $C_{1-6}$ alkyl;
M is a negative charge, H, or a pharmaceutically acceptable metal or ammonium salt, and provided that when W contains a moiety with multiple positive charges, there is an appropriate number of $L^\ominus$ present to provide overall neutrality;
$R^2$ and $R^5$ independently represent hydrogen, halogen, cyano, —$OR^1$, or $C_{1-6}$ alkyl;

X and Y independently are O, $NR^x$, (C=O), $SO_2$, $(CH_2)_n$, —$(CH_2)_n NR^1C(O)$—, —$(CH_2)_n S$—, or —$(CH_2)_n N(R^x)_2$—;
Z* is $(CH_2)_n$ which may be substituted with one to four $R^b$;
$R^6$ represents $C_{6-10}$ aryl, or $C_{5-10}$ heteroaryl, said aryl and heteroaryl optionally substituted;
Q is selected from the group consisting of:

wherein Z represents $N^+$ or carbon; and A is O, $CH_2$, $S(O)_{0-2}$, $NR^x$, or $N^+(R^x)_2$;
+ represents a positive charged ion;
$L^\ominus$ represents a pharmaceutically acceptable counterion that is present as needed to provide charge balance on the molecule;
a and b are 1, 2 or 3;
α represents O, S or $NR^s$;
β, δ, λ, μ and σ represent $CR^t$, N or $N^\ominus R^s$, provided that no more than one of β, δ, λ, μ and σ is $N^\ominus R^s$;
each $R^b$ independently represents halo; —CN; —$NO_2$; phenyl; —$NHSO_2R^c$; —$OR^c$, —$SR^c$; —$N(R^c)_2$; —$N^+(R^c)_3$; —$C(O)N(R^c)_2$; —$SO_2N(R^c)_2$; heteroaryl; heteroarylium; formamidinyl, —$CO_2R^c$; —$C(O)R^c$; —$OC(O)R^c$; —$NHC(O)R^c$; —$NHC(O)_2R^c$; guanidinyl; carbamimidoyl or ureido, said phenyl and heteroaryl optionally substituted;
each $R^c$ independently represents hydrogen, a —$C_{1-6}$ straight or branched-chain alkyl group, a —$C_3$-$C_6$ cycloalkyl group or $C_{6-10}$ aryl, said aryl optionally substituted with one to four groups of halogen; —CN; —$NO_2$; phenyl; —$NHSO_2R^j$; —$OR^1$, —$SR^j$; —$N(R^j)_2$; —$N^+(R^j)_3$; —$C(O)N(R^j)_2$; —$SO_2N(R^j)_2$; heteroaryl; heteroarylium; formamidinyl; —$CO_2R^j$; —$C(O)R^j$; —$OC(O)R^j$; —$NHC(O)R^j$; —$NHC(O)_2R^j$; guanidinyl; carbamimidoyl or ureido, said phenyl and heteroaryl optionally substituted, wherein Rj is selected from the group consisting of hydrogen, a —$C_{1-6}$ straight or branched-chain alkyl group, a —$C_3$-$C_6$ cycloalkyl group or $C_{6-10}$ aryl;
each $R^s$ independently represents hydrogen; phenyl or —$C_{1-6}$ straight- or branched-chain alkyl, unsubstituted or substituted with one to four $R^b$ groups;
each $R^t$ independently represents hydrogen; halo; phenyl; —CN; —$NO_2$; —$NR^uR^v$; —$OR^u$; —$SR^u$; —$C(O)NR^uR^v$; —$COOR^c$; —$SOR^u$; —$SO_2R^u$; —$SO_2NR^uR^v$; —$NR^uSO_2R^v$; —$C(O)R^u$; —$NR^uC(O)R^v$; —$OC(O)R^u$; —$OC(O)NR^uR^v$; —$NR^uCO_2R^v$; —$NR^uC(O)NR^vR^w$;

—OCO₂Rᵛ; —C$_{1-6}$ straight- or branched-chain alkyl, unsubstituted or substituted with one to four R$^b$ groups;

R$^u$ and R$^v$ represent hydrogen or —C$_{1-6}$ straight- or branched-chain alkyl, unsubstituted or substituted with one to four R$^b$ groups;

each R$^w$ independently represents hydrogen; —C$_{1-6}$ straight- or branched-chain alkyl, unsubstituted or substituted with one to four R$^b$ groups; C$_{3-6}$ cycloalkyl optionally substituted with one to four R$^b$ groups; phenyl optionally substituted with one to four R$^b$ groups, or heteroaryl optionally substituted with one to four R$^b$ groups;

R$^x$ represents hydrogen or a C$_{1-8}$ straight- or branched-alkyl chain, optionally interrupted by one or two of O, S, SO, SO₂, NR$^w$, N$^+$R$^c$R$^w$, or —C(O)—, said alkyl chain being unsubstituted or substituted with one to four of halo, CN, NO₂, —N₃, OR$^w$, SR$^w$, SOR$^w$, SO₂R$^w$, NR$^c$R$^w$, N$^+$(R$^c$)₂R$^w$, Q, —C(O)—R$^w$, C(O)NR$^c$R$^w$, SO₂NR$^c$R$^w$, CO₂R$^w$, OC(O)R$^w$, OC(O)NR$^c$R$^w$, NR$^c$C(O)R$^w$, NR$^c$C(NH)NH₂, NR$^c$C(NH)H, NR$^c$C(O)NR$^c$R$^w$, phenyl, naphthyl, heteroaryl, or heterocyclic group said phenyl, heteroaryl, and heterocyclic group optionally substituted with from one to four R$^b$ groups or with one to two C$_{1-3}$ straight- or branched-chain alkyl groups, said alkyl groups being unsubstituted or substituted with one to four R$^b$ groups;

R$^y$ and R$^z$ represent hydrogen; phenyl; —C$_{1-6}$ straight or branched chain alkyl, unsubstituted or substituted with one to four R$^b$ groups, and optionally interrupted by O, S, N$^w$, N$^+$R$^c$R$^w$ or —C(O)—; and m represents 0 to 1; n represents 0 to 6; wherein it is understood that when a value is zero, a bond exists.

2. The compound according to claim 1 wherein one of R$^3$ and R$^4$ is —X$_m$—Y$_m$—Z*$_m$-Q$^+$ and the other is —X$_m$—Y$_m$—Z*$_m$—R$^8$.

3. The compound according to claim 1 wherein X is O; and Y is (CH₂)$_n$NR$^1$CO—, a bond, —(CH₂)$_n$S—, or (CH₂)$_n$N(R$^x$)₂.

4. A compound which is:

4-cyano-3-fluorophenyl-[({[5-(2-pyridiniumethoxy)-1-benzothien-2-yl]sulfonyl}amino)methyl]-phosphonate;

4-cyano-3-fluorophenyl-[({[6-(2-pyridiniumethoxy)-4,5,7-trifluoro-1-benzothien-2-yl]-sulfonyl}amino)methyl]phosphonate;

4-cyano-3-fluorophenyl-[({[6-(2-pyridiniumethoxy)-4-fluoro-1-benzothien-2-yl]-sulfonyl}amino)methyl]phosphonate;

4-cyano-3-fluorophenyl-[({[6-(4-pyridiniumbutoxy)-4-fluoro-1-benzothien-2-yl]-sulfonyl}amino)methyl]phosphonate;

4-cyano-3-fluorophenyl[({[5-(2-pyridinium-1-ylethoxy)-1-benzothien-2-yl]-sulfonyl}amino)methyl]phosphonate;

4-cyano-3-fluorophenyl-[({[4-chloro-3-methyl-5-(2-pyridinium-1-ylethoxy)-1-benzothien-2-yl]sulfonyl}amino)methyl]phosphonate;

4-cyano-3-fluorophenyl-[({[7-chloro-3-methyl-5-(2-pyridinium-1-ylethoxy)-1-benzothien-2-yl]-sulfonyl}amino)methyl]phosphonate;

4-cyano-3-fluorophenyl-{[({5-[4-(2-pyridinium-1-ylethoxy)phenyl]-1,3,4-thiadiazol-2-yl}-sulfonyl)amino]methyl}phosphonate;

4-cyano-3-fluorophenyl-{[({5-[4-(3-pyridinium-1-ylpropoxy)phenyl]-1,3,4-thiadiazol-2-yl}sulfonyl)amino]methyl}phosphonate;

4-cyano-3-fluorophenyl-[({[5-(2-pyridinium-1-ylethoxy)-6-(2-chloroethoxy)-1-benzothien-2-yl]-sulfonyl}amino)methyl]phosphonate;

4-cyano-3-fluorophenyl-[({[6-(2-pyridinium-1-ylethoxy)-5-(2-chloroethoxy)-1-benzothien-2-yl]-sulfonyl}amino)methyl]phosphonate;

4-cyano-3-(trifluoromethyl)phenyl[({[5-(2-pyridinium-1-ylethoxy)-1-benzothien-2-yl]sulfonyl}amino)methyl]phosphonate;

4-cyano-3-(trifluoromethyl)phenyl-[({[5-(2-pyridinium-1-ylethoxy)-1-benzothien-2-yl]-sulfonyl}amino)methyl]phosphonate;

4-cyano-3-(trifluoromethyl)phenyl-[({[6-(4-pyridinium-1-ylbutoxy)-1-benzothien-2-yl]-sulfonyl}amino)methyl]phosphonate;

4-cyano-3-(trifluoromethyl)phenyl-[({[6-(5-pyridinium-1-ylpentoxy)-1-benzothien-2-yl]-sulfonyl}amino)methyl]phosphonate;

4-cyano-3-(trifluoromethyl)phenyl-[({[6-(2-pyridinium-1-ylethoxy)-1-benzothien-2-yl]sulfonyl}-amino)methyl]phosphonate;

4-cyano-3-(trifluoromethyl)phenyl-[({[6-(6-pyridinium-1-ylhexoxy)-1-benzothien-2-yl]-sulfonyl}amino)methyl]phosphonate;

4-cyano-3-(trifluoromethyl)phenyl-[({[4-chloro-3-methyl-5-(2-pyridinium-1-ylethoxy)-1-benzothien-2-yl]sulfonyl}amino)methyl]phosphonate;

4-cyano-3-(trifluoromethyl)phenyl-[({[4,5,7-trifluoro-6-(2-pyridinium-1-ylethoxy)-1-benzothien-2-yl]sulfonyl}amino)methyl]phosphonate;

4-cyano-3-(trifluoromethyl)phenyl-[({[7-chloro-3-methyl-5-(2-pyridinium-1-ylethoxy)-1-benzothien-2-yl]sulfonyl}amino)methyl]phosphonate;

4-cyano-3-(trifluoromethyl)phenyl-{[({5-[4-(2-pyridinium-1-ylethoxy)phenyl]-1,3,4-thiadiazol-2-yl}sulfonyl)amino]methyl}phosphonate;

Ammonium 4-cyano-3-fluorophenyl[({[5-(morpholin-4-yl-methyl)-1-benzothien-2-yl]sulfonyl}amino)methyl]phosphonate;

4-Cyano-3-fluorophenyl-({[(4,7-dichloro-5-{[(3-(pyridinium-1-ylpropyl)thio]methyl}-1-benzothien-2-yl)sulfonyl]amino}methyl)phosphonate;

4-cyano-3-(trifluoromethyl)phenyl-({[(4,7-dichloro-5-{[(3-(pyridinium-1-ylpropyl)thio]methyl}-1-benzothien-2-yl)sulfonyl]amino}methyl)phosphonate;

4-cyano-3-fluorophenyl hydrogen[({[5-(aminomethyl)-thieno[3,2-b]thien-2-yl]sulfonyl}amino)methyl]phosphonate; 4-cyano-3-fluorophenyl-({[(5-{[(3-aminopropyl)thio]methyl}thieno[3,2-b]thien-2-yl)sulfonyl]amino}methyl)phosphonate;

Ammonium-4-cyano-3-fluorophenyl-[({[5-(aminomethyl)thieno[2,3-b]thien-2-yl)sulfonyl}-amino)methyl]phosphonate;

4-cyano-3-fluorophenyl[({[5,6-bis(2-ammonioethoxy)-1-benzothien-2-yl]sulfonyl}amino)methyl]phosphonate;

4-cyano-3-(trifluoromethyl)phenyl[({[5,6-bis(2-ammonioethoxy)-1-benzothien-2-yl]-sulfonyl}amino)methyl]phosphonate;

3-fluoro-4-[(trifluoromethyl)sulfonyl]phenyl-[({[5,6-bis(2-ammonioethoxy)-1-benzothien-2-yl]-sulfonyl}amino)methyl]phosphonate;

6-cyanopyridin-2-yl-[({[5,6-bis(2-ammonioethoxy)-1-benzothien-2-yl]sulfonyl}amino)-methyl]-phosphonate;

4-cyano-3-fluorophenyl[({[5,6-bis(3-ammoniopropoxy)-1-benzothien-2-yl]sulfonyl}amino)-methyl]phosphonate;

4-cyano-3-fluorophenyl[({[5,6-bis(4-ammoniobutoxy)-1-benzothien-2-yl]sulfonyl}amino)-methyl]phosphonate;

4-cyano-3-(trifluoromethyl)phenyl[({[5,6-bis(3-ammoniopropoxy)-1-benzothien-2-yl]sulfonyl}-amino)methyl]phosphonate;

4-cyano-3-fluorophenyl[({[5,6-bis(2-ammonioethoxy)-4,7-dichloro-1-benzothien-2-yl]sulfonyl}-amino)methyl]phosphonate;

4-cyano-3-(trifluoromethyl)phenyl[({[5,6-bis(2-ammonioethoxy)-4,7-dichloro-1-benzothien-2-yl]sulfonyl}amino)methyl]phosphonate;

3-fluoro-4-[(trifluoromethyl)sulfonyl]phenyl-[({[5,6-bis(2-ammonioethoxy)-4,7-dichloro-1-benzothien-2-yl]sulfonyl}amino)methyl]phosphonate;

4-cyano-3-fluorophenyl[({[5,6-bis(2-ammonioethoxy)-4,7-difluoro-1-benzothien-2-yl]sulfonyl}-amino)methyl]phosphonate;

4-cyano-3-(trifluoromethyl)phenyl[({[5,6-bis(2-ammonioethoxy)-4,7-difluoro-1-benzothien-2-yl]sulfonyl}amino)methyl]phosphonate;

4-cyano-3-(trifluoromethyl)phenyl[({[5,6-bis(3-ammoniopropoxy)-4,7-difluoro-1-benzothien-2-yl]sulfonyl}amino)methyl]phosphonate;

4-cyano-3-fluorophenyl[({[5,6-bis(3-ammoniopropoxy)-3-methyl-1-benzothien-2-yl]-sulfonyl}amino)methyl]phosphonate;

4-cyano-3-fluorophenyl[({[5,6-bis(3-ammoniopropoxy)-4,7-difluoro-3-methyl-1-benzothien-2-yl]sulfonyl}amino)methyl]phosphonate;

4-cyano-3-fluorophenyl-[({[5-(2-ammonioethoxy)-1-benzothien-2-yl]sulfonyl}amino)methyl]-phosphonate;

4-cyano-3-(trifluoromethyl)phenyl-[({[5-(2-ammonioethoxy)-1-benzothien-2-yl]sulfonyl}amino) methyl]phosphonate;

6-cyanopyridin-3-yl-[({[5-(2-ammonioethoxy)-1-benzothien-2-yl]sulfonyl}amino)methyl]phosphonate;

6-methylsulfonylpyridin-3-yl-[({[5-(2-ammonioethoxy)-1-benzothien-2-yl]sulfonyl}amino) methyl]phosphonate;

4-cyano-3-fluorophenyl-[({[5-(2-ammonioethoxy)-4-chloro-1-benzothien-2-yl]sulfonyl}amino) methyl] phosphonate;

4-cyano-3-fluorophenyl-[({[5-(2-ammonioethoxy)-7-chloro-1-benzothien-2-yl]sulfonyl}amino) methyl] phoshonate;

4-cyano-3-(trifluoromethyl)phenyl-[({[5-(2-ammonioethoxy)-7-chloro-1-benzothien-2-yl]-sulfonyl}amino) methyl]phoshonate;

3-fluoro-4-[(trifluoromethyl)sulfonyl]phenyl-[({[5-(ammonioethoxy)-7-chloro-1-benzothien-2-yl] sulfonyl}amino)methyl]phosphonate;

4-cyano-3-fluorophenyl-[({[5-(2-ammonioethoxy)-4-chloro-3-methyl-1-benzothien-2-yl]sulfonyl}amino) methyl]phosphonate;

4-cyano-3-(trifluoromethyl)phenyl-[({[5-(2-ammonioethoxy)-4-chloro-3-methyl-1-benzothien-2-yl] sulfonyl}amino)methyl]phosphonate;

4-cyano-3-fluorophenyl-[({[5-(ammonioethoxy)-7-fluoro-3-methyl-1-benzothien-2-yl]sulfonyl}-amino) methyl]phosphonate;

3-fluoro-4-[(trifluoromethyl)phenyl-[({[5-(ammonioethoxy)-7-fluoro-3-methyl-1-benzothien-2-yl] sulfonyl}amino)methyl]phosphonate;

3-fluoro-4-[(trifluoromethyl)sulfonyl]phenyl-[({[5-(ammonioethoxy)-7-fluoro-3-methyl-1-benzothien-2-yl] sulfonyl}amino)methyl]phosphonate;

4-cyano-3-[(trifluoromethyl)sulfonyl]-phenyl-[({[5-(2-ammonioethoxy)-4-chloro-3-methyl-1-benzothien-2-yl] sulfonyl}amino)methyl]phosphonate;

4-cyano-3-fluorophenyl-[({[5-(2-ammonioethoxy)-7-chloro-3-methyl-1-benzothien-2-yl]sulfonyl}amino) methyl]phosphonate;

4-cyano-3-(trifluoromethyl)phenyl-[({[5-(2-ammonioethoxy)-7-chloro-3-methyl-1-benzothien-2-yl] sulfonyl}amino)methyl]phosphonate;

4-cyano-3-fluorophenyl-[({[6-(2-ammonioethoxy)-4,5,7-trifluoro-1-benzothien-2-yl]sulfonyl}-amino)methyl] phosphonate;

4-cyano-3-fluorophenyl-{[({5-[4-(2-ammonioethoxy) phenyl]-1,3,4-thiadiazol-2-yl}sulfonyl)-amino] methyl}phosphonate;

4-cyano-3-fluorophenyl-{[({5-[3,4-bis(3-ammoniopropoxy)phenyl]thiophen-2-yl}sulfonyl)-amino] methyl}phosphonate;

4-cyano-3-fluorophenyl-{[({5-[3,4-bis(3-ammoniopropoxy)-2-methylphenyl]thiophen-2-yl}sulfonyl)amino] methyl}phosphonate;

4-cyano-3-fluorophenyl-{[({5-[4,5-bis(3-ammoniopropoxy)-2-methylphenyl]thiophen-2-yl}-sulfonyl)amino] methyl}phosphonate;

4-cyano-3-fluorophenyl-[({[6-(2-ammonioethoxy)-5-(2-{[2,3-bis(benzyloxy)benzoyl]amino}-ethoxy-1-benzothien-2-yl)-sulfonyl]amino}methyl)phosphonate;

4-cyano-3-fluorophenyl-[({[5-(2-ammonioethoxy)-6-(2-{[2,3-bis(benzyloxy)benzoyl]amino}-ethoxy)-1-benzothien-2-yl)-sulfonyl]amino}methyl)phosphonate;

4-cyano-3-(trifluoromethyl)phenyl-[({[6-(2-ammonioethoxy)-5-(2-{[3,4-bis(benzyloxy)benzoyl]-amino}ethoxy)-1-benzothien-2-yl]sulfonyl}amino)methyl]phosphonate;

4-cyano-3-(trifluoromethyl)phenyl-[({[5-(2-ammonioethoxy)-6-(2-{[3,4-bis(benzyloxy)benzoyl]-amino}ethoxy)-1-benzothien-2-yl]sulfonyl}amino)methyl]phosphonate;

4-cyano-3-fluorophenyl({[(6-(2-ammonioethoxy)-5-{2-[(2,3-dihydroxybenzoyl)amino]ethoxy}-1-benzothien-2-yl]sulfonyl}amino)methyl]phosphonate;

4-cyano-3-fluorophenyl({[(5-(2-ammonioethoxy)-6-{2-[(2,3-dihydroxybenzoyl)amino]ethoxy}-1-benzothien-2-yl]sulfonyl}amino)methyl]phosphonate;

4-cyano-3-(trifluoromethyl)phenyl-({[(6-(2-ammonioethoxy)-5-{2-[(3,4-dihydroxybenzoyl)-amino]ethoxy}-1-benzothien-2-yl)sulfonyl]amino}methyl)phosphonate;

4-cyano-3-(trifluoromethyl)phenyl-({[(5-(2-ammonioethoxy)-6-{2-[(3,4-dihydroxybenzoyl)amino]ethoxy}-1-benzothien-2-yl)sulfonyl]amino}methyl)phosphonate;

4-cyano-3-fluorophenyl {[({5-[2-dimethylammonioethoxy]-1-benzothien-2-yl}sulfonyl)amino] methyl}phosphonate;

4-cyano-3-(trifluoromethyl)phenyl-({[(5-{2-[(iminiomethyl)amino]ethoxy}-1-benzothien-2-yl)sulfonyl]-amino}methyl)phosphonate;

4-cyano-3-fluorophenyl[({[5-(2-{[(dimethyliminio)-methyl]amino}ethoxy)-1-benzothien-2-yl] sulfonyl}amino)methyl]-phosphonate;

4-cyano-3-fluorophenyl-{[({5-(2-(4-aza-1-azoniabicyclo [2.2.2]oct-1-yl)ethoxy)-1-benzothien-2-yl}sulfonyl)-amino]methyl}phosphonate;

4-cyano-3-fluorophenyl-{[({6-(2-(4-aza-1-azoniabicyclo [2.2.2]oct-1-yl)ethoxy)-4,5,7-trifluoro-1-benzothien-2-yl}sulfonyl)amino]methyl}phosphonate;

4-cyano-3-(trifluoromethyl)phenyl-[({[5-(2-(4-methyl-1,4-diazoniabicyclo[2.2.2]oct-1-yl)ethoxy)-1-benzothien-2-yl]sulfonyl}-amino)methyl]-phosphonate;

4-cyano-3-fluorophenyl-({[(5-{2-[4-(3-azidopropyl)-1,4-diazoniabicylco[2.2.2]oct-1-yl]ethoxy}-1-benzothien-2-yl)sulfonyl]-amino}methyl)phosphonate;

4-cyano-3-fluorophenyl-({[(6-{2-[4-(3-azidopropyl)-1,4-diazoniabicylco[2.2.2]oct-1-yl]ethoxy}-4-fluoro-1-benzothien-2-yl)sulfonyl]amino}methyl)phosphonate;

4-cyano-3-fluorophenyl-({[(6-{2-[4-(3-azidopropyl)-1,4-diazoniabicylco[2.2.2]oct-1-yl]ethoxy}-4,5,7-trifluoro-1-benzothien-2-yl)sulfonyl]amino}methyl)phosphonate;

4-cyano-3-fluorophenyl hydrogen[({[5-{2-[bis(2-cyanoethyl)amino]ethoxy}-1-benzothien-2-yl]-sulfonyl}amino)methyl]phosphonate;

4-cyano-3-fluorophenyl[({[5-(2-{4-[3-(1,4-diazoniabicyclo[2.2.2]oct-1-yl)propyl]-1,4-diazoniabicyclo[2.2.2]oct-1-yl}ethoxy)-1-benzothien-2-yl]sulfonyl}amino)methyl]phosphonate;

4-cyano-3-fluorophenyl-{[({6-[2-(4-{3-[(2,3-dihydroxybenzoyl)amino]propyl}-1,4-diazoniabicyclo[2.2.2]oct-1-yl)ethoxy]-4,5,7-trifluoro-1-benzothien-2-yl}sulfonyl)-amino]methyl}phosphonate;

4-cyano-3-fluorophenyl hydrogen[({[5-{2-[bis(3-ammoniopropoxy)amino]ethoxy}-1-benzothien-2-yl]-sulfonyl}amino)methyl]phoshonate;

4-cyano-3-fluorophenyl hydrogen({[(5-{3-[bis(3-aminopropyl)amino]propoxy}-1-benzothien-2-yl)sulfonyl]amino}methyl)phosphonate;

4-cyano-3-fluorophenyl hydrogen({[(5-{3-[(4-aminobutyl)-(3-aminopropyl)amino]propoxy}-1-benzothien-2-yl)sulfonyl]amino}methyl)phosphonate;

4-cyano-3-fluorophenyl hydrogen({[(5-{3-[bis(3-aminopropyl)amino]propoxy}-3-methyl-1-benzothien-2-yl)sulfonyl]amino}methyl)phosphonate;

4-cyano-3-fluorophenyl hydrogen[({[5-(3-{bis[3-({[(4-methoxybenzyl)oxy]carbonyl}amino)propyl]-amino}propoxy)-1-benzothien-2-yl]sulfonyl}amino)methyl]phosphonate;

4-cyano-3-fluorophenyl hydrogen[({[5-(3-{[4-({[(4-methoxybenzyl)oxy]carbonyl}amino)butyl][3-({[(4-methoxybenzyl)oxy]carbonyl}amino)propyl]amino}propoxy)-1-benzothien-2-yl]-sulfonyl}amino)-methyl]phosphonate;

4-cyano-3-fluorophenyl hydrogen[({[5-(3-{bis[3-({[(4-methoxybenzyl)oxy]carbonyl}amino)propyl]-amino}propoxy)-3-methyl-1-benzothien-2-yl]sulfonyl}amino)methyl]phosphonate;

4-cyano-3-fluorophenyl hydrogen[({[5-(3-{[4-({[(4-methoxybenzyl)oxy]carbonyl}amino)butyl][3-({[(4-methoxybenzyl)oxy]carbonyl}amino)propyl]amino}propoxy)-3-methyl-1-benzothien-2-yl]sulfonyl}-amino)methyl]phosphonate;

4-cyano-3-fluorophenyl hydrogen({[(5-{3-[4-aminobutyl]-(3-aminopropyl)amino]propoxy}-3-methyl-1-benzothien-2-yl)sulfonyl]amino}methyl)phosphonate;

4-cyano-3-fluorophenyl-({[(5-{2-[4-(3-ammoniopropyl)-1,4-diazoniabicylco[2.2.2]oct-1-yl]-ethoxy}-1-benzothien-2-yl)sulfonyl]amino}methyl)phosphonate trifluoroacetate trifluoromethanesulfonate;

4-cyano-3-fluorophenyl-({[(6-{2-[4-(3-ammoniopropyl)-1,4-diazoniabicyclo[2.2.2]oct-1-yl]-ethoxy}-4-fluoro-1-benzothien-2-yl)sulfonyl]amino}methyl)phosphonate;

4-cyano-3-fluorophenyl-({[(6-{2-[4-(3-ammoniopropyl)-1,4-diazoniabicyclo[2.2.2]oct-1-yl]-ethoxy}-4,5,7-trifluoro-1-benzothien-2-yl)sulfonyl]amino}methyl)phosphonate;

4-{[4-({2-[({(4-cyano-3-fluorophenoxy)(hydroxyl)phosphoryl]methyl}amino)sulfonyl]-1-benzothien-6-yl}-oxy)butyl]thio}-1-methylpyridinium;

4-Cyano-3-fluorophenyl-({[(5-{[(3-(pyridinium-1-ylpropyl)thio]methyl}-1-benzothien-2-yl)sulfonyl]amino}methyl)phosphonate;

4-cyano-3-(trifluoromethyl)phenyl-({[(5-{[(3-(pyridinium-1-ylpropyl)thio]methyl}-1-benzothien-2-yl)sulfonyl]amino}methyl)phosphonate;

4-Cyano-3-fluorophenyl-({[(5-{[(3-(pyridinium-1-ylpropyl)sulfonyl]methyl}-1-benzothien-2-yl)sulfonyl]amino}methyl)phosphonate;

4-cyano-3-fluorophenyl[({[5,6-bis(2-ammonioethoxy)-3-methyl-1-benzothien-2-yl]sulfonyl}-amino)methyl]phosphonate;

4-cyano-3-fluorophenyl hydrogen[({[5,6-bis(3-ammoniopropoxy)-3-ethyl-1-benzothien-2-yl]-sulfonyl}amino)methyl]phosphonate;

4-cyano-3-fluorophenyl hydrogen[({[6-(4-ammoniobutoxy)-5-(3-ammoniopropoxy)-1-benzothien-2-yl]sulfonyl}amino)methyl]phosphonate;

4-cyano-3-fluorophenyl hydrogen[({[5-(4-ammoniobutoxy)-6-(3-ammoniopropoxy)-1-benzothien-2-yl]sulfonyl}amino)methyl]phosphonate;

4-cyano-3-fluorophenyl[({[5,6-bis(2-ammonioethoxy)-3-methyl-4,7-difluoro-1-benzothien-2-yl]sulfonyl}amino)methyl]phosphonate;

4-cyano-3-fluorophenyl[({[5,6-bis(2-ammonioethoxy)-3-ethyl-4,7-difluoro-1-benzothien-2-yl]sulfonyl}amino)methyl]phosphonate;

4-cyano-3-fluorophenyl[({[5,6-bis(3-ammoniopropoxy)-4,7-difluoro-3-ethyl-1-benzothien-2-yl]-sulfonyl}amino)methyl]phosphonate;

N'2',N'2'-bis(2-aminoethyl)-N-{2-[({[(4-cyano-3-fluorophenoxy)(hydroxy)phosphoryl]-methyl}amino)sulfonyl]-1-benzothien-5-yl}glycinamide;

2-(2-(N-(((4-cyano-3-fluorophenoxy)(hydroxy)phosphoryl)methyl)sulfamoyl)benzo[b]thiophen-5-ylamino)-N,N,N-trimethyl-2-oxoethanaminium;

4-cyano-3-fluorophenyl hydrogen[({[5,6-bis(3-{[amino(iminio)methyl]amino}propoxy)-4,7-difluoro-1-benzothien-2-yl]sulfonyl}amino)methyl]phosphonate;

4-cyano-3-fluorophenyl[({[5,6-bis(3-{[amino(iminio)methyl]amino}propoxy)-3-methyl-1-benzothien-2-yl]sulfonyl}amino)methyl]phosphonate;

4-cyano-3-fluorophenyl[({[5,6-bis(3-{[amino(iminio)methyl]amino}propoxy)-4,7-dichloro-1-benzothien-2-yl]sulfonyl}amino)methyl]phosphonate;

N'2',N'2'-bis{2-[(tert-butoxycarbonyl)amino]ethyl}-N-{2-[({[(4-cyano-3-fluorophenoxy)-(hydroxy)phosphoryl]methyl}amino)sulfonyl]-1-benzothien-5-yl}glycinamide;

4-cyano-3-fluorophenyl hydrogen[({[5-(2-{bis[3-({[(4-methoxybenzyl)oxy]carbonyl}amino)-propyl]amino}ethoxy)-1-benzothien-2-yl]sulfonyl}amino)methyl]phosphonate;

4-cyano-3-fluorophenyl hydrogen[5-(2-{[(8-hydroxyquinolin-5-yl)methyl](methyl)amino}-acetamido)-benzo[b]thiophene-2-sulfonamido]methyl phosphonate;

4-cyano-3-fluorophenyl[({[5,6-bis(3-{[amino(iminio)methyl]amino}propoxy)-3-ethyl-1-benzothien-2-yl]sulfonyl}amino)methyl]phosphonate;

4-cyano-3-fluorophenyl[({[5,6-bis(3-{[amino(iminio)methyl]amino}propoxy)-4,7-fluoro-3-ethyl-1-benzothien-2-yl]sulfonyl}amino)methyl]phosphonate;

4-cyano-3-fluorophenyl[({[5,6-bis(2-ammonioethoxy)-3-ethyl-1-benzothien-2-yl]sulfonyl}-amino)methyl]phosphonate;

4-cyano-3-fluorophenyl hydrogen[5-((S)-2,6-diaminohexanamido)benzo[b]thiophene-2-sulfonamido]methylphosphonate;

4-cyano-3-fluorophenyl-hydrogen-{5-[(S)-2-amino-3-(1H-imidazol-4-yl)propanamido]-benzo[b]thiophene-2-sulfonamido}methylphosphonate;

4-cyano-3-fluorophenyl hydrogen[({5-(2-{bis[3-({[(4-methoxybenzyl)oxy]-carbonyl}amino)-propyl]amino}ethoxy)-1-benzothien-2-yl]sulfonyl}amino)methyl]-phosphonate;

4-cyano-3-fluorophenyl(5-((3-(pyridinium-1-yl)propylthio)methyl)benzo[b]thiophene-2-sulfonamido)methylphosphonate;

4-cyano-3-fluorophenyl(5-((3-(pyridinium-1-yl)propylsulfonyl)methyl)benzo[b]thiophene-2-sulfonamido)methylphosphonate;

4-cyano-3-fluorophenyl aminooxy((7-cyano-6-(dimethylamino)benzo[b]thiophene-2-sulfonamido)methyl)phosphinate;

4-cyano-3-fluorophenyl hydrogen(5-(2-(bis(2-(3,4-dimethoxybenzamido)ethyl)-amino)acetamido)-benzo[b]thiophene-2-sulfonamido)methylphosphonate;

4-cyano-3-fluorophenyl hydrogen(5-(2-(bis(2-(3,4-dihydroxybenzamido)ethyl)-amino)acetamido)-benzo[b]thiophene-2-sulfonamido)methylphosphonate;

4-cyano-3-fluorophenyl hydrogen(5-(3,4-bis(3-aminopropoxy)benzamido)benzo[b]thiophene-2-sulfonamido)methylphosphonate;

4-cyano-3-fluorophenyl hydrogen(5-(3,4,5-tris(3-aminopropoxy)benzamido)-benzo[b]thiophene-2-sulfonamido)methylphosphonate;

4-cyano-3-fluorophenyl hydrogen(5-(3,5-bis(3-aminopropoxy)benzamido)benzo[b]thiophene-2-sulfonamido)methylphosphonate;

4-cyano-3-fluorophenyl hydrogen[({[5,6-bis(3-aminopropoxy)-3-methyl-1-benzothien-2-yl]sulfonyl}amino)methyl]phosphonate;

4-cyano-3-fluorophenyl hydrogen({[(5,6-bis{3-[(iminomethyl)amino]propoxy}-3-methyl-1-benzothien-2-yl)sulfonyl]amino}methyl)phosphonate;

4-cyano-3-fluorophenyl hydrogen[({[5,6-bis(3-{[amino(imino)methyl]amino}propoxy)-3-methyl-1-benzothien-2-yl]sulfonyl}amino)methyl]phosphonate;

6-cyanopyridin-3-yl hydrogen[({[5,6-bis(3-aminopropoxy)-3-methyl-1-benzothien-2-yl]sulfonyl}amino)methyl]phosphonate;

6-cyanopyridin-3-yl hydrogen({[(5,6-bis{3-[(iminomethyl)amino]propoxy}-3-methyl-1-benzothien-2-yl)sulfonyl]amino}methyl)phosphonate;

6-cyanopyridin-3-yl hydrogen[({[5,6-bis(3-{[amino(imino)methyl]amino}propoxy)-3-methyl-1-benzothien-2-yl]sulfonyl}amino)methyl]phosphonate;

6-cyanopyridin-3-yl[({[5,6-bis(3-ammoniopropoxy)-3-methyl-1-benzothien-2-yl]sulfonyl}amino)methyl]phosphonate;

6-cyanopyridin-3-yl hydrogen[({[5,6-bis(3-aminopropoxy)-4-fluoro-3-methyl-1-benzothien-2-yl]sulfonyl}amino)methyl]phosphonate;

6-cyanopyridin-3-yl hydrogen[({[5,6-bis(3-aminopropoxy)-7-fluoro-3-methyl-1-benzothien-2-yl]sulfonyl}amino)methyl]phosphonate;

6-cyanopyridin-3-yl hydrogen[({[5,6-bis(3-aminopropoxy)-4,7-difluoro-3-methyl-1-benzothien-2-yl]sulfonyl}amino)methyl]phosphonate;

4-cyano-3-fluorophenyl hydrogen[({[5,6-bis(3-aminopropoxy)-4-fluoro-3-methyl-1-benzothien-2-yl]sulfonyl}amino)methyl]phosphonate;

4-cyano-3-fluorophenyl hydrogen[({[5,6-bis(3-aminopropoxy)-7-fluoro-3-methyl-1-benzothien-2-yl]sulfonyl}amino)methyl]phosphonate;

4-cyano-3-fluorophenyl hydrogen[({[5,6-bis(3-aminopropoxy)-4,7-difluoro-3-methyl-1-benzothien-2-yl]sulfonyl}amino)methyl]phosphonate;

4-cyano-3-fluorophenyl({[(5-{3-[4-(3-ammoniopropyl)-1,4-diazoniabicyclo[2.2.2]oct-1-yl]propoxy}-3-methyl-1-benzothien-2-yl)sulfonyl]amino}methyl)phosphonate;

4-cyano-3-fluorophenyl({[(5-{3-[4-(3-{[(Z)-iminomethyl]amino}propyl)-1,4-diazoniabicyclo[2.2.2]oct-1-yl]propoxy}-3-methyl-1-benzothien-2-yl)sulfonyl]amino}methyl)phosphonate;

4-cyano-3-fluorophenyl({[(5-{3-[4-(3-{[(Z)-amino(imino)methyl]amino}propyl)-1,4-diazoniabicyclo[2.2.2]oct-1-yl]propoxy}-3-methyl-1-benzothien-2-yl)sulfonyl]amino}methyl)phosphonate;

6-cyanopyridin-3-yl({[(5-{3-[4-(3-ammoniopropyl)-1,4-diazoniabicyclo[2.2.2]oct-1-yl]propoxy}-3-methyl-1-benzothien-2-yl)sulfonyl]amino}methyl)phosphonate;

6-cyanopyridin-3-yl({[(5-{3-[4-(3-{[(Z)-iminomethyl]amino}propyl)-1,4-diazoniabicyclo[2.2.2]oct-1-yl]propoxy}-3-methyl-1-benzothien-2-yl)sulfonyl]amino}methyl)phosphonate; and 6-cyanopyridin-3-yl({[(5-{3-[4-(3-{[(Z)-amino(imino)methyl]amino}propyl)-1,4-diazoniabicyclo[2.2.2]oct-1-yl]propoxy}-3-methyl-1-benzothien-2-yl)sulfonyl]amino}methyl)phosphonate;

or pharmaceutically acceptable salts thereof.

5. A compound according to claim 4 wherein the pharmaceutically acceptable salts are selected from one or more of the groups consisting of chloride, trifluoroacetate, iodide, trifluoromethanesulfonate, acetate, phosphate, or a mixture thereof.

6. A compound according to claim 1, which is 4-cyano-3-fluorophenyl hydrogen(5-(3,4-bis(3-aminopropoxy)benzamido)benzo[b]thiophene-2-sulfonamido)methylphosphonate trifluoroacetate;

4-cyano-3-fluorophenyl hydrogen(5-(3,4,5-tris(3-aminopropoxy)benzamido)-benzo[b]thiophene-2-sulfonamido)methylphosphonate trifluoroacetate;

4-cyano-3-fluorophenyl hydrogen(5-(3,5-bis(3-aminopropoxy)benzamido)benzo[b]thiophene-2-sulfonamido)methylphosphonate trifluoroacetate;

6-cyanopyridin-3-yl[({[5,6-bis(3-ammoniopropoxy)-3-methyl-1-benzothien-2-yl]sulfonyl}amino)methyl]phosphonate chloride;

6-cyanopyridin-3-yl[({[5,6-bis(3-ammoniopropoxy)-3-methyl-1-benzothien-2-yl]sulfonyl}amino)methyl]phosphonate trifluoroacetate; or 4-cyano-3-fluorophenyl[({[5,6-bis(3-ammoniopropoxy)-3-methyl-1-benzothien-2-yl]sulfonyl}amino)methyl]phosphonate trifluoroacetate.

7. A pharmaceutical composition which is comprised of a compound in accordance with claim 1 and a pharmaceutically acceptable carrier.

8. The composition according to claim 7 in combination with a beta-lactam antibiotic.

9. The composition according to claim 8 wherein the beta-lactam antibiotic is selected from the group consisting of imipenem, Primaxin®, Amoxicillin, Ticarcillin, Ampicillin, Cefoperazone, Piperacillin, and ceftazidime.

10. The composition of claim 9 wherein the beta-lactam antibiotic is Primaxin®.

11. A method of treating bacterial infections or inhibiting beta-lactamase in a mammal, the method comprising administering a therapeutically effect amount of a compound according to claim 1.

12. A compound according to claim 1, which is 6-cyanopyridin-3-yl hydrogen[({[5,6-bis(3-aminopropoxy)-3-methyl-1-benzothien-2-yl]sulfonyl}amino)methyl]phosphonate or a pharmaceutically acceptable salt thereof.

13. A compound which is 4-cyano-3-fluorophenyl(5-((triethylammonio)methyl)thiophene-2-sulfonamido)methylphosphonate or a pharmaceutically acceptable salt thereof.

14. A compound according to claim 1:

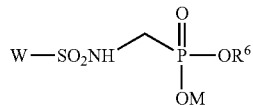

Formula I or a pharmaceutically acceptable salt thereof, wherein:
W represents:

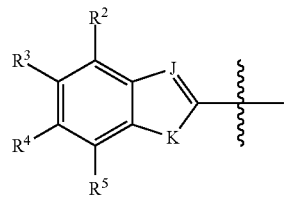

and
$R^3$ and $R^4$ independently represent cyano, $C_{1-6}$ alkyl, $-X_m-Y_m-Z^*_m-R^8$, or $-X_m-Y_m-Z^*_m-Q^+$;
or W represents

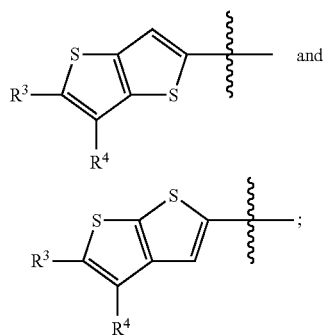

and
$R^3$ and $R^4$ independently represent hydrogen, halogen, cyano, $-OR^1$, $C_{1-6}$ alkyl, $-X_m-Y_m-Z^*_m-R^8$, or $-X_m-Y_m-Z^*_m-Q^+$;
or W represents

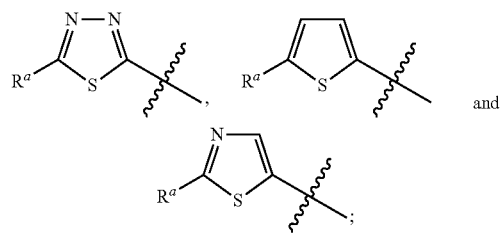

$R^a$ represents: $(CH_2)_n R^{aa}$;
Raa represents:

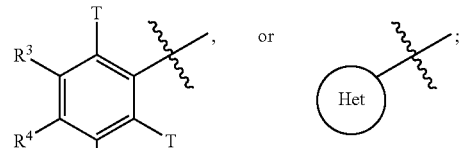

and
$R^3$ and $R^4$ independently represent halogen, cyano, $-OR^1$, $C_{1-6}$ alkyl, $-X_m-Y_m-Z^*_m-R^8$, or $-X_m-Y_m-Z^*_m-Q^+$;

J represents N or $CR^1$;

K represents O, S, or $NR^1$;

Het represents a 5-6 membered nitrogen containing heterocycle substituted with 0 to 4 groups of $R^2$;

T represents hydrogen, halogen, $OR^1$, or $C_{1-6}$ alkyl;

$R^1$ independently represents hydrogen, or $C_{1-6}$ alkyl;

M is a negative charge, H, or a pharmaceutically acceptable metal or ammonium salt, and provided that when W contains a moiety with multiple positive charges, there is an appropriate number of $L^\ominus$ present to provide overall neutrality;

$R^2$ and $R^5$ independently represent hydrogen, halogen, cyano, $-OR^1$, or $C_{1-6}$ alkyl;

$R^7$ represents hydrogen, halogen, cyano, $-OR^1$, $C_{1-6}$ alkyl, $-X_m-Y_m-Z^*_m-R^8$, or $-X_m-Y_m-Z^*_m-Q^+$;

X and Y independently are O, $NR^x$, (C=O), $SO_2$, $(CH_2)_n$, $-(CH_2)_n NR^1 C(O)-$, $-(CH_2)_n S-$, or $-(CH_2)_n N(R^x)_2-$;

$Z^*$ is $(CH_2)_n$ which may be substituted with one to four $R^b$, $R^6$ represents $C_{6-10}$ aryl, or $C_{5-10}$ heteroaryl, said aryl and heteroaryl optionally substituted;

$R^8$ represents halo, $N(R^c)_2$, $-C(O)R^5$, $NR^c C(NH)NH_2$, $NR^c C(NH)H$, $(CH_2)_n C_{5-10}$ heterocyclyl, or $(CH_2)_n C_{5-10}$ aryl, said heterocyclyl and aryl optionally substituted;

Q is selected from the group consisting of:

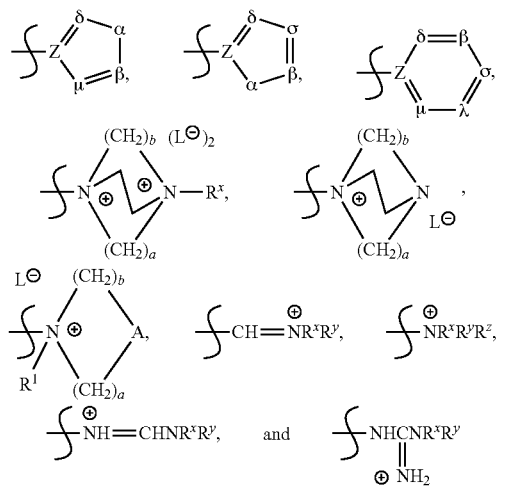

wherein Z represents N$^+$ or carbon; and A is O, CH$_2$, S(O)$_{0-2}$, NR$^x$, or N$^+$(R$^x$)$_2$;
$^+$ represents a positive charged ion;
L$^\ominus$ represents a pharmaceutically acceptable counterion that is present as needed to provide charge balance on the molecule;
a and b are 1, 2 or 3;
α represents O, S or NR$^s$;
β, δ, λ, μ and σ represent CR$^t$, N or N$^\ominus$R$^s$, provided that no more than one of β, δ, λ, μ and σ is N$^\ominus$R$^s$;
each R$^b$ independently represents halo; —CN; —NO$_2$; phenyl; —NHSO$_2$R$^c$; —OR$^c$, —SR$^c$; —N(R$^c$)$_2$; —N$^+$(R$^c$)$_3$; —C(O)N(R$^c$)$_2$; —SO$_2$N(R$^c$)$_2$; heteroaryl; heteroarylium; formamidinyl; —CO$_2$R$^c$; —C(O)R$^c$; —OC(O)R$^c$; —NHC(O)R$^c$; —NHC(O)$_2$R$^c$; guanidinyl; carbamimidoyl or ureido, said phenyl and heteroaryl optionally substituted;
each R$^c$ independently represents hydrogen, a —C$_{1-6}$ straight or branched-chain alkyl group, a —C$_3$-C$_6$ cycloalkyl group or C$_{6-10}$ aryl, said aryl optionally substituted with one to four groups of halogen; —CN; —NO$_2$; phenyl; —NHSO$_2$R$^j$; —OR$^j$, —SR$^j$; —N(R$^j$)$_2$; N$^+$(R$^j$)$_3$; —C(O)N(R$^j$)$_2$; —SO$_2$N(R$^j$)$_2$; heteroaryl; heteroarylium; formamidinyl; —CO$_2$R$^j$; —C(O)R$^j$; —OC(O)R$^j$; —NHC(O)R$^j$; —NHC(O)$_2$R$^j$; guanidinyl; carbamimidoyl or ureido, said phenyl and heteroaryl optionally substituted, wherein Rj is selected from the group consisting of hydrogen, a —C$_{1-6}$ straight or branched-chain alkyl group, a —C$_3$-C$_6$ cycloalkyl group or C$_{6-10}$ aryl;
each R$^s$ independently represents hydrogen; phenyl or —C$_{1-6}$ straight- or branched-chain alkyl, unsubstituted or substituted with one to four R$^b$ groups;
each R$^t$ independently represents hydrogen; halo; phenyl; —CN; —NO$_2$; —NR$^u$R$^v$; —OR$^u$; —SR$^u$; —C(O)NR$^u$R$^v$; —COOR$^c$; —SOR$^u$; —SO$_2$R$^u$; —SO$_2$NR$^u$R$^v$; —NR$^u$SO$_2$R$^v$; —C(O)R$^u$; —NR$^u$C(O)R$^v$; —OC(O)R$^u$; —OC(O)NR$^u$R$^v$; —NR$^u$CO$_2$R$^v$; —NR$^u$C(O)NR$^v$R$^w$; —OCO$_2$R$^v$; —C$_{1-6}$ straight- or branched-chain alkyl, unsubstituted or substituted with one to four R$^b$ groups;

R$^u$ and R$^v$ represent hydrogen or —C$_{1-6}$ straight- or branched-chain alkyl, unsubstituted or substituted with one to four R$^b$ groups;
each R$^w$ independently represents hydrogen; —C$_{1-6}$ straight- or branched-chain alkyl, unsubstituted or substituted with one to four R$^b$ groups; C$_{3-6}$ cycloalkyl optionally substituted with one to four R$^b$ groups; phenyl optionally substituted with one to four R$^b$ groups, or heteroaryl optionally substituted with one to four R$^b$ groups;
R$^x$ represents hydrogen or a C$_{1-8}$ straight- or branched-alkyl chain, optionally interrupted by one or two of O, S, SO, SO$_2$, NR$^w$, N$^+$R$^c$R$^w$, or —C(O)—, said alkyl chain being unsubstituted or substituted with one to four of halo, CN, NO$_2$, —N$_3$, OR$^w$, SR$^w$, SOR$^w$, SO$_2$R$^w$, NR$^c$R$^w$, N$^+$(R$^c$)$_2$R$^w$, Q, —C(O)—R$^w$, C(O)NR$^c$R$^w$, SO$_2$NR$^c$R$^w$, CO$_2$R$^w$, OC(O)R$^w$, OC(O)NR$^c$R$^w$, NR$^c$C(O)R$^w$, NR$^c$C(NH)NH$_2$, NR$^c$C(NH)H, NR$^c$C(O)NR$^c$R$^w$, phenyl, naphthyl, heteroaryl, or heterocyclic group said phenyl, heteroaryl, and heterocyclic group optionally substituted with from one to four R$^b$ groups or with one to two C$_{1-3}$ straight- or branched-chain alkyl groups, said alkyl groups being unsubstituted or substituted with one to four R$^b$ groups;
R$^y$ and R$^z$ represent hydrogen; phenyl; —C$_{1-6}$ straight or branched chain alkyl, unsubstituted or substituted with one to four R$^b$ groups, and optionally interrupted by O, S, N$^w$, N$^+$R$^c$R$^w$ or —C(O)—; and
m represents 0 to 1; n represents 0 to 6; wherein it is understood that when a value is zero, a bond exists.

15. The compound of claim 1 wherein W represents:

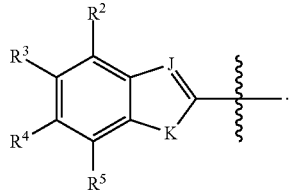

16. The compound of claim 15 wherein J is CR$^1$ and K is S.
17. The compound of claim 1 wherein R$^3$ and R$^4$ are —X$_m$—Y$_m$—Z*$_m$-Q$^+$.
18. The compound of claim 1 wherein X is O.
19. The compound of claim 18 wherein Y is a bond and Z* is (CH$_2$).
20. The compound of claim 1 wherein R$^6$ is C$_{6-10}$ aryl, C$_{5-10}$heteroaryl, said aryl and heteroaryl optionally substituted with 1-4 groups selected from halogen, cyano, nitro, C$_{1-6}$alkyl, OR$^1$, N(R$^1$)$_2$, COOR$^1$, and CON(R$^1$)$_2$.
21. The compound of claim 1 wherein Q$^+$ is

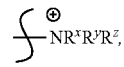

and L$^-$ is present if needed to provide neutrality.

* * * * *

UNITED STATES PATENT AND TRADEMARK OFFICE
CERTIFICATE OF CORRECTION

| | | |
|---|---|---|
| PATENT NO. | : 8,440,643 B2 | Page 1 of 1 |
| APPLICATION NO. | : 12/301797 | |
| DATED | : May 14, 2013 | |
| INVENTOR(S) | : Dininno et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1199 days.

Signed and Sealed this
Twenty-first Day of January, 2014

Michelle K. Lee
*Deputy Director of the United States Patent and Trademark Office*